(12) United States Patent
Keum et al.

(10) Patent No.: US 10,421,779 B2
(45) Date of Patent: Sep. 24, 2019

(54) CARBAZOLE COMPOUND HAVING ANTI-VIRUS ACTIVITY

(71) Applicants: KOREA INSTITUTE OF SCIENCE AND TECHNOLOGY, Seoul (KR); POSTECH ACADEMY-INDUSTRY FOUNDATION, Pohang-si, Gyeongsangbuk-do (KR)

(72) Inventors: Gyo Chang Keum, Seoul (KR); Eunice Eun Kyeong Kim, Seoul (KR); Sung Key Jang, Pohang-si (KR); Hee Sun Kim, Naju-si (KR); Ae Nim Pae, Seoul (KR); Hua Li, Seoul (KR); Jin Hyeong Park, Seoul (KR); Jin Sook Kwak, Seoul (KR)

(73) Assignees: KOREA INSTITUTE OF SCIENCE AND TECHNOLOGY, Seoul (KR); POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 0 days.

(21) Appl. No.: 15/687,203

(22) Filed: Aug. 25, 2017

(65) Prior Publication Data
US 2018/0057527 A1    Mar. 1, 2018

(30) Foreign Application Priority Data
Aug. 30, 2016 (KR) .......................... 10-2016-0110794

(51) Int. Cl.
*C07D 209/88* (2006.01)
*C07K 5/065* (2006.01)
*C07K 5/062* (2006.01)
*A61K 38/00* (2006.01)

(52) U.S. Cl.
CPC ...... *C07K 5/06078* (2013.01); *C07K 5/06052* (2013.01); *A61K 38/00* (2013.01)

(58) Field of Classification Search
CPC .................................................. C07D 209/88
See application file for complete search history.

(56) References Cited

U.S. PATENT DOCUMENTS

| | | | |
|---|---|---|---|
| 7,704,992 B2 * | 4/2010 | Bachand ............. | C07D 405/14 514/217 |
| 9,051,340 B2 * | 6/2015 | Bacon .................... | A61K 45/06 |

OTHER PUBLICATIONS

Huff, Joel R., Journal of Medicinal Chemistry, vol. 34. No. 8, Aug. 1991, pp. 2305-2314.*
Alter et al., "Chronic Consequences of Non-A, Non-B Hepatitis", Current Perspectives in Hepatology, 1989, Total No. pp. 17.
Davis et al., "Treatment of Chronic Hepatitis C Wth Recombinant Interferon Alfa", The New England Journal of Medicine:Treatment of Chronic Hepatitis C with Interferon, vol. 321, vol. 22, Nov. 30, 1989, pp. 1501-1506 (Total No. pp. 7).

* cited by examiner

*Primary Examiner* — Rebecca L Anderson
(74) *Attorney, Agent, or Firm* — Birch, Stewart, Kolasch & Birch, LLP

(57) ABSTRACT

The present invention relates to a carbazole compound having anti-virus activity, and more particularly, to a novel compound selected from the group of consisting of a carbazole compound which shows excellent anti-proliferative efficacy against hepatitis C virus (HCV), a pharmaceutically acceptable salt thereof, a hydrate thereof, and an isomer thereof; an anti-virus pharmaceutical composition including the novel compound as an active ingredient; a pharmaceutical composition for preventing or treating liver diseases caused by hepatitis C virus; and a method of preparing the novel compound.

6 Claims, No Drawings

CARBAZOLE COMPOUND HAVING ANTI-VIRUS ACTIVITY

CROSS-REFERENCE TO RELATED APPLICATION

This application claims under 35 U.S.C. § 119(a) the benefit of Korean Patent Application No. 10-2016-0110794 filed on Aug. 30, 2016, the entire contents of which are incorporated herein by reference.

BACKGROUND

(a) Technical Field

The present disclosure relates to a carbazole compound having anti-virus activity. More particularly, it relates to a novel compound selected from a carbazole compound which shows excellent anti-proliferative efficacy against hepatitis C virus (HCV), a pharmaceutically acceptable salt thereof, a hydrate thereof, or an isomer thereof, an anti-virus pharmaceutical composition including the novel compound as an active ingredient, a pharmaceutical composition for preventing or treating liver diseases caused by hepatitis C virus; and a method of preparing the novel compound.

(b) Background Art

It has been reported that hepatitis C virus (HCV) is caused by blood transfusion and a region specific infection, and about 70% of the infection cases are caused by kidney dialysis. Further, it has been known that about 20% of infection cases caused by hepatitis C virus causes acute hepatitis accompanied by cirrhosis within five years, and also develops into liver cancer (hepatocellular carcinoma: HCC) [see Non-Patent Documents 1 and 2]. Such a high chronic infection rate is a very rare occurrence seldom seen in RNA viruses, while at the sometime points out as evidence showing that hepatitis C virus is a medium which causes liver cancer at a high rate.

Since epidemiology shows that hepatitis C virus is prevalent all over the world, 3% of the global population have been infected, and 3 to 4 million per year are additionally infected, hepatitis C virus is emerging as an even more severe problem.

A vaccine for preventing and treating hepatitis C has not been currently developed. As a therapeutic agent for hepatitis C virus infection, a combination therapy of interferon and ribavirin as an antiviral agent has been used, but it has been reported that the combination therapy has efficacy for only 50% of the patients. Boceprevir (Merck & Co.) or telaprevir (Vertex Pharmaceuticals, Inc) approved by the FDA in 2011 increased the treatment rate by being administered in combination with a standard therapeutic agent, but could not obtain significant efficacy for chronic hepatitis patients. Further, the combination therapy of Daklinza (daclatasvir, DCV) as a genotype NS5A replication complex inhibitor and Sunvepra (asunaprevir, ASV) as an NS3/A4 protease inhibitor obtained the approval by the Ministry of Food and Drug Safety. In addition, Sovaldi (sofosbuvir) as an oral hepatitis C therapeutic agent which helps increase the cure rate was approved, followed by a recent approval of Harvoni (ledipasvir/sofosbuvir) as an oral hepatitis C therapeutic agent. Harvoni is a composite of ledipasvir as an NS5A inhibitor and sofosbuvir as an NS5B inhibitor, and shows overall sustained virologic response (SVR) rates for the treatment of patients with genotype 1 type chronic hepatitis C, which is relatively difficult to treat. Zepatier, which is a composite formulation of Grazoprevir as an NS3/4A protease inhibitor and Elbasvir as an NS5A inhibitor, has been most recently approved. Since a novel HCV therapeutic agent including the therapeutic agents needs to be combined with at least two target therapeutic agents, there is a need for a therapeutic agent for viruses resistant to NS5A inhibitors.

When a sustained virologic response fails to be obtained, there are problems with non-efficacy, recurrence, and tolerance to side effects. Furthermore, the standard therapy has not only the above-described problems, but also a problem in that 10 to 15% of the patients are in a state where a continuous treatment cannot be performed due to various side effects (influenza-like aches and pains, fever, fatigue, anemia, thrombocytopenia, leukopenia, baldness, and depression). In particular, patients, who are difficult to treat, are patients with genotype 1 HCV, HIV/HCV simultaneous infection, advanced cirrhosis, or liver transplant. Therefore, there is a desperate need for developing a more effective therapeutic agent.

The above information disclosed in this Background section is only for enhancement of understanding of the background of the invention and therefore it may contain information that does not form the prior art that is already known in this country to a person of ordinary skill in the art.

REFERENCES OF THE RELATED ART

[Non-Patent Documents]
(Non-Patent Document 1) Davis G L et al., Nev. Engl. J. Med. 321(1989) 1501-1506
(Non-Patent Document 2) Alter et al., Current Perspective in Hepatology, (1989) p. 83

SUMMARY OF THE DISCLOSURE

The present invention has been made in an effort to solve the above-described problems associated with prior art.

The present inventors have studied for many years in order to develop a new material capable of effectively inhibiting hepatitis C virus (HCV). As a result, the present inventors synthesized a novel carbazole compound which is useful as a functional inhibitor of NS5A nonstructural protein of HCV, confirmed that the compound exhibited excellent HCV inhibition activity and anti-proliferative efficacy while exhibiting low cytotoxicity, and revealed that the compound could be usefully used not only as an antiviral agent, but also as an agent for preventing or treating liver diseases caused by infection of hepatitis C virus due to the excellent HCV inhibition activity and anti-proliferative efficacy, thereby completing the present invention.

Thus, an object of the present invention is to provide a novel carbazole compound in which a pyrrolidin-2-yl carboxamide group and/or a 2-(pyrrolidin-2-yl)-1H-imidazol-5-yl group are/is substituted at C2 and C7 positions of the carbazole mother nucleus, a pharmaceutically acceptable salt thereof, a hydrate thereof, or an isomer thereof.

Another object of the present invention is to provide an anti-virus pharmaceutical composition including a novel carbazole compound, a pharmaceutically acceptable salt thereof, a hydrate thereof, or an isomer thereof as an active ingredient.

Still another object of the present invention is to provide a pharmaceutical composition for treating and preventing liver diseases caused by infection of hepatitis C virus, including a novel carbazole compound, a pharmaceutically acceptable salt thereof, a hydrate thereof, or an isomer thereof as an active ingredient.

Yet another object of the present invention is to provide a method of preparing a novel carbazole compound, a pharmaceutically acceptable salt thereof, a hydrate thereof, or an isomer thereof.

In one aspect, the present invention provides a carbazole compound represented by the following Formula 1, a pharmaceutically acceptable salt thereof, a hydrate thereof, or an isomer thereof.

[Formula 1]

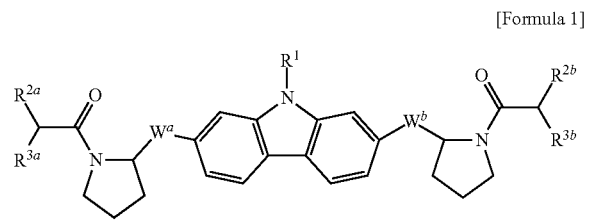

In Formula 1,
$W^a$ and $W^b$ are the same as or different from each other, and represent

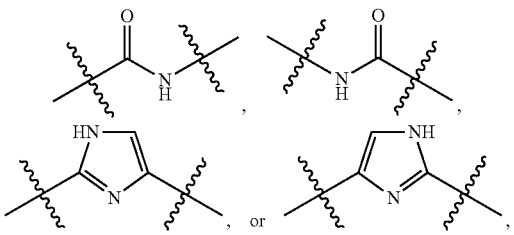

$R^1$ represents —($C_1$ to $C_{15}$ alkyl)-$R^4$, $R^{2a}$ and $R^{2b}$ are the same as or different from each other, and represent a $C_1$-$C_{10}$ alkyl group, or a $C_6$ to $C_{12}$ aryl group, $R^{3a}$ and $R^{3b}$ are the same as or different from each other, and represent —N($R^5$)—C(O)O$R^6$, $R^4$ represents a hydrogen atom, a $C_3$ to $C_7$ cycloalkyl group, di($C_3$ to $C_7$ cycloalkyl), —O$C_1$-$C_{10}$ alkyl, —(O$C_1$-$C_{10}$alkyl)$_n$(O$C_1$-$C_{10}$alkyl) (here, n is an integer from 0 to 5), a $C_6$ to $C_{12}$ aryl group, a pentagonal to heptagonal heterocyclic group including 1 to 3 heteroatoms selected from nitrogen and oxygen, or a pentagonal to heptagonal heteroaryl group including 1 to 3 heteroatoms selected from nitrogen and oxygen, $R^5$ and $R^6$ represent a hydrogen atom, or a $C_1$-$C_{10}$ alkyl group, or $R^5$ and $R^6$ may be bonded to each other to form

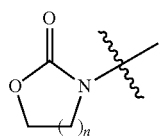

(here, n is an integer from 0 to 9), and the aryl group, the heterocyclic group, or the heteroaryl group may be each unsubstituted or substituted with 1 to 3 substituents selected from the group consisting of a halogen atom, nitro, amine, $C_1$-$C_{10}$ alkyl, —O$C_1$-$C_{10}$ haloalkyl including 1 to 15 halogen atoms, —O$C_1$-$C_{10}$ alkyl, —O$C_3$-$C_7$ cycloalkyl, —(O$C_1$-$C_{10}$alkyl)$_n$(O$C_1$-$C_{10}$alkyl) (here, n is an integer from 0 to 5), and —NH—C(O)—$C_1$-$C_{10}$ alkyl.

In another aspect, the present invention provides an anti-virus pharmaceutical composition including the carbazole compound represented by Formula 1, a pharmaceutically acceptable salt thereof, a hydrate thereof, or an isomer thereof as an active ingredient. In particular, the compound of the present invention has excellent activities of inhibiting the function of HCV NS5A nonstructural protein and of inhibiting replication/proliferation of HCV virus.

In still another aspect, the present invention provides a pharmaceutical composition for preventing or treating liver diseases caused by infection of hepatitis C virus, including the carbazole compound represented by Formula 1, a pharmaceutically acceptable salt thereof, a hydrate thereof, or an isomer thereof as an active ingredient. The liver disease caused by infection of hepatitis C virus may be selected from the group consisting of acute hepatitis C, chronic hepatitis C, cirrhosis, and hepatocellular carcinoma.

In yet another aspect, the present invention provides a method of preventing or treating infectious diseases caused by HCV, the method including administering a therapeutically effective amount of the pharmaceutical composition. In addition, the anti-virus composition against HCV may be combined with other HCV antiviral agents, if appropriate.

In still yet another aspect, the present invention provides a method of preparing the carbazole compound represented by Formula 1, a pharmaceutically acceptable salt thereof, a hydrate thereof, or an isomer thereof.

The carbazole compound represented by Formula 1 according to the present invention, a pharmaceutically acceptable salt thereof, a hydrate thereof, or an isomer thereof has an anti-virus activity, and thus may be used for the purpose of treating and preventing virus diseases. In particular, the compound of the present invention has excellent activities of inhibiting the function of HCV NS5A nonstructural protein and inhibiting replication/proliferation of HCV virus, and thus is effective as an agent for preventing or treating liver diseases caused by hepatitis C virus, for example, acute hepatitis C, chronic hepatitis C, cirrhosis, and hepatocellular carcinoma.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Hereinafter, the present invention will be described in more detail.

The term "hepatitis C virus (HCV)" as used herein means all the hepatitis C virus strains, and also includes homologues and mutants thereof.

The term 'treatment' as used herein is used as a meaning including all of the alleviation or improvement of symptoms, the reduction of the scope of disease, the retardation or alleviation of disease progression, the improvement, alleviation or stabilization of a disease state, partial or full recovery, the prolongation of survival, or other beneficial therapeutic results, and the like.

S substituent used to define a compound according to the present invention will be described in more detail as follows.

The term 'a halogen atom' or 'halo' as used herein specifically means fluorine, chlorine, bromine, and iodine.

The term 'alkyl' as used herein means an aliphatic hydrocarbon group having 1 to 15 carbon atoms. The alkyl may be 'saturated alkyl' or 'unsaturated alkyl' including at least one alkenyl or alkynyl moiety. The alkyl may be straight, branched, or cyclic when used either alone or in combination. Specific examples of the straight and branched alkyl include methyl, ethyl, normal propyl, isopropyl, normal butyl, isobutyl, tert-butyl, normal pentyl, neo-pentyl, normal hexyl, isohexyl, normal heptyl, normal octyl, normal nonyl, normal decyl, normal undecyl, normal dodecyl, and the like. The cyclic alkyl may be a cycloalkyl group having 3 to 7 carbon atoms, and specific examples thereof include cyclopropyl, cyclobutyl, cyclohexyl, and cycloheptyl.

The term 'aryl' as used herein means an aromatic hydrocarbon group having 6 to 12 carbon atoms, or an aromatic hydrocarbon in which a cycloalkyl group, a heterocycloalkyl group or a heteroaryl group is fused with an aromatic hydrocarbon ring. Specific examples of the aryl include phenyl, indanyl, 1-naphthyl, 2-naphthyl, tetrahydronaphthyl, 2,3-dihydrobenzo[b][1,4]dioxin, and the like, but are not limited thereto. The aryl may be connected to another group at a suitable position on the aromatic ring.

As used herein, the term "heteroaryl" means a heteroaromatic cyclic group including one or more heteroatoms selected from the group consisting of N, O, and S, unless otherwise mentioned. Specific examples of the heteroaryl include pyridinyl, pyrazinyl, pyrimidinyl, pyridazinyl, pyrazolyl, imidazolyl, triazolyl, indolyl, oxadiazolyl, thiadiazolyl, quinolinyl, isoquinolinyl, isoxazolyl, oxazolyl, thiazolyl, pyrrolyl, and the like, but are not limited thereto.

As used herein, the term "heterocycle" means a saturated or unsaturated non-aromatic cyclic group including one or more heteroatoms selected from the group consisting of N, O, and S, unless otherwise mentioned. Specific examples of the heterocycle include pyrrolidinyl, furanyl, morpholinyl, piperazinyl, piperidinyl, and the like, but are not limited thereto.

The aryl, the heteroaryl, or the heterocycle may be unsubstituted or substituted with one or more substituents. In this case, the substituent may be 1 to 3 substituents selected from the group consisting of a halogen atom, nitro, amine, $C_1$-$C_{10}$ alkyl, $C_1$-$C_{10}$ haloalkyl including 1 to 15 halogen atoms, —$OC_1$-$C_{10}$ alkyl, —$OC_3$-$C_7$ cycloalkyl, —$(OC_1$-$C_{10}$alkyl$)_n(OC_1$-$C_{10}$alkyl) (here, n is an integer from 0 to 5), and —NH—C(O)—$C_1$-$C_{10}$ alkyl.

The compound represented by Formula 1 according to the present invention may have one or more asymmetric centers, and in the case of the compound, an enantiomer or a diastereomer may be present. Accordingly, the present invention includes each isomer or an isomer mixture thereof.

Since the compound represented by Formula 1 can also be present in the form of tautomer, the present invention also includes each tautomer or a mixture thereof.

The present invention includes radioactive derivatives of the compound represented by Formula 1, and these radioactive compounds are useful in the bio research field.

According to an exemplary embodiment of the present invention, the present invention provides a compound selected from a carbazole compound represented by the following Formula 1, a pharmaceutically acceptable salt thereof, a hydrate thereof, or an isomer thereof.

[Formula 1]

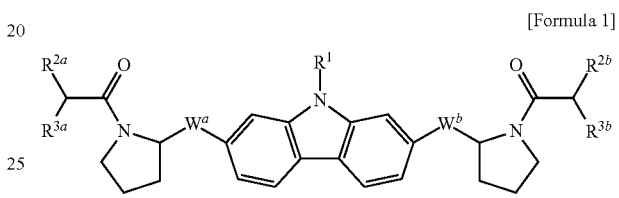

In Formula 1, $W^a$ and $W^b$ are the same as or different from each other, and represent

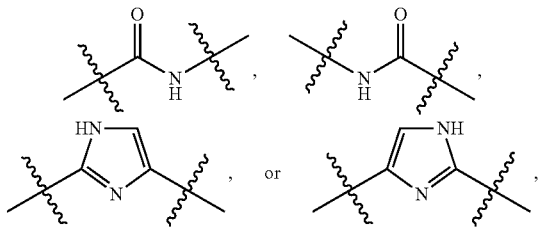

$R^1$ represents —($C_1$ to $C_{15}$ alkyl)-$R^4$, $R^{2a}$ and $R^{2b}$ are the same as or different from each other, and represent a $C_1$-$C_{10}$ alkyl group, or a $C_6$ to $C_{12}$ aryl group, $R^{3a}$ and $R^{3b}$ are the same as or different from each other, and represent —N($R^5$)—C(O)O$R^6$, $R^4$ represents a hydrogen atom, a $C_3$ to $C_7$ cycloalkyl group, di($C_3$ to $C_7$ cycloalkyl), —O$C_1$-$C_{10}$alkyl), —(O$C_1$-$C_{10}$ alkyl$)_n$(O$C_1$-$C_{10}$ alkyl) (here, n is an integer from 0 to 5), a $C_6$ to $C_{12}$ aryl group, a pentagonal to heptagonal heterocyclic group including 1 to 3 heteroatoms selected from nitrogen and oxygen, or a pentagonal to heptagonal heteroaryl group including 1 to 3 heteroatoms selected from nitrogen and oxygen, $R^5$ and $R^6$ represent a hydrogen atom, or a $C_1$-$C_{10}$ alkyl group, or $R^5$ and $R^6$ may be bonded to each other to form

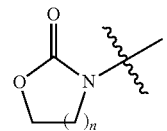

(here, n is an integer from 0 to 9), and the aryl group, the heterocyclic group, or the heteroaryl group may be each unsubstituted or substituted with 1 to 3 substituents selected from the group consisting of a halogen atom, nitro, amine, $C_1$-$C_{10}$ alkyl, $C_1$-$C_{10}$ haloalkyl including 1 to 15 halogen atoms, —$OC_1$-$C_{10}$ alkyl, —$OC_3$-$C_7$ cycloalkyl, —$(OC_1$-$C_{10}$alkyl$)_n(OC_1$-$C_{10}$alkyl) (here, n is an integer from 0 to 5), and —NH—C(O)—$C_1$-$C_{10}$ alkyl.

According to a preferred exemplary embodiment of the present invention, in the compound represented by Formula 1, $W^a$ and $W^b$ are the same as or different from each other, and represent

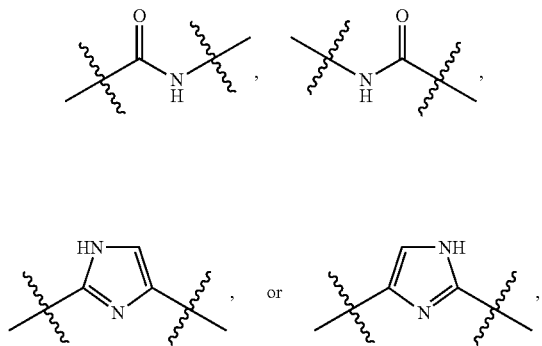

$R^1$ represents a $C_1$ to $C_{15}$ alkyl group, —($C_1$-$C_{10}$ alkyl)-($C_3$ to $C_7$ cycloalkyl), —($C_1$-$C_{10}$ alkylene)-($C_3$ to $C_7$ cycloalkyl)$_2$, —($C_1$-$C_{10}$ alkyl)-($OC_1$ to $C_6$ alkyl), —($C_1$-$C_{10}$ alkyl)($OC_1$ to $C_6$ alkyl)$_n$($OC_1$ to $C_6$ alkyl) (here, n is an integer from 1 to 3), —($C_1$-$C_{10}$ alkyl)-morpholino, —($C_1$-$C_{10}$ alkyl)-piperidine, —($C_1$-$C_{10}$ alkyl)-piperazine, —($C_1$-$C_{10}$ alkyl)-(N—$C_1$ to $C_6$ alkylpiperazine), alkyl)-pyridine, and —($C_1$-$C_{10}$ alkyl)-phenyl, the pyridine may be unsubstituted or substituted with 1 to 2 substituents selected from the group consisting of $C_1$ to $C_6$ alkyl, and the phenyl may be unsubstituted or substituted with 1 to 3 substituents selected from the group consisting of halo, —$NO_2$, —$NH_2$, —$CF_3$, —$OC_1$ to $C_6$ alkyl, —$OC_3$-$C_7$ cycloalkyl, —$(OC_1$ to $C_6$ alkyl$)_n(OC_1$ to $C_6$ alkyl) (here, n is an integer from 1 to 3), and —NH—C(O)—$C_1$ to $C_6$ alkyl, $R^{2a}$ and $R^{2b}$ are the same as or different from each other, and represent a $C_1$-$C_{10}$ alkyl group, or a phenyl group, $R^{3a}$ and $R^{3b}$ are the same as or different from each other, and represent —N($R^5$)—C(O)$OR^6$, and $R^5$ and $R^6$ represent a hydrogen atom, or a $C_1$-$C_{10}$ alkyl group, or $R^5$ and $R^6$ may be bonded to each other to form

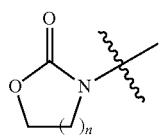

(here, n is an integer from 0 to 9).

According to a more preferred exemplary embodiment of the present invention, the compound represented by Formula 1 may also be classified into the following Formula 1a, 1 b, or 1c by $W^a$ and $W^b$.

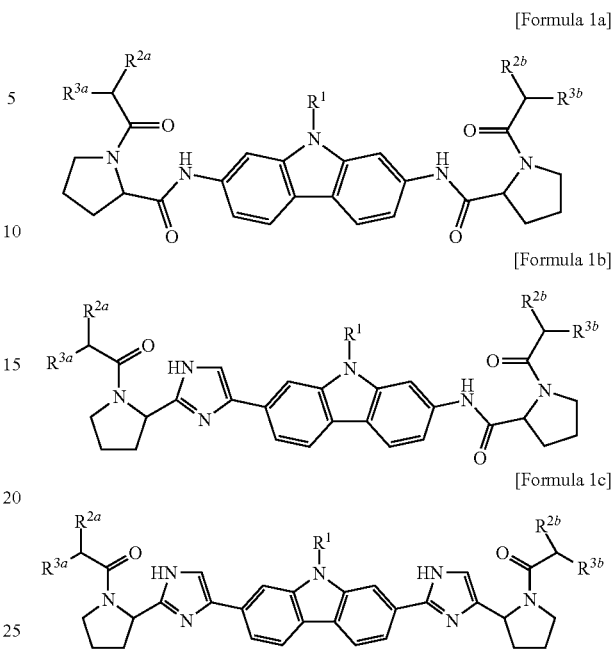

(In Formula 1a, 1 b, or 1c, $R^1$, $R^{2a}$, $R^{2b}$, $R^{3a}$, and $R^{3b}$ are each the same as those defined in Formula 1.)

According to a more preferred exemplary embodiment of the present invention, the compound of the present invention may be a compound selected from below, or a pharmaceutically acceptable salt thereof, or a hydrate thereof, or an isomer thereof:

(Compound No. 1) dimethyl ((1R,1'R)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 2) dimethyl ((2R,2'R)-((2S,2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 3) dimethyl ((1S,1'S)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))carbamate, (Compound No. 4) dimethyl ((2S,2'S)-((2S,2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 5) (2S,2'S)—N,N'-(9-butyl-9H-carbazole-2,7-diyl)bis(1-((S)-3-methyl-3-2-(2-oxooxazolidine-3-yl)butanoyl)pyrrolidine-2-carboxamide), (Compound No. 6) dimethyl ((1R,1'R)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 7) dimethyl ((2R,2'R)-((2S,2'S)-(((9-methyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 8) dimethyl ((1S,1'S)-((2S,2'S)-(((9-methyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 9) dimethyl ((2S,2'S)-((2S,2'S)-(((9-methyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 10) (2S,2'S)—N,N'-(9-methyl-9H-carbazole-2,7-diyl)bis(1-((S)-3-methyl-2-(2-oxazolidine-3-yl)butanoyl)pyrrolidine-2-carboxamide), (Compound No. 11) dimethyl ((1R,1'R)-((2 S,2'S)-(((9-(2-(4-methylpiperazine-1-yl)ethyl-9H-carbazole-2,7-diyl) bis(azanediyl))bis(carbonyl))bis(pyrrolidine-2,1-diyl))bis(2-oxo-1-phenylethane-2,1-diyl))carbamate, (Compound No. 12) dimethyl ((1R,1'R)-((2S,2'S)-(((9-(2-morpholinoethyl)-9H-carbazole-2,7-diyl)bis(azanediyl))bis(carbonyl))bis(pyrrolidine-2,1-diyl))bis(2-oxo-1-phenylethane-2,1-diyl))carbamate, (Compound No. 13) dimethyl ((1R,1'R)-((2S,2'S)-(((9-benzyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 14) dimethyl ((1R,1'R)-((2S,2'S)-(((9-(4-methoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 15) dimethyl ((1R,1'R)-((2S,2'S)-(((9-(1-phenylethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 16) dimethyl ((1R,1'R)-((2S,2'S)-(((9-(cyclopropylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 17) dimethyl ((1R,1'R)-((2S,2'S)-(((9-(pyridine-2-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 18) dimethyl ((1R,1'R)-((2S,2'S)-(((9-(pyridine-3-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 19) dimethyl ((1R,1'R)-((2S,2'S)-(((9-(pyridine-4-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 20) dimethyl ((1R,1'R)-((2S,2'S)-(((9-((6-methylpyridine-2-yl)methyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 21) dimethyl ((1R,1'R)-((2S,2'S)-(((9-(2-methoxyethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 22) dimethyl ((1R,1'R)-((2S,2'S)-(((9-(2-(2-methoxyethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 23) dimethyl ((1R,1'R)-((2S,2'S)-(((9-(2-(2-(2-methoxyethoxy)ethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 24) dimethyl ((1R,1'R)-((2S,2'S)-(((9-decyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 25) dimethyl ((2R,2'R)-((2S,2'S)-(((9-decyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 26) dimethyl ((1R,1'R)-((2S,2'S)-(((9-octyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 27) dimethyl ((1R,1'R)-((2S,2'S)-(((9-dodecyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 28) dimethyl ((1R,1'R)-((2S,2'S)-(((9-(1-phenylbutyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 29) dimethyl ((1R,1'R)-((2S,2'S)-(((9-(1-phenyloctyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 30) dimethyl ((1R,1'R)-((2S,2'S)-(((9-(3-(pentyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 31) dimethyl ((1R,1'R)-((2S,2'S)-(((9-(4-(hexyloxy)benzyl)-9H-carbonyl-2,7-diyl)bis(azanediyl))bis(carbonyl))bis(pyrrolidine-2,1-diyl))bis(2-oxo-1-phenylethane-2,1-diyl))dicarbamate, (Compound No. 32) dimethyl ((1R,1'R)-((2S,2'S)-(((9-(2-butoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 33) dimethyl ((1R,1'R)-((2S,2'S)-(((9-(10-(4-methylpiperazine-1-yl)decyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 34) dimethyl ((1R,1'R)-((2S,2'S)-(((9-(10-morpholinodecyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 35) dimethyl ((1R,1'R)-((2S,2'S)-(((9-(2-(hexyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 36) dimethyl ((1R,1'R)-((2S,2'S)-(((9-(4-butoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 37) dimethyl ((1R,1'R)-((2S,2'S)-(((9-(3-nitrobenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 38) dimethyl ((1R,1'R)-((2S,2'S)-(((9-(3-pivalamidobenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 39) dimethyl ((1R,1'R)-((2S,2'S)-(((9-(3-(cyclopentyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 40) dimethyl ((1R,1'R)-((2S,2'S)-(((9-(3-(2-(2-methoxyethoxy)ethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 41) dimethyl ((1R,1'R)-((2S,2'S)-(((9-(3-(2-methoxyethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 42) dimethyl ((1R,1'R)-((2S,2'S)-(((9-(1-phenyldecyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 43) dimethyl ((1R,1'R)-((2S,2'S)-(((9-(2-(trifluoromethyl)benzyl)-9H-carbazole-2,7-diyl)bis (azanediyl))biscarbonyl))bis(pyrrolidine-2,1-diyl))bis(2-oxo-1-phenylethane-2,1-diyl))dicarbamate, (Compound No. 44) dimethyl ((1R,1'R)-((2S,2'S)-(((9-(3-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 45) dimethyl ((1R,1'R)-((2S,2'S)-(((9-(4-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 46) dimethyl ((1R,1'R)-((2S,2'S)-(((9-(nonane-5-yl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 47) dimethyl ((1R,1'R)-((2S,2'S)-(((9-(cyclopentylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 48) dimethyl ((1R,1'R)-((2S,2'S)-(((9-(cyclohexylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 49) dimethyl ((1R,1'R)-((2S,2'S)-(((9-(dicyclopropylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 50) dimethyl ((1R,1'R)-((2S,2'S)-(((9-pentyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 51) methyl ((R)-2-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-2-oxo-1-phenylethyl)carbamate, (Compound No. 52) methyl ((R)-2-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-2-oxo-1-phenylethyl)carbamate, (Compound No. 53) methyl ((S)-1-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-3-methyl-1-oxobutane-2-yl) carbamate, and (Compound No. 54) methyl ((S)-1-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-3-methyl-1-oxobutane-2-yl) carbamate.

The compound according to the present invention may include the carbazole compound represented by Formula 1, a pharmaceutically acceptable salt thereof, or a hydrate thereof.

A pharmaceutically acceptable salt of the carbazole compound represented by Formula 1 may be prepared by a typical method in the art. The pharmaceutically acceptable salt may be used in the form of a pharmaceutically acceptable acid addition salt derived from an inorganic acid or an organic acid. An acid which may be used for the preparation of the pharmaceutically acceptable salt may be specifically one or more selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

A hydrate of the carbazole compound represented by Formula 1 according to the present invention may mean a compound formed by bonding the compound of Formula 1 to water molecules.

The carbazole compound represented by Formula 1 according to the present invention may have one or more asymmetric centers in the molecular structure, and in the case of the compound, an enantiomer or a diastereomer may be present.

Accordingly, unless there is a particular limitation in the present specification, the term 'the compound represented by Formula 1' may be interpreted to mean all of a carbazole compound, a pharmaceutically acceptable salt thereof or a hydrate thereof, or an isomer thereof.

Meanwhile, the compound represented by Formula 1 has an excellent HCV inhibition activity while exhibiting low cytotoxicity, and thus may be used as an active ingredient of a pharmaceutical composition for treating and preventing virus-infected diseases. By having excellent HCV inhibition activity and anti-proliferative efficacy as described above, the carbazole compound represented by Formula 1, a pharmaceutically acceptable salt thereof, or a hydrate thereof is very useful not only as an anti-virus composition against HCV, but also as a composition for preventing or treating hepatitis as diseases associated with hepatitis C.

Thus, another exemplary embodiment of the present invention provides a pharmaceutical composition for preventing or treating hepatitis and an anti-virus composition against HCV, including the compound represented by Formula 1, a pharmaceutically acceptable salt thereof, or a hydrate thereof as an active ingredient.

The pharmaceutical composition may be applied to an experimental animal such as a mouse, a rabbit, a rat, a guinea pig, or a hamster, or a primate including a human, but is not limited thereto, and may be applied to preferably a primate including a human, and more preferably a human.

The term 'treatment' as used herein may be used as a meaning including all of the alleviation or improvement of symptoms, the reduction of the scope of disease, the retardation or alleviation of disease progression, the improvement, alleviation or stabilization of a disease state, partial or full recovery, the prolongation of survival, or other beneficial therapeutic results, and the like.

In accordance with the use aspect and use method of the pharmaceutical composition of the present invention, the content of the compound represented by Formula 1, which is an active ingredient, may be used by being appropriately adjusted according to the selection of the person skilled in the art.

The pharmaceutical composition of the present invention includes the compound represented by Formula 1 as an active ingredient, and the active ingredient may be included in a content of 0.1 to 10 wt %, more preferably 0.5 to 5 wt % based on a total weight of the pharmaceutical composition.

In the pharmaceutical composition of the present invention, the compound represented by Formula 1 as an active ingredient may be included alone in the pharmaceutical composition, or may also be included together with a pharmacologically acceptable carrier, excipient, diluent, or adjuvant.

Examples of the pharmacologically acceptable carrier, excipient, or diluent include one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil, dextrin, calcium carbonate, propylene glycol, liquid paraffin, and a physiological saline, but are not limited thereto, and all the typical carriers, excipients, or diluents can be used. Further, the pharmaceutical composition may additionally include typical fillers, extenders, binders, disintegrating agents, anticoagulants, lubricants, wetting agents, pH adjusting agents, nutrients, vitamins, electrolytes, alginic acid and salts thereof, pectic acid and salts thereof, protective colloids, glycerin, flavors, emulsifiers or preservatives, and the like.

The pharmaceutical composition of the present invention may be used as a combination therapy which is simultaneously or at different times applied by further including one or more other antiviral agents, which are publicly known to be effective for treating or preventing HCV, or other therapeutic agents, in addition to the compound represented by Formula 1. The one or more antiviral agents or other therapeutic agents may include one or more compounds selected from the group consisting of interferon, an interferon-ribavirin combination therapy, an HCV protease inhibitor, an NS5A inhibitor, an HCV polymerase inhibitor or an HCV serine protease inhibitor, and further, the one or more antiviral agents may include a vaccine selected from therapeutic vaccines or DNA vaccines.

The pharmaceutical composition may be administered both orally and parenterally, and as an example, the composition may be administered through various routes including oral, percutaneous, subcutaneous, intravenous and intramuscular administration. Furthermore, the dosage form of the composition may vary according to the use method, and the composition may be formulated by using a method well-known in the art to which the present invention pertains so as to provide a rapid, continued or delayed release of the active ingredient after administration to a mammal. In general, examples of solid preparations for oral administration include tablets, caplets, soft or hard capsules, pills, powders, granules, and the like, and the preparation may be prepared by mixing one or more excipients, for example, starch, calcium carbonate, sucrose or lactose, gelatin, and the like. Further, in addition to simple excipients, lubricants such as magnesium stearate and talc may also be used. Examples of liquid preparations for oral administration include suspensions, liquids for internal use, emulsions, syrups, and the like, and may include various excipients, for example, wetting agents, flavoring agents, aromatics, preservatives, and the like, in addition to water and liquid paraffin, which are frequently used simple diluents. Preparations for parenteral administration may be in the form of creams, lotions, ointments, plasters, liquids and solutions, aerosols, fluid extracts, elixirs, infusions, sachets, patches, or injections, and in the case of a dosage form for injection, the preparations for parenteral administration may be preferably in the form of an isotonic aqueous solution or a suspension.

The pharmaceutical composition may further contain adjuvants such as sterile agents, preservatives, stabilizers, hydrating agents or emulsifying accelerants, salts for controlling osmotic pressure and/or buffering agents, and other therapeutically useful materials, and the composition may be prepared by typical mixing, granulating or coating method, and may be formulated by using an appropriate method publicly known in the art, in addition to the methods.

The administration amount of the pharmaceutical composition may be determined in consideration of an administration method, age and gender of a taker, severity and condition of a patient, absorption of active ingredient in the body, inert rate, and drugs to be combined, and the pharmaceutical composition may be administered once or several times. The active ingredient of the pharmaceutical composition may be administered once or several times daily via an oral or parenteral route to preferably a mammal including a human in an amount of 0.001 to 100 mg/kg body weight, preferably 0.01 to 35 mg/kg body weight.

Still another exemplary embodiment of the present invention provides a method of preventing or treating virus infection symptoms, the method including: administering a therapeutically effective amount of the pharmaceutical composition.

Preferably, the treatment method includes treating cells infected with HCV. The cells infected with HCV means any cell infected with HCV, and prokaryotic or eukaryotic cells, and include, for example, immortalized cell lines or primary cell lines, bacterial culture, and in-situ cells.

Preferably, the treatment method may additionally include: identifying a patient in need of preventing or treating the infection symptoms caused by HCV.

The same described above in association with a subject to which the pharmaceutical composition may be applied may be applied to a subject to which the treatment method is applied.

The term "therapeutically effective amount" of the present invention means an amount of active ingredient for a mammal, which is effective in treating and/or alleviating HCV infection. The therapeutically effective amount may be adjusted according to various factors such as the kind and severity of the disease, the kinds and contents of active ingredient and other ingredients contained in the composition, the kind of dosage form, age, body weight, general medical conditions, gender and a diet of a patient, a duration and a route of administration, a blood clearance rate of the composition, a treatment duration, and drugs used together. Specifically, the therapeutically effective amount may be an amount of 0.001 to 100 mg/kg-body weight, preferably 0.01 to 35 mg/kg-body weight based on the daily administration amount, and may be administered once or several times daily via an oral or parenteral route.

The present invention provides a method of preparing the compound represented by Formula 1.

The method of preparing the compound represented by Formula 1 according to the present invention may be changed in accordance with $W^a$ and $W^b$.

The following Reaction Formula 1 is an example of a method of preparing the carbazole compound represented by Formula 1, in which $W^a$ and $W^b$ are each

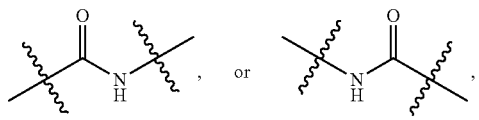 [SMILES: *NC(*)=O ; *NC(*)=O]

and includes:

1) a process of preparing a 9-substituted 2,7-dihalo-9H-carbazole compound represented by the following Formula 4 by performing a reaction in which a 2,7-dihalo-9H-carbazole compound represented by the following Formula 2 is substituted with a halide compound represented by the following Formula 3;

2) a process of preparing a 2,7-diphenylmethaneimine-9H-carbazole compound represented by the following Formula 6 by reacting the compound represented by the following Formula 4 with benzophenoneimine represented by the following Formula 5;

3) a process of preparing a 9H-carbazole-2,7-diamine compound represented by the following Formula 7 by reacting the compound represented by the following Formula 6 under acid conditions; and 4) a process of preparing a 2,7-bis(pyrrolidine-2-ylcarboxamide)-9H-carbazole compound represented by the following Formula 1a by performing a reaction in which the compound represented by the following Formula 7 is bonded to a pyrroline-2-carboxylic acid compound represented by the following Formula 8.

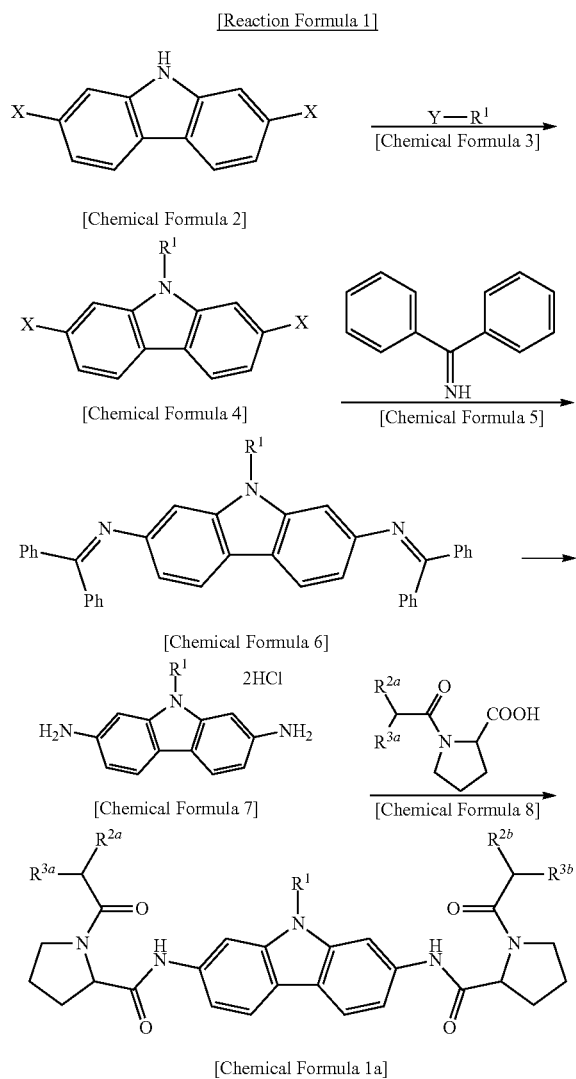

(In Reaction Formula 1, $R^1$, $R^{2a}$, $R^{2b}$, $R^{3a}$, and $R^{3b}$ are each the same as those defined in Formula 1; and X and Y each represent a halogen atom.)

The preparation method according to Reaction Formula 1 will be described for each step in more detail as follows.

The process 1) is a reaction in which a substituent $R^1$ is introduced into a C9 position of the 2,7-dihalo-9H-carbazole compound represented by Formula 2. Specifically, the reaction is performed by using an alkyl halide reagent (Y—$R^1$) in the presence of sodium hydride (NaH). In this case, dichloromethane, acetonitrile, tetrahydrofuran (THF), N,N-dimethylformamide (DMF), dimethyl sulfoxide (DMSO), and the like may be used as a reaction solvent. The reaction temperature is −20° C. to 50° C., and the reaction may smoothly proceed even at a temperature around room temperature.

The process 2) is a reaction in which a diphenylmethaneimine group is introduced into both C2 and C7 by reacting 2 equivalents of benzophenoneimine with the compound represented by Formula 4. Specifically, the reaction may be performed by using a 2-di-tert-butylphosphino-2',4',6'-triisopropyldiphenyl (tBuXPhos) or (1,1'-binaphthalene-2,2'-diyl)bis(diphenylphosphine) (BINAP) reagent in the presence of a palladium catalyst such as $Pd_2(dba)_3$ and a base such as sodium tert-butoxide ($^tBuONa$). In this case, a hydrocarbon solvent such as toluene may be used as a reaction solvent, and a condition under which the temperature is increased to 50° C. to 120° C. as a reaction temperature may be maintained.

The process 3) is a reaction in which a diphenylmethaneimide group of the compound represented by Formula 6 is converted into an amine ($NH_2$) group by being reacted under acidic conditions. The reaction is performed within a temperature range of −20° C. to 50° C. by using an HCl-methanol solution, and the reaction may smoothly proceed even at a temperature around room temperature.

The process 4) is a process in which the compound represented by Formula 1a is prepared via an amidization bonding reaction between the 9H-carbazole-2,7-diamine compound represented by Formula 7 and the pyrrolidine-2-carboxylic acid compound represented by Formula 8. The amidization bonding reaction may be performed in the presence or absence of additive under a reaction solvent such as dichloromethane, acetonitrile, tetrahydrofuran (THF), N,N-dimethylformamide (DMF), and dimethyl sulfoxide (DMSO). In this case, it is possible to use an organic base such as triethylamine (TEA) and N,N-diisopropylethylamine (DIPEA) or an inorganic base of an alkali metal carbonate such as $Cs_2CO_3$, $K_2CO_3$, and $NaHCO_3$ as the additive. Alternatively, in order to promote the bonding reaction, it is possible to use a catalyst such as 1,3-dicyclohexylcarbodiimide (DCC), 1-ethyl-3-(3-dimethylaminopropyl)carbodiimide (EDC), 1-[bis(dimethylamino)methylene-1H-1,2,3-triazole[4,5-b]pyridinium 3-oxide hexafluorophosphate (HATU), and 1-hydroxybenzotriazole (HOBt) as the additive. Further, it is preferred that the bonding reaction is performed at −78° C. to 100° C. for 1 hour to 200 hours.

The following Reaction Formula 2 as a preparation method of the present invention is an example of a method of preparing the carbazole compound represented by Formula 1, in which one of $W^a$ and $W^b$ is

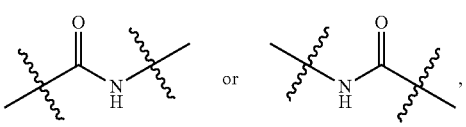 [SMILES: *NC(*)=O ; *NC(*)=O]

and the other is

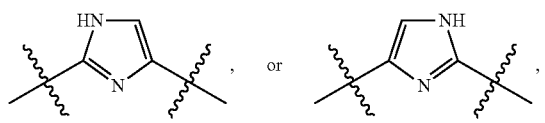 [SMILES: *c1c[nH]c(*)n1 ; *c1c[nH]c(*)n1]

and includes:

a) a process of preparing a 9-substituted 2,7-dihalo-9H-carbazole compound represented by the following Formula 4 by performing a reaction in which a 2,7-dihalo-9H-carbazole compound represented by the following Formula 2 is substituted with a halide compound represented by the following Formula 3;

b) a process of preparing a 2-halo-7-(diphenylmethaneimine)-9H-carbazole compound represented by the following Formula 9 by reacting the compound represented by the following Formula 4 with a benzophenoneimine compound represented by the following Formula 5;

c) a process of preparing a 2-(4,4,5,5-tetramethyl-1,3,2-dioxaborolane-2-yl)-7-(diphenylmethaneimine)-9H-carbazole compound represented by the following Formula 11 by reacting the compound represented by the following Formula 9 with bis(pinacolato)diboron represented by the following Formula 10;

d) a process of preparing a 2-(2-pyrrolidine-5-halo-1H-imidazole)-7-(diphenylmethaneimine)-9H-carbazole compound represented by the following Formula 13 by reacting the compound represented by the following Formula 11 with a 2-pyrrolidine-5-halo-1H-imidazole compound represented by the following Formula 12;

e) a process of preparing a 2-(2-(pyrrolidine-2-yl)-1H-imidazole-5-yl)-7-(amino)-9H-carbazole compound represented by the following Formula 14 by hydrolyzing the compound represented by the following Formula 13 under acid conditions; and f) a process of preparing a 2-(2-(pyrrolidine-2-yl)-1H-imidazole-5-yl)-7-(pyrrolidine-2-ylcarboxamide)-9H-carbazole compound represented by the following Formula 1 b by performing a reaction in which the compound represented by the following Formula 14 is bonded to a pyrroline-2-carboxylic acid compound represented by the following Formula 8.

[Reaction Formula 2]

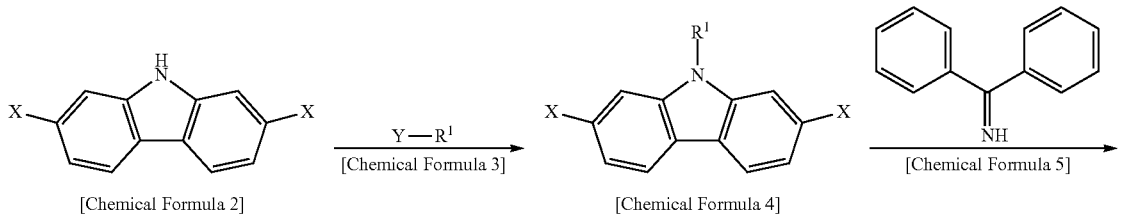

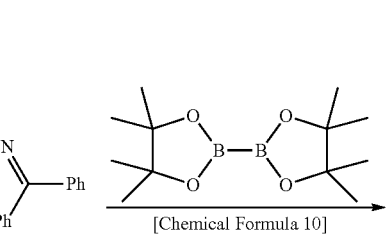

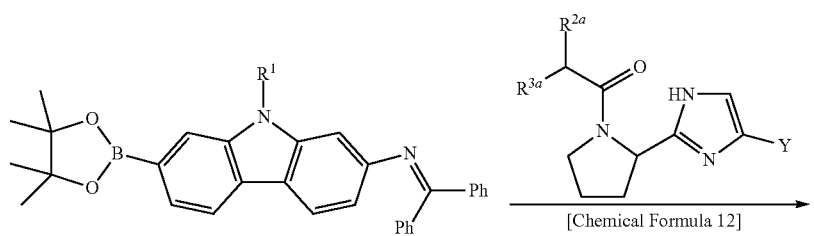

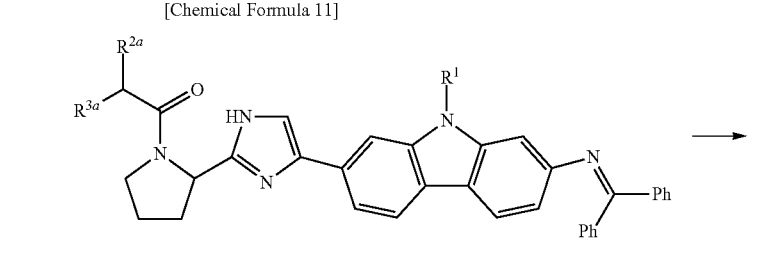

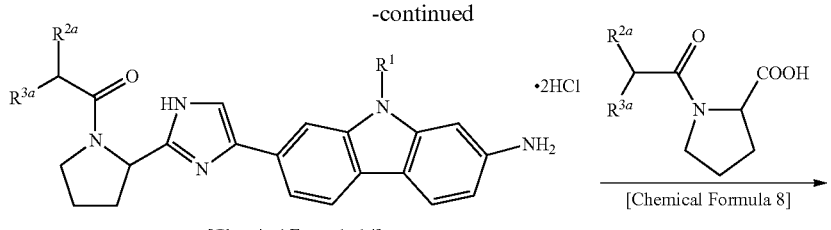

[Chemical Formula 14]

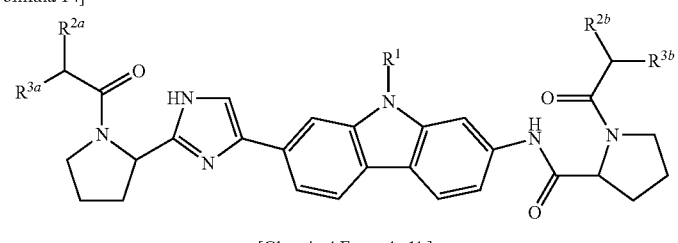

[Chemical Formula 1b]

(In Reaction Formula 2, $R^1$, $R^{2a}$, $R^{2b}$, $R^{3a}$, and $R^{3b}$ are each the same as those defined in Formula 1; and X and Y each represent a halogen atom.)

The preparation method according to Reaction Formula 2 will be described for each step in more detail as follows.

The process a) is a reaction in which a substituent $R^1$ is introduced into a C9 position of the 2,7-dihalo-9H-carbazole compound represented by Formula 2. Specifically, the reaction is performed by using an alkyl halide reagent (Y—$R^1$) in the presence of sodium hydride (NaH). In this case, dichloromethane, acetonitrile, tetrahydrofuran (THF), N,N-dimethylformamide (DMF), dimethyl sulfoxide (DMSO), and the like may be used as a reaction solvent. The reaction temperature is −20° C. to 50° C., and the reaction may smoothly proceed even at a temperature around room temperature.

The process b) is a reaction in which a diphenylmethaneimine group is introduced into one of a C2 and C7 positions of the compound represented by Formula 4. Specifically, the reaction may be performed by using a 2-di-tert-butylphosphino-2',4',6'-triisopropyldiphenyl (tBuXPhos) or (1,1'-binaphthalene-2,2'-diyl)bis(diphenylphosphine) (BI NAP) reagent in the presence of a palladium catalyst such as $Pd_2(dba)_3$ and $Pd(dppf)Cl_2$ and a base such as sodium tert-butoxide ($^t$BuONa) and potassium acetoxide (KOAc). In this case, a hydrocarbon solvent such as toluene may be used as a reaction solvent, and a condition under which the temperature is increased to 50° C. to 120° C. as a reaction temperature may be maintained.

The process c) is a process of performing a standard Suzuki bonding reaction on a halide group of the compound represented by Formula 9 and bis(pinacolato)diboron. Specifically, the halide group of the compound represented by Formula 9 is reacted with a bis(pinacolato)diboron reagent in the presence of a palladium catalyst such as $Pd_2(dba)_3$ and $Pd(dppf)Cl_2$ and a base such as sodium tert-butoxide ($^t$BuONa) and potassium acetoxide (KOAc). In this case, 1,4-dioxane, and the like may be used as a reaction solvent, and a condition under which the temperature is increased to 50° C. to 120° C. as a reaction temperature may be maintained.

The process d) is a process of substituting a dioxaborolane group of the compound represented by Formula 11 with a pyrrolidine-2-yl-1H-imidazole group. Specifically, the dioxaborolane group of the compound represented by Formula 11 is reacted with a 1H-imidazole halide compound in the presence of a palladium catalyst such as $Pd_2(dba)_3$ and $Pd(dppf)Cl_2$ and an alkali metal salt base such as sodium hydrogen carbonate. In this case, as a reaction solvent, it is possible to use a single solvent or a mixed solvent selected from water, N,N-dimethylformamide (DMF), and dimethyl sulfoxide (DMSO), and a mixed solvent of water and N,N-dimethylformamide was used in the Examples of the present invention. A condition under which the temperature is heated to 50° C. to 120° C. as a reaction temperature may be maintained.

The process e) is a reaction in which a diphenylmethaneimide group of the compound represented by Formula 13 is converted into an amine ($NH_2$) group by being reacted under acidic conditions. The reaction is performed within a temperature range of −20° C. to 50° C. by using an HCl-methanol solution, and the reaction may smoothly proceed even at a temperature around room temperature.

The process f) is a process of preparing the compound represented by Formula 1 b by subjecting an amine group of the compound represented by Formula 14 to an amidization reaction. The amidization reaction may be performed in the presence or absence of additive under a reaction solvent such as dichloromethane, acetonitrile, tetrahydrofuran (THF), N,N-dimethylformamide (DMF), and dimethyl sulfoxide (DMSO). In this case, it is possible to use an organic base such as triethylamine (TEA) and N,N-diisopropylethylamine (DIPEA) or an inorganic base of an alkali metal carbonate such as $CS_2CO_3$, $K_2CO_3$, and $NaHCO_3$ as the additive. Alternatively, in order to promote the bonding reaction, it is possible to use a catalyst such as 1,3-dicyclohexylcarbodiimide (DCC), 1-ethyl-3-(3-dimethylaminopropyl)carbodiimide (EDC), 1-[bis(dimethylamino)methylene-1H-1,2,3-triazole[4,5-b]pyridinium 3-oxide hexafluorophosphate (HATU), and 1-hydroxybenzotriazole (HOBt) as the additive. Further, it is preferred that the bonding reaction is performed at −78° C. to 100° C. for 1 hour to 200 hours.

The following Reaction Formula 3 as a preparation method of the present invention is an example of a method of preparing the carbazole compound represented by Formula 1, in which $W^a$ and $W^b$ are each

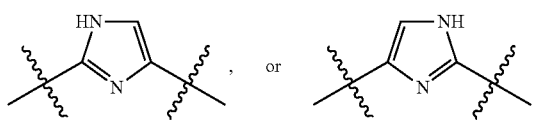 [SMILES: *c1c[nH]c(*)n1 ; *c1c[nH]c(*)n1]

in, and includes:

i) a process of preparing a 9-substituted 2,7-dihalo-9H-carbazole compound represented by the following Formula 4 by performing a reaction in which a 2,7-dihalo-9H-carbazole compound represented by the following Formula 2 is substituted with a halide compound represented by the following Formula 3;

ii) a process of preparing a 2,7-bis(4,4,5,5-tetramethyl-1,3,2-dioxaborolane-2-yl)-9H-carbazole compound represented by the following Formula 15 by reacting the compound represented by the following Formula 4 with bis(pinacolato)diboron represented by the following Formula 10; and iii) a process of preparing a 2,7-bis(2-(pyrrolidine-2-yl)-1H-imidazole-5-yl)-9H-carbazole compound represented by the following Formula 1c by reacting the compound represented by the following Formula 15 with a 2-pyrrolidine-5-halo-1H-imidazole compound represented by the following Formula 12.

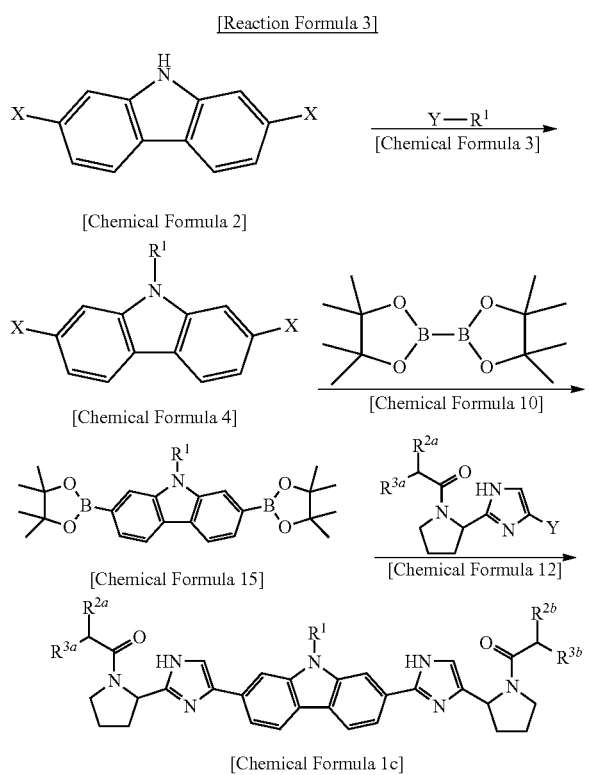

(In Reaction Formula 3, $R^1$, $R^{2a}$, $R^{2b}$, $R^{3a}$, and $R^{3b}$ are each the same as those defined in Formula 1; and X and Y each represent a halogen atom.)

The preparation method according to Reaction Formula 3 will be described for each step in more detail as follows.

The process i) is a reaction in which a substituent $R^1$ is introduced into a C9 position of the 2,7-dihalo-9H-carbazole compound represented by Formula 2. Specifically, the reaction is performed by using an alkyl halide reagent (Y—$R^1$) in the presence of sodium hydride (NaH). In this case, dichloromethane, acetonitrile, tetrahydrofuran (THF), N,N-dimethylformamide (DMF), dimethyl sulfoxide (DMSO), and the like may be used as a reaction solvent. The reaction temperature is −20° C. to 50° C., and the reaction may smoothly proceed even at a temperature around room temperature.

The process ii) is a process of performing a standard Suzuki bonding reaction on a halide group at the C2 and C9 positions of the compound represented by Formula 4 and bis(pinacolato)diboron. Specifically, the halide group of the compound represented by Formula 9 is reacted with a bis(pinacolato)diboron reagent in the presence of a palladium catalyst such as $Pd_2(dba)_3$ and $Pd(dppf)Cl_2$ and a base such as sodium tert-butoxide ($^tBuONa$) and potassium acetoxide (KOAc). In this case, 1,4-dioxane, and the like may be used as a reaction solvent, and a condition under which the temperature is increased to 50° C. to 120° C. as a reaction temperature may be maintained.

The process iii) is a process of preparing the compound represented by Formula 1c by substituting a dioxaborolane group of the compound represented by Formula 15 with a pyrrolidine-2-yl-1H-imidazole group. Specifically, the dioxaborolane group of the compound represented by Formula 15 is reacted with a 1H-imidazole halide compound in the presence of a palladium catalyst such as $Pd_2(dba)_3$ and $Pd(dppf)Cl_2$ and an alkali metal salt base such as sodium hydrogen carbonate. In this case, as a reaction solvent, it is possible to use a single solvent or a mixed solvent selected from water, N,N-dimethylformamide (DMF), and dimethyl sulfoxide (DMSO), and a mixed solvent of water and N,N-dimethylformamide was used in the Examples of the present invention. A condition under which the temperature is increased to 50° C. to 120° C. as a reaction temperature may be maintained.

EXAMPLES

The following examples illustrate the invention and are not intended to limit the same.

Hereinafter, the present invention will be described in more detail through preferred Examples for help understanding of the present invention. However, the following Examples are only for exemplifying the present invention, and the scope of the present invention is not limited to the following Examples.

EXAMPLES

Example 1. Preparation of dimethyl ((1R,1'R)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate

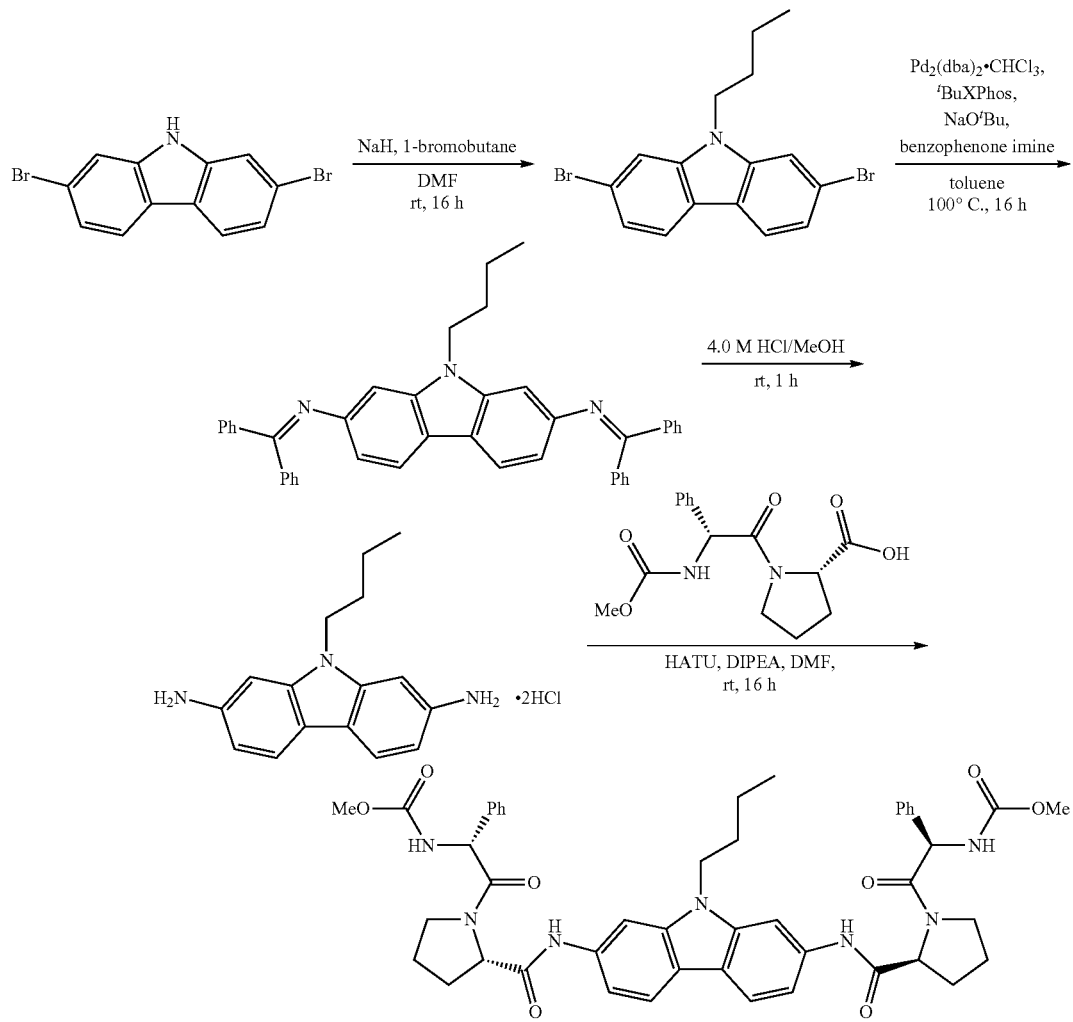

Step (1). Preparation of 2,7-dibromo-9-butyl-9H-carbazole 2,7-dibromo-9H-carbazole (3.0 g, 9.231 mmol) was dissolved in DMF (50 mL) under an argon atmosphere, and then NaH (60% in mineral oil, 480 mg, 12.00 mmol) was added thereto at 0° C., and the resulting mixture was stirred at room temperature for 30 minutes. 1-bromobutane (1.19 mL, 11.08 mmol) was added to the mixture, and then the resulting mixture was stirred at room temperature for 16 hours. H$_2$O was slowly added to the reaction mixture. The mixture completely reacted was extracted by using ethyl acetate and H$_2$O, and the collected organic layer was washed with brine. The separated organic layer was dried by using anhydrous magnesium sulfate, and then filtered and concentrated under reduced pressure. The concentrated solution was purified with column chromatography (hexane/EtOAc=50/1, v/v) to obtain a white solid target compound (3.52 g, 100%).

$^1$H NMR (400 MHz, CDCl$_3$) δ 7.87 (d, J=8.3 Hz, 2H), 7.54 (d, J=1.5 Hz, 2H), 7.36 (dd, J=8.3, 1.6 Hz, 2H), 4.16 (t, J=7.3 Hz, 2H), 1.87-1.79 (m, 2H), 1.47-1.37 (m, 2H), 0.99 (t, J=7.4 Hz, 3H); $^{13}$C NMR (100 MHz, CDCl$_3$) δ 141.32, 122.51, 121.46, 121.25, 119.70, 111.98, 43.13, 30.94, 20.56, 13.89.

Step (2). Preparation of N,N'-(9-butyl-9H-carbazole-2,7-diyl)bis(1,1-diphenylmethaneimine)

The 2,7-dibromo-9-butyl-9H-carbazole (500 mg, 1.312 mmol) prepared in Step (1), Pd$_2$(dba)$_3$·CHCl$_3$ (41 mg, 0.039 mmol), 2-di-tert-butylphosphino-2',4',6'-triisopropyldiphenyl ($^t$BuXPhos; 50 mg, 0.118 mmol), and $^t$BuONa (378 mg, 3.936 mmol) was added to toluene (5 mL) under an argon atmosphere. Benzophenoneimine (0.51 mL, 3.018 mmol) was added to the mixture, and then the resulting mixture was stirred at 100° C. for 16 hours. The mixture completely reacted was cooled to room temperature, and then extracted by using ethyl acetate and H$_2$O, and the collected organic layer was washed with brine. The separated organic layer was dried by using anhydrous magnesium sulfate, and then filtered and concentrated under reduced pressure. The concentrated solution was separated and purified with column chromatography (hexane/EtOAc=20/1 to 10/1, v/v) to obtain a viscous yellow solid target compound (591 mg, 77%).

$^1$H NMR (400 MHz, CDCl$_3$) δ 7.83 (d, J=7.1 Hz, 4H), 7.75 (d, J=8.2 Hz, 2H), 7.54-7.51 (m, 2H), 7.48-7.44 (m, 4H), 7.29-7.24 (m, 6H), 7.22-7.20 (m, 4H), 6.72 (s, 2H), 6.68 (dd, J=8.2, 1.5 Hz, 2H), 3.95 (t, J=7.1 Hz, 2H), 1.48 (p, J=7.4 Hz, 2H), 1.19-1.09 (m, 2H), 0.87 (t, J=7.3 Hz, 3H); $^{13}$C NMR (100 MHz, CDCl$_3$) δ 167.94, 148.82, 141.27, 140.06, 136.67, 130.71, 129.71, 129.44, 128.59, 128.27, 128.05, 119.75, 119.08, 113.82, 101.37, 42.73, 30.57, 20.48, 13.93.

Step (3). Preparation of 9-butyl-9H-carbazole-2,7-diamine dihydrochloride

The N,N'-(9-butyl-9H-carbazole-2,7-diyl)bis(1,1-diphenylmethaneimine) (652 mg, 1.121 mmol) prepared in Step (2) was dissolved in a minimum amount of methanol under an argon atmosphere. 4.0 M HCl/methanol (11.2 mL, 44.83 mmol) was added to the mixture, and then the resulting mixture was stirred at room temperature for 1 hour. The mixture completely reacted was concentrated under reduced pressure. The concentrated residue was filtered while being washed several times with acetone to obtain a light yellow solid target compound (290 mg, 100%).

$^1$H NMR (400 MHz, DMSO-d$_6$) δ 10.58 (bs, 6H), 8.26 (d, J=8.2 Hz, 2H), 7.66 (d, J=0.9 Hz, 2H), 7.26 (dd, J=8.2, 1.3 Hz, 2H), 4.33 (t, J=6.8 Hz, 2H), 1.75 (p, J=7.2 Hz, 2H), 1.32-1.23 (m, 2H), 0.88 (t, J=7.3 Hz, 3H); $^{13}$C NMR (100 MHz, DMSO-d$_6$) δ 140.95, 130.70, 122.08, 121.32, 114.68, 104.69, 42.99, 30.81, 22.26, 14.15.

Step (4). Preparation of dimethyl ((1R,1'R)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate The 9-butyl-9H-carbazole-2,7-diamine dihydrochloride (100 mg, 0.395 mmol) prepared in Step (3) and ((R)-2-((methoxycarbonyl)amino)-2-phenylacetyl)-L-proline (278 mg, 0.908 mmol) were added to DMF (3 mL) under an argon atmosphere. 1-[bis(dimethylamino)methylene-1H-1,2,3-triazole[4,5-b]pyridinium 3-oxide hexafluorophosphate (HATU; 345 mg, 0.908 mmol) was added thereto, and then diisopropylethylamine (DIPEA; 0.28 ml, 1.579 mmol) was added dropwise thereto, and the resulting mixture was stirred at room temperature for 16 hours. A saturated aqueous sodium hydrogen carbonate solution was added to the mixture completely reacted, the resulting mixture was extracted by using ethyl acetate, and the collected organic layer was washed with brine. The separated organic layer was dried over anhydrous sodium sulfate, and then filtered and concentrated under reduced pressure. The concentrated solution was separated and purified with column chromatography (CH$_2$Cl$_2$/EtOAc=1/1, v/v) to obtain a pale grey solid target compound (130 mg, 39.6%).

$^1$H NMR (400 MHz, CDCl$_3$) δ 9.70 (s, 2H), 7.64 (s, 2H), 7.58 (d, J=8.2 Hz, 2H), 7.48-7.47 (m, 4H), 7.40-7.38 (m, 6H), 7.17-7.15 (m, 2H), 6.31 (d, J=7.0 Hz, 2H), 5.60 (d, J=7.1 Hz, 2H), 4.76-4.74 (m, 2H), 4.08-4.06 (m, 2H), 3.99-3.95 (m, 2H), 3.64 (s, 6H), 3.37 (q, J=8.2 Hz, 2H), 2.45-2.40 (m, 2H), 2.36-2.29 (m, 2H), 2.05-1.98 (m, 2H), 1.94-1.90 (m, 2H), 1.76-1.67 (m, 2H), 1.31-1.20 (m, 2H), 0.86 (t, J=7.3 Hz, 3H); $^{13}$C NMR (100 MHz, CDCl$_3$) δ 169.76, 168.90, 156.03, 140.59, 136.77, 135.85, 129.17, 128.77, 127.90, 119.54, 118.78, 111.17, 99.44, 61.78, 57.22, 52.33, 47.54, 42.24, 31.02, 28.66, 24.82, 20.46, 13.87. LC/MS (ESI-TOF) m/z calcd for C$_{46}$H$_{52}$N$_7$O$_8$ [M+H]$^+$: 830.38 found 830.35.

Example 2. Preparation of dimethyl ((2R,2'R)-((2S,2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate

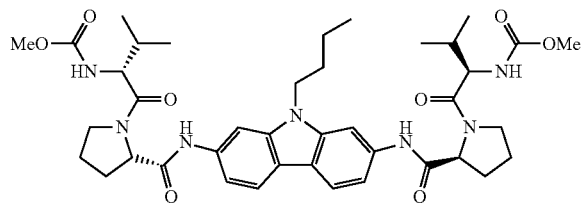

((R)-2-((methoxycarbonyl)amino)-2-phenylacetyl)-L-proline (100.2 mg, 0.368 mmol), 1-hydroxybenzotriazole (HOBt; 52 mg, 0.383 mmol), and 1-ethyl-3-(3-dimethylaminopropyl)carbodiimide (EDC; 71 mg, 0.368 mmol) were added to acetonitrile (3 mL) under an argon atmosphere, and the resulting mixture was stirred at room temperature for 1 hour. The 9-butyl-9H-carbazole-2,7-diamine dihydrochloride (50 mg, 0.153 mmol) prepared in Step (3) of Example 1 was added thereto, diisopropylethylamine (0.11 mL, 0.613 mmol) was added dropwise thereto at 0° C., and then the resulting mixture was stirred at room temperature for 16 hours. A saturated aqueous sodium hydrogen carbonate solution was added to the mixture completely reacted, the resulting mixture was extracted by using ethyl acetate, and the collected organic layer was washed with brine. The separated organic layer was dried over anhydrous sodium sulfate, and then filtered and concentrated under reduced pressure. The concentrated solution was separated and purified with column chromatography (CH$_2$Cl$_2$/EtOAc=1/2, v/v) to obtain a pale light yellow solid target compound (84 mg, 71.9%).

$^1$H NMR (400 MHz, CDCl$_3$) δ 9.40 (s, 2H), 7.87 (s, 2H), 7.71 (d, J=8.3 Hz, 2H), 7.08 (d, J=8.2 Hz, 2H), 5.41 (d, J=8.0 Hz, 2H), 4.82 (d, J=6.8 Hz, 2H), 4.35 (t, J=7.8 Hz, 2H), 4.18 (t, J=7.0 Hz, 2H), 4.04-3.99 (m, 2H), 3.73-3.67 (m, 2H), 3.65 (s, 6H), 2.56-2.52 (m, 2H), 2.30-2.23 (m, 2H), 2.13-2.02 (m, 6H), 1.86-1.75 (m, 4H), 1.36-1.28 (m, 2H), 1.05 (d, J=6.6 Hz, 12H), 0.91 (t, J=7.3 Hz, 3H); $^{13}$C NMR (100 MHz, CDCl$_3$) δ 172.13, 168.99, 157.25, 140.87, 135.86, 119.39, 118.91, 111.55, 99.99, 61.25, 58.13, 52.38, 47.76, 42.43, 31.09, 30.99, 28.61, 24.72, 20.37, 19.41, 17.90, 13.81. LC/MS (ESI-TOF) m/z calcd for C$_{40}$H$_{56}$N$_7$O$_8$ [M+H]$^+$: 762.41 found 762.20.

Example 3. Preparation of dimethyl ((1S,1'S)-((2S, 2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))carbamate

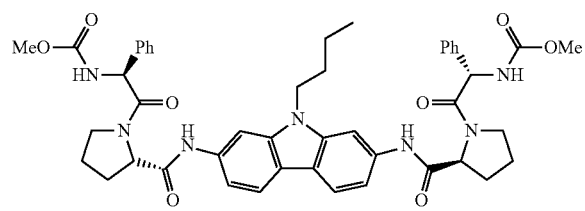

The method in Example 2 was performed, and a target compound (46 mg, 40.7%) was obtained by using 9-butyl-9H-carbazole-2,7-diamine dihydrochloride (44 mg, 0.136 mmol) and ((S)-2-((methoxycarbonyl)amino)-2-phenylacetyl)-L-proline (100 mg, 0.326 mmol).

$^1$H NMR (400 MHz, CDCl$_3$) δ 9.64 (s, 2H), 7.62-7.55 (m, 8H), 7.45-7.29 (m, 6H), 7.05-7.03 (m, 2H), 5.94 (d, J=8.0 Hz, 2H), 5.62 (d, J=8.0 Hz, 2H), 4.94-4.91 (m, 2H), 4.15-4.12 (m, 2H), 3.77-3.71 (m, 8H), 3.39-3.35 (m, 2H), 2.37-2.34 (m, 2H), 2.16-2.09 (m, 4H), 2.08-2.04 (m, 2H), 1.72-1.65 (m, 2H), 1.21-1.10 (m, 2H), 0.74 (t, J=7.3 Hz, 3H); $^{13}$C NMR (100 MHz, CDCl$_3$) δ 170.00, 169.06, 156.39, 140.66, 136.25, 135.74, 129.34, 128.82, 127.98, 119.47, 118.77, 111.36, 99.67, 61.56, 57.02, 52.38, 47.52, 42.27, 31.27, 29.71, 28.15, 25.12, 20.43, 13.94. LC/MS (ESI-TOF) m/z calcd for C$_{46}$H$_{52}$N$_7$O$_8$ [M+H]$^+$: 830.38 found 830.25.

Example 4. Preparation of dimethyl ((2S,2'S)-((2S, 2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate

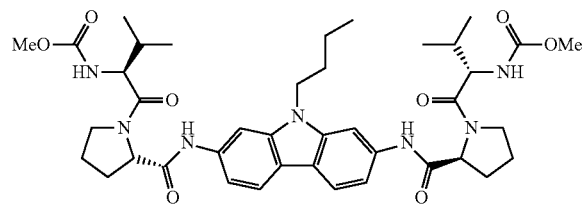

The method in Step (4) of Example 1 was performed, and a target compound (90 mg, 29.9%) was obtained by using 9-butyl-9H-carbazole-2,7-diamine dihydrochloride (100 mg, 0.395 mmol) and (methoxycarbonyl)-L-valyl-L-proline (247 mg, 0.908 mmol).

$^1$H NMR (400 MHz, DMSO-d$_6$) δ 10.16 (s, 2H), 7.96 (d, J=8.4 Hz, 2H), 7.93 d, J=1.0 Hz, 2H), 7.36 (d, J=8.4 Hz, 2H), 7.31 (dd, J=8.4, 1.4 Hz, 2H), 4.55-4.51 m, 2H), 4.23-4.19 (m, 2H), 4.08 (t, J=8.4 Hz, 2H), 3.89-3.81 (m, 2H), 3.71-3.65 (m, 2H), 3.55 (s, 6H), 2.21-2.15 (m, 2H), 2.10-2.04 (m, 2H), 2.01-1.90 (m, 6H), 1.80-1.73 (m, 2H), 1.34-1.25 (m, 2H), 0.98 (d, J=6.7 Hz, 6H), 0.94-0.90 (m, 11H), $^{13}$C NMR (100 MHz, CDCl$_3$) δ 169.95, 157.08, 140.09, 135.84, 119.07, 118.37, 111.01, 99.03, 61.34, 57.64, 52.38, 48.20, 41.91, 31.44, 31.30, 29.21, 25.34, 20.36, 19.50, 17.60, 13.97. LC/MS (ESI-TOF) m/z calcd for C$_{40}$H$_{56}$N$_7$O$_6$ [M+H]$^+$: 762.41 found 762.30.

Example 5. Preparation of (2S,2'S)—N,N'-(9-butyl-9H-carbazole-2,7-diyl)bis(1-((S)-3-methyl-3-2-(2-oxooxazolidine-3-yl)butanoyl)pyrrolidine-2-carboxamide)

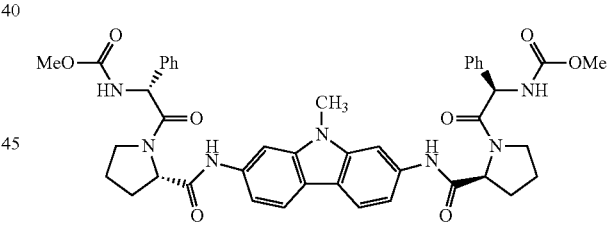

The method in Step (4) of Example 1 was performed, and a target compound (216 mg, 69.6%) was obtained by using 9-butyl-9H-carbazole-2,7-diamine dihydrochloride (100 mg, 0.395 mmol) and ((S)-3-methyl-2-(2-oxooxazolidine-3-yl)butanoyl)-L-proline (269 mg, 0.947 mmol).

$^1$H NMR (400 MHz, CDCl$_3$) δ 9.95 (s, 2H), 7.29-7.13 (m, 6H), 4.81-4.78 (m, 2H), 4.46 (s, 1H), 4.43 (s, 1H), 4.37 (t, J=8.4 Hz, 4H), 4.18-4.10 (m, 2H), 3.98-3.90 (m, 5H), 3.66-3.60 (m, 2H), 2.36-2.25 (m, 4H), 2.23-2.10 (m, 4H), 2.08-2.00 (m, 2H), 1.50-1.41 (m, 2H), 1.23 (d, J=6.5 Hz, 6H), 1.12-1.06 (m, 1H), 1.01 (d, J=6.6 Hz, 6H), 0.96-0.91 (m, 2H), 0.64 (t, J=7.3 Hz, 3H); $^{13}$C NMR (100 MHz, CDCl$_3$) δ 169.94, 169.65, 158.57, 139.91, 135.78, 118.87, 118.26, 111.09, 99.04, 62.77, 61.20, 59.98, 48.55, 41.70, 31.51, 29.83, 28.37, 25.00, 20.30, 19.03, 18.85, 13.94. LC/MS (ESI-TOF) m/z calcd for C$_{42}$H$_{55}$N$_7$O$_8$Na [M+Na]$^+$: 808.40 found 808.35.

Example 6. Preparation of dimethyl ((1R,1'R)-((2S, 2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate Step (1). Preparation of 2,7-dibromo-9-methyl-9H-carbazole The method in Step (1) of Example 1 was performed, and a target compound (440 mg, 84.4%) was obtained by using 2,7-dibromo-9H-carbazole (500 mg, 1.54 mmol) and iodomethane (0.2 mL, 3.23 mmol).

$^1$H NMR (400 MHz, CDCl$_3$) δ 7.89 (d, J=8.2 Hz, 2H), 7.55 (d, J=1.4 Hz, 2H), 7.35 (dd, J=8.2, 1.5 Hz, 2H), 3.79 (s, 3H); $^{13}$C NMR (100 MHz, CDCl$_3$) δ 141.91, 122.64, 121.43, 121.24, 119.76, 111.89, 29.30.

Step (2). Preparation of N,N'-(9-methyl-9H-carbazole-2,7-diyl)bis(1,1-diphenylmethaneimine)

The method in Step (2) of Example 1 was performed, and 484 mg (0.90 mmol, 75.9%) of a viscous yellow solid target compound was obtained by using 2,7-dibromo-9-methyl-9H-carbazole (400 mg, 1.18 mmol) and benzophenoneimine (0.46 mL, 2.71 mmol).

¹H NMR (400 MHz, CDCl₃) δ 7.77 (d, J=7.0 Hz, 4H), 7.63 (d, J=8.2 Hz, 2H), 7.47-7.37 (m, 6H), 7.23-7.15 (m, 10H), 6.76 (d, J=1.5 Hz, 2H), 6.51 (dd, J=1.5, 8.2 Hz, 2H), 3.50 (s, 3H); ¹³C NMR (100 MHz, CDCl₃) δ 167.88, 149.06, 141.99, 140.09, 136.70, 130.66, 129.40, 128.57, 128.26, 128.03, 119.64, 113.40, 101.39, 28.90.

Step (3). Preparation of 9-methyl-9H-carbazole-2,7-diamine dihydrochloride

The method in Step (3) of Example 1 was performed, and a yellow solid target compound (240 mg, 94.1%) was obtained by using N,N'-(9-methyl-9H-carbazole-2,7-diyl)bis(1,1-diphenylmethaneimine) (484 mg, 0.897 mmol).

¹H NMR (400 MHz, DMSO-d₆) δ 9.52 (s, 6H), 8.11 (d, J=8.2 Hz, 2H), 7.33 (s, 2H), 7.05 (d, J=8.1 Hz, 2H), 3.83 (s, 3H); ¹³C NMR (100 MHz, DMSO-d₆) δ 141.72, 131.54, 121.91, 120.92, 114.49, 103.79, 29.85.

Step (4). Preparation of dimethyl ((1R,1'R)-((2S,2'S)-(((9-methyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (43 mg, 31.3%) was obtained by using 9-butyl-9H-carbazole-2,7-diamine dihydrochloride (50 mg, 0.176 mmol) and ((S)-3-methyl-2-(2-oxoxazolidine-3-yl)butanoyl)-L-proline (124 mg, 0.410 mmol).

¹H NMR (400 MHz, CDCl₃) δ 9.65 (s, 2H), 7.57-7.55 (m, 4H), 7.45-7.43 (m, 4H), 7.36-7.35 (m, 6H), 7.15 (d, J=8.2 Hz, 2H), 6.22 (d, J=7.0 Hz, 2H), 5.58 (d, J=7.1 Hz, 2H), 4.75 (dd, J=8.2, 2.6 Hz, 2H), 3.95-3.93 (m, 2H), 3.61 (s, 6H), 3.53 (s, 3H), 3.34 (q, J=8.3 Hz, 2H), 2.40-2.25 (m, 4H), 2.02-1.95 (m, 2H), 1.92-1.87 (m, 2H); ¹³C NMR (100 MHz, CDCl₃) δ 169.60, 169.39, 156.10, 140.89, 136.87, 135.92, 129.14, 128.73, 127.86, 119.39, 118.60, 111.16, 99.05, 61.79, 57.20, 52.36, 47.63, 29.16, 28.71, 24.81. LC/MS (ESI-TOF) m/z calcd for C₄₃H₄₅N₇O₆Na [M+Na]⁺: 810.32 found 810.20.

Example 7. Preparation of dimethyl ((2R,2'R)-((2S,2'S)-(((9-methyl-9H-carbazole-2,7-diyl)bis(azanediyl))bis(carbonyl))bis(pyrrolidine-2,1-diyl))bis(3-methyl-1-oxobutane-1,2-diyl))dicarbamate

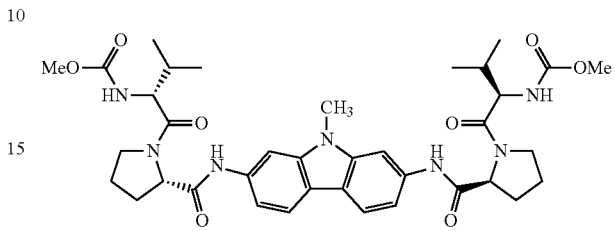

The method in Example 2 was performed, and a target compound (62.3 mg, 24.7%) was obtained by using 9-methyl-9H-carbazole-2,7-diamine dihydrochloride (100 mg, 0.35 mmol) and (methoxycarbonyl)-L-valyl-L-proline (211 mg, 0.77 mmol).

¹H NMR (400 MHz, CDCl₃) δ 9.92 (s, 2H), 7.28-6.97 (m, 6H), 5.33 (d, J=9.2 Hz, 2H), 4.8 (t, J=6.7 Hz, 2H), 4.48-4.44 (m, 2H), 3.93-3.82 (m, 4H), 3.70 (s, 6H), 3.47 (s, 3H), 2.36-2.27 (m, 2H), 2.25-2.19 (m, 6H), 2.10-2.00 (m, 2H), 1.14 (d, J=6.8 Hz, 6H), 1.03 (d, J=6.7 Hz, 6H); ¹³C NMR (100 MHz, CDCl₃) δ 171.35, 170.23, 157.12, 140.45, 135.97, 119.02, 118.22, 111.00, 98.64, 61.28, 57.56, 52.35, 48.14, 31.20, 29.37, 28.59, 25.32, 19.49, 17.45. LC/MS (ESI-TOF) m/z calcd for C₃₇H₄₉N₇O₈Na [M+Na]⁺: 742.35 found 742.20.

Example 8. Preparation of dimethyl ((1S,1'S)-((2S,2'S)-(((9-methyl-9H-carbazole-2,7-diyl)bis(azanediyl))bis(carbonyl))bis(pyrrolidine-2,1-diyl))bis(2-oxo-1-phenylethane-2,1-diyl))dicarbamate

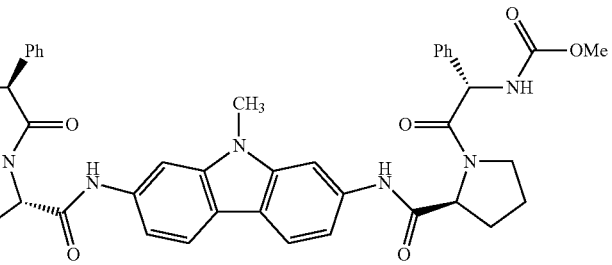

The method in Example 2 was performed, and a target compound (39 mg, 35.5%) was obtained by using 9-methyl-9H-carbazole-2,7-diamine dihydrochloride (40 mg, 0.14 mmol) and ((S)-2-((methoxycarbonyl)amino)-2-phenylacetyl)-L-proline (99 mg, 0.32 mmol).

¹H NMR (400 MHz, CDCl₃) δ 9.78 (s, 2H), 7.57-7.55 (m, 4H), 7.45-7.37 (m, 10H), 7.02 (d, J=8.3 Hz, 2H), 5.89 (d, J=8.0 Hz, 2H), 5.62 (d, J=8.2 Hz, 2H), 4.91-4.73 (m, 2H), 3.74-3.72 (m, 2H), 3.68 (s, 6H), 3.62 (s, 3H), 3.49-3.37 (m, 2H), 2.31-2.18 (m, 6H), 2.06-2.02 (m, 2H); ¹³C NMR (100 MHz, CDCl₃) δ 169.61, 169.54, 156.41, 140.73, 136.16, 135.90, 129.24, 128.83, 128.04, 119.29, 118.44, 111.17, 98.98, 61.57, 56.95, 52.36, 47.61, 29.71, 28.81, 25.13. LC/MS (ESI-TOF) m/z calcd for C₄₃H₄₅N₇O₈Na [M+Na]⁺: 810.32 found 810.20.

Example 9. Preparation of dimethyl ((2S,2'S)-((2S, 2'S)-(((9-methyl-9H-carbazole-2,7-diyl)bis (azanediyl))bis(carbonyl))bis(pyrrolidine-2,1-diyl)) bis(3-methyl-1-oxobutane-1,2-diyl))dicarbamate

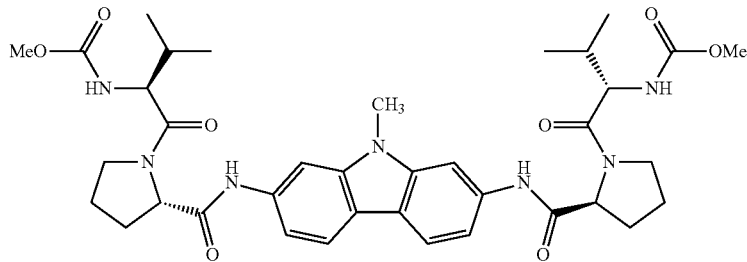 [SMILES: COC(=O)N[C@H](C(=O)N1CCC[C@H]1C(=O)Nc1ccc2c3ccc(NC(=O)[C@@H]4CCCN4C(=O)[C@@H](NC(=O)OC)C(C)C)cc3n(C)c2c1)C(C)C]

The method in Example 2 was performed, and a target compound (60 mg, 58.9%) was obtained by using 9-methyl-9H-carbazole-2,7-diamine dihydrochloride (40 mg, 0.14 mmol) and (methoxycarbonyl)-D-valyl-L-proline (84 mg, 0.31 mmol).

$^1$H NMR (400 MHz, CDCl$_3$) δ 9.53 (s, 2H), 7.66 (s, 2H), 7.57 (d, J=8.2 Hz, 2H), 7.07 (d, J=8.1 Hz, 2H), 5.46 (d, J=8.1 Hz, 2H), 4.77 (d, J=5.9 Hz, 2H), 4.38 (t, J=7.7 Hz, 2H), 4.03 (t, J=7.3 Hz, 2H), 3.71-3.66, 3.63 (s, 6H), 3.60 (s, 3H), 2.44-2.42 (m, 2H), 2.32-2.27 (m, 2H), 2.09-1.98 (m, 6H), 1.03 (t, J=7.3 Hz, 12H); $^{13}$C NMR (100 MHz, CDCl$_3$) δ 172.03, 169.18, 157.23, 141.21, 135.92, 119.40, 118.72, 111.45, 99.50, 61.23, 58.04, 52.47, 47.80, 31.10, 29.71, 28.85, 24.76, 19.48, 17.89. LC/MS (ESI-TOF) m/z calcd for C$_{37}$H$_{49}$N$_7$O$_8$Na [M+Na]$^+$: 742.35 found 742.20.

Example 10. Preparation of (2S,2'S)—N,N'-(9-methyl-9H-carbazole-2,7-diyl)bis(1-((S)-3-methyl-2-(2-oxazolidine-3-yl)butanoyl)pyrrolidine-2-carboxamide)

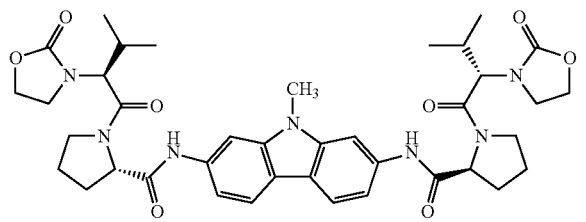 [SMILES: CC(C)[C@@H](C(=O)N1CCC[C@H]1C(=O)Nc1ccc2c3ccc(NC(=O)[C@@H]4CCCN4C(=O)[C@H](C(C)C)N4CCOC4=O)cc3n(C)c2c1)N1CCOC1=O]

The method in Example 2 was performed, and a target compound (54 mg, 45.6%) was obtained by using 9-methyl-9H-carbazole-2,7-diamine dihydrochloride (45 mg, 0.158 mmol) and ((S)-3-methyl-2-(2-oxooxazolidine-3-yl)butanoyl)-L-proline (110 mg, 0.39 mmol).

$^1$H NMR (400 MHz, CDCl$_3$) δ 9.99 (s, 2H), 7.29-6.97 (m, 6H), 4.85-4.82 (m, 2H), 4.46 (d, J=10.9 Hz, 2H), 4.41-4.37 (m, 4H), 4.18-4.12 (m, 2H), 4.00-3.91 (m, 4H), 3.64 (q, J=7.9 Hz, 2H), 3.49 (s, 3H), 2.42-2.25 (m, 4H), 2.19-2.00 (m, 6H), 1.11 (dd, J=79.6, 6.6 Hz, 12H); $^{13}$C NMR (100 MHz, CDCl$_3$) δ 170.12, 169.62, 158.59, 140.40, 135.93, 118.98, 118.22, 111.11, 98.71, 62.77, 61.13, 59.96, 48.51, 41.68, 29.70, 28.61, 28.33, 25.01, 18.95, 18.74. LC/MS (ESI-TOF) m/z calcd for C$_{39}$H$_{49}$N$_7$O$_8$Na [M+Na]$^+$: 766.35 found 766.15.

Example 11. Preparation of dimethyl ((1R,1'R)-((2S,2'S)-(((9-(2-(4-methylpiperazine-1-yl)ethyl-9H-carbazole-2,7-diyl)bis(azanediyl))bis(carbonyl))bis (pyrrolidine-2,1-diyl))bis(2-oxo-1-phenylethane-2,1-diyl))carbamate

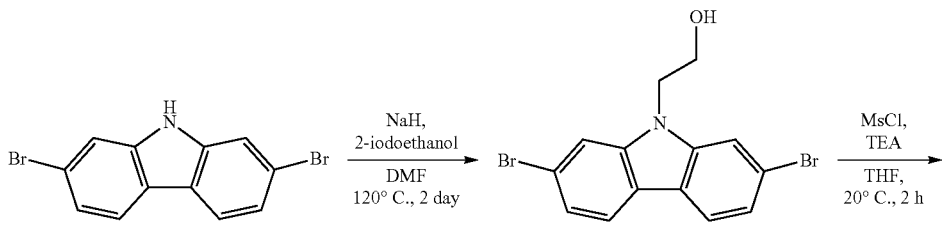

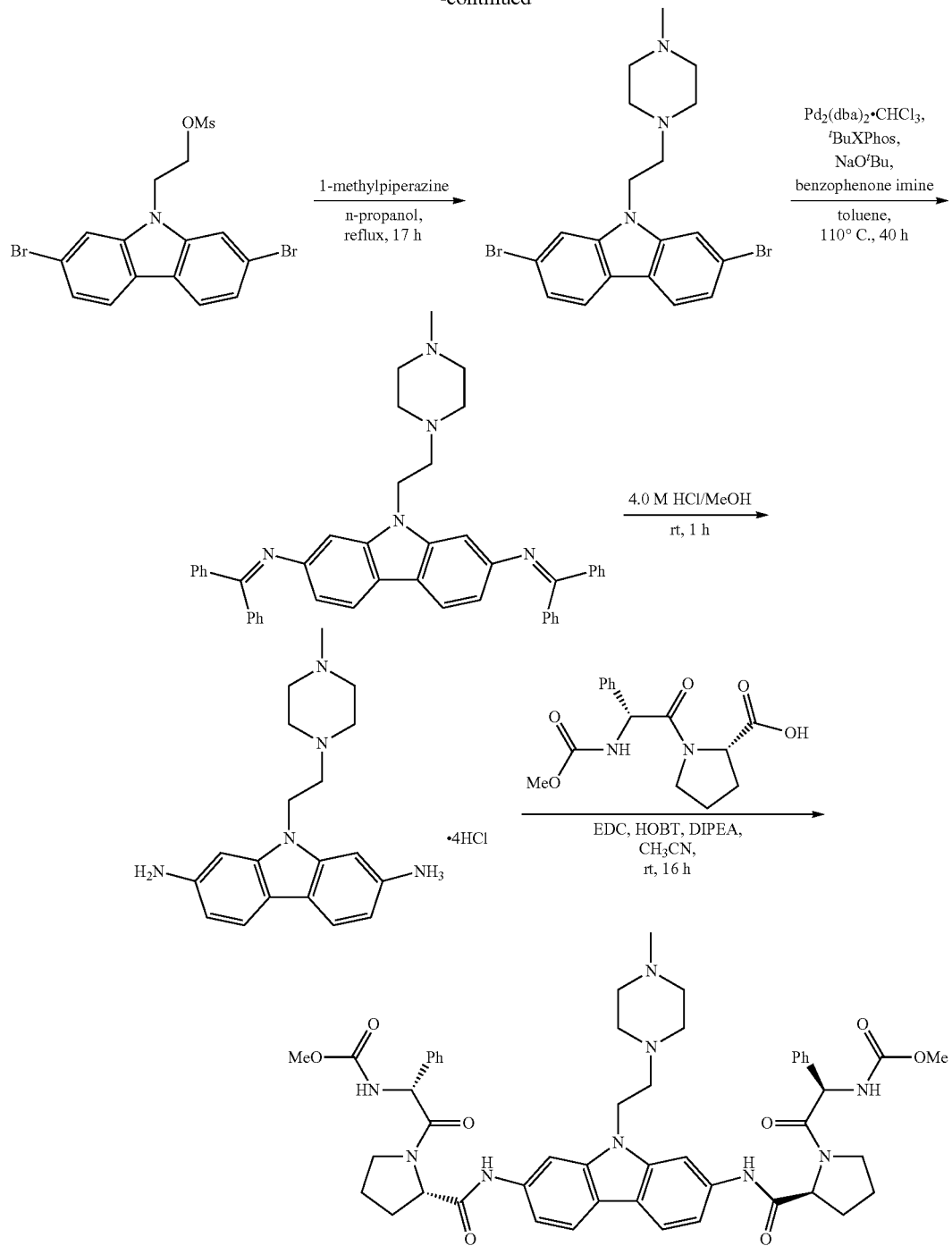

Step (1). Preparation of 2-(2,7-dibromo-9H-carbazole-9-yl)ethane-1-ol 2,7-dibromo-9H-carbazole (1.0 g, 3.077 mmol) was dissolved in DMF (10 mL) under an argon atmosphere, and then NaH (60% in mineral oil, 185 mg, 4.615 mmol) was added thereto at 0° C., and the resulting mixture was stirred at room temperature for 30 minutes. 2-iodoethanol (0.36 mL, 4.615 mmol) was added to the mixture, and then the resulting mixture was stirred at 120° C. for 48 hours. The mixture was cooled to room temperature, and then H$_2$O was slowly added thereto. The mixture completely reacted was extracted by using ethyl acetate and H$_2$O, and the collected organic layer was washed with brine. The separated organic layer was dried by using anhydrous magnesium sulfate, and then filtered and concentrated under reduced pressure. The concentrated solution was purified with column chromatography (hexane/EtOAc=20/1 to 5/1, v/v) to obtain a white solid target compound (775 mg, 63.6%).

$^1$H NMR (400 MHz, CDCl$_3$) δ 7.88 (d, J=8.3 Hz, 2H), 7.62 (d, J=1.6 Hz, 2H), 7.37 (dd, J=8.3, 1.4 Hz, 2H), 4.37 (t,

J=5.4 Hz, 2H), 4.04 (t, J=5.4 Hz, 2H), 1.63 (s, 1H); $^{13}$C NMR (100 MHz, CDCl$_3$) δ 141.65, 122.99, 121.46, 121.41, 119.89, 122.27, 61.23, 45.64.

Step (2). Preparation of 2-(2,7-dibromo-9H-carbazole-9-yl) ethyl methanesulfonate The 2-(2,7-dibromo-9H-carbazole-9-yl)ethane-1-ol (761 mg, 2.062 mmol) prepared in Step (1) was dissolved in THF (7.6 mL) under an argon atmosphere, and then triethylamine (0.32 mL, 2.268 mmol) and methanesulfonyl chloride (0.18 mL, 2.068 mmol) were added thereto at 20° C., and the resulting mixture was stirred at room temperature for 2 hours. The mixture completely reacted was concentrated under reduced pressure. The concentrated solution was diluted with dichloromethane, and washed with H$_2$O. The separated organic layer was dried over anhydrous sodium sulfate, and then filtered and concentrated under reduced pressure. The concentrated solution was separated and purified with column chromatography (hexane/EtOAc=5/1, v/v) to obtain a target compound (844 mg, 92.0%).

$^1$H NMR (400 MHz, Acetone-d$_6$) δ 8.11 (dd, J=8.3, 2.0 Hz, 2H), 7.92 (d, J=1.5 Hz, 2H), 7.42 (dt, J=8.3 Hz, 2.0 Hz, 2H), 4.88 (t, J=4.7 Hz, 2H), 4.73 (t, J=4.7 Hz, 2H), 2.90 (s, 3H); $^{13}$C NMR (100 MHz, Acetone-d$_6$) δ 141.71, 122.90, 121.79, 121.53, 119.52, 112.73, 67.92, 42.35, 36.24.

Step (3). Preparation of 2,7-dibromo-9-(2-(4-methylpiperazine-1-yl)ethyl-9H-carbazole The 2-(2,7-dibromo-9H-carbazole-9-yl)ethyl methanesulfonate (739 mg, 1.661 mmol) prepared in Step (2) was dissolved in n-propanol (7.4 mL) under an argon atmosphere, and then 1-methylpiperazine (0.55 mL, 4.983 mmol) was added thereto, and the resulting mixture was refluxed under heating for 17 hours. The mixture completely reacted was cooled to room temperature, and then concentrated under reduced pressure. The concentrated solution was purified with column chromatography (CH$_2$Cl$_2$/MeOH=15/1+1% NH$_3$, v/v) to obtain a white solid target compound (545 mg, 73.1%).

$^1$H NMR (400 MHz, CDCl$_3$) δ 7.84 (d, J=8.3 Hz, 2H), 7.54 (d, J=1.5 Hz, 2H), 7.33 (dd, J=8.3, 1.5 Hz, 2H), 4.26 (t, J=6.8 Hz, 2H), 2.75 (t, J=6.8 Hz, 2H), 2.64-2.57 (m, 8H), 2.39 (s, 3H); $^{13}$C NMR (100 MHz, CDCl$_3$) δ 141.32, 122.74, 121.46, 121.30, 119.65, 112.15, 56.03, 54.79, 52.83, 45.50, 41.66.

Step (4). Preparation of N,N'-(9-(2-(4-methylpiperazine-1-yl)ethyl-9H-carbazole-2,7-diyl)bis(1,1-diphenylmethaneimine)

The method in Step (2) of Example 1 was performed, and a target compound (113 mg, 55.9%) was obtained by using 2,7-dibromo-9-(2-(4-methylpiperazine-1-yl)ethyl-9H-carbazole (140 mg, 0.310 mmol).

$^1$H NMR (400 MHz, CDCl$_3$) δ 7.82 (d, J=7.7 Hz, 4H), 7.73 (d, J=8.2 Hz, 2H), 7.53-7.43 (m, 6H), 7.29-7.25 (m, 6H), 7.24-7.20 (m, 4H), 6.74 (d, J=1.4 Hz, 2H), 6.65 (dd, J=8.2, 1.7 Hz, 2H), 4.12 (t, J=7.7 Hz, 2H), 2.56 (bs, 8H), 2.44 (t, J=7.7 Hz, 2H), 2.36 (s, 3H); $^{13}$C NMR (100 MHz, CDCl$_3$) δ 167.94, 149.09, 141.13, 140.04, 136.62, 130.67, 129.69, 129.37, 128.61, 128.25, 128.05, 119.77, 119.07, 113.80, 101.11, 55.38, 55.07, 53.25, 45.99, 40.71.

Step (5). Preparation of 9-(2-(4-methylpiperazine-1-yl)ethyl-9H-carbazole-2,7-diamine tetrahydrochloride The method in Step (3) of Example 1 was performed, and a target compound (64 mg, 75.1%) was obtained by using N,N'-(9-(2-(4-methylpiperazine-1-yl)ethyl-9H-carbazole-2,7-diyl)bis(1,1-diphenylmethaneimine) (113 mg, 0.173 mmol).

$^1$H NMR (400 MHz, MeOD) δ 7.51 (d, J=8.2 Hz, 2H), 6.56 (d, J=1.7 Hz, 2H), 6.49 (dd, J=8.2, 1.8 Hz, 2H), 4.82 (s, 4H), 3.98 (t, J=7.4 Hz, 2H), 2.47 (t, J=7.4 Hz, 2H), 2.37 (bs, 8H), 2.18 (s, 3H).

Step (6). Preparation of dimethyl ((1R,1'R)-((2S,2'S)-(((9-(2-(4-methylpiperazine-1-yl)ethyl-9H-carbazole-2,7-diyl)bis(azanediyl))bis(carbonyl))bis(pyrrolidine-2,1-diyl))bis(2-oxo-1-phenylethane-2,1-diyl))carbamate The method in Example 2 was performed, and a target compound (53 mg, 51.2%) was obtained by using 9-(2-(4-methylpiperazine-1-yl)ethyl-9H-carbazole-2,7-diamine tetrahydrochloride (54 mg, 0.115 mmol).

$^1$H NMR (400 MHz, CDCl$_3$) δ 9.50 (s, 2H), 7.83 (s, 2H), 7.75 (d, J=8.0 Hz, 2H), 7.48-7.39 (m, 10H), 7.15 (d, J=8.1 Hz, 2H), 6.21 (d, J=6.8 Hz, 2H), 5.57 (d, J=6.9 Hz, 2H), 4.78 (d, J=7.9 Hz, 2H), 4.13-3.85 (m, 4H), 3.66 (s, 6H), 3.36-3.29 (m, 2H), 2.83-2.72 (m, 10H), 2.56 (s, 3H), 2.45-2.38 (m, 2H), 2.24-2.20 (m, 2H), 2.07-1.19 (m, 4H); $^{13}$C NMR (100 MHz, CDCl$_3$) δ 169.91, 169.19, 156.22, 140.75, 136.30, 135.89, 129.20, 128.82, 127.96, 119.62, 119.01, 112.02, 100.15, 61.68, 57.40, 55.61, 54.08, 52.44, 51.11, 47.44, 44.12, 29.70, 28.64, 24.75. LC/MS (ESI-TOF) m/z calcd for C$_{49}$H$_{58}$N$_9$O$_8$ [M+H]$^+$: 900.44 found 900.25.

Example 12. Preparation of dimethyl ((1R,1'R)-((2S,2'S)-(((9-(2-morpholinoethyl)-9H-carbazole-2,7-diyl)bis(azanediyl))bis(carbonyl))bis(pyrrolidine-2,1-diyl))bis(2-oxo-1-phenylethane-2,1-diyl))carbamate

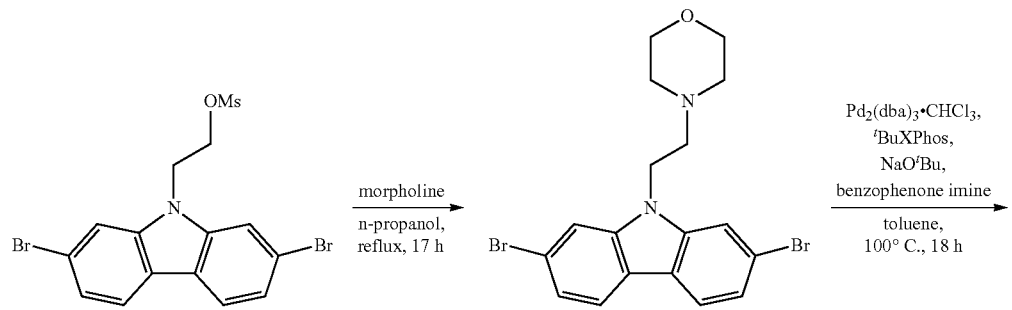

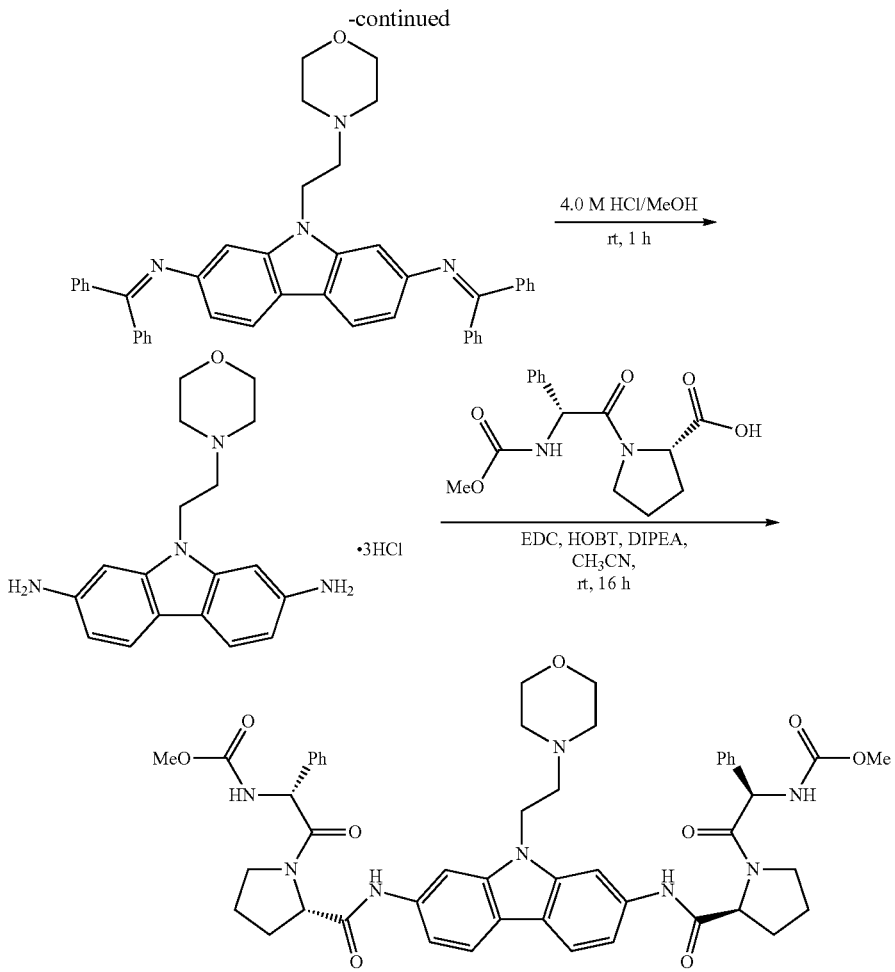

Step (1). Preparation of 4-(2-(2,7-dibromo-9H-carbazole-9-yl)ethyl)morpholine The method in Step (3) of Example 11 was performed, and a target compound (786 mg, 86.9%) was obtained by using 2-(2,7-dibromo-9H-carbazole-9-yl)ethyl methanesulfonate (918 mg, 2.063 mmol) and morpholine (0.54 mL, 6.190 mmol).

$^1$H NMR (400 MHz, CDCl$_3$) δ 7.86 (d, J=8.3 Hz, 2H), 7.57 (d, J=1.4 Hz, 2H), 7.36 (dd, J=8.3, 1.6 Hz, 2H), 4.29 (t, J=6.9 Hz, 2H), 3.72 (t, J=4.3 Hz, 4H), 2.74 (t, J=6.9 Hz, 2H), 2.54 (s, 4H); $^{13}$C NMR (100 MHz, CDCl$_3$) δ 141.31, 122.77, 121.47, 121.33, 119.71, 112.08, 66.90, 56.63, 54.06, 41.39.

Step (2). Preparation of N,N'-(9-(2-morpholinoethyl)-9H-carbazole-2,7-diyl)bis(1,1-diphenylmethaneimine)

The method in Step (4) of Example 11 was performed, and a target compound (251 mg, 63.5%) was obtained by using 4-(2-(2,7-dibromo-9H-carbazole-9-yl)ethyl)morpholine (273 mg, 0.623 mmol).

$^1$H NMR (400 MHz, CDCl$_3$) δ 7.83-7.81 (m, 4H), 7.73 (d, J=8.2 Hz, 2H), 7.54-7.50 (m, 2H), 7.48-7.44 (m, 4H), 7.30-7.25 (m, 4H), 7.24-7.21 (m, 4H), 6.75 (d, J=1.4 Hz, 2H), 6.66 (dd, J=8.2, 1.7 Hz, 2H), 4.16 (s, 2H), 3.75 (s, 4H), 2.50-2.46 (m, 6); $^{13}$C NMR (100 MHz, CDCl$_3$) δ 167.97, 149.14, 141.04, 140.01, 136.63, 130.70, 129.72, 129.38, 128.60, 128.26, 128.05, 119.82, 119.11, 113.91, 101.06, 66.71, 55.75, 53.76.

Step (3). Preparation of 9-(2-morpholinoethyl)-9H-carbazole-2,7-diamine trihydrochloride The method in Step (5) of Example 11 was performed, and a target compound (125 mg, 75.3%) was obtained by using N,N'-(9-(2-(4-mophlinoethyl)-9H-carbazole-2,7-diyl) bis(1,1-diphenylmethaneimine) (251 mg, 0.395 mmol).

$^1$H NMR (400 MHz, DMSO-d$_6$) δ 12.21 (bs, 1H), 10.74 (bs, 6H), 8.29 (d, J=8.2 Hz, 2H), 7.84 (d, J=1.1 Hz, 2H), 7.33 (dd, J=8.3, 1.4 Hz, 2H), 4.95 (t, J=7.6 Hz, 2H), 4.05-4.02 (m, 2H), 3.90 (t, J=12.0 Hz, 2H), 3.64-3.61 (m, 2H), 3.48 (t, J=7.7 Hz, 2H), 3.28 (t, J=12.5 Hz); $^{13}$C NMR (100 MHz, CDCl$_3$) δ 140.49, 130.82, 122.28, 121.83, 115.75, 105.09, 63.68, 52.82, 51.78, 37.36.

Step (4). Preparation of dimethyl ((1R,1'R)-((2S,2'S)-(((9-(2-morpholinoethyl)-9H-carbazole-2,7-diyl)bis(azanediyl))bis(carbonyl))bis(pyrrolidine-2,1-diyl))bis(2-oxo-1-phenylethane-2,1-diyl)) carbamate The method in Example 2 was performed, and a target compound (55 mg, 52.0%) was obtained by using 9-(2-(morpholinoethyl)-9H-carbazole-2,7-diamine trihydrochloride (50 mg, 0.119 mmol).

¹H NMR (400 MHz, CDCl₃) δ 9.75 (s, 2H), 7.56-7.46 (m, 8H), 7.39-7.37 (m, 6H), 7.18-7.17 (m, 2H), 6.41 (d, J=6.4 Hz, 2H), 5.62 (d, J=7.2 Hz, 2H), 4.76-4.73 (m, 2H), 4.10-3.94 (m, 4H), 3.72-3.63 (m, 10H), 3.41-3.35 (m, 2H), 2.63-2.52 (m, 6H), 2.36-2.30 (m, 4H), 2.06-1.98 (m, 2H), 1.95-1.90 (m, 2H); ¹³C NMR (100 MHz, CDCl₃) δ 169.73, 169.15, 156.06, 140.34, 136.79, 135.93, 129.14, 128.74, 127.89, 119.54, 118.85, 111.59, 99.37, 66.74, 57.25, 53.73, 52.36, 47.59, 29.71, 28.87, 24.81. LC/MS (ESI-TOF) m/z calcd for $C_{48}H_{55}N_8O_9$ [M+H]⁺: 887.40 found 887.35.

Example 13. Preparation of dimethyl ((1R,1'R)-((2S,2'S)-(((9-benzyl-9H-carbazole-2,7-diyl)bis(azanediyl))bis(carbonyl))bis(pyrrolidine-2,1-diyl))bis(2-oxo-1-phenylethane-2,1-diyl))dicarbamate

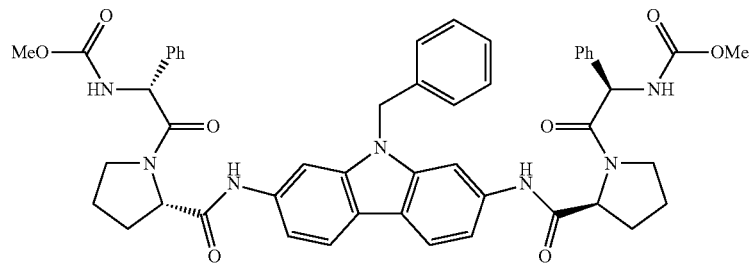 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3ccccc3)c2c1)c1ccccc1]

Step (1). Preparation of 9-benzyl-2,7-dibromo-9H-carbazole

The method in Step (1) of Example 1 was performed, and a while solid target compound (546 mg, 85.6%) was obtained by using 2,7-dibromo-9H-carbazole (500 mg, 1.54 mmol) and benzyl bromide (0.4 mL, 3.38 mmol).

¹H NMR (400 MHz, CDCl₃) δ 7.87 (d, J=8.3 Hz, 2H), 7.46 (s, 2H), 7.33 (dd, J=8.3, 1.6 Hz, 2H), 7.29-7.23 (m, 3H), 7.06 (d, J=7.2 Hz, 2H), 5.35 (s, 2H); ¹³C NMR (100 MHz, CDCl₃) δ 141.61, 135.99, 129.04, 127.89, 126.24, 123.09, 121.55, 121.49, 119.98, 112.25, 46.71.

Step (2). Preparation of N,N'-(9-benzyl-9H-carbazole-2,7-diyl)bis(1,1-diphenylmethaneimine)

The method in Step (2) of Example 1 was performed, and a target compound (311 mg, 69.8%) was obtained by using 9-benzyl-2,7-dibromo-9H-carbazole (300 mg, 0.72 mmol) and benzophenoneimine (0.27 mL, 1.59 mmol).

¹H NMR (400 MHz, CDCl₃) δ 7.75-7.69 (m, 6H), 7.46-7.42 (m, 2H), 7.40-7.35 (m, 4H), 7.20-7.12 (m, 9H), 7.09-7.06 (m, 4H), 6.87-6.84 (m, 2H), 6.65 (d, J=1.4 Hz, 2H), 6.60 (dd, J=8.2, 1.7 Hz, 2H), 5.11 (s, 2H); ¹³C NMR (100 MHz, CDCl₃) δ 168.01, 149.26, 141.51, 139.94, 137.11, 136.53, 130.62, 129.48, 129.32, 128.62, 128.45, 128.20, 127.92, 127.20, 126.47, 119.73, 119.13, 113.88, 101.38, 46.42.

Step (3). Preparation of 9-benzyl-9H-carbazole-2,7-diamine dihydrochloride

The method in Step (3) of Example 1 was performed, and a target compound (170 mg, 93.5%) was obtained by using N,N'-(9-benzyl-9H-carbazole-2,7-diyl)bis(1,1-diphenylmethaneimine) (311 mg, 0.51 mmol).

¹H NMR (400 MHz, DMSO-d₆) δ 10.48 (s, 6H), 8.29 (d, J=8.2 Hz, 2H), 7.65 (s, 2H), 7.32-7.23 (m, 5H), 7.16 (d, J=7.3 Hz, 2H), 5.64 (s, 2H); ¹³C NMR (100 MHz, DMSO-d₆) δ 140.68, 136.71, 130.65, 128.76, 127.54, 126.57, 121.64, 120.89, 114.62, 104.07, 45.98.

Step (4). Preparation of dimethyl ((1R,1'R)-((2S,2'S)-(((9-benzyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (51 mg, 42.4%) was obtained by using 9-benzyl-9H-carbazole-2,7-diamine dihydrochloride (50 mg, 0.14 mmol) and ((R)-2-((methoxycarbonyl)amino)-2-phenylacetyl)-L-proline (98 mg, 0.32 mmol).

¹H NMR (400 MHz, CDCl₃) δ 9.50 (s, 2H), 7.69 (d, J=7.9 Hz, 4H), 7.45-7.4 (m, 4H), 7.38-7.34 (m, 6H), 7.26-7.12 (m, 5H), 7.11-7.07 (m, 2H), 6.12 (d, J=7.0 Hz, 2H), 5.52 (d, J=7.0 Hz, 2H), 5.29 (q, J=13.6 Hz, 2H), 4.74-4.71 (m, 2H), 3.88 (t, J=7.5 Hz, 2H), 3.57 (s, 6H), 3.29 (q, J=8.1 Hz, 2H), 2.40-2.36 (m, 2H), 2.25-2.17 (m, 2H), 1.95-1.83 (m, 4H); ¹³C NMR (100 MHz, CDCl₃) δ 169.80, 168.90, 156.07, 140.81, 137.38, 136.63, 136.06, 129.16, 128.76, 128.53, 127.91, 127.03, 126.77, 119.68, 119.06, 111.90, 99.82, 61.69, 57.28, 52.29, 47.49, 45.91, 28.57, 24.76. LC/MS (ESI-TOF) m/z calcd for $C_{49}H_{49}N_7O_8Na$ [M+Na]⁺: 886.35 found 886.15.

Example 14. Preparation of dimethyl ((1R,1'R)-((2S,2'S)-(((9-(4-methoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

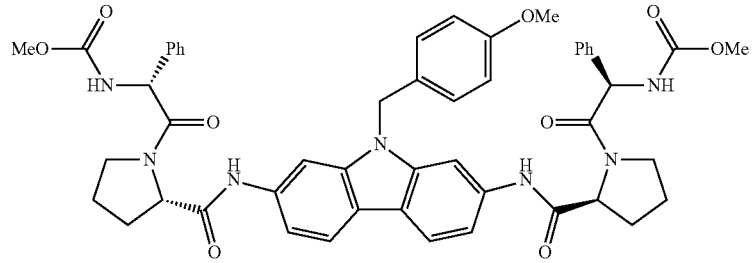 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3ccc(OC)cc3)c2c1)c1ccccc1]

Step (1). Preparation of 2,7-dibromo-9-methyl-(4-methoxybenzyl)-9H-carbazole The method in Step (1) of Example 1 was performed, and a target compound (204 mg, 49.6%) was obtained by using 2,7-dibromo-9H-carbazole (300 mg, 0.92 mmol) and 4-methoxybenzyl chloride (0.28 mL, 2.02 mmol).

$^1$H NMR (400 MHz, CDCl$_3$) δ 7.86 (d, J=0.3 Hz, 1H), 7.84 (d, J=0.2 Hz, 1H), 7.46 (d, J=1.5 Hz, 2H), 7.32 (dd, J=8.3, 1.6 Hz, 2H), 7.00 (dt, J=9.3, 2.5 Hz, 2H), 6.78 (dt, J=9.3, 2.6 Hz, 2H), 5.26 (s, 2H), 3.72 (s, 3H); $^{13}$C NMR (100 MHz, CDCl$_3$) 159.25, 141.55, 127.99, 127.60, 122.99, 121.52, 121.47, 119.94, 114.42, 112.27, 55.30, 46.22.

Step (2). Preparation of N,N'-(9-(4-methoxybenzyl)-9H-carbazole-2,7-diyl)bis(1,1-diphenylmethaneimine)

The method in Step (2) of Example 1 was performed, and a target compound (222 mg, 65.2%) was obtained by using 2,7-dibromo-9-(4-methoxybenzyl)-9H-carbazole (235 mg, 0.53 mmol) and benzophenoneimine (0.09 mL, 1.16 mmol).

$^1$H NMR (400 MHz, CDCl$_3$) δ 7.74 (d, J=7.4 Hz, 4H), 7.70 (d, J=8.2 Hz, 2H), 7.47-7.37 (m, 6H), 7.22-7.08 (m, 10H), 6.75 (dd, J=36.2, 8.3 Hz, 4H), 6.66 (s, 2H), 6.60 (d, J=8.2 Hz, 2H), 5.05 (s, 2H), 3.77 (s, 3H); $^{13}$C NMR (100 MHz, CDCl$_3$) 167.98, 158.77, 149.21, 141.46, 139.97, 136.54, 130.64, 129.54, 129.34, 129.25, 128.44, 128.21, 127.94, 127.76, 119.72, 119.12, 114.02, 113.83, 101.39, 55.31, 45.91.

Step (3). Preparation of 9-(4-methoxybenzyl)-9H-carbazole-2,7-diamine dihydrochloride The method in Step (3) of Example 1 was performed, and 126 mg (0.32 mmol, 93.9%) of a target compound was obtained by using N,N'-(9-(4-methoxybenzyl)-9H-carbazole-2,7-diyl)bis(1,1-diphenylmethaneimine) (222 mg, 0.34 mmol).

$^1$H NMR (400 MHz, DMSO-d$_6$) δ 10.48 (s, 6H), 8.29 (d, J=8.2 Hz, 2H), 7.65 (s, 2H), 7.32-7.23 (m, 5H), 7.16 (d, J=7.3 Hz, 2H), 5.64 (s, 2H); $^{13}$C NMR (100 MHz, DMSO-d$_6$) δ 140.68, 136.71, 130.65, 128.76, 127.54, 126.57, 121.64, 120.89, 114.62, 104.07, 45.98.

Step (4). Preparation of dimethyl ((1R,1'R)-((2S,2'S)-(((9-(4-methoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (58 mg, 50.8%) was obtained by using 9-(4-methoxybenzyl)-9H-carbazole-2,7-diamine dihydrochloride (50 mg, 0.13 mmol) and ((R)-2-((methoxycarbonyl)amino)-2-phenylacetyl)-L-proline (90 mg, 0.29 mmol).

$^1$H NMR (400 MHz, CDCl$_3$) δ 9.54 (s, 2H), 7.66-7.62 (m, 4H), 7.41-7.33 (m, 10H), 7.17 (d, J=7.7 Hz, 2H), 7.03 (d, J=8.6 Hz, 2H), 6.70 (d, J=8.7 Hz, 2H), 6.18 (d, J=7.0 Hz, 2H), 5.54 (d, J=7.0 Hz, 2H), 5.18 (q, J=13.4 Hz, 2H), 4.73 (d, J=5.6 Hz, 2H), 3.90 (t, J=7.8 Hz, 2H), 3.68 (s, 3H), 3.57 (s, 6H), 3.30 (q, J=8.0 Hz, 2H), 2.38-2.34 (m, 2H), 2.28-2.19 (m, 2H), 1.97-1.83 (m, 4H); $^{13}$C NMR (100 MHz, CDCl$_3$) δ 169.82, 168.88, 158.70, 156.09, 140.74, 136.64, 136.02, 129.54, 129.13, 128.72, 128.06, 127.89, 119.62, 119.05, 113.97, 111.79, 99.83, 61.69, 57.29, 55.14, 52.28, 47.47, 45.36, 28.58, 24.74. LC/MS (ESI-TOF) m/z calcd for C$_{50}$H$_{51}$N$_7$O$_9$Na [M+Na]$^+$: 916.36 found 916.10.

Example 15. Preparation of dimethyl ((1R,1'R)-((2S,2'S)-(((9-(1-phenylethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

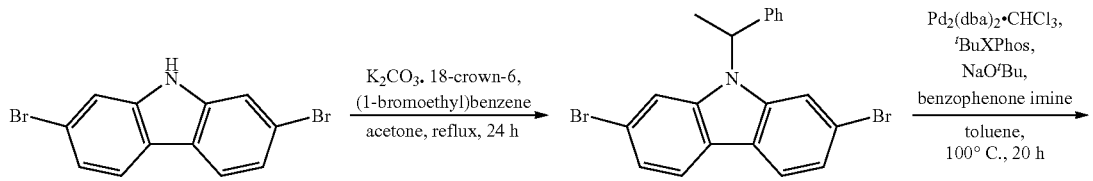

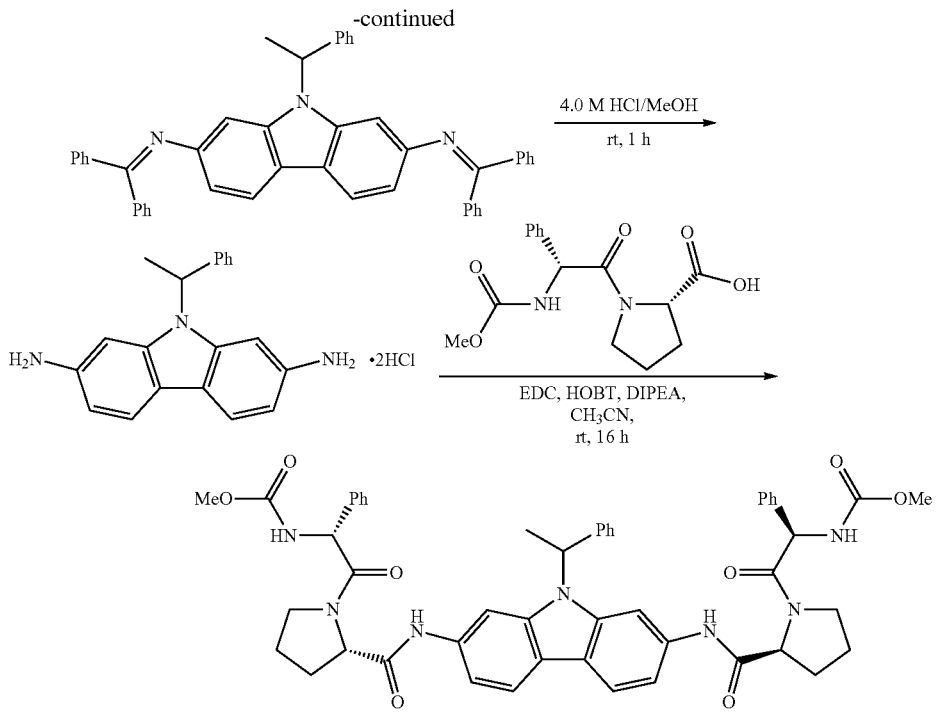

Step (1). Preparation of 2,7-dibromo-9-(1-phenylethyl)-9H-carbazole 2,7-dibromo-9H-carbazole (625 mg, 0.923 mmol) was dissolved in acetone (6 mL), and then potassium carbonate (1.063 g, 7.692 mmol), 18-crown-6 (51 mg, 0.192 mmol), and (1-bromoethyl)benzene (1.57 mL, 11.54 mmol) were added thereto, and the resulting mixture was refluxed under heating for 24 hours. The mixture completely reacted was concentrated under reduced pressure. The concentrated solution was separated and purified with column chromatography (100% hexane) to obtain a white solid target compound (754 mg, 91.4%).

$^1$H NMR (400 MHz, CDCl$_3$) δ 7.95 (d, J=8.3 Hz, 2H), 7.46 (d, J=1.5 Hz, 2H), 7.42-7.36 (m, 5H), 7.33-7.29 (m, 2H), 6.00 (q, J=7.1 Hz, 1H), 2.03 (d, J=7.2 Hz, 1H), $^{13}$C NMR (100 MHz, CDCl$_3$) δ 140.85, 139.57, 128.96, 127.88, 126.39, 122.86, 121.93, 121.47, 119.66, 113.47, 52.86, 17.51.

Step (2). Preparation of N,N'-(9-(1-phenylethyl)-9H-carbazole-2,7-diyl)bis(1,1-diphenylmethaneimine)

The method in Step (2) of Example 1 was performed, and a target compound (118 mg, 61.9%) was obtained by using 2,7-dibromo-9-(1-phenylethyl)-9H-carbazole (130 mg, 0.303 mmol).

$^1$H NMR (400 MHz, CDCl$_3$) δ 7.80-7.76 (m, 6H), 7.53-7.48 (m, 2H), 7.46-7.42 (m, 4H), 7.32-7.21 (m, 9H), 7.11-7.09 (m, 6H), 6.69 (dd, J=8.2, 1.7 Hz, 2H), 6.57 (s, 2H), 5.64 (q, J=7.1 Hz, 1H), 1.66 (d, J=7.1 Hz, 3H); $^{13}$C NMR (100 MHz, CDCl$_3$) 167.98, 148.68, 140.63, 140.61, 139.84, 136.57, 130.68, 129.51, 129.37, 128.49, 128.45, 128.21, 127.99, 127.18, 126.47, 119.63, 113.90, 102.77, 52.15, 16.83.

Step (3). Preparation of 9-(1-phenylethyl)-9H-carbazole-2,7-diamine dihydrochloride The method in Step (2) of Example 1 was performed, and a target compound (51 mg, 72.7%) was obtained by using N,N'-(9-(1-phenylethyl)-9H-carbazole-2,7-diyl)bis(1,1-diphenylmethaneimine) (118 mg, 0.187 mmol).

$^1$H NMR (400 MHz, DMSO-d$_6$) δ 10.04 (bs, 6H), 8.26 (d, J=8.3 Hz, 2H), 7.48 (s, 2H), 7.38-7.29 (m, 3H), 7.26 (d, J=7.5 Hz, 2H), 7.17 (dd, J=8.3, 1.5 Hz, 2H), 6.22 (q, J=5.4 Hz, 1H), 2.02 (d, J=7.1 Hz, 3H).

Step (4). Preparation of dimethyl ((1R,1'R)-((2S,2'S)-(((9-(1-phenylethyl)-9H-carbazole-2,7-diyl)bis(azanediyl))bis(carbonyl))bis(pyrrolidine-2,1-diyl))bis(2-oxo-1-phenylethane-2,1-diyl))dicarbamate ((R)-2-((methoxycarbonyl)amino)-2-phenylacetyl)-L-proline (100 mg, 0.327 mmol), HOBt (46 mg, 0.341 mmol), and EDC (63 mg, 0.327 mmol) were added to acetonitrile (2 mL) under an argon atmosphere, and the resulting mixture was stirred at room temperature for 1 hour. The 9-(1-phenylethyl)-9H-carbazole-2,7-diamine dihydrochloride (51 mg, 0.136 mmol) prepared in Step (3) was added thereto, DIPEA (95 μL 0.545 mmol) was added dropwise thereto at 0° C., and then the resulting mixture was stirred at room temperature for 16 hours. H$_2$O was added to the mixture completely reacted, the resulting mixture was extracted by using ethyl acetate, and the collected organic layer was washed with brine. The separated organic layer was dried over anhydrous sodium sulfate, and then filtered and concentrated under reduced pressure. The concentrated solution was separated and purified with column chromatography (CH$_2$Cl$_2$/MeOH=40/1, v/v) to obtain a pale light yellow solid target compound (52 mg, 43.5%).

$^1$H NMR (400 MHz, CDCl$_3$) δ 9.28 (s, 2H), 7.95 (s, 2H), 7.87 (dd, J=8.1, 2.1 Hz, 7.47-7.49 (m, 4H),7.47-7.46 (m,

4H), 7.40-7.39 (m, 6H), 7.32-7.29 (m, 4H), 7.27-7.20 (m, 3H), 6.21 (d, J=7.0 Hz, 1H), 6.17 (d, J=7.0 Hz, 1H), 6.05 (t, J=7.0 Hz, 1H), 5.51-5.48 (m, 2H) 4.78 (d, J=7.3 Hz, 2H), 3.84-3.80 (m, 2H), 3.62 (s, 6H), 3.27-3.21 (m, 2H), 2.50-2.47 (m, 2H), 2.16-2.12 (m, 2H), 2.05 (dd, J=12.7 Hz, 7.1 Hz, 3H), 1.88-1.78 (m, 4H); $^{13}$C NMR (100 MHz, CDCl$_3$) δ 170.42, 168.44, 156.43, 140.62, 135.72, 129.24, 128.87, 128.60, 127.20, 126.54, 119.80, 112.19, 101.78, 61.53, 57.56, 52.38, 47.16, 27.59, 24.64, 17.67, 17.61. LC/MS (ESI-TOF) m/z calcd for C$_{50}$H$_{52}$N$_7$O$_8$ [M+H]$^+$: 878.38 found 878.25.

Example 16. Preparation of dimethyl ((1R,1'R)-((2S,2'S)-(((9-(cyclopropylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate J=8.2, 1.6 Hz, 2H), 3.85 (d, J=6.2 Hz, 2H), 0.97-0.87 (m, 1H), 0.26 (q, J=6.2 Hz, 2H), 0.02 (q, J=5.3 Hz, 2H); $^{13}$C NMR (100 MHz, CDCl$_3$) δ 167.81, 148.94, 141.47, 140.10, 136.66, 130.59, 129.64, 129.35, 128.44, 128.20, 128.01, 119.66, 119.03, 113.76, 101.34, 46.56, 10.26, 3.54.

Step (3). Preparation of 9-(cyclopropylmethyl)-9H-carbazole-2,7-diamine dihydrochloride The method in Step (3) of Example 1 was performed, and a target compound (303 mg, 91.3%) was obtained by using N,N'-(9-(cyclopropylmethyl)-9H-carbazole-2,7-diyl)bis(1,1-diphenylmethaneimine) (593 mg, 1.02 mmol).

$^1$H NMR (400 MHz, DMSO-d$_6$) δ 10.50 (s, 6H), 8.25 (d, J=8.3 Hz, 2H), 7.67 (d, J=1.5 Hz, 2H), 7.24 (dd, J=8.3, 1.7 Hz, 2H), 4.28 (d, J=6.7 Hz, 2H), 1.24 (sp, J=6.5 Hz, 1H),

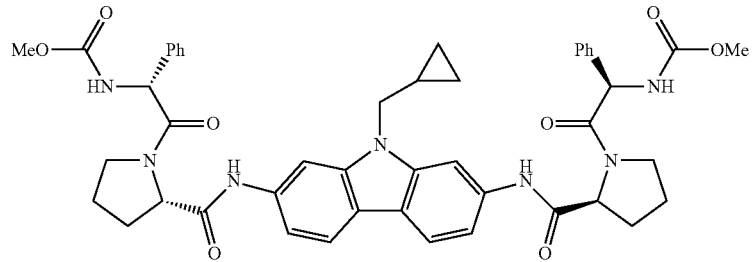 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(CC3CC3)c2c1)c1ccccc1]

Step (1). Preparation of 2,7-dibromo-9-(cyclopropylmethyl)-9H-carbazole

The method in Step (1) of Example 1 was performed, and a target compound (463 mg, 79.4%) was obtained by using 2,7-dibromo-9H-carbazole (500 mg, 1.54 mmol) and (chloromethyl)cyclopropane (0.30 mL, 3.23 mmol).

$^1$H NMR (400 MHz, CDCl$_3$) δ 7.84 (d, J=8.2 Hz, 2H), 7.53 (d, J=1.2 Hz, 2H), 7.31 (dd, J=8.3, 0.9 Hz, 2H), 4.08 (d, J=6.5 Hz, 2H), 1.32-1.23 (m, 1H), 0.56 (q, J=6.3 Hz, 2H), 0.38 (q, J=5.2 Hz, 2H); $^{13}$C NMR (100 MHz, CDCl$_3$) δ 141.54, 122.61, 121.45, 121.35, 119.74, 112.18, 47.32, 10.56, 4.11.

Step (2). Preparation of N,N'-(9-(cyclopropylmethyl)-9H-carbazole-2,7-diyl)bis(1,1-diphenylmethaneimine)

The method in Step (2) of Example 1 was performed, and a target compound (593 mg, 68.0%) was obtained by using 2,7-dibromo-9-(cyclopropylmethyl)-9H-carbazole (570 mg, 1.50 mmol) and benzophenoneimine (0.58 mL, 3.31 mmol).

$^1$H NMR (400 MHz, CDCl$_3$) δ 7.78-7.76 (m, 4H), 7.71 (d, J=8.2 Hz, 2H), 7.49-7.46 (m, 2H), 7.43-7.39 (m, 4H), 7.23-7.21 (m, 6H), 7.18-7.15 (m, 4H), 6.67 (s, 2H), 6.63 (dd, 0.54-0.47 (m, 4H); $^{13}$C NMR (100 MHz, DMSO-d$_6$) δ 140.60, 130.64, 121.47, 120.72, 114.23, 104.09, 48.55, 46.72, 10.40, 3.64.

Step (4). Preparation of dimethyl ((1R,1'R)-((2S,2'S)-(((9-(cyclopropylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (46 mg, 36.4%) was obtained by using 9-(cyclopropylmethyl)-9H-carbazole-2,7-diamine dihydrochloride (50 mg, 0.15 mmol) and ((R)-2-((methoxycarbonyl)amino)-2-phenylacetyl)-L-proline (108 mg, 0.35 mmol).

$^1$H NMR (400 MHz, CDCl$_3$) δ 9.56 (s, 2H), 7.75-7.62 (m, 4H), 7.45-7.36 (m, 10H), 7.12 (d, J=8.2 Hz, 2H), 6.20 (s, 2H), 5.56 (d, J=6.9 Hz, 2H), 4.76 (d, J=6.2 Hz, 2H), 4.06-3.88 (m, 4H), 3.62 (s, 6H), 3.31 (q, J=8.2 Hz, 2H), 2.46-2.21 (m, 4H), 1.96-1.87 (m, 4H), 1.24-1.19 (m, 1H), 0.45-0.35 (m, 4H); $^{13}$C NMR (100 MHz, CDCl$_3$) δ 169.92, 168.81, 156.10, 140.81, 136.61, 135.87, 129.18, 128.78, 127.92, 119.56, 118.93, 111.39, 99.79, 61.73, 57.29, 52.32, 47.47, 46.53, 28.43, 24.79, 10.66, 4.22, 3.56. LC/MS (ESI-TOF) m/z calcd for C$_{46}$H$_{49}$N$_7$O$_8$Na [M+Na]$^+$: 850.35 found 850.10.

Example 17. Preparation of dimethyl ((1R,1'R)-((2S,2'S)-(((9-(pyridine-2-ylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

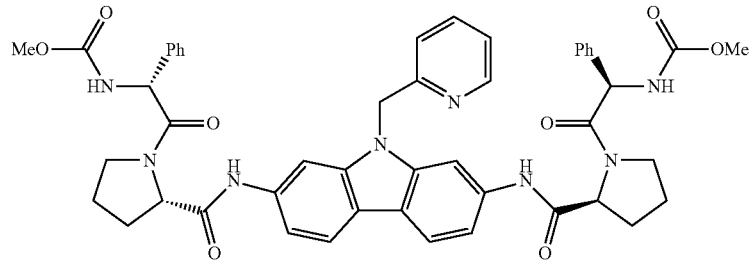 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3ccccn3)c2c1)c1ccccc1]

Step (1). Preparation of 2,7-dibromo-9-((6-methylpyridine-2-yl)methyl)-9H-carbazole The method in Step (1) of Example 1 was performed, and a white solid target compound (213 mg, 40%) was obtained by using 2,7-dibromo-9H-carbazole (400 mg, 1.23 mmol) and 2-(bromomethyl)-6-methylpyridine (251 mg, 1.35 mmol).

$^1$H NMR (400 MHz, CDCl$_3$) δ 7.97 (dd, J=8.4, 0.4 Hz, 2H), 7.57 (d, J=1.6 Hz, 2H), 7.42 (m, 3H), 7.09 (d, J=7.6 Hz, 1H), 6.42 (d, 7.6 Hz, 1H), 5.53 (s, 2H).

Step (2). Preparation of N,N'-(9-(pyridine-2-ylmethyl)-9H-carbazole-2,7-diyl)bis(1,1-diphenylmethaneimine)

The method in Step (2) of Example 1 was performed, and a yellow solid target compound (102 mg, 30%) was obtained by using 2,7-dibromo-9-((6-methylpyridine-2-yl)methyl)-9H-carbazole (230 mg, 0.55 mmol) and benzophenoneimine (142 μL, 1.27 mmol).

$^1$H NMR (400 MHz, CDCl$_3$) δ 8.58 (dd, J=4.8, 0.8 Hz, 1H), 7.78 (m, 6H), 7.50 (m, 7H), 7.15 (m, 11H), 6.69 (dd, J=8.4, 2.0 Hz, 2H), 6.64 (d, J=1.6 Hz, 2H), 6.26 (d, J=8.0 Hz, 1H), 5.28 (s, 2H).

Step (3). Preparation of 9-(pyridine-2-ylmethyl)-9H-carbazole-2,7-diamine dihydrochloride The method in Step (3) of Example 1 was performed, and a white solid target compound (53 mg, 90%) was obtained by using N,N'-(9-(pyridine-2-ylmethyl)-9H-carbazole-2,7-diyl)bis(1,1-diphenylmethaneimine) (100 mg, 0.16 mmol).

$^1$H NMR (400 MHz, MeOD) δ 8.88 (d, J=6.4 Hz, 1H), 8.38 (m, 3H), 7.97 (t, J=8.4 Hz, 1H), 7.74 (d, J=2.4 Hz, 2H), 7.42 (m, 3H), 6.22 (s, 2H).

Step (4). Preparation of dimethyl ((1R,1'R)-((2S,2'S)-(((9-(pyridine-2-ylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate EDC (49 mg, 0.25 mmol), HOBt (32 mg, 0.23 mmol), and ((R)-2-((methoxycarbonyl)amino)-2-phenylacetyl)-L-proline (72 mg, 0.24 mmol) were added to DMF (1 mL), and then the resulting mixture was stirred at room temperature for 1 hour. N-methylmorpholine (NMM; 17 μL, 0.15 mmol) and the 9-(pyridine-2-ylmethyl)-9H-carbazole-2,7-diamine dihydrochloride (25 mg, 0.07 mmol) prepared in Step (3) were added to the reaction mixture, and then the resulting mixture was stirred for 15 hours. The mixture completely reacted was concentrated under reduced pressure. The mixture was extracted by using ethyl acetate and distilled water, and the organic layer was dried by putting anhydrous sodium sulfate thereto, and then filtered and concentrated under reduced pressure. The concentrated solution was separated and purified with column chromatography (CH$_2$Cl$_2$/MeOH=30/1, v/v) to obtain a white solid target compound (26 mg, 43%).

$^1$H NMR (400 MHz, CDCl$_3$) δ 9.64 (s, 2H), 8.59 (d, J=4.4 Hz, 1H), 7.59 (m, 3H), 7.42-7.32 (m, 12H), 7.22 (s, 1H), 7.11 (m, 1H), 6.68 (d, J=5.6 Hz, 1H), 6.55 (d, J=8 Hz, 1H), 5.59 (d, J=6.8 Hz, 2H), 5.44 (d, J=6.4 Hz, 2H), 4.68 (d, J=5.6 Hz, 2H), 3.97 (br s, 2H), 3.59 (s, 6H), 3.41 (m, 2H), 2.96 (br s, 2H), 2.32 (m, 4H), 1.94 (m, 4H); $^{13}$C NMR (100 MHz, CDCl$_3$) δ 169.7, 169.1, 157.2, 156.1, 149.2, 140.5, 136.9, 136.8, 136.1, 129.0, 128.5, 127.9, 122.1, 120.5, 119.6, 119.0, 111.9, 99.4, 61.7, 57.3, 52.2, 47.5, 28.5, 24.8. LC/MS (ESI-TOF) m/z calcd for C$_{48}$H$_{49}$N$_8$O$_8$ [M+H]$^+$: 865.37 found 865.45.

Example 18. Preparation of dimethyl ((1R,1'R)-((2S,2'S)-(((9-(pyridine-3-ylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

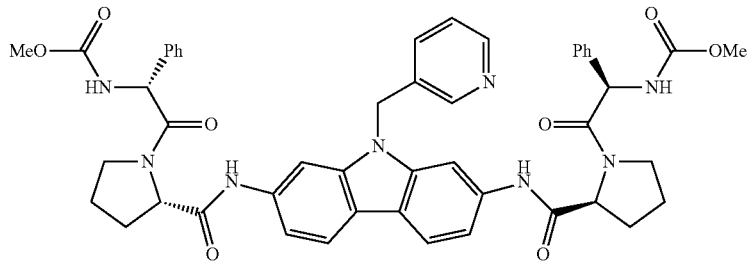

Step (1). Preparation of 2,7-dibromo-9-(pyridine-3-ylmethyl)-9H-carbazole

The method in Step (1) of Example 1 was performed, and a white solid target compound (51 mg, 32%) was obtained by using 2,7-dibromo-9H-carbazole (125 mg, 0.38 mmol) and 3-(chloromethyl)pyridine hydrochloride (63 mg, 0.38 mmol). $^1$H NMR (400 MHz, CDCl$_3$) δ 8.58 (d, J=5.2 Hz, 2H), 7.97 (d, J=8.0 Hz, 2H), 7.52 (d, J=1.6 Hz, 2H), 7.43 (dd, J=8.4, 1.6 Hz, 2H), 7.34 (m, 1H), 7.25 (dd, J=7.6, 4.8 Hz, 1H), 5.48 (s, 2H).

Step (2). Preparation of N,N'-(9-(pyridine-3-ylmethyl)-9H-carbazole-2,7-diyl)bis(1,1-diphenylmethaneimine)

The method in Step (2) of Example 1 was performed, and a yellow solid target compound (140 mg, 47%) was obtained by using 2,7-dibromo-9-(pyridine-3-ylmethyl)-9H-carbazole (200 mg, 0.48 mmol) and benzophenoneimine (124 μL, 1.10 mmol).
$^1$H NMR (400 MHz, CDCl$_3$) δ 8.53 (d, J=4.4 Hz, 1H), 8.38 (s, 1H), 7.78 (d, J=11.2 Hz, 6H), 7.52 (m, 6H), 7.21-7.07 (m, 11H), 6.96 (d, J=10.4 Hz, 1H), 6.71 (dd, J=10.8, 2.4 Hz, 2H), 6.62 (d, J=2.0 Hz, 2H), 5.15 (s, 2H).

Step (3). Preparation of 9-(pyridine-3-ylmethyl)-9H-carbazole-2,7-diamine dihydrochloride The method in Step (3) of Example 1 was performed, and a white solid target compound (56 mg, 86%) was obtained by using N,N'-(9-(pyridine-3-ylmethyl)-9H-carbazole-2,7-diyl)bis(1,1-diphenylmethaneimine) (111 mg, 0.18 mmol).

$^1$H NMR (400 MHz, MeOD) δ 8.84 (d, J=10.8 Hz, 2H), 8.42 (d, J=10.8 Hz, 2H), 8.31 (d, J=10.8 Hz, 1H), 8.04 (dd, J=10.8, 8 Hz, 1H), 7.76 (d, J=2 Hz, 2H), 7.39 (dd, J=11.2, 2.4 Hz, 2H), 6.08 (s, 2H).

Step (4). Preparation of dimethyl ((1R,1'R)-((2S,2'S)-(((9-(pyridine-3-ylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Step (4) of Example 17 was performed, and a while solid target compound (29 mg, 41%) was obtained by using 9-(pyridine-3-ylmethyl)-9H-carbazole-2,7-diamine dihydrochloride (30 mg, 0.08 mmol) and ((R)-2-((methoxycarbonyl)amino)-2-phenylacetyl)-L-proline (86 mg, 0.28 mmol).
$^1$H NMR (400 MHz, CDCl$_3$) δ 9.61 (s, 2H), 8.63 (s, 1H), 8.45 (dd, J=4.8, 1.6 Hz, 1H), 7.68 (m, 3H), 7.44-7.32 (m, 10H), 7.18 (br s, 2H), 7.12 (m, 1H), 6.72 (br s, 2H), 5.62 (d, J=7.2 Hz, 2H), 5.29 (m, 1H), 5.08 (m, 1H), 4.66 (d, J=4.8 Hz, 2H), 3.96 (d, J=6.8 Hz, 2H), 3.64 (s, 6H); $^{13}$C NMR (100 MHz, CDCl$_3$) δ 169.8, 169.5, 156.3, 149.1, 148.3, 140.0, 137.2, 136.1, 135.3, 133.0, 128.9, 128.4, 127.9, 123.6, 119.5, 118.8, 112.1, 99.4, 61.7, 57.1, 52.3, 47.7, 43.2, 29.3, 24.9. LC/MS (ESI-TOF) m/z calcd for C$_{48}$H$_{49}$N$_8$O$_8$ [M+H]$^+$: 865.37 found 865.40.

Example 19. Preparation of dimethyl ((1R,1'R)-((2S,2'S)-(((9-(pyridine-4-ylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

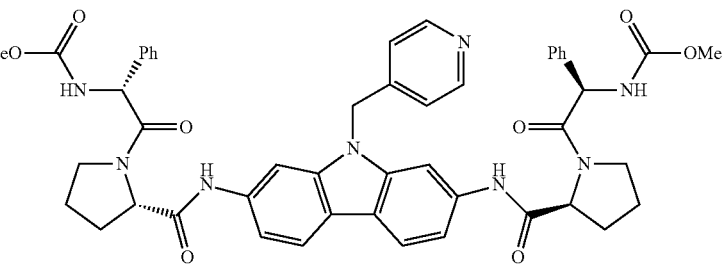

Step (1). Preparation of 2,7-dibromo-9-(pyridine-4-ylmethyl)-9H-carbazole

The method in Step (1) of Example 1 was performed, and a white solid target compound (380 mg, 74%) was obtained by using 2,7-dibromo-9H-carbazole (400 mg, 1.23 mmol) and 4-(chloromethyl)pyridine hydrochloride (173 mg, 1.35 mmol).

$^1$H NMR (400 MHz, CDCl$_3$) δ 8.58 (d, J=5.2 Hz, 2H), 7.98 (dd, J=8.4, 0.8 Hz, 2H), 7.45 (m, 3H), 7.00 (d, J=6.0 Hz, 2H), 5.44 (s, 2H).

Step (2). Preparation of N,N'-(9-(pyridine-4-ylmethyl)-9H-carbazole-2,7-diyl)bis(1,1-diphenylmethaneimine)

The method in Step (2) of Example 1 was performed, and a yellow solid target compound (110 mg, 37%) was obtained by using 2,7-dibromo-9-(pyridine-4-ylmethyl)-9H-carbazole (200 mg, 0.48 mmol) and benzophenoneimine (123 μL, 1.10 mmol).

$^1$H NMR (400 MHz, CDCl$_3$) δ 8.44 (d, J=4.8 Hz, 2H), 7.80 (m, 6H), 7.50 (m, 7H), 7.21 (m, 7H), 7.09 (m, 4H), 6.71 (m, 4H), 6.53 (s, 2H), 5.12 (s, 2H).

Step (3). Preparation of 9-(pyridine-4-ylmethyl)-9H-carbazole-2,7-diamine dihydrochloride The method in Step (3) of Example 1 was performed, and a white solid target compound (15 mg, 48%) was obtained by using N,N'-(9-(pyridine-4-ylmethyl)-9H-carbazole-2,7-diyl)bis(1,1-diphenylmethaneimine) (53 mg, 0.09 mmol).

$^1$H NMR (400 MHz, MeOD) δ 8.80 (d, J=6.4 Hz, 2H), 8.43 (d, J=8 Hz, 2H), 7.76 (d, J=6.8 Hz, 2H), 7.61 (d, J=1.6 Hz, 2H), 7.38 (dd, J=8.4, 2.0 Hz, 2H), 6.15 (s, 2H).

Step (4). Preparation of dimethyl ((1R,1'R)-((2S,2'S)-(((9-(pyridine-4-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Step (4) of Example 17 was performed, and a white solid target compound (15 mg, 37%) was obtained by using 9-(pyridine-4-ylmethyl)-9H-carbazole-2,7-diamine dihydrochloride (15 mg, 0.04 mmol) and ((R)-2-((methoxycarbonyl)amino)-2-phenylacetyl)-L-proline (30 mg, 0.09 mmol).

$^1$H NMR (400 MHz, CDCl$_3$) δ 9.62 (s, 2H), 8.43 (d, J=6 Hz, 2H), 7.73 (d, J=8.4 Hz, 2H), 7.62 (s, 2H), 7.44-7.38 (m, 10H), 7.22 (s, 2H), 6.96 (d, J=5.2 Hz, 2H), 6.11 (d, J=6.8 Hz, 2H), 5.57 (d, J=7.2 Hz, 2H), 5.26 (s, 2H), 4.73 (m, 2H), 3.94 (t, J=5.6 Hz, 2H), 3.61 (m, 6H), 3.36 (m, 2H), 2.40 (m, 2H). LC/MS (ESI-TOF) m/z calcd for C$_{48}$H$_{49}$N$_8$O$_8$ [M+H]$^+$: 865.37 found 865.45.

Example 20. Preparation of dimethyl ((1R,1'R)-((2S,2'S)-(((9-((6-methylpyridine-2-yl)methyl)-9H-carbazole-2,7-diyl)bis(azanediyl))bis(carbonyl))bis(pyrrolidine-2,1-diyl))bis(2-oxo-1-phenylethane-2,1-diyl))dicarbamate

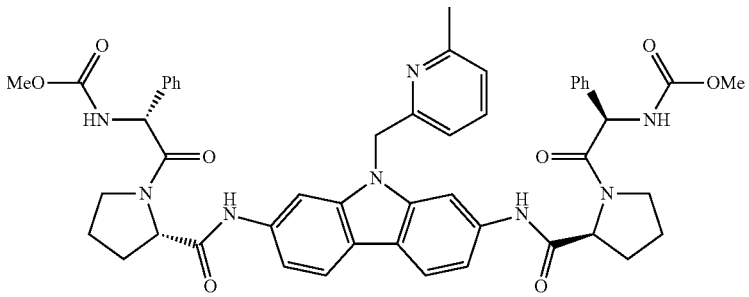 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3cccc(C)n3)c2c1)c1ccccc1]

Step (1). Preparation of 2,7-dibromo-9-((6-methylpyridine-2-yl)methyl)-9H-carbazole The method in Step (1) of Example 1 was performed, and a white solid target compound (213 mg, 40%) was obtained by using 2,7-dibromo-9H-carbazole (400 mg, 1.23 mmol) and 2-(bromomethyl)-6-methylpyridine (251 mg, 1.35 mmol).

$^1$H NMR (400 MHz, CDCl$_3$) δ 7.97 (dd, J=8.4, 0.4 Hz, 2H), 7.57 (d, J=1.6 Hz, 2H), 7.42 (m, 3H), 7.09 (d, J=7.6 Hz, 1H), 6.42 (d, J=7.6 Hz, 1H), 5.53 (s, 2H).

Step (2). Preparation of N,N'-(9-((6-methylpyridine-2-yl)methyl)-9H-carbazole-2,7-diyl)bis(1,1-diphenylmethaneimine)

The method in Step (2) of Example 1 was performed, and a yellow solid target compound (103 mg, 57%) was obtained by using 2,7-dibromo-9-((6-methylpyridine-2-yl)methyl)-9H-carbazole (125 mg, 0.29 mmol) and benzophenoneimine (74 μL, 0.66 mmol).

$^1$H NMR (400 MHz, CDCl$_3$) δ 7.77 (m, 6H), 7.48-7.39 (m, 7H), 7.26-7.12 (m, 10H), 7.02 (d, J=6.4 Hz, 1H), 6.67 (dd, J=6.4, 1.6 Hz, 2H), 6.63 (d, J=1.6 Hz, 2H), 6.03 (d, J=7.9 Hz, 1H), 5.25 (s, 2H).

Step (3). Preparation of 9-((6-methylpyridine-2-yl)methyl)-9H-carbazole-2,7-diamine dihydrochloride The method in Step (3) of Example 1 was performed, and a white solid target compound (28 mg, 46%) was obtained by using N,N'-(9-((6-methylpyridine-2-yl)methyl)-9H-carbazole-2,7-diyl)bis(1,1-diphenylmethaneimine) (103 mg, 0.16 mmol).

$^1$H NMR (400 MHz, MeOD) δ 8.45 (d, J=8 Hz, 2H), 8.22 (t, J=8 Hz, 1H), 7.83 (d, J=8 Hz, 1H), 7.77 (d, J=2 Hz, 2H), 7.41 (dd, J=8.0, 1.6 Hz, 2H), 6.95 (d, J=8.0 Hz, 1H), 6.20 (s, 2H), 2.94 (s, 3H).

Step (4). Preparation of dimethyl ((1R,1'R)-((2S,2'S)-(((9-((6-methylpyridine-2-yl)methyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Step (4) of Example 17 was performed, and a white solid target compound (51 mg, 87%) was obtained by using 9-((6-methylpyridine-2-yl)methyl)-9H-carbazole-2,7-diamine dihydrochloride (25 mg, 0.07 mmol) and ((R)-2-((methoxycarbonyl)amino)-2-phenylacetyl)-L-proline (45 mg, 0.15 mmol).

$^1$H NMR (400 MHz, CDCl$_3$) δ 9.31 (s, 2H), 7.94 (d, J=8.4 Hz, 2H), 7.86 (s, 2H), 7.45 (m, 10H), 7.34 (d, J=7.2 Hz, 2H), 7.01 (d, J=7.6 Hz, 1H), 6.33 (d, J=7.6 Hz, 1H), 6.09 (d, J=6.8 Hz, 1H), 5.57 (s, 2H), 5.49 (d, J=6.4 Hz, 2H), 4.79 (d, J=7.6 Hz, 2H), 3.84 (t, J=8.8 Hz, 2H), 3.63 (m, 6H), 3.26 (m, 2H), 2.65 (s, 3H), 2.53 (m, 2H), 2.13 (m, 2H), 1.91 (m, 4H); $^{13}$C NMR (75 MHz, CDCl$_3$) δ 169.9, 168.9, 158.2, 156.4, 156.2, 140.7, 137.2, 136.6, 136.1, 129.0, 128.6, 127.9, 121.7, 119.7, 119.1, 116.9, 112.1, 99.7, 61.6, 57.4, 52.2, 47.4, 30.9, 28.2, 24.8, 24.1. LC/MS (ESI-TOF) m/z calcd for C$_{49}$H$_{51}$N$_8$O$_8$ [M+H]$^+$: 879.39 found 879.45.

Example 21. Preparation of dimethyl ((1R,1'R)-((2S,2'S)-(((9-(2-methoxyethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

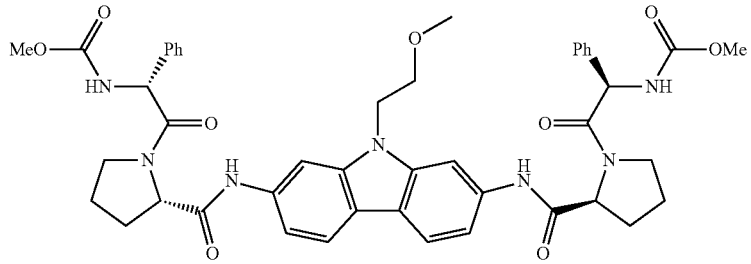 [SMILES: COCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-(2-methoxyethyl)-9H-carbazole

The method in Step (1) of Example 1 was performed, and a white solid target compound (419 mg, 89%) was obtained by using 2,7-dibromo-9H-carbazole (400 mg, 1.23 mmol) and 1-bromo-2-methoxyethane (127 µL, 1.35 mmol).

$^1$H NMR (400 MHz, CDCl$_3$) δ 7.92 (d, J=8.0 Hz, 2H), 7.63 (d, J=1.2 Hz, 2H), 7.39 (dd, J=8.0, 1.6 Hz, 2H), 4.43 (t, J=5.6 Hz, 2H), 3.33 (s, 3H).

Step (2). Preparation of N,N'-(9-(2-methoxyethyl)-9H-carbazole-2,7-diyl)bis(1,1-diphenylmethaneimine)

The method in Step (2) of Example 1 was performed, and a yellow solid target compound (148 mg, 48%) was obtained by using 2,7-dibromo-9-(2-methoxyethyl)-9H-carbazole (200 mg, 0.52 mmol) and benzophenoneimine (134 µL, 1.20 mmol).

$^1$H NMR (400 MHz, CDCl$_3$) δ 7.80 (d, J=2.0 Hz, 3H), 7.73 (d, J=10.8 Hz, 2H), 7.51 (m, 7H), 7.27 (m, 10H), 6.76 (d, J=2 Hz, 2H), 6.65 (dd, J=10.8, 2.0 Hz, 2H), 4.18 (m, 2H), 3.55 (t, J=9.6 Hz, 2H), 3.45 (m, 4H), 3.36 (s, 3H).

Step (3). Preparation of 9-(2-methoxyethyl)-9H-carbazole-2,7-diamine dihydrochloride The method in Step (3) of Example 1 was performed, and a white solid target compound (40 mg, 48%) was obtained by using N,N'-(9-(2-methoxyethyl)-9H-carbazole-2,7-diyl)bis(1,1-diphenylmethaneimine) (148 mg, 0.25 mmol).

$^1$H NMR (400 MHz, MeOD) δ 8.34 (d, J=8 Hz, 2H), 7.69 (d, J=2.0 Hz, 2H), 7.31 (dd, J=8.0, 2.0 Hz, 2H), 4.66 (t, J=5.2 Hz, 2H), 3.87 (t, J=4.8 Hz, 2H), 3.27 (s, 3H).

Step (4). Preparation of dimethyl ((1R,1'R)-((2S,2'S)-(((9-(2-methoxyethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Step (4) of Example 17 was performed, and a white solid target compound (53 mg, 84%) was obtained by using 9-(2-methoxyethyl)-9H-carbazole-2,7-diamine dihydrochloride (25 mg, 0.08 mmol) and ((R)-2-((methoxycarbonyl)amino)-2-phenylacetyl)-L-proline (51 mg, 0.17 mmol).

$^1$H NMR (400 MHz, CDCl$_3$) δ 9.48 (s, 2H), 7.88 (s, 2H), 7.77 (d, J=8.4 Hz, 2H), 7.48 (m, 4H), 7.41 (m, 6H), 7.20 (d, J=8.0 Hz, 2H), 6.22 (d, J=7.2 Hz, 2H), 5.56 (d, J=7.2 Hz, 2H), 4.82 (d, J=6.0 Hz, 2H), 4.34 (t, J=5.6 Hz, 2H), 3.92 (t, J=8.4 Hz, 2H), 3.73 (m, 8H), 3.32 (m, 2H), 3.29 (s, 3H), 2.52 (m, 2H), 2.27 (m, 2H), 1.95 (m, 4H); $^{13}$C NMR (75 MHz, CDCl$_3$) δ 170.0, 168.7, 156.1, 140.8, 136.5, 135.8, 129.1, 128.7, 127.9, 119.5, 119.0, 111.6, 99.7, 70.4, 61.6, 58.9, 57.3, 52.3, 47.4, 42.4, 30.9, 28.3, 24.7. LC/MS (ESI-TOF) m/z calcd for C$_{45}$H$_{50}$N$_7$O$_9$ [M+H]$^+$: 832.37 found 832.50.

Example 22. Preparation of dimethyl ((1R,1'R)-((2S,2'S)-(((9-(2-(2-methoxyethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate

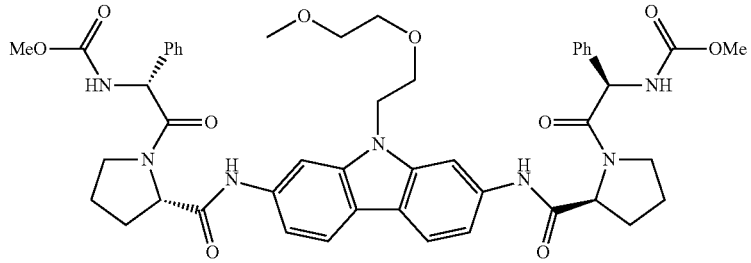 [SMILES: COCCOCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-(2-(2-methoxyethoxy)ethyl)-9H-carbazole The method in Step (1) of Example 1 was performed, and a white solid target compound (451 mg, 86%) was obtained by using 2,7-dibromo-9H-carbazole (400 mg, 1.23 mmol) and 1-bromo-2-(2-methoxyethoxy)ethane (189 µL, 1.35 mmol).

$^1$H NMR (400 MHz, CDCl$_3$) δ 7.93 (d, J=11.2 Hz, 2H), 7.67 (d, J=1.6 Hz, 2H), 7.40 (dd, J=11.2, 2.4 Hz, 2H), 4.47 (t, J=7.6 Hz, 2H), 3.91 (t, J=7.6 Hz, 2H), 3.57 (m 2H), 3.49 (m, 2H), 3.37 (s, 3H).

Step (2). Preparation of N,N'-(9-(2-(2-methoxyethoxy)ethyl)-9H-carbazole-2,7-diyl)bis(1,1-diphenylmethaneimine)

The method in Step (2) of Example 1 was performed, and a yellow solid target compound (175 mg, 80%) was obtained by using 2,7-dibromo-9-(2-(2-methoxyethoxy)ethyl)-9H-carbazole (250 mg, 0.59 mmol) and benzophenoneimine (151 µL, 1.35 mmol).

$^1$H NMR (400 MHz, CDCl$_3$) δ 7.81 (m, 4H), 7.72 (d, J=8.0 Hz, 2H), 7.51 (m, 6H), 7.27 (m, 6H), 7.21 (m, 4H), 6.75 (d, J=1.2 Hz, 2H), 6.64 (dd, J=8.4, 2.0 Hz, 2H), 4.16 (t, J=6.8 Hz, 2H), 3.55 (t, J=9.6 Hz, 2H), 3.45 (s, 4H), 3.35 (s, 3H).

Step (3). Preparation of 9-(2-(2-methoxyethoxy)ethyl)-9H-carbazole-2,7-diamine dihydrochloride The method in Step (3) of Example 1 was performed, and a white solid target compound (70 mg, 86%) was obtained by using N,N'-(9-(2-(2-methoxyethoxy)ethyl)-9H-carbazole-2,7-diyl)bis(1,1-diphenylmethaneimine) (138 mg, 0.21 mmol).

$^1$H NMR (400 MHz, CDCl$_3$) δ 8.34 (d, J=8.4 Hz, 2H), 7.71 (d, J=2.0 Hz, 2H), 7.32 (dd, J=8.0, 2.0 Hz, 2H), 4.67 (t, J=5.2 Hz, 2H), 3.97 (t, J=4.8 Hz, 2H), 3.53 (m, 2H), 3.39 (m, 2H), 3.15 (s, 3H).

Step (4). Preparation of dimethyl ((1R,1'R)-((2S,2'S)-(((9-(2-(2-methoxyethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Step (4) of Example 17 was performed, and a white solid target compound (33 mg, 47%) was obtained by using 9-(2-(2-methoxyethoxy)ethyl)-9H-carbazole-2,7-diamine dihydrochloride (30 mg, 0.08 mmol) and ((R)-2-((methoxycarbonyl)amino)-2-phenylacetyl)-L-proline (54 mg, 0.18 mmol).

$^1$H NMR (400 MHz, CDCl$_3$) δ 9.41 (s, 2H), 7.90 (br s, 2H), 7.80 (d, J=8 Hz, 2H), 7.49-7.39 (m, 10H), 7.21 (d, J=8.4 Hz, 2H), 6.19 (d, J=6.8 Hz, 2H), 5.56 (d, J=7.2 Hz, 2H), 4.82 (d, J=6.4 Hz, 2H), 4.37 (m, 2H), 3.92 (t, J=9.2 Hz, 2H), 3.83 (t, J=6 Hz, 2H), 3.67 (s, 6H), 3.54 (t, J=2 Hz, 2H), 3.47 (t, J=4.4 Hz, 2H), 3.31 (m, 5H); $^{13}$C NMR (75 MHz, CDCl$_3$) δ 169.9, 168.9, 156.2, 140.7, 136.6, 135.8, 129.1, 128.7, 127.9, 119.4, 119.0, 111.6, 99.9, 71.8, 70.5, 68.9, 61.6, 58.8, 57.3, 52.3, 47.4, 42.4, 28.5, 24.7. LC/MS (ESI-TOF) m/z calcd for C$_{47}$H$_{53}$N$_7$C$_{10}$Na [M+Na]$^+$: 898.38 found 898.40.

Example 23. Preparation of dimethyl ((1R,1'R)-((2S,2'S)-(((9-(2-(2-(2-methoxyethoxy)ethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate

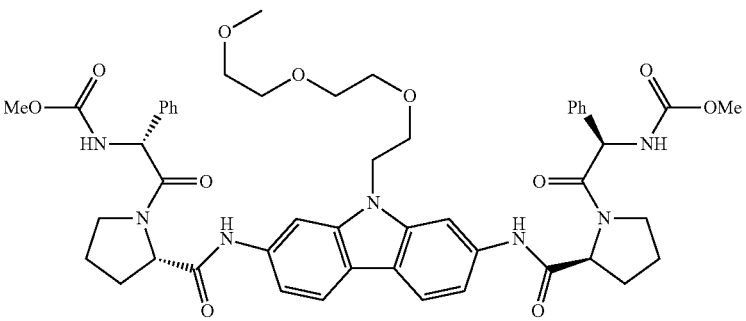 [SMILES: COCCOCCOCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-(2-(2-(2-methoxyethoxy)ethoxy)ethyl)-9H-carbazole The method in Step (1) of Example 1 was performed, and a white solid target compound (418 mg, 72%) was obtained by using 2,7-dibromo-9H-carbazole (400 mg, 1.23 mmol) and 1-bromo-2-(2-(2-methoxyethoxy)ethoxy)ethane (184 μL, 1.35 mmol).

$^1$H NMR (400 MHz, CDCl$_3$) δ 7.93 (d, J=10.8 Hz, 2H), 7.66 (d, J=2 Hz, 2H), 7.39 (dd, J=11.2, 2.4 Hz, 2H), 4.46 (t, J=7.6 Hz, 2H), 3.91 (t, J=8 Hz, 2H), 3.57 (m, 6H), 3.50 (t, J=4 Hz, 2H), 3.37 (s, 3H).

Step (2). Preparation of N,N'-(9-(2-(2-(2-methoxyethoxy)ethoxy)ethyl)-9H-carbazole-2,7-diyl)bis(1,1-diphenylmethaneimine)

The method in Step (2) of Example 1 was performed, and a yellow solid target compound (223 mg, 63%) was obtained by using 2,7-dibromo-9-(2-(2-(2-methoxyethoxy)ethoxy)ethyl)-9H-carbazole (250 mg, 0.53 mmol) and benzophenoneimine (136 μL, 1.22 mmol).

$^1$H NMR (400 MHz, CDCl$_3$) δ 7.83 (m, 4H), 7.72 (d, J=10.8 Hz, 2H), 7.51 (m, 6H), 7.29 (m, 6H), 7.23 (m, 4H), 6.76 (d, J=2 Hz, 2H), 6.64 (dd, J=11.2, 2.0 Hz, 2H), 4.17 (m, 2H), 3.58-3.46 (m, 10H), 3.35 (s, 3H).

Step (3). Preparation of 9-(2-(2-methoxyethoxy)ethyl)-9H-carbazole-2,7-diamine dihydrochloride The method in Step (3) of Example 1 was performed, and a white solid target compound (110 mg, 80%) was obtained by using N,N'-(9-(2-(2-(2-methoxyethoxy)ethoxy)ethyl)-9H-carbazole-2,7-diyl)bis(1,1-diphenylmethaneimine) (222 mg, 0.33 mmol).

$^1$H NMR (400 MHz, CDCl$_3$) δ 8.33 (d, J=8.4 Hz, 2H), 7.73 (d, J=1.6 Hz, 2H), 7.32 (dd, J=8.4, 2.0 Hz, 2H), 4.67 (t, J=4.8 Hz, 2H), 3.97 (t, J=5.2 Hz, 2H), 3.53 (m, 2H), 3.48 (m, 2H), 3.36 (m, 4H), 3.26 (s, 3H).

Step (4). Preparation of dimethyl ((1R,1'R)-((2S,2'S)-(((9-(2-(2-(2-methoxyethoxy)ethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Step (4) of Example 17 was performed, and a white solid target compound (51 mg, 57%) was obtained by using 9-(2-(2-(2-methoxyethoxy)ethoxy)ethyl)-9H-carbazole-2,7-diamine dihydrochloride (40 mg, 0.09 mmol) and ((R)-2-((methoxycarbonyl)amino)-2-phenylacetyl)-L-proline (100 mg, 0.32 mmol).

$^1$H NMR (400 MHz, CDCl$_3$) δ 9.60 (s, 2H), 7.59 (m, 4H), 7.47 (m, 4H), 7.40 (m, 6H), 7.16 (d, J=7.6 Hz, 2H), 6.40 (d, J=7.2 Hz, 2H), 5.62 (d, J=7.2 Hz, 2H), 4.75 (m, 2H), 4.14 (br s, 2H), 3.97 (br s, 2H), 3.68 (t, J=8 Hz, 2H), 3.47 (s, 6H), 3.46-3.33 (m, 12H), 3.28 (s, 3H), 2.39 (m, 4H), 1.92 (m, 4H); $^{13}$C NMR (75 MHz, CDCl$_3$) δ 169.8, 168.9, 156.2, 140.7, 136.6, 135.8, 129.1, 128.7, 127.9, 119.4, 118.9, 111.6, 99.9, 71.8, 70.8, 70.3, 69.0, 61.7, 58.8, 57.3, 52.3, 47.4, 42.4, 28.6, 24.7. LC/MS (ESI-TOF) m/z calcd for C$_{49}$H$_{57}$N$_7$O$_{11}$Na [M+Na]$^+$: 942.40 found 942.45.

Example 24. Preparation of dimethyl ((1R,1'R)-((2S,2'S)-(((9-decyl-9H-carbazole-2,7-diyl)bis(azanediyl))bis(carbonyl))bis(pyrrolidine-2,1-diyl))bis(2-oxo-1-phenylethane-2,1-diyl))dicarbamate

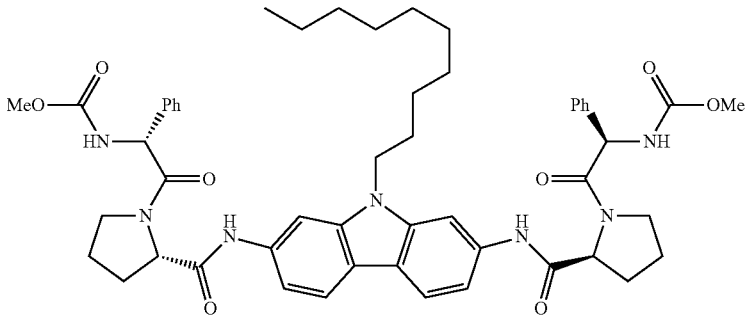 [SMILES: CCCCCCCCCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-decyl-9H-carbazole

The method in Step (1) of Example 1 was performed, and a target compound (1.418 g, 98.6%) was obtained by using 2,7-dibromo-9H-carbazole (1.0 g, 3.077 mmol) and 1-bromodecane (0.77 mL, 3.692 mmol).

$^1$H NMR (400 MHz, CDCl$_3$) δ 7.85-7.82 (m, 4H), 7.74 (d, J=8.2 Hz, 2H), 7.55-7.50 (m, 2H), 7.48-7.44 (m, 4H), 7.30-7.26 (m, 6H), 7.25-7.21 (m, 4H), 6.75 (d, J=1.2 Hz, 2H), 6.65 (dd, J=8.2, 1.7 Hz, 2H), 3.96 (t, J=7.1 Hz, 2H), 1.52 (p, J=7.4 Hz, 2H), 1.37-1.21 (m, 14H), 0.93 (t, J=5.4 Hz, 3H); $^{13}$C NMR (100 MHz, CDCl$_3$) 167.95, 148.74, 141.24, 140.01, 136.65, 130.69, 129.68, 129.41, 128.58, 128.24, 128.01, 119.70, 119.07, 113.66, 101.47, 42.98, 31.92, 29.67, 29.61, 29.43, 29.36, 28.43, 27.24, 22.72, 14.16.

Step (2). Preparation of N,N'-(9-decyl-9H-carbazole-2,7-diyl)bis(1,1-diphenylmethaneimine)

The method in Step (2) of Example 1 was performed, and a target compound (837 mg, 41.3%) was obtained by using 2,7-dibromo-9-decyl-9H-carbazole (1.418 mg, 3.048 mmol).

$^1$H NMR (400 MHz, CDCl$_3$) δ 7.83-7.81 (m, 4H), 7.73 (d, J=8.2 Hz, 2H), 7.54-7.50 (m, 2H), 7.48-7.44 (m, 4H), 7.30-7.25 (m, 4H), 7.24-7.21 (m, 4H), 6.75 (d, J=1.4 Hz, 2H), 6.66 (dd, J=8.2, 1.7 Hz, 2H), 4.16 (s, 4H), 3.75 (s, 4H), 2.50-2.46 (m, 6); $^{13}$C NMR (100 MHz, CDCl$_3$) δ 167.97, 149.14, 141.04, 140.01, 136.63, 130.70, 129.72, 129.38, 128.60, 128.26, 128.05, 119.82, 119.11, 113.91, 101.06, 66.71, 55.75, 53.76.

Step (3). Preparation of 9-decyl-9H-carbazole-2,7-diamine dihydrochloride

The method in Step (3) of Example 1 was performed, and a target compound (441 mg, 85.5%) was obtained by using N,N'-(9-decyl-9H-carbazole-2,7-diyl)bis(1,1-diphenyl-methaneimine) (837 mg, 1.257 mmol).

$^1$H NMR (400 MHz, DMSO-$d_6$) δ 10.25 (bs, 6H), 8.24 (d, J=8.3 Hz, 2H), 7.57 (d, J=1.3 Hz, 2H), 7.20 (dd, J=8.2, 1.6 Hz, 2H), 4.35 (t, J=7.0 Hz, 2H), 1.79 (t, J=6.7 Hz, 2H), 1.28-1.20 (m, 14H), 0.85 (t, J=6.9 Hz, 3H); $^{13}$C NMR (100 MHz, CDCl$_3$) δ 141.00, 137.47, 133.17, 130.07, 129.05, 104.52, 43.32, 31.72, 29.43, 29.39, 29.30, 29.11, 28.72, 27.03, 22.54, 14.42.

Example 4. Preparation of dimethyl ((1R,1'R)-((2S,2'S)-(((9-decyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (88 mg, 79.0%) was obtained by using 9-decyl-9H-carbazole-2,7-diamine dihydrochloride (50 mg, 0.122 mmol).

$^1$H NMR (400 MHz, CDCl$_3$) 9.67 (s, 2H), 7.65 (s, 2H), 7.58 (d, J=8.3 Hz, 2H), 7.48-7.47 (m, 4H), 7.41-7.38 (m, 6H), 7.16-7.14 (m, 2H), 6.30 (d, J=7.0 Hz, 2H), 5.60 (d, J=7.1 Hz, 2H), 4.77-4.75 (m, 2H), 4.08-4.04 (m, 2H), 3.99-3.94 (m, 2H), 3.64 (s, 6H), 3.40-3.34 (m, 2H), 2.43-2.39 (m, 2H), 2.35-2.28 (m, 2H), 2.07-1.98 (m, 2H), 1.96-1.72 (m, 2H), 1.30-1.21 (m, 16H), 0.87 (t, J=6.9 Hz, 3H); $^{13}$C NMR (100 MHz, CDCl$_3$) δ 169.76, 168.93, 156.07, 140.60, 136.74, 135.84, 129.13, 128.73, 127.88, 119.47, 118.80, 111.19, 99.52, 61.77, 57.25, 52.30, 47.52, 42.46, 31.86, 29.61, 29.55, 29.52, 29.29, 28.85, 28.72, 27.16, 24.78, 22.63, 14.08. LC/MS (ESI-TOF) m/z calcd for C$_{52}$H$_{64}$N$_7$O$_8$ [M+H]$^+$: 914.48 found 914.20.

Example 25. Preparation of dimethyl ((2R,2'R)-((2S,2'S)-(((9-decyl-9H-carbazole-2,7-diyl)bis(azanediyl))bis(carbonyl))bis(pyrrolidine-2,1-diyl))bis(3-methyl-1-oxobutane-1,2-diyl))dicarbamate

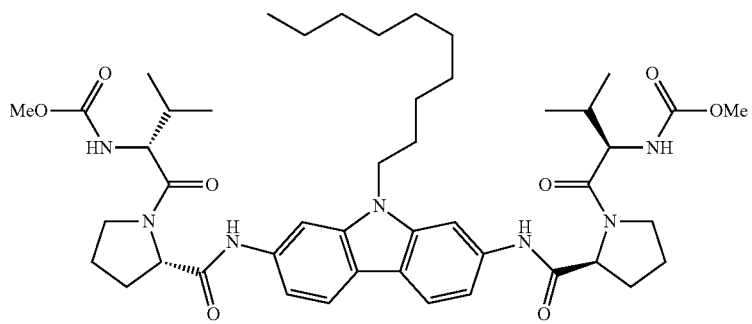 [SMILES: CCCCCCCCCCn1c2cc(NC(=O)[C@@H]3CCCN3C(=O)[C@H](NC(=O)OC)C(C)C)ccc2c2ccc(NC(=O)[C@@H]3CCCN3C(=O)[C@H](NC(=O)OC)C(C)C)cc21]

The method in Example 2 was performed, and a target compound (77 mg, 74.2%) was obtained by using 9-decyl-9H-carbazole-2,7-diamine dihydrochloride (50 mg, 0.122 mmol) and (methoxycarbonyl)-D-valyl-L-proline (80 mg, 0.292 mmol).

$^1$H NMR (400 MHz, CDCl$_3$) δ 9.51 (s, 2H), 7.77 (s, 2H), 7.62 (d, J=8.3 Hz, 2H), 7.07 (d, J=7.8 Hz, 2H), 5.54 (d, J=8.3 Hz, 2H), 4.79 (dd, J=7.9, 2.4 Hz, 2H), 4.38 (t, J=7.7 Hz, 2H), 4.15-4.12 (m, 2H), 4.06-4.02 (m, 2H), 3.71-3.68 (m, 2H), 3.64 (s, 6H), 2.49-2.45 (m, 2H), 2.32-2.25 (m, 2H), 2.14-2.02 (m, 6H), 1.76-1.72 (m, 2H), 1.28-1.21 (m, 16H), 1.06-1.03 (m, 12H), 0.87 (t, J=7.0 Hz, 3H); $^{13}$C NMR (100 MHz, CDCl$_3$) δ 172.05, 169.04, 157.25, 140.74, 135.82, 119.38, 118.80, 111.42, 99.85, 61.24, 58.07, 52.45, 47.80, 42.62, 31.85, 31.10, 29.69, 29.59, 29.54, 29.27, 28.87, 28.76, 27.16, 24.75, 22.64, 19.46, 17.94, 14.10. LC/MS (ESI-TOF) m/z calcd for C$_{46}$H$_{67}$N$_7$O$_8$Na [M+Na]$^+$: 868.49 found 868.35.

Example 26. Preparation of dimethyl ((1R,1'R)-((2S,2'S)-(((9-octyl-9H-carbazole-2,7-diyl)bis(azanediyl))bis(carbonyl))bis(pyrrolidine-2,1-diyl))bis(2-oxo-1-phenylethane-2,1-diyl))dicarbamate

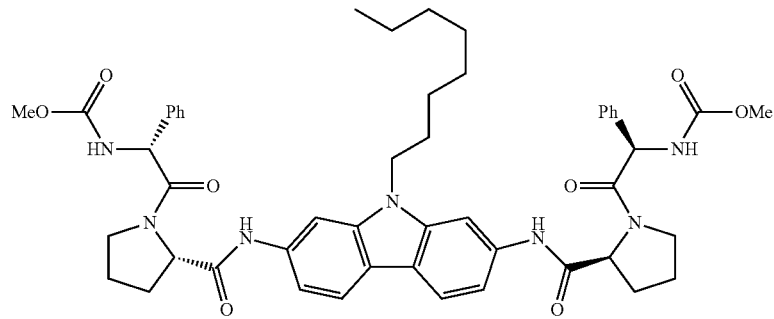 [SMILES: CCCCCCCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-octyl-9H-carbazole

The method in Step (1) of Example 1 was performed, and a target compound (324 mg, 80.3%) was obtained by using 2,7-dibromo-9H-carbazole (300 mg, 0.92 mmol) and 1-bromooctane (0.34 mL, 1.93 mmol).

$^1$H NMR (400 MHz, CDCl$_3$) δ 7.83 (d, J=8.2 Hz, 2H), 7.49 (d, J=1.5 Hz, 2H), 7.31 (dd, J=8.3, 1.6 Hz, 2H), 4.12 (t, J=7.4 Hz, 2H), 1.83-1.76 (m, 2H), 1.33-1.24 (m, 10H), 0.87 (t, J=6.9 Hz, 3H); $^{13}$C NMR (100 MHz, CDCl$_3$) δ 141.36, 122.52, 121.45, 121.29, 119.70, 112.00, 43.33, 31.79, 29.29, 29.17, 28.77, 27.18, 22.63, 14.09.

Step (2). Preparation of N,N'-(9-octyl-9H-carbazole-2,7-diyl)bis(1,1-diphenylmethaneimine)

The method in Step (2) of Example 1 was performed, and a target compound (151 mg, 41.4%) was obtained by using 2,7-dibromo-9-octyl-9H-carbazole (250 mg, 0.57 mmol) and benzophenoneimine (0.21 mL, 1.26 mmol).

$^1$H NMR (400 MHz, CDCl$_3$) δ 7.78-7.76 (m, 4H), 7.67 (d, J=8.2 Hz, 2H), 7.47-7.37 (m, 6H), 7.23-7.14 (m, 10H), 6.68 (d, J=1.5 Hz, 2H), 6.59 (dd, J=8.2, 1.7 Hz, 2H), 3.89 (t, J=7.3 Hz, 2H), 1.49-1.42 (m, 2H), 1.32-1.15 (m, 10H), 0.88 (t, J=7.0 Hz, 3H); $^{13}$C NMR (100 MHz, CDCl$_3$) δ 167.86, 148.92, 141.27, 140.14, 136.73, 130.65, 129.69, 129.39, 128.56, 128.26, 128.03, 119.72, 119.07, 113.67, 101.44, 42.99, 31.95, 29.42, 29.31, 28.46, 27.26, 22.73, 14.19.

Step (3). Preparation of 9-octyl-9H-carbazole-2,7-diamine dihydrochloride

The method in Step (3) of Example 1 was performed, and a target compound (84 mg, 92.8%) was obtained by using N,N'-(9-octyl-9H-carbazole-2,7-diyl)bis(1,1-diphenylmethaneimine) (151 mg, 0.24 mmol).

$^1$H NMR (400 MHz, DMSO-d$_6$) δ 10.47 (s, 6H), 8.26 (d, J=8.2 Hz, 2H), 7.63 (s, 2H), 7.24 (d, J=8.1 Hz, 2H), 4.35 (t, J=6.4 Hz, 2H), 1.78 (t, J=6.3 Hz, 2H), 1.27-1.19 (m, 10H), 0.82 (t, J=6.6 Hz, 3H); $^{13}$C NMR (100 MHz, DMSO-d$_6$) δ 140.53, 130.67, 121.48, 120.65, 114.18, 103.80, 42.81, 31.11, 28.71, 28.54, 28.19, 26.50, 21.95, 13.87.

Step (4). Preparation of dimethyl ((1R,1'R)-((2S,2'S)-(((9-octyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (71 mg, 76.2%) was obtained by using 9-octyl-9H-carbazole-2,7-diamine dihydrochloride (40 mg, 0.11 mmol) and ((R)-2-((methoxycarbonyl)amino)-2-phenylacetyl)-L-proline (71 mg, 0.23 mmol).

$^1$H NMR (400 MHz, CDCl$_3$) δ 9.60 (s, 2H), 7.69 (s, 2H), 7.60 (d, J=8.3 Hz, 2H), 7.45 (d, J=3.7 Hz, 4H), 7.39-7.35 (m, 6H), 7.12 (d, J=7.7 Hz, 2H), 6.23 (d, J=6.9 Hz, 2H), 5.56 (d, J=7.0 Hz, 2H), 4.74 (d, J=5.6 Hz, 2H), 4.08 (t, J=6.3 Hz, 2H), 3.93-3.90 (m, 2H), 3.61 (s, 6H), 3.33 (dd, J=8.3, 16.6 Hz, 2H), 2.43-2.39 (m, 2H), 2.30-2.22 (m, 2H), 2.05-1.87 (m, 4H), 1.26-1.18 (m, 12H), 0.83 (t, J=6.9 Hz, 3H); $^{13}$C NMR (100 MHz, CDCl$_3$) δ 169.87, 168.79, 156.07, 140.68, 136.59, 135.83, 129.16, 128.76, 127.90, 119.54, 118.84, 111.25, 99.60, 61.73, 57.26, 52.33, 47.47, 42.53, 31.88, 29.46, 29.22, 28.84, 28.47, 27.14, 24.77, 22.62, 14.09. LC/MS (ESI-TOF) m/z calcd for C$_{50}$H$_{59}$N$_7$O$_8$Na [M+Na]$^+$: 908.44 found 908.15.

Example 27. Preparation of dimethyl ((1R,1'R)-((2S,2'S)-(((9-dodecyl-9H-carbazole-2,7-diyl)bis(azanediyl))bis(carbonyl))bis(pyrrolidine-2,1-diyl))bis(2-oxo-1-phenylethane-2,1-diyl))dicarbamate

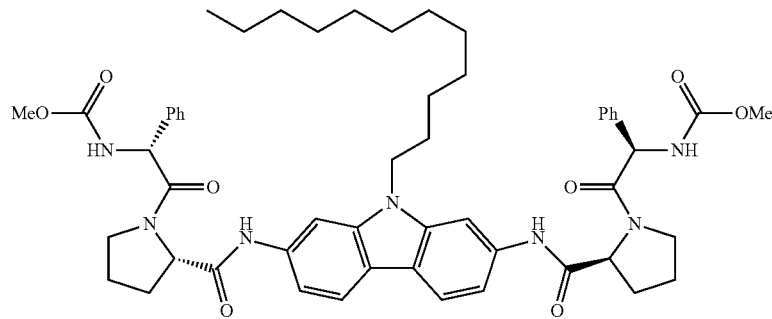 [SMILES: CCCCCCCCCCCCn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of 2,7-dibromo-9-dodecyl-9H-carbazole

The method in Step (1) of Example 1 was performed, and a target compound (312 mg, 68.5%) was obtained by using 2,7-dibromo-9H-carbazole (300 mg, 0.92 mmol) and 1-bromododecane (0.47 mL, 1.93 mmol).

$^1$H NMR (400 MHz, CDCl$_3$) δ 7.87 (d, J=8.3 Hz, 2H), 7.51 (d, J=1.6 Hz, 2H), 7.33 (dd, J=1.6, 8.3 Hz, 2H), 4.16 (t, J=7.4 Hz, 2H), 1.86-1.78 (m, 2H), 1.35-1.24 (m, 18H), 0.87 (t, J=6.9 Hz, 3H); $^{13}$C NMR (100 MHz, CDCl$_3$) δ 141.36, 122.52, 121.49, 121.28, 119.70, 112.02, 43.86, 31.94, 29.63, 29.59, 29.56, 29.52, 29.35, 28.79, 28.75, 27.19, 22.72, 14.16.

Step (2). Preparation of N,N'-(9-dodecyl-9H-carbazole-2,7-diyl)bis(1,1-diphenylmethaneimine)

The method in Step (2) of Example 1 was performed, and a target compound (140 mg, 34.5%) was obtained by using 2,7-dibromo-9-dodecyl-9H-carbazole (289 mg, 0.59 mmol) and benzophenoneimine (0.22 mL, 1.29 mmol).

$^1$H NMR (400 MHz, CDCl$_3$) δ 7.78-7.76 (m, 4H), 7.67 (d, J=8.2 Hz, 2H), 7.48-7.37 (m, 6H), 7.22-7.15 (m, 10H), 6.68 (d, J=1.1 Hz, 2H), 6.59 (dd, J=1.5, 8.2 Hz, 2H), 3.90 (t, J=7.3 Hz, 2H), 1.49-1.42 (m, 2H), 1.31-1.15 (m, 18H), 0.87 (t, J=6.8 Hz, 3H); $^{13}$C NMR (100 MHz, CDCl$_3$) δ 167.84, 148.90, 141.26, 140.13, 136.73, 130.64, 129.68, 129.38, 128.54, 128.25, 128.02, 119.70, 119.05, 113.65, 101.43, 42.99, 31.97, 29.74, 29.73, 29.70, 29.64, 29.46, 29.41, 28.45, 27.26, 22.75, 14.20.

Step (3). Preparation of 9-dodecyl-9H-carbazole-2,7-diamine dihydrochloride

The method in Step (3) of Example 1 was performed, and a target compound (82 mg, 92.6%) was obtained by using N,N'-(9-dodecyl-9H-carbazole-2,7-diyl)bis(1,1-diphenylmethaneimine) (140 mg, 0.20 mmol).

$^1$H NMR (400 MHz, DMSO-d$_6$) δ 10.45 (s, 6H), 8.24 (d, J=8.2 Hz, 2H), 7.59 (d, J=1.0 Hz, 2H), 7.21 (dd, J=1.3, 8.2 Hz, 2H), 4.35 (t, J=6.8 Hz, 2H), 1.77 (t, J=6.8 Hz, 2H), 1.26-1.18 (m, 18H), 0.84 (t, J=6.8 Hz, 3H); $^{13}$C NMR (100 MHz, DMSO-d$_6$) δ 141.08, 131.32, 122.01, 121.05, 114.51, 104.08, 43.27, 31.74, 29.45, 29.44, 29.43, 29.30, 29.21, 29.14, 28.72, 27.01, 22.54, 14.41.

Step (4). Preparation of dimethyl ((1R,1'R)-((2S,2'S)-(((9-dodecyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (77 mg, 90.1%) was obtained by using 9-dodecyl-9H-carbazole-2,7-diamine dihydrochloride (40 mg, 0.09 mmol) and ((R)-2-((methoxycarbonyl)amino)-2-phenylacetyl)-L-proline (61 mg, 0.20 mmol).

$^1$H NMR (400 MHz, CDCl$_3$) δ 9.58 (s, 2H), 7.72 (s, 2H), 7.62 (d, J=8.3 Hz, 2H), 7.45-7.44 (m, 4H), 7.39-7.36 (m, 6H), 7.12 (d, J=7.8 Hz, 2H), 6.20 (d, J=6.9 Hz, 2H), 5.55 (d, J=7.1 Hz, 2H), 4.74 (d, J=5.6 Hz, 2H), 4.09 (t, J=7.0 Hz, 2H), 3.93-3.89 (m, 2H), 3.62 (s, 6H), 3.32 (q, J=8.2 Hz, 2H), 2.45-2.41 (m, 2H), 2.27-2.21 (m, 2H), 1.99-1.87 (m, 4H), 1.27-1.19 (m, 20H), 0.85 (t, J=6.9 Hz, 3H); $^{13}$C NMR (100 MHz, CDCl$_3$) δ 169.95, 168.76, 156.11, 140.75, 136.53, 135.85, 129.19, 128.80, 127.93, 119.58, 118.89, 111.31, 99.67, 61.74, 57.30, 52.36, 47.46, 42.62, 31.93, 29.72, 29.68, 29.65, 29.60, 29.58, 29.35, 28.90, 28.39, 27.22, 24.79, 22.69, 14.13. LC/MS (ESI-TOF) m/z calcd for C$_{54}$H$_{67}$N$_7$O$_8$Na [M+Na]$^+$: 964.51 found 964.20.

Example 28. Preparation of dimethyl ((1R,1'R)-((2S,2'S)-(((9-(1-phenylbutyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

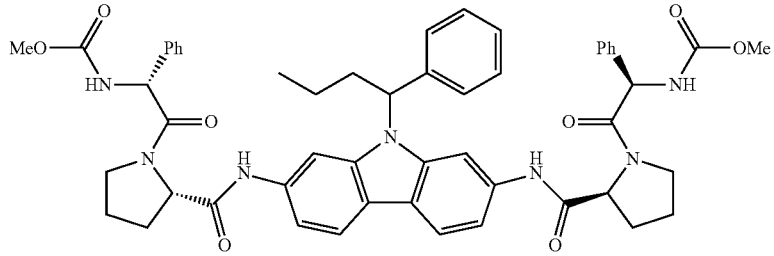 [SMILES: CCCC(c1ccccc1)n1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of (1-bromobutyl)benzene n-butylbenzene (1 mL, 6.41 mmol), N-bromosuccinimide (NBS; 1.37 g, 7.69 mmol), and benzene (5 mL) were added to a reaction vessel under a dry argon atmosphere, and then the resulting mixture was refluxed under heating at 80° C. for 2 hours. It was confirmed by TLC that the reaction was completed, and then the temperature of the reaction mixture was lowered to 0° C., and the reaction mixture was filtered under reduced pressure and concentrated, and then filtered by using n-hexane. The filtrate was filtered and concentrated under reduced pressure and to obtain 1.01 g (4.73 mmol, 73.8%) of a target compound.

$^1$H NMR (400 MHz, CDCl$_3$) δ 7.36-7.19 (m, 5H), 4.93 (dd, J=8.0, 7.0 Hz, 1H), 2.28-2.19 (m, 1H), 2.11-2.02 (m, 1H), 1.53-1.40 (m, 1H), 1.36-1.23 (m, 1H), 0.89 (t, J=7.4 Hz, 3H); $^{13}$C NMR (100 MHz, CDCl$_3$) δ 142.47, 128.77, 128.36, 127.42, 55.57, 42.23, 21.63, 13.53.

Step (2). Preparation of 2,7-dibromo-9-(1-phenylbutyl)-9H-carbazole

The method in Step (1) of Example 1 was performed, and a target compound (573 mg, 81.5%) was obtained by using 2,7-dibromo-9H-carbazole (500 mg, 1.54 mmol) and (1-bromobutyl)benzene (360 mg, 1.69 mmol).

$^1$H NMR (400 MHz, CDCl$_3$) δ 7.89 (d, J=8.3 Hz, 2H), 7.46 (d, J=1.3 Hz, 2H), 7.33-7.24 (m, 7H), 5.74 (q, J=5.2 Hz, 1H), 2.61-2.51 (m, 1H), 2.48-2.40 (m, 1H), 1.34-1.22 (m, 1H), 1.06-1.94 (m, 1H), 0.89 (t, J=7.2 Hz, 3H); $^{13}$C NMR (100 MHz, CDCl$_3$) δ 141.27, 139.26, 128.86, 127.79, 126.55, 122.82, 121.71, 121.42, 119.65, 113.50, 57.65, 33.61, 20.07, 13.94.

Step (3). Preparation of N,N'-(9-(1-phenylbutyl)-9H-carbazole-2,7-diyl)bis(1,1-diphenylmethaneimine)

The method in Step (2) of Example 1 was performed, and a target compound (217 mg, 50.3%) was obtained by using 2,7-dibromo-9-(1-phenylbutyl)-9H-carbazole (300 mg, 0.66 mmol) and benzophenoneimine (0.25 mL, 1.45 mmol).

$^1$H NMR (400 MHz, CDCl$_3$) δ 7.72 (d, J=7.6 Hz, 6H), 7.46-7.42 (m, 2H), 7.39-7.35 (m, 4H), 7.22-7.14 (m, 9H), 7.05-7.03 (m, 6H), 6.64 (dd, J=8.2, 1.2 Hz, 2H), 6.53 (s, 2H), 5.39 (q, J=5.2 Hz, 1H), 2.25-2.06 (m, 2H), 0.94-0.75 (m, 2H), 0.74 (t, J=3.5 Hz, 3H); $^{13}$C NMR (100 MHz, CDCl$_3$) δ 167.96, 148.94, 141.03, 140.32, 139.94, 136.60, 130.64, 129.50, 129.34, 128.42, 128.33, 128.22, 127.96, 127.13, 126.70, 119.64, 119.36, 113.81, 102.47, 56.82, 33.02, 19.81, 13.94.

Step (4). Preparation of 9-(1-phenylbutyl)-9H-carbazole-2,7-diamine dihydrochloride The method in Step (3) of Example 1 was performed, and a target compound (122 mg, 91.8%) was obtained by using N,N'-(9-(1-phenylbutyl)-9H-carbazole-2,7-diyl)bis(1,1-diphenylmethaneimine) (217 mg, 0.33 mmol).

$^1$H NMR (400 MHz, DMSO-d$_6$) δ 10.23 (s, 6H), 8.28-8.23 (m, 2H), 7.77-7.55 (m, 2H), 7.37-7.29 (m, 5H), 7.21-7.15 (m, 2H), 6.02 (d, J=4.9 Hz, 1H), 2.63-2.60 (m, 2H), 1.21-0.86 (m, 2H), 0.88 (t, J=5.3 Hz, 3H); $^{13}$C NMR (100 MHz, DMSO-d$_6$) 140.84, 140.02, 131.04, 129.23, 128.05, 126.98, 122.04, 121.63, 115.04, 105.74, 57.66, 33.13, 19.87, 14.07.

Step (5). Preparation of dimethyl ((1R,1'R)-((2S,2'S)-(((9-(1-phenylbutyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (41 mg, 45.5%) was obtained by using 9-(1-phenylbutyl)-9H-carbazole-2,7-diamine dihydrochloride (40 mg, 0.10 mmol) and ((R)-2-((methoxycarbonyl)amino)-2-phenylacetyl)-L-proline (67 mg, 0.22 mmol).

$^1$H NMR (400 MHz, CDCl$_3$) δ 9.26 (s, 2H), 8.03-7.86 (m, 4H), 7.44-7.26 (m, 14H), 7.25-7.15 (m, 3H), 6.09 (t, J=8.0 Hz, 2H), 5.88-5.82 (m, 1H), 5.46 (d, J=5.5 Hz, 2H), 4.76 (d, J=7.8 Hz, 2H), 3.77 (t, J=7.0 Hz, 2H), 3.61 (s, 6H), 3.21-3.19 (m, 2H), 2.74-2.71 (m, 1H), 2.52-2.45 (m, 2H), 2.44-2.36 (m, 1H), 2.11-2.09 (m, 2H), 1.86-1.72 (m, 4H), 1.37-1.26 (m, 1H), 1.06-1.04 (m, 1H), 0.89 (td, J=7.2, 3.9 Hz, 3H); $^{13}$C NMR (100 MHz, CDCl$_3$) δ 170.51, 168.23, 156.40, 141.11, 140.29, 140.12, 135.83, 135.74, 129.26, 129.07, 128.89, 128.53, 128.49, 128.04, 127.21, 126.90, 119.74, 119.65, 112.16, 112.05, 101.81, 61.54, 57.56, 57.23, 52.40, 47.15, 33.62, 33.44, 27.37, 24.65, 20.10, 13.99. LC/MS (ESI-TOF) m/z calcd for C$_{52}$H$_{55}$N$_7$O$_8$Na [M+Na]$^+$: 928.41 found 928.15.

Example 29. Preparation of dimethyl ((1R,1'R)-((2S,2'S)-(((9-(1-phenyloctyl)-9H-carbazole-2,7-diyl)bis(azanediyl))bis(carbonyl))bis(pyrrolidine-2,1-diyl))bis(2-oxo-1-phenylethane-2,1-diyl))dicarbamate

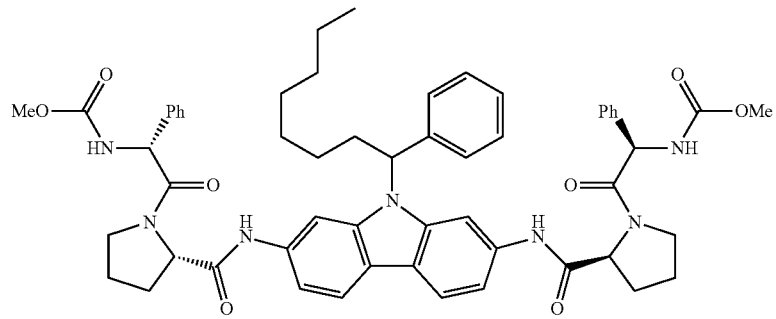 [SMILES: CCCCCCCC(c1ccccc1)n1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of (1-bromooctyl)benzene

The method in Step (1) of Example 28 was performed, and a target compound (1.04 g, 85.4%) was obtained by using n-octylbenzene (1 mL, 4.61 mmol) and NBS (0.99 g, 5.53 mmol).

$^1$H NMR (400 MHz, CDCl$_3$) δ 7.37-7.21 (m, 5H), 4.93 (t, J=7.5 Hz, 1H), 2.31-2.23 (m, 1H), 2.15-2.11 (m, 1H), 1.46 (s, 1H), 1.28-1.25 (m, 10H), 0.86 (t, J=6.7 Hz, 3H); $^{13}$C NMR (100 MHz, CDCl$_3$) δ 142.46, 128.72, 128.31, 127.36, 55.84, 40.16, 31.86, 29.19, 29.00, 28.37, 22.73, 14.21.

Step (2). Preparation of 2,7-dibromo-9-(1-phenyloctyl)-9H-carbazole

The method in Step (1) of Example 1 was performed, and a target compound (328 mg, 41.5%) was obtained by using 2,7-dibromo-9H-carbazole (500 mg, 1.54 mmol) and (1-bromooctyl)benzene (455 mg, 1.69 mmol).

$^1$H NMR (400 MHz, CDCl$_3$) δ 7.87 (d, J=8.3 Hz, 2H), 7.47 (d, J=1.4 Hz, 2H), 7.31 (dd, J=1.6, 8.3 Hz, 2H), 7.28-7.21 (m, 5H), 5.70 (q, J=5.2 Hz, 1H), 2.57-2.50 (m, 1H), 2.49-2.43 (m, 1H), 1.30-1.08 (m, 9H), 0.99-0.94 (m, 1H), 0.80 (t, J=7.1 Hz, 3H); $^{13}$C NMR (100 MHz, CDCl$_3$) δ 141.30, 139.36, 128.86, 127.79, 126.58, 122.83, 121.74, 121.43, 119.68, 113.53, 57.87, 31.71, 31.46, 29.32, 29.00, 26.61, 22.60, 14.10.

Step (3). Preparation of N,N'-(9-(1-phenyloctyl)-9H-carbazole-2,7-diyl)bis(1,1-diphenylmethaneimine)

The method in Step (2) of Example 1 was performed, and a target compound (109 mg, 26.2%) was obtained by using 2,7-dibromo-9-(1-phenyloctyl)-9H-carbazole (300 mg, 0.58 mmol) and benzophenoneimine (0.23 mL, 1.29 mmol).

$^1$H NMR (400 MHz, CDCl$_3$) δ 7.74-7.70 (m, 6H), 7.48-7.43 (m, 2H), 7.41-7.37 (m, 4H), 7.22-7.14 (m, 9H), 7.06-7.02 (m, 6H), 6.61-6.58 (m, 4H), 5.38 (dd, J=10.0, 5.7 Hz, 1H), 2.29-2.14 (m, 2H), 1.28-1.21 (m, 2H), 1.17-1.10 (m, 6H), 1.01-0.98 (m, 1H), 0.85 (t, J=7.1 Hz, 3H), 0.81-0.77 (m, 1H); $^{13}$C NMR (100 MHz, CDCl$_3$) δ 167.90, 148.88, 140.34, 139.94, 136.60, 130.58, 129.47, 128.36, 128.18, 127.90, 127.08, 126.70, 119.56, 119.36, 113.61, 102.56, 100.85, 99.14, 57.14, 31.87, 30.98, 29.41, 29.16, 26.60, 22.64, 14.09.

Step (4). Preparation of 9-(1-phenyloctyl)-9H-carbazole-2,7-diamine dihydrochloride The method in Step (3) of Example 1 was performed, and a target compound (64 mg, 91.5%) was obtained by using N,N'-(9-(1-phenyloctyl)-9H-carbazole-2,7-diyl)bis(1,1-diphenylmethaneimine) (109 mg, 0.15 mmol).

$^1$H NMR (400 MHz, DMSO-d$_6$) δ 10.06 (s, 6H), 8.24 (d, J=7.8 Hz, 2H), 7.58 (s, 2H), 7.34-7.28 (m, 5H), 7.17 (d, J=7.3 Hz, 2H), 5.97 (dd, J=10.0, 4.8 Hz, 1H), 2.57-2.55 (m, 2H), 1.32-1.24 (m, 3H), 1.16-1.09 (m, 6H), 0.76 (t, J=6.8 Hz, 3H); $^{13}$C NMR (75 MHz, DMSO-d$_6$): δ 140.44, 139.65, 131.56, 128.69, 127.49, 126.44, 121.32, 120.61, 113.96, 104.26, 57.29, 31.00, 30.49, 28.53, 28.39, 26.02, 21.88, 13.86.

Step (5). Preparation of dimethyl ((1R,1'R)-((2S,2'S)-(((9-(1-phenyloctyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (27 mg, 32.2%) was obtained by using 9-(1-phenyloctyl)-9H-carbazole-2,7-diamine dihydrochloride (40 mg, 0.09 mmol) and ((R)-2-((methoxycarbonyl)amino)-2-phenylacetyl)-L-proline (59 mg, 0.19 mmol).

$^1$H NMR (400 MHz, CDCl$_3$) δ 9.25 (s, 2H), 8.04 (d, J=7.8 Hz, 2H), 7.89 (d, J=8.3 Hz, 2H), 7.45-7.16 (m, 17H), 6.03 (t, J=6.8 Hz, 2H), 5.86-5.80 (m, 1H), 5.45 (d, J=8.0 Hz, 2H), 4.77 (d, J=7.8 Hz, 2H), 3.77 (t, J=8.7 Hz, 2H), 3.62 (s, 6H), 3.20 (q, J=8.8 Hz, 2H), 2.76-2.67 (m, 1H), 2.54-2.44 (m, 3H), 2.16-2.02 (m, 2H), 1.87-1.82 (m, 2H), 1.80-1.72 (m, 2H), 1.30-1.25 (m, 3H), 1.21-1.14 (m, 6H), 1.04-1.00 (m, 1H), 0.80 (t, J=7.0 Hz, 3H); $^{13}$C NMR (100 MHz, CDCl$_3$) δ 170.52, 168.18, 156.35, 141.12, 140.33, 140.16, 135.74, 129.27, 128.91, 128.53, 128.48, 128.04, 127.20, 126.92, 119.72, 119.64, 112.11, 112.00, 101.78, 61.54, 57.78, 57.55, 52.41, 47.14, 31.75, 31.51, 31.32, 29.44, 29.06, 27.34, 26.76, 24.65, 22.56, 14.05. LC/MS (ESI-TOF) m/z calcd for C$_{56}$H$_{63}$N$_7$O$_8$Na [M+Na]$^+$: 984.47 found 984.15.

Example 30. Preparation of dimethyl ((1R,1'R)-((2S,2'S)-(((9-(3-(pentyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

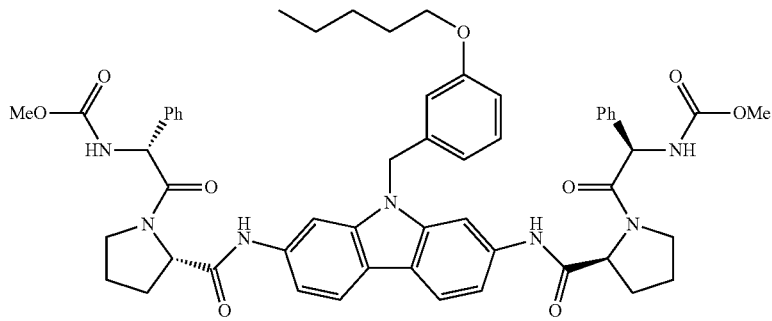 [SMILES: CCCCCOc1cccc(Cn2c3cc(NC(=O)[C@@H]4CCCN4C(=O)[C@H](NC(=O)OC)c4ccccc4)ccc3c3ccc(NC(=O)[C@@H]4CCCN4C(=O)[C@H](NC(=O)OC)c4ccccc4)cc32)c1]

Step (1). Preparation of 2,7-dibromo-9-(3-methoxybenzyl)-9H-carbazole

The method in Step (1) of Example 1 was performed, and a target compound (274 mg, 100%) was obtained by using 2,7-dibromo-9H-carbazole (200 mg, 0.615 mmol) and 1-(bromomethyl)-3-methoxybenzene (0.10 mL, 0.738 mmol).

$^1$H NMR (400 MHz, CDCl$_3$) δ 7.93 (d, J=8.3 Hz, 2H), 7.52 (d, J=1.5 Hz, 2H), 7.39 (dd, J=8.3, 1.6 Hz, 2H), 7.24 (t, J=7.9 Hz, 1H), 6.83 (dd, J=8.2, 2.1 Hz, 1H), 6.70 (dt, J=7.6, 0.7 Hz, 1H), 6.66 (d, J=2.0 Hz, 1H), 5.39 (s, 2H), 3.76 (s, 3H); $^{13}$C NMR (100 MHz, CDCl$_3$) δ 160.11, 141.62, 137.65, 130.15, 123.09, 121.54, 121.48, 119.97, 118.43, 112.67, 112.36, 112.24, 55.22, 46.63.

Step (2). Preparation of 3-((2,7-dibromo-9H-carbazole-9-yl)methyl)phenol

The 2,7-dibromo-9-(3-methoxybenzyl)-9H-carbazole (274 mg, 0.616 mmol) prepared in Step (1) was dissolved in dichloromethane (2.7 mL) under an argon atmosphere, and then a boron tribromide solution (a BBr$_3$ solution, 1.2 mL, 1.0 M in dichloromethane, 1.231 mmol) was added thereto at 0° C. The reaction mixture was stirred at room temperature for 30 minutes, and then H$_2$O was slowly added thereto. The mixture was extracted by using dichloromethane, and the organic layer was washed with brine. The collected organic layer was dried over magnesium sulfate, and then filtered and concentrated under reduced pressure. The concentrated solution was separated and purified with column chromatography (hexane/EtOAc=5/1, v/v) to obtain a white solid target compound (266 mg, 100%).

$^1$H NMR (400 MHz, Acetone-d$_6$) δ 8.40 (s, 1H), 8.08 (d, J=8.3 Hz, 2H), 7.78 (d, J=1.5 Hz, 2H), 7.39 (dd, J=8.3, 1.7 Hz, 2H), 7.16 (t, J=7.9 Hz, 1H), 6.78-6.75 (m, 1H), 6.74-6.71 (m, 1H), 6.58 (t, J=1.9 Hz, 1H), 5.60 (s, 2H); $^{13}$C NMR (100 MHz, Acetone-d$_6$) δ 157.84, 141.77, 138.59, 129.92, 122.77, 121.87, 121.40 119.56, 117.66, 114.60, 113.13, 112.59, 45.96.

Step (3). Preparation of 2,7-dibromo-9-(3-pentyloxy)benzyl)-9H-carbazole

The 3-((2,7-dibromo-9H-carbazole-9-yl)methyl)phenol (266 mg, 0.617 mmol) prepared in Step (2), potassium carbonate (193 mg, 1.234 mmol), and 1-bromopentane (0.15 mL, 1.234 mmol) were added to acetonitrile (5 mL) under an argon atmosphere, and the resulting mixture was refluxed under heating for 16 hours. The mixture completely reacted was filtered to remove the solid, and then the filtrate was concentrated under reduced pressure. The concentrated solution was separated and purified with column chromatography (hexane/EtOAc=50/1, v/v) to obtain a target compound (220 mg, 71.1%).

$^1$H NMR (400 MHz, CDCl$_3$) δ 7.89 (d, J=8.3 Hz, 2H), 7.52 (d, J=1.4 Hz, 2H), 7.39 (dd, J=8.3, 1.6 Hz, 2H), 7.22 (t, J=8.2 Hz, 1H), 6.84-6.82 (m, 1H), 6.70-6.68 (m, 2H), 5.30 (s, 2H), 3.90 (t, J=6.6 Hz, 2H), 1.77 (p, J=6.9 Hz, 2H), 1.49-1.38 (m, 4H), 0.98 (t, J=7.0 Hz, 3H); $^{13}$C NMR (100 MHz, CDCl$_3$) δ 159.73, 141.62, 137.61, 130.10, 123.07, 121.50, 121.48, 119.99, 118.28, 113.37, 112.91, 112.26, 68.03, 46.66, 28.94, 28.21, 22.52, 14.09.

Step (4). Preparation of N,N'-(9-(3-pentyloxy)benzyl)-9H-carbazole-2,7-diyl)bis(1,1-diphenylmethaneimine)

The method in Step (2) of Example 1 was performed, and a target compound (179 mg, 58.1%) was obtained by using 2,7-dibromo-9-(3-(pentyloxy)benzyl)-9H-carbazole (220 mg, 0.439 mmol).

$^1$H NMR (400 MHz, CDCl$_3$) δ 7.83-7.78 (m, 4H), 7.77 (d, J=8.2 Hz, 2H), 7.53-7.49 (m, 2H), 7.47-7.43 (m, 4H), 7.29-7.23 (m, 6H), 7.22-7.14 (m, 5H), 6.81 (dd, J=8.2, 2.0 Hz, 1H), 6.74 (d, J=1.4 Hz, 2H), 6.67 (dd, J=8.2, 1.7 Hz, 2H), 6.55 (d, J=1.9 Hz, 1H), 6.49 (d, J=7.6 Hz, 1H), 5.16 (s, 2H), 3.90 (t, J=6.6 Hz, 2H), 1.80 (p, J=7.0 Hz, 2H), 1.52 (m, 4H), 0.98 (t, J=6.7 Hz, 3H); $^{13}$C NMR (100 MHz, CDCl$_3$) 168.08, 159.47, 149.13, 141.62, 139.87, 138.69, 136.51, 130.68, 129.66, 129.50, 129.37, 128.49, 128.31, 128.21, 127.92, 119.72, 119.20, 118.45, 113.89, 112.94, 112.94, 112.79, 101.57, 67.86, 46.45, 29.02, 28.26, 22.51, 14.05.

Step (5). Preparation of 9-(3-(pentyloxy)benzyl)-9H-carbazole-2,7-diamine dihydrochloride The method in Step (3) of Example 1 was performed, and a target compound (104 mg, 91.4%) was obtained by using N,N'-(9-(3-(pentyloxy)benzyl)-9H-carbazole-2,7-diyl)bis(1,1-diphenylmethaneimine) (179 mg, 0.255 mmol).

$^1$H NMR (400 MHz, CDCl$_3$) δ 7.70 (d, J=7.9 Hz, 7.14 (t, J=7.4 Hz, 1H), 6.76-6.66 (m, 3H), 6.56-6.50 (m, 4H), 5.19 (s, 2H), 3.84 (s, 2H), 3.60 (bs, 4H), 1.71 (s, 2H), 1.36-1.28 (m, 4H), 0.91 (s, 3H); $^{13}$C NMR (100 MHz, CDCl$_3$) δ

159.59, 144.19, 142.32, 139.09, 129.80, 119.87, 118.45, 116.34, 112.94, 112.85, 108.55, 94.92, 67.94, 46.36, 28.96, 28.21, 22.49, 14.04.

Step (6). Preparation of dimethyl ((1R,1'R)-((2S,2'S)-(((9-(3-(pentyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (48 mg, 32.2%) was obtained by using 9-(3-(pentyloxy)benzyl)-9H-carbazole-2,7-diamine dihydrochloride (70 mg, 0.157 mmol).

$^1$H NMR (400 MHz, CDCl$_3$) 9.57 (s, 2H), 7.69-7.64 (m, 4H), 7.46-7.44 (m, 4H), 7.38-7.36 (m, 6H), 7.22-7.15 (m, 2H), 7.09 (t, J=7.9 Hz, 1H), 6.70-6.62 (m, 3H), 6.25 (d, J=6.7 Hz, 2H), 5.57 (d, J=6.9 Hz, 2H), 5.27-5.16 (m, 2H), 4.76-4.75 (m, 2H), 3.95-3.91 (m, 2H), 3.83 (t, J=5.9 Hz, 2H), 3.59 (s, 6H), 3.36-3.30 (m, 2H), 2.40-2.35 (m, 2H), 2.32-2.20 (m, 2H), 2.00-1.87 (m, 4H), 1.72-1.65 (m, 2H), 1.40-1.33 (m, 4H), 0.91 (t, J=7.1 Hz, 3H); $^{13}$C NMR (100 MHz, CDCl$_3$) 169.78, 168.92, 159.33, 156.09, 140.85, 138.91, 136.63, 136.04, 129.47, 129.13, 128.72, 127.92, 119.60, 119.06, 118.77, 113.14, 112.67, 111.88, 99.85, 67.77, 61.67, 57.28, 52.26, 47.46, 45.86, 28.93, 28.61, 28.17, 24.73, 22.46, 14.01. LC/MS (ESI-TOF) m/z calcd for C$_{54}$H$_{60}$N$_7$O$_9$ [M+H]$^+$: 950.44 found 950.20.

Example 31. Preparation of dimethyl ((1R,1'R)-((2S,2'S)-(((9-(4-(hexyloxy)benzyl)-9H-carbonyl-2,7-diyl)bis(azanediyl))bis(carbonyl))bis(pyrrolidine-2,1-diyl))bis(2-oxo-1-phenylethane-2,1-diyl)) dicarbamate

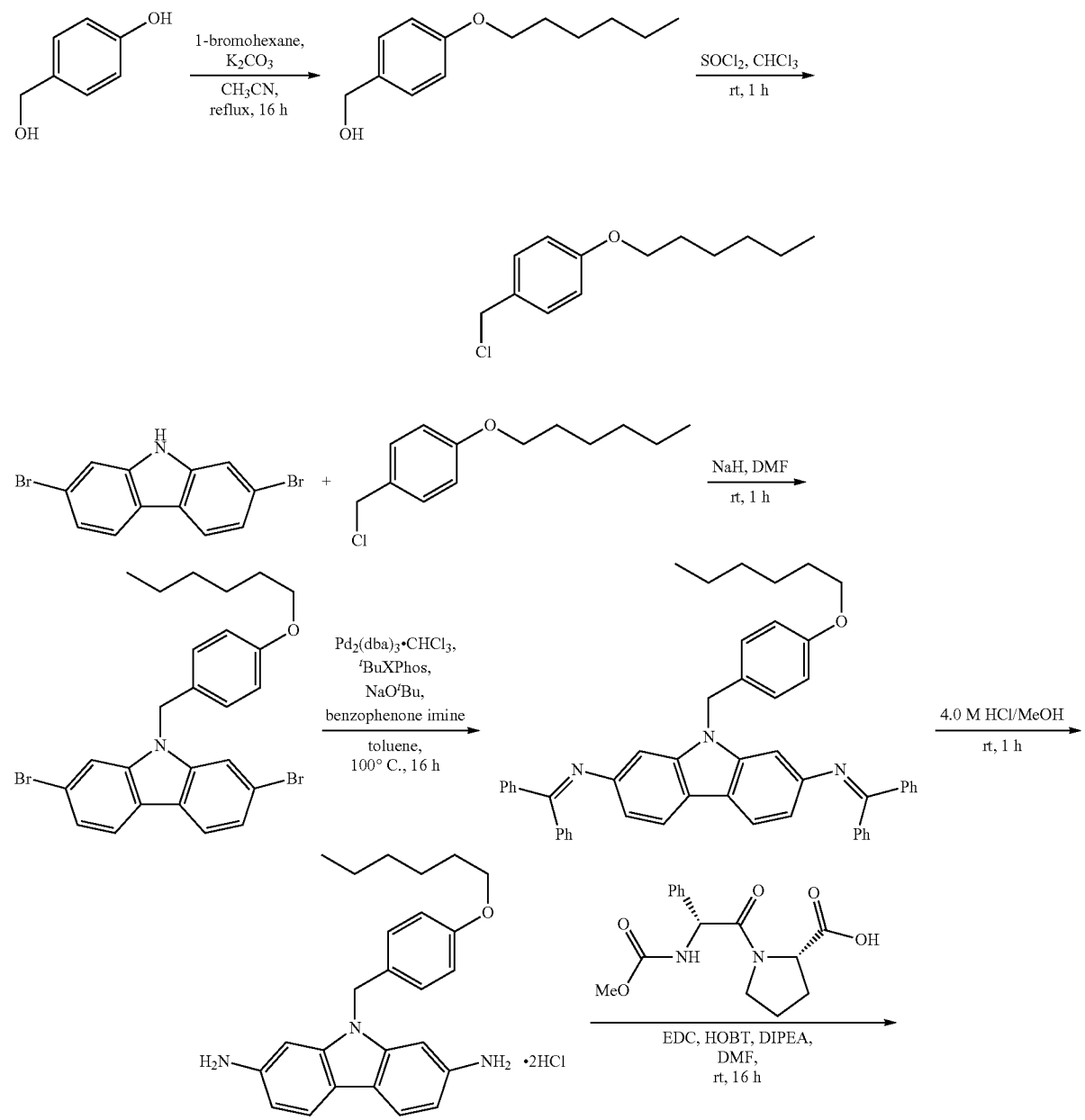

-continued

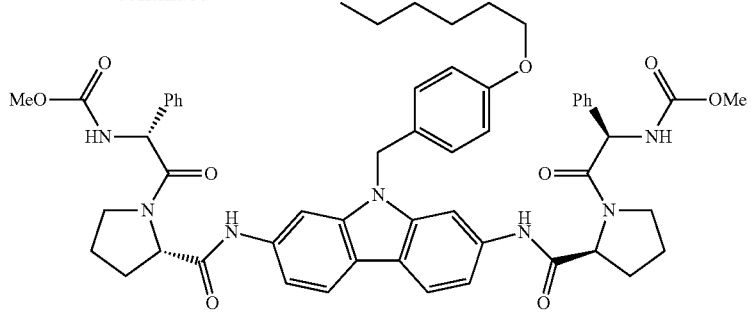

Step (1). Preparation of (4-(hexyloxy)phenyl)methanol 4-(hydroxymethyl)phenol (200 mg, 1.611 mmol), potassium carbonate (505 mg, 3.222 mmol), and 1-bromohexane (0.45 mL, 1.176 mmol) were added to acetonitrile (4 mL) under an argon atmosphere, and the resulting mixture was refluxed under heating for 16 hours. The mixture completely reacted was filtered to remove the solid, and then the filtrate was concentrated under reduced pressure. The concentrated solution was separated and purified with column chromatography (hexane/EtOAc=5/1, v/v) to obtain a target compound (242 mg, 72.1%).

$^1$H NMR (400 MHz, CDCl$_3$) δ 7.15 (d, J=6.8 Hz, 2H), 6.79 (dd, J=6.6, 2.0 Hz, 1H), 4.45 (s, 2H), 3.86 (t, J=6.6 Hz, 2H), 2.67 (s, 1H), 1.70 (p, J=7.1 Hz, 2H), 1.43-1.36 (m, 2H), 1.30-1.26 (m, 4H), 0.86 (t, J=7.0 Hz, 3H); $^{13}$C NMR (100 MHz, CDCl$_3$) δ 158.68, 133.08, 128.58, 114.50, 68.08, 64.72, 31.52, 29.26, 25.74, 22.62, 14.03.

Step (2). Preparation of 1-(chloromethyl)-4-(hexyloxy)benzene

The (4-(hexyloxy)phenyl)methanol (982 mg, 4.714 mmol) prepared in Step (1) was dissolved in chloroform (15 mL), and then SOCl$_2$ (1.03 mL, 14.14 mmol) was slowly added dropwise thereto at 0° C. The reaction mixture was stirred at room temperature for 1 hour, and then filtered and concentrated under reduced pressure to obtain a colorless oil target compound (770 mg, 72%).

Step (3). Preparation of 2,7-dibromo-9-(4-(hexyloxy)benzyl)-9H-carbazole

The method in Step (1) of Example 1 was performed, and a target compound (1.35 g, 100%) was obtained by using 2,7-dibromo-9H-carbazole (849 mg, 2.612 mmol) and 1-(chloromethyl)-2-(hexyloxy)benzene (770 mg, 3.396 mmol).

$^1$H NMR (400 MHz, CDCl$_3$) δ 7.90 (d, J=8.3 Hz, 2H), 7.53 (d, J=1.5 Hz, 2H), 7.39 (dd, J=8.3, 1.6 Hz, 2H), 7.05 (d, J=8.7 Hz, 2H), 6.83 (dd, J=6.8, 2.0 Hz, 2H), 5.29 (s, 2H), 3.91 (t, J=6.6 Hz, 2H), 1.78 (p, J=7.1 Hz, 2H), 1.51-1.41 (m, 2H), 1.39-1.33 (m, 4H), 0.96 (t, J=6.9 Hz, 3H); $^{13}$C NMR (100 MHz, CDCl$_3$) δ 158.82, 141.52, 127.72, 127.57, 122.96, 121.50, 121.43, 119.93, 114.93, 112.27, 68.05, 46.22, 31.63, 29.24, 25.76, 25.76, 22.66, 14.12.

Step (4). Preparation of N,N'-(9-(4-(hexyloxy)benzyl)-9H-carbazole-2,7-diyl)bis(1,1-diphenylmethaneimine)

The method in Step (2) of Example 1 was performed, and a target compound (1.446 g, 68.9%) was obtained by using 2,7-dibromo-9-(4-(hexyloxy)benzyl)-9H-carbazole (1.51 g, 2.930 mmol).

$^1$H NMR (400 MHz, CDCl$_3$) δ 7.85-7.83 (m, 4H), 7.79 (d, J=8.2 Hz, 2H), 7.54-7.50 (m, 2H), 7.48-7.44 (m, 4H), 7.29-7.22 (m, 6H), 7.20-7.17 (m, 4H), 6.88 (d, J=8.7 Hz, 2H), 6.81-6.77 (m, 4H), 6.71 (dd, J=8.2, 1.7 Hz, 2H), 5.13 (s, 2H), 4.00 (t, J=6.5 Hz, 2H), 1.86 (p, J=7.1 Hz, 2H), 1.58-1.53 (m, 2H), 1.45-1.35 (m, 4H), 1.01-0.97 (m, 3H); $^{13}$C NMR (100 MHz, CDCl$_3$) δ 168.04, 158.40, 149.16, 141.50, 139.94, 136.54, 130.71, 129.57, 129.41, 129.03, 128.50, 128.25, 127.98, 127.79, 119.76, 119.18, 114.65, 113.87, 101.49, 68.07, 45.99, 31.66, 29.33, 25.82, 22.69, 14.14.

Step (5). Preparation of 9-(4-(hexyloxy)benzyl)-9H-carbazole-2,7-diamine dihydrochloride The method in Step (3) of Example 1 was performed, and a target compound (675 mg, salt free, 86.2%) was obtained by using N,N'-(9-(4-(hexyloxy)benzyl)-9H-carbazole-2,7-diyl)bis(1,1-diphenylmethaneimine) (1.446 g, 2.020 mmol).

$^1$H NMR (400 MHz, CDCl$_3$) δ 7.74 (d, J=8.1 Hz, 2H), 7.08 (d, J=8.6 Hz, 2H), 6.81 (d, J=8.6 Hz, 2H), 6.61-6.57 (m, 4H), 5.24 (s, 2H), 3.91 (t, J=6.5 Hz, 2H), 3.71 (bs, 4H), 1.77 (p, J=7.0 Hz, 2H), 1.48-1.43 (m, 2H), 1.37-1.30 (m, 4H), 0.93 (t, J=6.7 Hz, 3H); $^{13}$C NMR (100 MHz, MeOD) δ 158.17, 144.50, 142.05, 129.46, 127.39, 119.20, 116.12, 114.12, 108.70, 95.34, 67.53, 44.80, 31.40, 28.95, 25.47, 22.33, 13.18.

Step (6). Preparation of dimethyl ((1R,1'R)-((2S,2'S)-(((9-(4-(hexyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (131 mg, 65.6%) was obtained by using 9-(4-(hexyloxy)benzyl)-9H-carbazole-2,7-diamine dihydrochloride (100 mg, 0.217 mmol).

$^1$H NMR (400 MHz, CDCl$_3$) δ 9.64 (s, 2H), 7.64-7.60 (m, 4H), 7.45-7.36 (m, 10H), 7.21-7.19 (m, 2H), 7.03 (d, J=8.5 Hz, 2H), 6.72 (d, J=8.6 Hz, 2H), 6.29 (d, J=6.7 Hz, 2H), 5.60 (d, J=6.9 Hz, 2H), 5.23-5.13 (m, 2H), 4.76-4.74 (m, 2H), 3.98-3.94 (m, 2H), 3.86-3.83 (m, 2H), 3.61 (s, 6H), 3.39-3.33 (m, 2H), 2.36-2.27 (m, 4H), 2.01-1.87 (m, 4H), 1.71 (p, J=7.0 Hz, 2H), 1.42-1.37 (m, 2H), 1.32-1.30 (m, 4H), 0.89 (t, J=6.8 Hz, 3H); $^{13}$C NMR (100 MHz, CDCl$_3$) δ 169.64, 169.04, 158.23, 156.04, 140.57, 136.82, 136.00, 129.38, 129.12, 128.70, 128.06, 127.87, 119.55, 118.94, 114.48, 111.61, 99.65, 67.83, 61.73, 57.22, 52.29, 47.56, 45.27, 31.56, 29.24, 28.89, 25.70, 24.77, 22.57, 14.02. LC/MS (ESI-TOF) m/z calcd for C$_{55}$H$_{61}$N$_7$O$_9$Na [M+Na]$^+$: 986.44 found 986.20.

Example 32. Preparation of dimethyl ((1R,1'R)-((2S,2'S)-(((9-(2-butoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

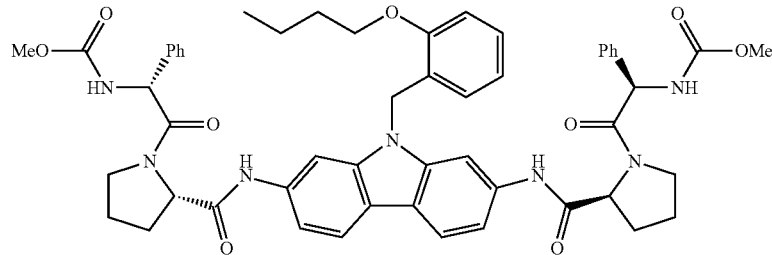 [SMILES: CCCCOc1ccccc1Cn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of (2-butoxyphenyl)methanol

The method in Step (1) of Example 31 was performed, and a white solid target compound (270 mg, 93.0%) was obtained by using 2-(hydroxymethyl)phenol (200 mg, 1.611 mmol) and 1-bromobutane (0.42 mL, 3.222 mmol).

$^1$H NMR (400 MHz, CDCl$_3$) δ 7.34-7.27 (m, 2H), 6.98 (td, J=7.4, 0.9 Hz, 1H), 6.91 (d, J=8.2 Hz, 1H), 4.73 (s, 2H), 4.05 (t, J=6.4 Hz, 2H), 2.84 (s, 1H), 1.87-1.80 (m, 2H), 1.61-1.51 (m, 2H), 1.05 (t, J=7.4 Hz, 3H); $^{13}$C NMR (100 MHz, CDCl$_3$) 156.91, 129.29, 128.77, 128.53, 120.50, 111.04, 67.99, 62.09, 31.59, 29.29, 25.87, 22.64, 14.06.

Step (2). Preparation of 1-butoxy-2-(chloromethyl)benzene

The method in Step (2) of Example 31 was performed, and a target compound (724 mg, 78.2%) was obtained by using (2-butoxyphenyl)methanol (840 mg, 4.660 mmol) and SOCl$_2$ (1.02 mL, 13.98 mmol).

Step (3). Preparation of 2,7-dibromo-9-(2-butoxybenzyl)-9H-carbazole

The method in Step (3) of Example 31 was performed, and a target compound (1.63 g, 100%) was obtained by using 2,7-dibromo-9H-carbazole (911 mg, 2.803 mmol) and 1-butoxy-2-(chloromethyl)benzene (724 mg, 3.644 mmol).

$^1$H NMR (400 MHz, CDCl$_3$) δ 7.92 (d, J=8.3 Hz, 2H), 7.59 (d, J=1.5 Hz, 2H), 7.39 (dd, J=8.3, 1.7 Hz, 2H), 7.27 (td, J=7.8, 1.4 Hz, 1H), 6.96 (d, J=7.7 Hz, 1H), 6.79 (td, J=7.5, 0.9 Hz, 1H), 6.69 (dd, J=7.5, 1.5 Hz, 1H), 5.41 (s, 2H), 4.12 (t, J=6.5 Hz, 2H), 1.96-1.89 (m, 2H), 1.65-1.56 (m, 2H), 1.11 (t, J=7.4 HZ, 3H); $^{13}$C NMR (100 MHz, CDCl$_3$) δ 156.42, 141.75, 128.90, 127.28, 124.00, 122.81, 121.39, 120.50, 119.84, 112.55, 111.09, 67.89, 42.10, 31.47, 19.53, 14.05.

Step (4). Preparation of N,N'-(9-(2-butoxybenzyl)-9H-carbazole-2,7-diyl)bis(1,1-diphenylmethaneimine)

The method in Step (2) of Example 1 was performed, and a target compound (1.849 g, 80.4%) was obtained by using 2,7-dibromo-9-(2-butoxybenzyl)-9H-carbazole (1.63 g, 3.345 mmol).

$^1$H NMR (400 MHz, CDCl$_3$) δ 7.87-7.81 (m, 6H), 7.55-7.51 (m, 2H), 7.49-7.45 (m, 4H), 7.27-7.18 (m, 12H), 6.95 (d, J=8.0 Hz, 1H), 6.82 (d, J=1.4 Hz, 2H), 6.74 (d, J=7.5 Hz, 1H), 6.70 (dd, J=8.2, 1.6 Hz, 2H), 6.33 (d, J=7.5 Hz, 1H), 5.33 (s, 2H), 4.14 (t, J=6.4 Hz, 2H), 1.95 (p, J=6.9 Hz, 2H), 1.70-1.61 (m, 2H), 1.11 (t, J=7.4 Hz, 3H); $^{13}$C NMR (100 MHz, CDCl$_3$) δ 140.82, 139.55, 128.95, 127.86, 126.37, 122.83, 121.91, 121.46, 119.63, 113.44, 52.83, 17.50.

Step (5). Preparation of 9-(2-butoxybenzyl)-9H-carbazole-2,7-diamine dihydrochloride The method in Step (2) of Example 1 was performed, and a target compound (837 mg, salt free, 86.6%) was obtained by using N,N'-(9-(2-butoxybenzyl)-9H-carbazole-2,7-diyl)bis(1,1-diphenylmethaneimine) (1.849 g, 2.688 mmol).

$^1$H NMR (400 MHz, CDCl$_3$) δ 7.54 (d, J=8.1 Hz, 2H), 6.98 (t, J=7.7 Hz, 1H), 6.72 (d, J=8.1 Hz, 1H), 6.47 (t, J=7.4 Hz, 1H), 6.38 (d, J=7.5 Hz, 1H), 6.33 (dd, J=8.1, 1.7 Hz, 2H), 6.29 (d, J=1.4 Hz, 2H), 5.11 (s, 2H), 3.91 (t, J=6.4 Hz, 2H), 3.50 (s, 4H), 1.71 (p, J=7.0 Hz, 2H), 1.48-1.39 (m, 2H), 0.89 (t, J=7.4 Hz, 3H); $^{13}$C NMR (100 MHz, MeOD) δ 156.36, 144.27, 142.21, 127.84, 126.45, 125.16, 119.90, 119.11, 116.26, 110.76, 108.75, 95.37, 67.54, 60.18, 40.84, 31.21, 19.16, 13.12, 13.00.

Step (6). Preparation of dimethyl ((1R,1'R)-((2S, 2'S)-(((9-(2-butoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (136 mg, 62.8%) was obtained by using 9-(2-butoxybenzyl)-9H-carbazole-2,7-diamine dihydrochloride (100 mg, 0.231 mmol).

$^1$H NMR (400 MHz, CDCl$_3$) δ 9.29 (s, 2H), 7.90 (d, J=8.3 Hz, 2H), 7.75 (s, 2H), 7.45-7.38 (m, 10H), 7.29-7.27 (m, 2H), 7.15 (t, J=8.1 Hz, 1H), 6.88 (d, J=7.9 Hz, 1H), 6.65 (t, J=7.4 Hz, 1H), 6.44 (d, J=7.2 Hz, 1H), 6.11 (d, J=6.8 Hz, 2H), 5.51 (d, J=6.5 Hz, 2H), 5.44-5.32 (m, 2H), 4.79-4.78 (m, 2H), 4.10 (t, J=6.6 Hz, 2H), 3.86-3.80 (m, 2H), 3.62 (s, 6H), 3.27-3.23 (m, 2H), 2.45-2.42 (m, 2H), 2.19-2.15 (m, 2H), 1.95-1.87 (m, 6H), 1.64-1.55 (m, 2H), 1.07 (t, J=7.4 Hz, 3H); $^{13}$C NMR (100 MHz, CDCl$_3$) δ 170.17, 168.46, 156.44, 156.30, 141.48, 136.05, 135.93, 129.19, 128.81, 127.98, 126.73, 125.01, 120.20, 119.69, 119.33, 112.26, 110.63, 100.59, 67.71, 61.51, 57.46, 52.32, 47.22, 41.73, 31.43, 27.90, 24.61, 19.46, 14.03. LC/MS (ESI-TOF) m/z calcd for $C_{53}H_{58}N_7O_9$ [M+H]$^+$: 936.43 found 936.20.

Example 33. Preparation of dimethyl ((1R,1'R)-((2S,2'S)-(((9-(10-(4-methylpiperazine-1-yl)decyl)-9H-carbazole-2,7-diyl)bis(azanediyl))bis(carbonyl))bis(pyrrolidine-2,1-diyl))bis(2-oxo-1-phenylethane-2,1-diyl))dicarbamate
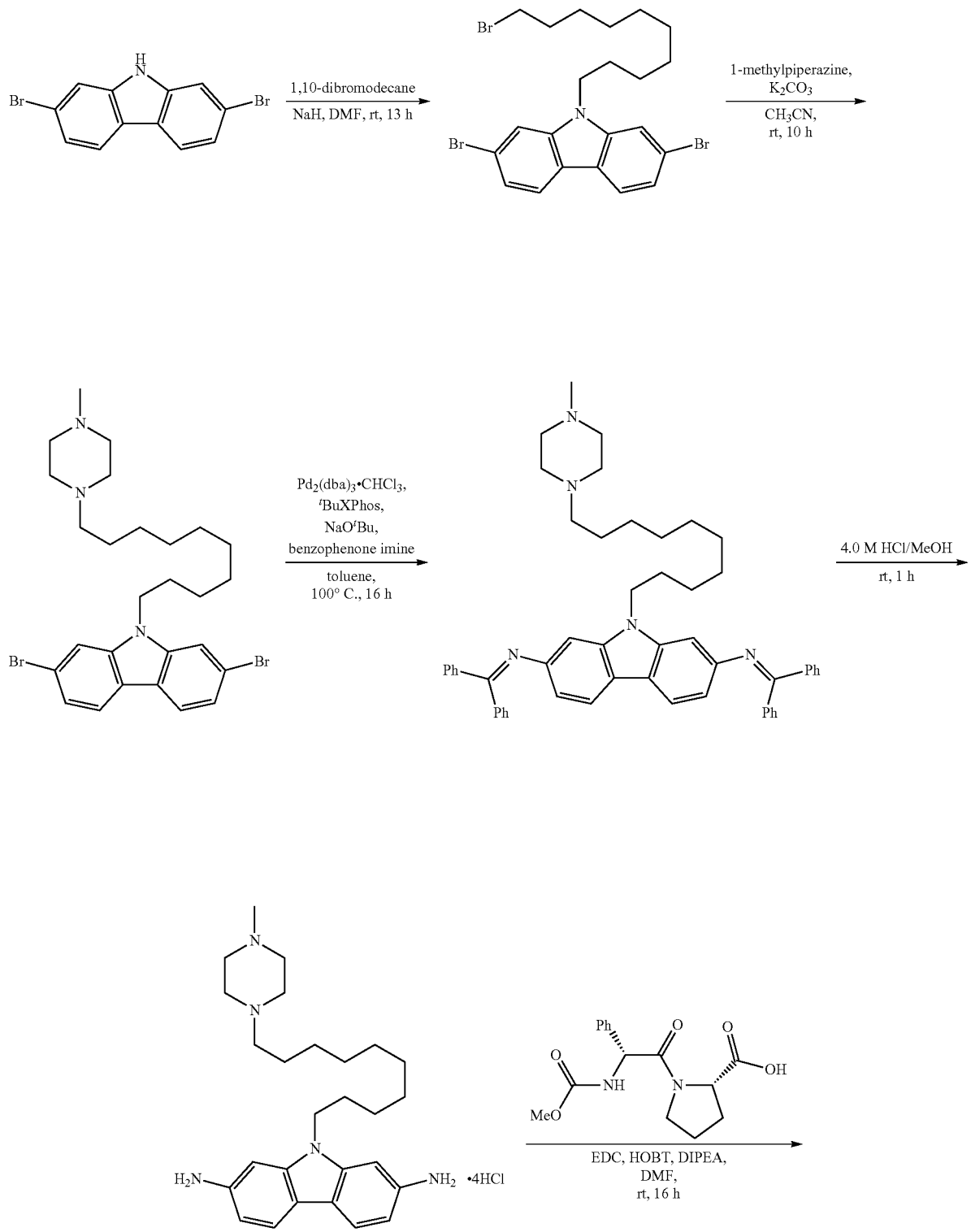

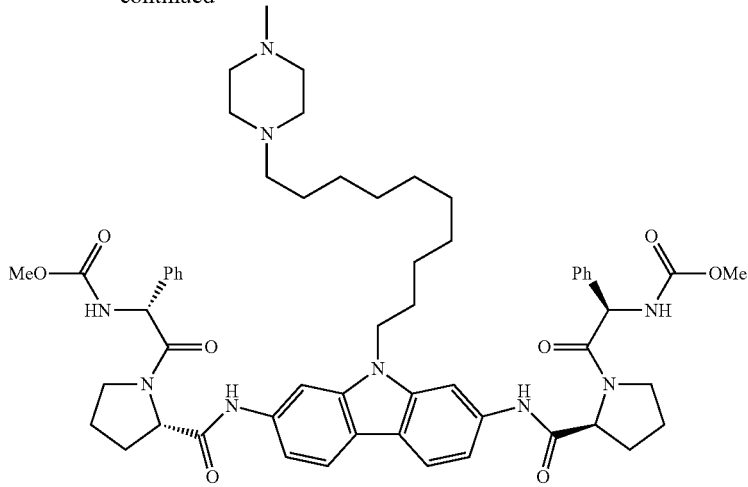

Step (1). Preparation of 2,7-dibromo-9-(10-bromodecyl)-9H-carbazole

The method in Step (1) of Example 1 was performed, and a white solid target compound (82 mg, 99%) was obtained by using 2,7-dibromo-9H-carbazole (50 mg, 0.15 mmol) and 1,10-dibromodecane (52 μL, 0.23 mmol).

$^1$H NMR (400 MHz, CDCl$_3$) δ 7.93 (t, J=7.6 Hz, 2H), 7.56 (dd, J=3.2, 1.6 Hz), 7.38 (m, 2H), 4.24 (m, 2H), 3.45 (m, 2H), 1.90 (m, 4H), 1.47 (m, 12H).

Step (2). Preparation of 2,7-dibromo-9-(10-(4-methylpiperazine-1-yl)decyl)-9H-carbazole 1-methylpiperazine (437 μL, 1.31 mmol), potassium carbonate (545 mg, 3.94 mmol), and the 2,7-dibromo-9-(10-bromodecyl)-9H-carbazole (715 mg, 1.31 mmol) obtained in Step (1) were added to MeCN (6 mL), and then the resulting mixture was stirred at room temperature for 10 hours. The mixture completely reacted was concentrated under reduced pressure. The mixture was extracted by using ethyl acetate and distilled water, and the organic layer was dried by putting anhydrous sodium sulfate thereto, and then filtered and concentrated under reduced pressure. The concentrated solution was purified with column chromatography (CH$_2$Cl$_2$/MeOH=30/1, v/v) to obtain a white solid target compound (314 mg, 42%).

$^1$H NMR (400 MHz, CDCl$_3$) δ 7.93 (d, J=8.4 Hz, 2H), 7.55 (d, J=1.6 Hz, 2H), 7.38 (dd, J=8.4, 1.6 Hz, 2H), 4.24 (t, J=7.2 Hz, 2H), 2.48 (m, 8H), 2.31 (s, 3H), 1.88 (m, 2H), 1.48 (m, 2H), 1.36 (m, 2H), 1.29 (m, 12H).

Step (3). Preparation of N,N'-(9-(10-(4-methylpiperazine-1-yl)decyl)-9H-carbazole-2,7-diyl)bis(1,1-diphenylmethaneimine)

The method in Step (2) of Example 1 was performed, and a yellow solid target compound (260 mg, 61%) was obtained by using 2,7-dibromo-9-(10-(4-methylpiperazine-1-yl)decyl)-9H-carbazole (314 mg, 0.56 mmol) and benzophenoneimine (175 μL, 1.56 mmol).

$^1$H NMR (400 MHz, CDCl$_3$) δ 7.81 (m, 4H), 7.72 (d, J=8.4 Hz, 2H), 7.50 (m, 6H), 7.26 (m, 10H), 6.71 (d, J=1.2 Hz, 2H), 6.62 (dd, J=8.4, 1.6 Hz, 2H), 3.95 (t, J=7.2 Hz, 2H), 2.59 (br s, 8H), 2.37 (m, 2H), 2.32 (s, 3H), 1.51 (m, 2H), 1.30 (m, 14H).

Step (4). Preparation of 9-(10-(4-methylpiperazine-1-yl)decyl)-9H-carbazole-2,7-diamine tetrahydrochloride The method in Step (3) of Example 1 was performed, and a white solid target compound (80 mg, 44%) was obtained by using N,N'-(9-(10-(4-methylpiperazine-1-yl)decyl)-9H-carbazole-2,7-diyl)bis(1,1-diphenylmethaneimine) (238 mg, 0.31 mmol).

$^1$H NMR (400 MHz, MeOD) δ 8.37 (d, J=8 Hz, 2H), 7.66 (d, J=2 Hz, 2H), 7.32 (dd, J=8.4, 2 Hz, 2H), 4.51 (t, J=6.8 Hz, 2H), 3.70 (br s, 8H), 3.27 (m, 2H), 3.03 (s, 3H), 2.04 (m, 2H), 1.82 (m, 2H), 1.38 (m, 12H).

Step (5). Preparation of dimethyl ((1R,1'R)-((2S,2'S)-(((9-(10-(4-methylpiperazine-1-yl)decyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Step (4) of Example 17 was performed, and a white solid target compound (17 mg, 16%) was obtained by using 9-(10-(4-methylpiperazine-1-yl)decyl)-9H-carbazole-2,7-diamine tetrahydrochloride (60 mg, 0.10 mmol) and ((R)-2-((methoxycarbonyl)amino)-2-phenylacetyl)-L-proline (69 mg, 0.22 mmol).

$^1$H NMR (400 MHz, CDCl$_3$) δ 9.57 (s, 2H), 7.80 (s, 2H), 7.70 (d, J=8.4 Hz, 2H), 7.47 (m, 10H), 7.16 (d, J=7.6 Hz, 2H), 6.23 (d, J=7.2 Hz, 2H), 5.57 (d, J=6.8 Hz, 2H), 4.78 (d, J=5.6 Hz, 2H), 4.13 (m, 2H), 3.94 (m, 2H), 3.65 (s, 6H), 3.34 (m, 2H), 2.53 (m, 8H), 2.48 (m, 2H), 2.32 (s, 6H), 2.29 (m, 2H), 1.96 (m, 4H), 1.48 (m, 2H), 1.23 (m, 12H). LC/MS (ESI-TOF) m/z calcd for C$_{57}$H$_{74}$N$_9$O$_8$ [M+H]$^+$: 1012.57 found 1012.45.

Example 34. Preparation of dimethyl ((1R,1'R)-((2S,2'S)-(((9-(10-morpholinodecyl)-9H-carbazole-2,7-diyl)bis(azanediyl))bis(carbonyl))bis(pyrrolidine-2,1-diyl))bis(2-oxo-1-phenylethane-2,1-diyl)) carbamate

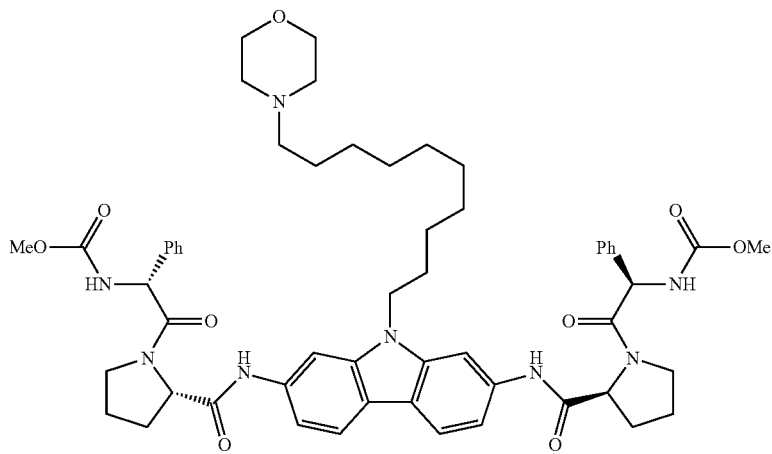 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(CCCCCCCCCCN3CCOCC3)c2c1)c1ccccc1]

Step (1). Preparation of 4-(10-(2,7-dibromo-9H-carbazole-9-yl)decyl)morpholine The method in Step (2) of Example 33 was performed, and a white solid target compound (441 mg, 47%) was obtained by using 2,7-dibromo-9-(10-bromodecyl)-9H-carbazole (715 mg, 1.31 mmol) and morpholine (491 μL, 5.11 mmol).

$^1$H NMR (400 MHz, CDCl$_3$) δ 7.93 (d, J=8 Hz, 2H), 7.55 (s, 2H), 7.38 (dd, J=8.0, 0.8 Hz, 2H), 4.24 (m, 2H), 3.75 (t, J=0.8 Hz, 4H), 2.45 (br s, 4H), 2.35 (t, J=7.2 Hz, 2H), 1.87 (m, 2H), 1.45 (m, 2H), 1.37 (m, 14H).

Step (2). Preparation of N,N'-(9-(10-morpholinodecyl)-9H-carbazole-2,7-diyl)bis(1,1-diphenylmethaneimine)

The method in Step (2) of Example 1 was performed, and a yellow solid target compound (425 mg, 73%) was obtained by using 4-(10-(2,7-dibromo-9H-carbazole-9-yl)morpholine (426 mg, 0.77 mmol) and benzophenoneimine (243 μL, 2.17 mmol).

$^1$H NMR (400 MHz, CDCl$_3$) δ 7.81 (m, 4H), 7.72 (d, J=8.0 Hz, 2H), 7.51 (m, 6H), 7.26 (m, 10H), 6.72 (d, J=1.6 Hz, 2H), 6.61 (dd, J=8.4, 1.6 Hz, 2H), 3.93 (m, 2H), 3.75 (t, J=4.4 Hz, 4H), 2.45 (m, 4H), 2.35 (t, J=7.6 Hz, 2H), 1.50 (m, 2H), 1.31 (m, 14H).

Step (3). Preparation of 9-(10-morpholinodecyl)-9H-carbazole-2,7-diamine trihydrochloride The method in Step (3) of Example 1 was performed, and a white solid target compound (215 mg, 71%) was obtained by using N,N'-(9-(10-morpholinodecyl)-9H-carbazole-2,7-diyl)bis(1,1-diphenylmethaneimine) (425 mg, 0.56 mmol).

$^1$H NMR (400 MHz, MeOD) δ 8.36 (d, J=8 Hz, 2H), 7.67 (d, J=2 Hz, 2H), 7.32 (dd, J=8.0, 1.6 Hz, 2H), 4.51 (t, J=6.8 Hz, 2H), 4.09 (dd, J=13.2, 3.2 Hz, 2H), 3.85 (dd, J=13.6, 1.6 Hz, 2H), 3.51 (t, J=3.2 Hz, 2H), 3.16 (m, 4H), 1.94 (m, 2H), 1.76 (m, 2H), 1.37 (m, 12H).

Step (4). Preparation of dimethyl ((1R,1'R)-((2S,2'S)-(((9-(10-morpholinodecyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Step (4) of Example 17 was performed, and a white solid target compound (42 mg, 37%) was obtained by using 9-(10-morpholinodecyl)-9H-carbazole-2,7-diamine trihydrochloride (60 mg, 0.11 mmol) and ((R)-2-((methoxycarbonyl)amino)-2-phenylacetyl)-L-proline (76 mg, 0.25 mmol).

$^1$H NMR (400 MHz, CDCl$_3$) δ 9.67 (s, 2H), 7.68 (s, 2H), 7.61 (d, J=8.0 Hz, 2H), 7.46 (m, 10H), 7.15 (m, 2H), 6.30 (d, J=7.2 Hz, 2H), 5.59 (d, J=7.2 Hz, 2H), 4.75 (t, J=5.6 Hz, 2H), 4.06 (m, 2H), 3.94 (m, 2H), 3.79 (t, J=4.8 Hz, 4H), 3.62 (s, 6H), 3.36 (m, 2H), 2.64 (br s, 4H), 2.48 (t, J=7.6 Hz, 2H), 2.37 (m, 2H), 2.02 (m, 4H), 1.48 (m, 2H), 1.15 (m, 12H). LC/MS (ESI-TOF) m/z calcd for C$_{56}$H$_{71}$N$_8$O$_9$ [M+H]$^+$: 999.54 found 999.50.

Example 35. Preparation of dimethyl ((1R,1'R)-((2S,2'S)-(((9-(2-(hexyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

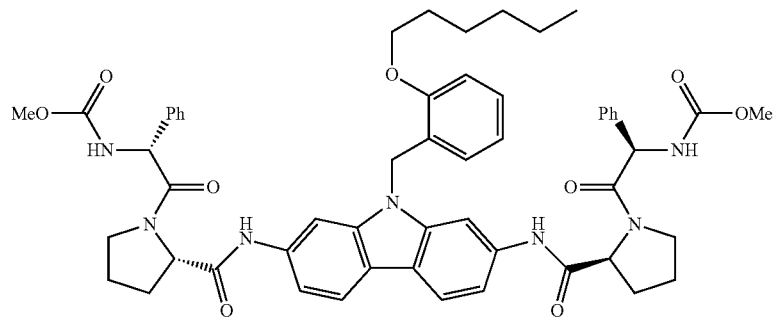 [SMILES: CCCCCCOc1ccccc1Cn1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of (2-(hexyloxy)phenyl)methanol

The method in Step (1) of Example 31 was performed, and a white solid target compound (312 mg, 93.0%) was obtained by using 2-(hydroxymethyl)phenol (200 mg, 1.611 mmol) and 1-bromohexane (0.25 mL, 1.772 mmol).

$^1$H NMR (400 MHz, CDCl$_3$) δ 7.32 (dd, J=6.9, 1.6 Hz, 1H), 7.28 (dd, J=7.9, 1.7 Hz, 1H), 6.97 (td, J=7.4, 0.9 Hz, 1H), 6.91 (d, J=8.1 Hz, 1H), 4.73 (s, 2H), 4.04 (t, J=6.5 Hz, 2H), 2.74 (s, 1H), 1.89-1.82 (m, 2H), 1.54-1.48 (m, 2H), 1.43-1.38 (m, 4H), 0.98 (t, J=7.0 Hz, 3H); $^{13}$C NMR (100 MHz, CDCl$_3$) δ 156.91, 129.29, 128.77, 128.53, 120.50, 111.04, 67.99, 62.09, 31.59, 29.29, 25.87, 22.64, 14.06.

Step (2). Preparation of 1-(chloromethyl)-2-(hexyloxy)benzene

The method in Step (2) of Example 31 was performed, and a target compound (245 mg, 72.1%) was obtained by using (2-(hexyloxy)phenyl)methanol (312 mg, 1.498 mmol) and SOCl$_2$ (0.33 mL, 4.494 mmol).

Step (3). Preparation of 2,7-dibromo-9-(2-(hexyloxy)benzyl)-9H-carbazole

The method in Step (3) of Example 31 was performed, and a while solid target compound (428 mg, 100%) was obtained by using 2,7-dibromo-9H-carbazole (270 mg, 0.831 mmol) and 1-(chloromethyl)-2-(hexyloxy)benzene (245 mg, 1.081 mmol).

$^1$H NMR (400 MHz, CDCl$_3$) δ 7.92 (d, J=8.3 Hz, 2H), 7.61 (d, J=1.5 Hz, 2H), 7.41 (dd, J=8.3, 1.6 Hz, 2H), 7.30-7.26 (m, 1H), 6.96 (d, J=7.7 Hz, 1H), 6.81 (td, J=7.5, 0.8 Hz, 1H), 6.73 (dd, J=7.5, 1.5 Hz, 1H), 4.12 (t, J=6.6 Hz, 2H), 1.94 (p, J=7.1 Hz, 2H), 1.60-1.54 (m, 2H), 1.50-1.45 (m, 4H), 1.05 (t, J=7.0 Hz, 3H); $^{13}$C NMR (100 MHz, CDCl$_3$) δ 156.46, 141.76, 128.93, 127.39, 124.02, 122.81, 120.51, 119.86, 112.58, 111.12, 68.22, 42.15, 31.75, 29.40, 26.01, 22.78, 14.26, 14.22.

Step (4). Preparation of N,N'-(9-(2-(hexyloxy)benzyl)-9H-carbazole-2,7-diyl)bis(1,1-diphenylmethaneimine)

The method in Step (2) of Example 1 was performed, and a target compound (415 mg, 69.8%) was obtained by using 2,7-dibromo-9-(2-(hexyloxy)benzyl)-9H-carbazole (428 mg, 0.831 mmol).

$^1$H NMR (400 MHz, CDCl$_3$) δ 7.84-7.79 (m, 6H), 7.52-7.44 (m, 6H), 7.26-7.16 (m, 11H), 6.93 (d, J=7.7 Hz, 1H), 6.73 (d, J=0.7 Hz, 2H), 6.71 (td, J=7.5, 0.7 Hz, 1H), 6.67 (dd, J=8.2, 1.7 Hz, 2H), 6.31 (dd, J=7.5, 1.3 Hz, 1H), 5.31 (s, 2H), 4.12 (t, J=6.5 Hz, 2H), 1.94 (p, J=7.0 Hz, 2H), 1.62-1.58 (m, 2H), 1.47-1.43 (m, 2H), 0.99 (t, J=7.0 Hz, 3H); $^{13}$C NMR (100 MHz, CDCl$_3$) δ 168.01, 156.13, 149.16, 141.78, 139.94, 136.52, 130.66, 129.54, 129.37, 128.53, 128.22, 127.95, 127.91, 126.70, 125.06, 120.47, 119.69, 119.15, 113.59, 110.66, 101.75, 68.05, 41.32, 31.69, 29.40, 25.99, 22.71, 14.16.

Step (5). Preparation of 9-(2-(hexyloxy)benzyl)-9H-carbazole-2,7-diamine dihydrochloride The method in Step (3) of Example 1 was performed, and a target compound (245 mg, 91.8%) was obtained by using N,N'-(9-(2-(hexyloxy)benzyl)-9H-carbazole-2,7-diyl)bis(1,1-diphenylmethaneimine) (415 mg, 0.580 mmol).

$^1$H NMR (400 MHz, DMSO-d$_6$) δ 10.48 (bs, 6H), 8.31 (d, J=8.3 Hz, 2H), 7.53 (d, J=1.5 Hz, 2H), 7.27 (dd, J=8.3, 1.7 Hz, 2H), 7.24-7.22 (m, 1H), 7.06 (d, J=7.9 Hz, 1H), 6.76 (t, J=7.4 Hz, 1H), 6.57 (dd, J=7.5 Hz, 1H), 5.53 (s, 2H), 4.08 (t, J=6.6 Hz, 2H), 1.71-1.66 (m, 2H), 1.30-1.24 (m, 6H), 0.86 (t, J=6.9 Hz, 3H); $^{13}$C NMR (100 MHz, DMSO-d$_6$) δ 156.66, 141.39, 131.09, 129.39, 129.06, 127.45, 124.33, 122.06, 121.37, 120.72, 115.02, 112.25, 104.63, 68.22, 42.43, 31.47, 28.97, 25.53, 22.52, 14.40.

Step (6). Preparation of dimethyl ((1R,1'R)-((2S,2'S)-(((9-(2-(hexyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (68 mg, 65.0%) was obtained by using 9-(2-(hexyloxy)benzyl)-9H-carbazole-2,7-diamine dihydrochloride (50 mg, 0.109 mmol).

$^1$H NMR (400 MHz, CDCl$_3$) δ 9.35 (s, 2H), 7.85 (d, J=8.3 Hz, 2H), 7.68 (s, 2H), 7.45-7.44 (m, 4H), 7.37-7.35 (m, 6H), 7.27 (d, J=8.1 Hz, 2H), 7.13 (t, J=7.3 Hz, 2H), 6.86 (d, J=8.2 Hz, 1H), 6.62 (t, J=7.4 Hz, 1H), 6.44 (d, J=7.2 Hz, 1H), 6.23 (d, J=6.8 Hz, 2H), 5.53 (d, J=6.8 Hz, 2H), 5.35 (d, J=17.7 Hz, 1H), 5.24 (d, J=17.7 Hz, 1H), 4.77 (d, J=6.2 Hz, 2H), 4.07 (t, J=6.7 Hz, 2H), 3.89-3.85 (m, 2H), 3.61 (s, 6H), 3.30-3.24 (m, 2H), 2.40-2.37 (m, 2H), 2.19-2.15 (m, 2H), 1.95-1.87 (m, 6H), 1.56-1.51 (m, 2H), 1.45-1.41 (m, 4H), 0.97 (t, J=6.9 Hz, 3H); $^{13}$C NMR (100 MHz, CDCl$_3$) δ 169.96, 168.70, 156.49, 156.27, 141.34, 136.25, 135.93, 129.16, 128.76, 127.97, 126.84, 125.07, 120.13, 119.60, 119.23, 112.15, 110.62, 100.50, 68.03, 61.56, 57.41, 52.30, 47.32, 41.72, 31.78, 28.28 25.89, 24.63, 22.68, 14.16. LC/MS (ESI-TOF) m/z calcd for $C_{55}H_{61}N_7O_9Na$ [M+Na]$^+$: 986.44 found 986.20.

Example 36. Preparation of dimethyl ((1R,1'R)-((2S,2'S)-(((9-(4-butoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

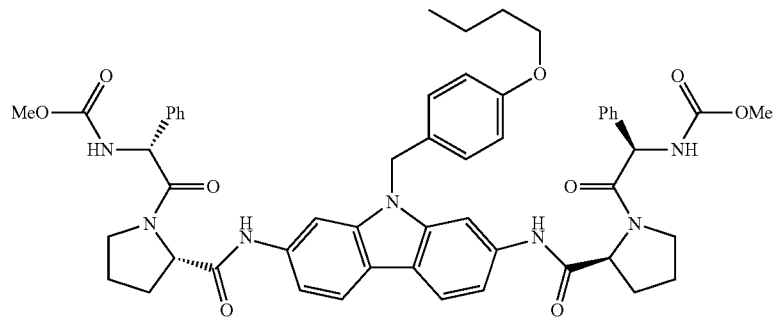 [SMILES: CCCCOc1ccc(Cn2c3cc(NC(=O)[C@@H]4CCCN4C(=O)[C@H](NC(=O)OC)c4ccccc4)ccc3c3ccc(NC(=O)[C@@H]4CCCN4C(=O)[C@H](NC(=O)OC)c4ccccc4)cc32)cc1]

Step (1). Preparation of (4-butoxyphenyl)methanol

The method in Step (1) of Example 31 was performed, and a target compound (167 mg, 76.7%) was obtained by using 2-(hydroxymethyl)phenol (200 mg, 0.403 mmol) and 1-bromobutane (0.35 mL, 3.222 mmol).

$^1$H NMR (400 MHz, CDCl$_3$) δ 7.27 (dt, J=9.2, 2.5 Hz, 2H), 6.90 (dt, J=7.4, 0.9 Hz, 2H), 4.57 (s, 2H), 3.98 (t, J=6.5 Hz, 2H), 2.54 (bs, 1H), 1.84-1.77 (m, 2H), 1.58-1.49 (m, 2H), 1.02 (t, J=7.4 Hz, 3H); $^{13}$C NMR (100 MHz, CDCl$_3$) δ 158.71, 133.00, 128.64, 114.52, 67.77, 64.83, 31.35, 19.28, 13.90.

Step (2). Preparation of 1-butoxy-4-(chloromethyl)benzene

The method in Step (2) of Example 31 was performed, and a target compound (280 mg, 79.9%) was obtained by using (4-butoxyphenyl)methanol (318 mg, 1.748 mmol) and SOCl$_2$ (0.38 mL, 5.243 mmol).

Step (3). Preparation of 2,7-dibromo-9-(4-butoxybenzyl)-9H-carbazole

The method in Step (1) of Example 1 was performed, and a target compound (528 mg, 100%) was obtained by using 2,7-dibromo-9H-carbazole (352 mg, 1.084 mmol) and 1-butoxy-4-(chloromethyl)benzene (280 mg, 1.409 mmol).

$^1$H NMR (400 MHz, CDCl$_3$) δ 7.92 (dd, J=8.3, 0.2 Hz, 2H), 7.53 (d, J=1.5 Hz, 2H), 7.39 (dd, J=8.3, 1.7 Hz, 2H), 7.05 (d, J=8.8 Hz, 2H), 6.83 (dt, J=9.3, 2.5 Hz, 1H), 5.33 (s, 2H), 3.93 (t, J=6.5 Hz, 2H), 1.80-1.73 (m, 2H), 1.53-1.48 (m, 2H), 1.00 (t, J=7.4 Hz, 3H); $^{13}$C NMR (100 MHz, CDCl$_3$) δ 158.82, 141.55, 127.71, 127.54, 122.96, 121.50, 121.44, 119.92, 114.94, 112.28, 67.73, 46.25, 31.29, 19.25, 13.87.

Step (4). Preparation of N,N'-(9-(4-butoxybenzyl)-9H-carbazole-2,7-diyl)bis(1,1-diphenylmethaneimine)

The method in Step (2) of Example 1 was performed, and a target compound (588 g, 78.9%) was obtained by using 2,7-dibromo-9-(4-butoxybenzyl)-9H-carbazole (528 mg, 1.084 mmol).

$^1$H NMR (400 MHz, CDCl$_3$) δ 7.88 (s, 2H), 7.86 (d, J=1.5 Hz, 2H), 7.81 (d, J=8.2 Hz, 2H), 7.56-7.52 (m, 2H), 7.50-7.46 (m, 4H), 7.30-7.24 (m, 6H), 7.22-7.19 (m, 4H), 6.91 (d, J=8.7 Hz, 2H), 6.84-6.80 (m, 4H), 6.74 (dd, J=8.2, 1.7 Hz, 2H), 4.03 (t, J=6.5 Hz, 2H), 1.90-1.83 (m, 2H), 1.65-1.55 (m, 2H), 1.08 (t, J=7.4 Hz, 3H); $^{13}$C NMR (100 MHz, CDCl$_3$) δ 168.05, 158.44, 149.22, 141.55, 139.97, 136.58, 130.75, 129.61, 129.45, 129.07, 128.55, 128.29, 128.03, 127.83, 119.81, 119.22, 114.68, 113.92, 101.53, 67.77, 46.02, 31.45, 19.39, 14.00.

Step (5). Preparation of 9-(4-butoxybenzyl)-9H-carbazole-2,7-diamine dihydrochloride The method in Step (2) of Example 1 was performed, and a target compound (336 mg, 90.9%) was obtained by using N,N'-(9-(4-butoxybenzyl)-9H-carbazole-2,7-diyl)bis(1,1-diphenylmethaneimine) (588 mg, 0.855 mmol).

$^1$H NMR (400 MHz, CDCl$_3$) δ 7.73 (d, J=8.2 Hz, 2H), 7.01 (d, J=8.6 Hz, 2H), 6.75 (d, J=8.7 Hz, 2H), 6.56 (dd, J=8.2, 1.7 Hz, 2H), 6.47 (d, J=1.6 Hz, 2H), 5.09 (s, 2H), 3.85 (t, J=6.5 Hz, 2H), 3.65 (bs, 4H), 1.77-1.70 (m, 2H), 1.53-1.43 (m, 2H), 1.00 (t, J=3H); $^{13}$C NMR (100 MHz, CDCl$_3$) δ 158.45, 144.33, 142.26, 129.25, 127.60, 119.87, 116.25, 114.75, 108.55, 94.99, 67.74, 45.66, 31.38, 19.33, 13.97.

Step (6). Preparation of dimethyl ((1R,1'R)-((2S,2'S)-(((9-(4-butoxybenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (68.7 mg, 63.4%) was obtained by using 9-(4-butoxybenzyl)-9H-carbazole-2,7-diamine dihydrochloride (50 mg, 0.116 mmol).

$^1$H NMR (400 MHz, CDCl$_3$) δ 9.56 (s, 2H), 7.71-7.65 (m, 4H), 7.46-7.44 (m, 4H), 7.38-7.36 (m, 6H), 7.21-7.19 (m, 2H), 7.04 (d, J=8.6 Hz, 2H), 6.73 (d, J=8.7 Hz, 2H), 6.22 (d, J=7.0 Hz, 2H), 5.57 (d, J=7.0 Hz, 2H), 5.27-5.18 (m, 2H), 4.76-4.74 (m, 2H), 3.94-3.89 (m, 2H), 3.88-3.84 (m, 2H), 3.61 (s, 6H), 3.37-3.31 (m, 2H), 2.42-2.38 (m, 2H), 2.31-

2.24 (m, 2H), 2.00-1.86 (m, 4H), 1.73-1.66 (m, 2H), 1.49-1.39 (m, 2H), 0.94 (t, J=7.4 Hz, 3H); $^{13}$C NMR (100 MHz, CDCl$_3$) δ 169.74, 168.95, 158.26, 156.08, 140.66, 136.72, 136.01, 129.34, 129.14, 128.73, 128.05, 127.90, 119.59, 118.99, 114.51, 111.69, 99.74, 67.53, 61.72, 57.26, 52.30, 47.52, 45.33, 31.33, 28.73, 24.76, 19.22, 13.84. LC/MS (ESI-TOF) m/z calcd for C$_{53}$H$_{58}$N$_7$O$_9$ [M+H]$^+$: 936.43 found 936.20.

Example 37. Preparation of dimethyl ((1R,1'R)-((2S,2'S)-(((9-(3-nitrobenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate

Step (3). Preparation of 9-(3-nitrobenzyl)-9H-carbazole-2,7-diamine dihydrochloride The method in Step (3) of Example 1 was performed, and a target compound (173 mg, 39.3%) was obtained by using N,N'-(9-(3-nitrobenzyl)-9H-carbazole-2,7-diyl)bis(1,1-diphenylmethaneimine) (718 mg, 1.087 mmol).

$^1$H NMR (400 MHz, DMSO-d$_6$) δ 10.41 (bs, 6H), 8.31 (d, J=8.3 Hz, 2H), 8.15-8.13 (m, 1H), 8.06-8.05 (m, 1H), 7.63-7.59 (m, 3H), 7.47 (d, J=7.7 Hz, 1H), 7.30 (dd, J=8.3, 1.7 Hz, 2H), 5.76 (s, 2H); $^{13}$C NMR (100 MHz, DMSO-d$_6$) δ 148.47, 141.15, 139.82, 133.42, 131.58, 131.01, 123.04, 122.26, 121.70, 121.43, 115.39, 104.38, 45.74.

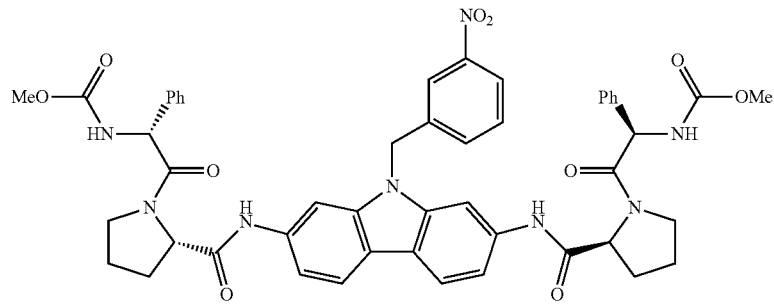 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3cccc([N+](=O)[O-])c3)c2c1)c1ccccc1]

Step (1). Preparation of 2,7-dibromo-9-(3-nitrobenzyl)-9H-carbazole

The method in Step (1) of Example 1 was performed, and a target compound (1.327 g, 93.7%) was obtained by using 2,7-dibromo-9H-carbazole (1.0 g, 3.077 mmol) and 3-nitrobenzyl bromide (798 mg, 3.692 mmol).

$^1$H NMR (400 MHz, CDCl$_3$) δ 8.18 (dd, J=8.2, 1.3 Hz, 1H), 8.07 (s, 1H), 7.98 (d, J=8.2 Hz, 2H), 7.52-7.42 (m, 5H), 7.33 (dd, J=7.7, 0.7 Hz, 1H), 5.54 (s, 2H); $^{13}$C NMR (100 MHz, CDCl$_3$) δ 148.75, 141.27, 138.24, 131.96, 130.25, 123.65, 123.08, 121.83, 121.70, 121.24, 120.24, 111.90, 46.05.

Step (2). Preparation of N,N'-(9-(3-nitrobenzyl)-9H-carbazole-2,7-diyl)bis(1,1-diphenylmethaneimine)

The method in Step (2) of Example 1 was performed, and a target compound (718 mg, 100%) was obtained by using N,N'-(9-(3-nitrobenzyl)-9H-carbazole-2,7-diyl)bis(1,1-diphenylmethaneimine) (500 mg, 1.087 mmol).

$^1$H NMR (400 MHz, CDCl$_3$) δ 8.13 (dd, J=8.2, 1.3 Hz, 1H), 7.83-7.80 (m, 7H), 7.52-7.48 (m, 2H), 7.45-7.41 (m, 4H), 7.34 (t, J=7.9 Hz, 1H), 7.20-7.13 (m, 10H), 7.08 (d, J=8.1 Hz, 1H), 6.79 (dd, J=8.2, 1.7 Hz, 2H), 6.64 (d, J=1.4 Hz, 2H), 5.23 (s, 2H); $^{13}$C NMR (100 MHz, CDCl$_3$) δ 168.19, 149.50, 148.50, 141.16, 139.79, 139.48, 136.41, 132.33, 130.82, 129.76, 129.54, 129.41, 128.52, 128.28, 127.93, 122.44, 121.18, 120.12, 119.33, 114.71, 100.94, 60.44, 45.59, 21.12, 14.32.

Step (4). Preparation of dimethyl ((1R,1'R)-((2S,2'S)-(((9-(3-nitrobenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (79 mg, 70.4%) was obtained by using 9-(3-nitrobenzyl)-9H-carbazole-2,7-diamine dihydrochloride (50 mg, 0.123 mmol).

$^1$H NMR (400 MHz, CDCl$_3$) δ 9.80 (s, 2H), 8.07 (s, 1H), 8.02-7.99 (m, 1H), 7.64-7.62 (m, 2H), 7.44-7.43 (m, 6H), 7.37-7.32 (m, 9H), 7.22 (s, 1H), 6.17 (d, J=6.9 Hz, 2H), 5.59 (d, J=6.9 Hz, 2H), 5.22-5.06 (m, 2H), 4.73-7.71 (m, 2H), 4.04-3.99 (m, 2H), 3.68-3.56 (m, 6H), 3.40-3.34 (m, 2H), 2.39-2.31 (m, 4H), 2.08-2.02 (m, 2H), 1.96-1.88 (m, 2H); $^{13}$C NMR (100 MHz, CDCl$_3$) δ 169.53, 155.78, 148.35, 140.18, 139.74, 136.90, 136.22, 132.94, 129.48, 129.12, 128.71, 127.83, 122.24, 121.85, 119.72, 118.98, 112.35, 99.35, 61.77, 57.14, 52.23, 47.66, 45.06, 29.21, 24.79.

Example 38. Preparation of dimethyl ((1R,1'R)-((2S,2'S)-(((9-(3-pivalamidobenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate
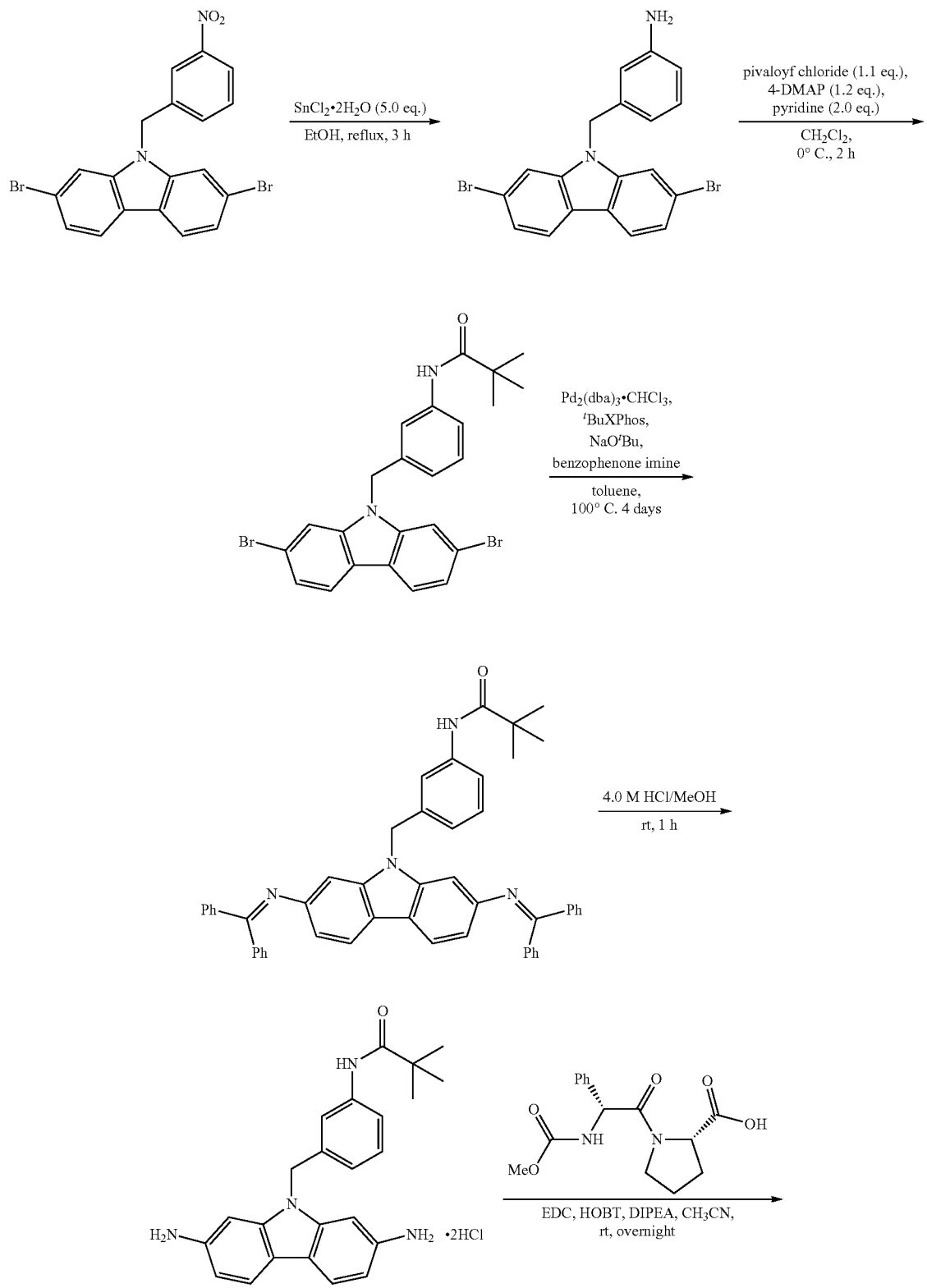

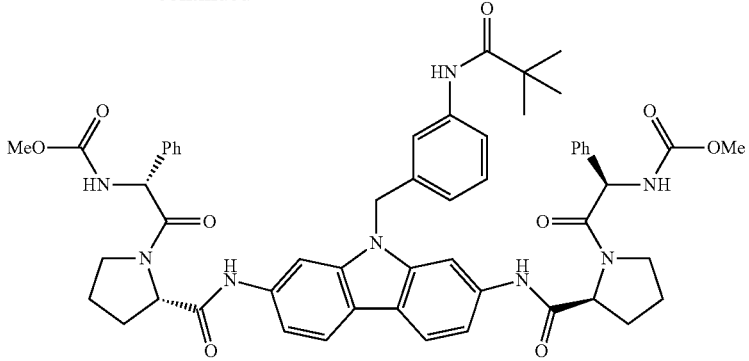

Step (1). Preparation of 3-((2,7-dibromo-9H-carbazole-9-yl)methyl)aniline

The 2,7-dibromo-9-(3-nitrobenzyl)-9H-carbazole (818 mg, 1.778 mmol) prepared in Step (1) of Example 37 was dissolved in ethanol (24 mL), and then $SnCl_2$ (2.005 g, 8.889 mmol) was added thereto, and the resulting mixture was refluxed under heating for 3 hours. When the reaction was completed, the temperature was reduced to room temperature, pH was adjusted to 9 by using 2 N sodium hydroxide, and then the mixture was extracted with ethyl acetate. The collected organic layer was washed with brine, dried over anhydrous sodium sulfate, and then filtered and concentrated under reduced pressure. The concentrated solution was separated and purified with column chromatography (hexane/EtOAc=5/1, v/v) to obtain a white solid target compound (679 mg, 88.8%).

$^1$H NMR (400 MHz, $CDCl_3$) δ 7.94 (d, J=8.3 Hz, 2H), 7.53 (d, J=1.4 Hz, 2H), 7.39 (dd, J=8.3, 1.5 Hz, 2H), 7.12 (t, J=7.8 Hz, 1H), 6.61-6.57 (m, 2H), 6.33 (s, 1H), 5.35 (s, 2H), 3.63 (bs, 2H); $^{13}$C NMR (100 MHz, $CDCl_3$) δ 147.04, 141.69, 137.30, 129.97, 123.01, 121.49, 121.42, 119.95, 116.38, 114.53, 112.33, 46.69.

Step (2). Preparation of N-3-((2,7-dibromo-9H-carbazole-9-yl)methyl)phenyl)pivalamide The 3-((2,7-dibromo-9H-carbazole-9-yl)methyl)aniline (679 mg, 1.579 mmol) prepared in Step (1), pyridine (0.26 mL, 3.157 mmol), and 4-dimethylaminopyridine (4-DMAP; 231 mg, 1.894 mmol) were dissolved in dichloromethane (7 mL), and then pivaloyl chloride (0.21 mL, 1.736 mmol) was slowly added dropwise thereto at 0° C., and the resulting mixture was stirred at room temperature for 2 hours. When the reaction was completed, the reaction mixture was slowly added dropwise to cold 1 M HCl, and extracted with dichloromethane. The collected organic layer was washed with 1 M HCl and brine, dried over anhydrous sodium sulfate, and then filtered and concentrated under reduced pressure. The concentrated solution was separated and purified with column chromatography (hexane/EtOAc=8/1, v/v) to obtain a target compound (706 mg, 87.0%).

$^1$H NMR (400 MHz, Acetone-$d_6$) δ 8.61 (bs, 1H), 8.16 (d, J=8.3 Hz, 2H), 7.80 (dd, J=1.5 Hz, 2H), 7.68 (d, J=8.1 Hz, 1H), 7.59 (s, 1H), 7.42 (dd, J=8.3, 1.7 Hz, 2H), 7.24 (t, J=7.9 Hz, 1H), 6.84 (dd, J=7.6, 0.6 Hz, 1H), 5.69 (s, 2H), 1.23 (s, 9H); $^{13}$C NMR (100 MHz, Acetone-$d_6$) δ 141.91, 140.27, 137.51, 128.92, 122.80, 121.92, 121.48, 121.14, 119.53, 119.21, 117.79, 112.65, 46.31, 39.28, 26.76.

Step (3). Preparation of N-(3-((2,7-bis((diphenylmethylene) amino)-9H-carbazole-9-yl)methyl)phenyl) pivalamide The method in Step (2) of Example 1 was performed, and a target compound (850 mg, 86.6%) was obtained by using N-(3-(2,7-dibromo-9H-carbazole-9-yl)methyl)phenyl)pivalamide (706 mg, 1.373 mmol).

$^1$H NMR (400 MHz, $CDCl_3$) δ 7.80-7.75 (m, 6H), 7.64 (dd, J=8.1, 1.3 Hz, 1H), 7.52-7.47 (m, 2H), 7.44-7.40 (m, 4H), 7.33 (bs, 1H), 7.23-7.17 (m, 7H), 7.15-7.12 (m, 5H), 6.68-6.67 (m, 3H), 6.66-6.65 (m, 1H), 6.57 (d, J=7.7 Hz, 1H), 5.14 (s, 1H), 1.34 (s, 9H); $^{13}$C NMR (100 MHz, $CDCl_3$) δ 176.67, 168.13, 149.24, 141.52, 139.85, 138.45, 138.03, 136.49, 130.69, 129.48, 129.38, 129.33, 128.48, 128.21, 127.91, 121.93, 119.72, 119.11, 119.02, 117.47, 114.00, 101.46, 46.38, 39.67, 27.68.

Step (4). Preparation of N-(3-((2,7-diamino-9H-carbazole-9-yl)methyl)phenyl)pivalamide dihydrochloride The method in Step (3) of Example 1 was performed, and a target compound (409 mg, 74.9%) was obtained by using N-(3-((2,7-bis((diphenylmethylene)amino)-9H-carbazole-9-yl)methyl)phenyl)pivalamide (850 mg, 1.189 mmol).

$^1$H NMR (400 MHz, MeOD) δ 7.63 (d, J=8.2 Hz, 2H), 7.42 (dd, J=8.1, 1.0 Hz, 1H), 7.33 (s, 1H), 7.14 (t, J=7.9 Hz, 1H), 6.81 (d, J=7.6 Hz, 1H), 6.64 (d, J=1.8, 2H), 6.58 (dd, J=8.2, 1.9 Hz, 2H), 5.24 (s, 2H), 1.22 (s, 9H); $^{13}$C NMR (100 MHz, MeOD) δ 178.50, 144.57, 142.09, 138.74, 138.64, 128.47, 122.21, 120.10, 119.25, 119.05, 116.05, 108.76, 95.26, 45.56, 39.07, 26.35.

Step (5). Preparation of dimethyl ((1R,1'R)-((2S, 2'S)-(((9-(3-pivalamidobenzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (45 mg, 42.9%) was obtained by using N-(3-(2,7-diamino-9H-carbazole-9-yl)methyl)phenyl)pivalamide dihydrochloride (50 mg, 0.109 mmol).

$^1$H NMR (400 MHz, $CDCl_3$) δ 9.57 (s, 2H), 7.82 (d, J=7.7 Hz, 1H), 7.70-7.60 (m, 5H), 7.45-7.44 (m, 4H), 7.38-7.37 (m, 6H), 7.26-7.17 (m, 3H), 6.89-6.84 (m, 2H), 6.35 (d, J=6.3 Hz, 2H), 5.55 (d, J=7.0 Hz, 2H), 5.07 (d, J=16.5 Hz, 1H), 4.89 (d, J=17.2 Hz, 1H), 4.76-4.74 (m, 2H), 3.89-3.85 (m, 2H), 3.59 (s, 6H), 3.34-3.28 (m, 2H), 2.41-2.38 (m, 2H), 2.27-2.22 (m, 2H), 1.98-1.86 (m, 4H), 1.29-1.27 (m, 9H); $^{13}$C NMR (100 MHz, CDCl$_3$) δ 206.97, 169.77, 168.97, 156.10, 140.80, 138.59, 137.88, 136.61, 136.00, 129.22, 129.13, 128.72, 127.90, 122.63, 119.80, 119.61, 119.08, 118.37, 111.99, 99.91, 61.64, 57.29, 52.29, 47.46, 39.52, 30.92, 28.62, 27.55, 24.74.

Example 39. Preparation of dimethyl ((1R,1'R)-((2S,2'S)-(((9-(3-(cyclopentyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

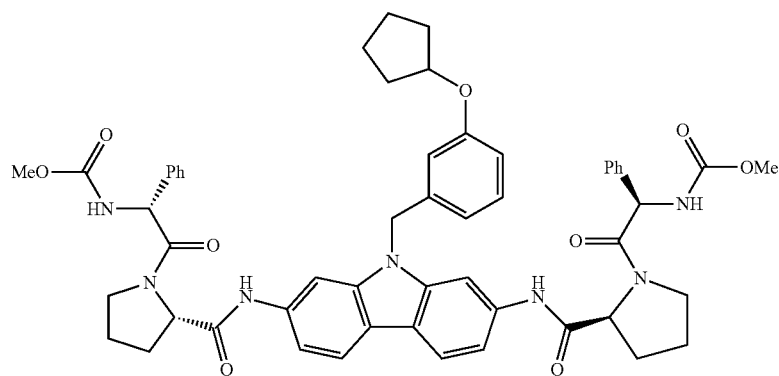 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3cccc(OC4CCCC4)c3)c2c1)c1ccccc1]

Step (1). Preparation of 2,7-dibromo-9-(3-(cyclopentyloxy)benzyl)-9H-carbazole The 3-((2,7-dibromo-9H-carbazole-9-yl)methyl)phenol (400 mg, 0.928 mmol) prepared in Step (2) of Example 30 and bromocyclopentane (0.15 mL, 1.392 mmol) were dissolved in DMF (4 mL), and then the resulting mixture was stirred at 90° C. for 5 hours. When the reaction was completed, the temperature was cooled to room temperature, and then the reaction product was diluted by adding ethyl acetate thereto, and washed by using H$_2$O and brine. The collected organic layer was dried over sodium sulfate, and then filtered and concentrated under reduced pressure. The concentrated solution was separated and purified with column chromatography (hexane/EtOAc, 50/1, v/v) to obtain a target compound (169 mg, 36.5%).
$^1$H NMR (400 MHz, CDCl$_3$) δ 7.91 (d, J=8.3 Hz, 2H), 7.52 (d, J=1.5 Hz, 2H), 7.39 (dd, J=8.3, 1.6 Hz, 2H), 7.21 (t, J=7.9 Hz, 1H), 6.81 (dd, J=8.2, 2.0 Hz, 1H), 6.67 (dd, J=7.6, 0.7 Hz, 1H), 6.63 (d, J=1.9 Hz, 1H), 5.34 (s, 2H), 4.69-4.65 (m, 1H), 1.90-1.74 (m, 6H), 1.66-1.58 (m, 2H); $^{13}$C NMR (100 MHz, CDCl$_3$) δ 158.68, 141.63, 137.52, 130.01, 123.04, 121.51, 121.47, 119.95, 117.98, 114.39, 113.77, 112.30, 79.25, 46.68, 32.80, 24.09.

Step (2). Preparation of N,N'-(9-(3-(cyclopentyloxy)benzyl)-9H-carbazole-2,7-diyl)bis(1,1-diphenylmethaneimine)

The method in Step (2) of Example 1 was performed, and a target compound (88 mg, 37.1%) was obtained by using 2,7-dibromo-9-(3-(cyclopentyloxy)benzyl)-9H-carbazole (169 mg, 0.339 mmol) and benzophenoneimine (0.13 mL, 0.779 mmol).
$^1$H NMR (400 MHz, CDCl$_3$) δ 7.81-7.73 (m, 6H), 7.54-7.42 (m, 7H), 7.25-7.18 (m, 6H), 7.16-7.10 (m, 4H), 6.77-6.74 (m, 3H), 6.67-6.66 (m, 2H), 6.50-6.44 (m, 2H), 5.14 (s, 2H), 4.67-4.66 (m, 1H), 1.88-1.77 (m, 6H), 1.66-1.61 (m, 2H).

Step (3). Preparation of 9-(3-(cyclopentyloxy)benzyl)-9H-carbazole-2,7-diamine dihydrochloride The method in Step (3) of Example 1 was performed, and a yellow solid target compound (32 mg, 57.2%) was obtained by using N,N'-(9-(3-(cyclopentyloxy)benzyl)-9H-carbazole-2,7-diyl)bis(1,1-diphenylmethaneimine) (88 mg, 0.126 mmol).
$^1$H NMR (400 MHz, DMSO-d$_6$) δ 10.38 (bs, 6H), 8.29 (d, J=8.3 Hz, 2H), 7.60 (d, J=1.4 Hz, 2H), 7.26 (dd, J=8.3, 1.7 Hz, 2H), 7.19 (t, J=7.9 Hz, 1H), 6.78 (dd, J=8.0, 2.2 Hz, 1H), 6.66 (d, J=7.6 Hz, 1H), 6.61 (s, 1H), 5.61 (s, 2H), 4.73-4.70 (m, 1H), 1.85-1.81 (m, 2H), 1.64-1.52 (m, 6H).

Step (4). Preparation of dimethyl ((1R,1'R)-((2S,2'S)-(((9-(3-(cyclopentyloxy)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (25 mg, 53.3%) was obtained by using 9-(3-(cyclopentyloxy)benzyl)-9H-carbazole-2,7-diamine dihydrochloride (22 mg, 0.050 mmol).
$^1$H NMR (400 MHz, CDCl$_3$) δ 9.51 (s, 2H), 7.72-7.70 (m, 4H), 7.45-7.44 (m, 4H), 7.41-7.37 (m, 6H), 7.23-7.20 (m, 2H), 7.09 (t, J=7.9 Hz, 1H), 6.68-6.64 (m, 2H), 6.59 (s, 1H), 6.20 (d, J=6.7 Hz, 2H), 5.55 (d, J=7.0 Hz, 2H), 5.29-5.19 (m, 2H), 4.76-4.75 (m, 2H), 4.63-4.61 (m, 1H), 3.93-3.89 (m, 2H), 3.60 (s, 6H), 3.35-3.28 (m, 2H), 2.42-2.39 (m, 2H), 2.26-2.19 (m, 2H), 1.97-1.86 (m, 4H), 1.81-1.68 (m, 6H), 1.57-1.55 (m, 2H); $^{13}$C NMR (100 MHz, CDCl$_3$) δ 169.95, 168.72, 158.32, 156.13, 141.01, 138.77, 136.44, 136.03, 129.47, 129.16, 128.76, 127.95, 119.68, 119.15, 118.47, 114.12, 113.73, 111.97, 100.03, 78.95, 61.63, 57.34, 52.29, 47.39, 45.97, 32.75, 32.73, 28.32, 24.71, 24.06. LC/MS (ESI-TOF) m/z calcd for C$_{53}$H$_{58}$N$_7$O$_9$ [M+H]$^+$: 936.43 found 936.30.

Example 40. Preparation of dimethyl ((1R,1'R)-((2S,2'S)-(((9-(3-(2-(2-methoxyethoxy)ethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate

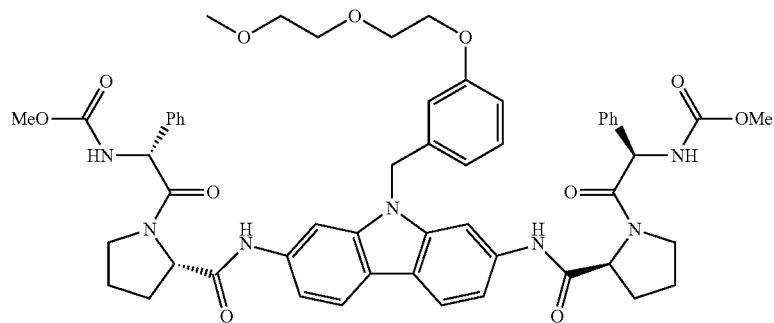 [SMILES: COCCOCCOc1cccc(Cn2c3cc(NC(=O)[C@@H]4CCCN4C(=O)[C@H](NC(=O)OC)c4ccccc4)ccc3c3ccc(NC(=O)[C@@H]4CCCN4C(=O)[C@H](NC(=O)OC)c4ccccc4)cc32)c1]

Step (1). Preparation of 2,7-dibromo-9-(3-(2-(2-methoxyethoxy)ethoxy)benzyl)-9H-carbazole The 3-((2,7-dibromo-9H-carbazole-9-yl)methyl)phenol (400 mg, 0.928 mmol) prepared in Step (2) of Example 30 was dissolved in dimethoxyethane (10 mL), and then potassium carbonate (256 mg, 1.856 mmol) and 1-bromo-2-(2-methoxyethoxy)ethane (0.25 mL, 1.856 mmol) were added thereto, and the resulting mixture was refluxed under heating for two and half days. When the reaction was completed, the temperature was cooled to room temperature, and then the filtrate was concentrated under reduced pressure by filtering the reaction mixture. The concentrated solution was separated and purified with column chromatography (hexane/EtOAc, 10/1, v/v) to obtain a target compound (450 mg, 91.0%).

$^1$H NMR (400 MHz, CDCl$_3$) δ 7.87 (d, J=8.2 Hz, 2H), 7.47 (d, J=1.5 Hz, 2H), 7.37 (dd, J=8.3, 1.6 Hz, 2H), 7.21 (t, J=7.9 Hz, 1H), 6.81 (dd, J=8.1, 2.2 Hz, 1H), 6.69 (d, J=7.6 Hz, 1H), 6.64 (d, J=1.9 Hz, 1H), 5.29 (s, 2H), 4.05 (t, J=4.9 Hz, 2H), 3.82-3.79 (m, 2H), 3.70-3.68 (m, 2H), 3.58-3.56 (m, 2H), 3.40 (s, 3H); $^{13}$C NMR (100 MHz, CDCl$_3$) δ 159.34, 141.55, 137.64, 130.09, 123.06, 121.52, 121.43, 119.96, 118.67, 113.31, 113.06, 112.20, 71.94, 70.73, 69.64, 67.32, 59.09, 46.56.

Step (2). Preparation of N,N'-(9-(3-(2-(2-methoxyethoxy)ethoxy)benzyl)-9H-carbazole-2,7-diyl)bis(1,1-diphenylmethaneimine)

The method in Step (2) of Example 1 was performed, and a target compound (508 mg, 82.0%) was obtained by using 2,7-dibromo-9-(3-(2-(2-methoxyethoxy)ethoxy)benzyl)-9H-carbazole (450 mg, 0.844 mmol).

$^1$H NMR (400 MHz, CDCl$_3$) δ 7.82-7.80 (m, 4H), 7.77 (d, J=8.2 Hz, 2H), 7.52-7.48 (m, 2H), 7.46-7.42 (m, 4H), 7.26-7.19 (m, 6H), 7.17-7.13 (m, 5H), 6.82 (dd, J=8.1, 2.1 Hz, 1H), 6.72-6.71 (m, 2H), 6.68 (dd, J=8.2, 1.7 Hz, 2H), 6.53-6.49 (m, 2H), 5.15 (s, 2H), 4.06 (t, J=4.9 Hz, 2H), 3.86 (t, J=4.9 Hz, 2H), 3.74-3.72 (m, 2H), 3.61-3.58 (m, 2H), 3.41 (s, 3H); $^{13}$C NMR (100 MHz, CDCl$_3$) δ 168.16, 159.08, 149.10, 141.57, 139.83, 138.73, 136.43, 130.74, 129.71, 129.52, 129.41, 128.60, 128.24, 127.96, 119.77, 119.19, 118.81, 113.98, 113.00, 112.84, 101.54, 71.98, 70.77, 69.74, 67.23, 59.11, 46.36.

Step (3). Preparation of 9-(3-(2-(2-methoxyethoxy)ethoxy)benzyl)-9H-carbazole-2,7-diamine dihydrochloride The method in Step (3) of Example 1 was performed, and a target compound (324 mg, 97.8%) was obtained by using N,N'-(9-(3-(2-(2-methoxyethoxy)ethoxy)benzyl)-9H-carbazole-2,7-diyl)bis(1,1-diphenylmethaneimine).

$^1$H NMR (400 MHz, DMSO-d$_6$) δ 10.50 (bs, 6H), 8.29 (d, J=8.3 Hz, 2H), 7.64 (d, J=1.5 Hz, 2H), 7.28 (dd, J=8.3, 1.7 Hz, 2H), 7.21 (t, J=8.1 Hz, 1H), 6.84 (dd, J=8.2, 1.8 Hz, 1H), 6.70-6.69 (m, 2H), 5.61 (s, 2H), 4.03-4.01 (m, 2H), 3.68-3.66 (m, 2H), 3.54-3.52 (m, 2H), 3.43-3.40 (m, 2H), 3.21 (s, 3H); $^{13}$C NMR (100 MHz, DMSO-d$_6$) δ 159.19, 141.20, 138.87, 131.25, 130.48, 122.17, 121.35, 119.15, 115.17, 113.61, 113.34, 104.56, 71.69, 70.08, 69.28, 67.50, 58.50, 46.32.

Step (4). Preparation of dimethyl ((1R,1'R)-((2S,2'S)-(((9-(3-(2-(2-methoxyethoxy)ethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (30 mg, 29.2%) was obtained by using 9-(3-(2-(2-methoxyethoxy)ethoxy)benzyl)-9H-carbazole-2,7-diamine dihydrochloride (50 mg, 0.105 mmol).

$^1$H NMR (400 MHz, CDCl$_3$) δ 9.34 (s, 2H), 7.82-7.80 (m, 4H), 7.45-7.38 (m, 10H), 7.23-7.12 (m, 3H), 6.79-6.68 (m, 3H), 6.08 (d, J=7.0 Hz, 2H), 5.53-5.52 (m, 2H), 5.35-5.25 (m, 2H), 4.79-4.78 (m, 2H), 4.04 (t, J=5.0 Hz, 2H), 3.88-3.84 (m, 2H), 3.78-3.76 (m, 2H), 3.67-3.62 (m, 8H), 3.54-3.52 (m, 2H), 3.36 (s, 3H), 3.32-3.26 (m, 2H), 2.48-2.44 (m, 2H), 2.21-2.18 (m, 2H), 1.88-1.85 (m, 4H); $^{13}$C NMR (100 MHz, CDCl$_3$) δ 170.20, 168.56, 159.15, 156.26, 141.26, 138.83, 136.31, 136.12, 129.60, 129.12, 128.72, 127.94, 119.70, 119.36, 119.25, 113.64, 112.97, 112.24, 100.33, 71.94, 70.62, 69.69, 67.39, 61.60, 58.87, 57.53, 52.23, 47.25, 46.18, 28.05, 24.65.

Example 41. Preparation of dimethyl ((1R,1'R)-((2S,2'S)-(((9-(3-(2-methoxyethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate

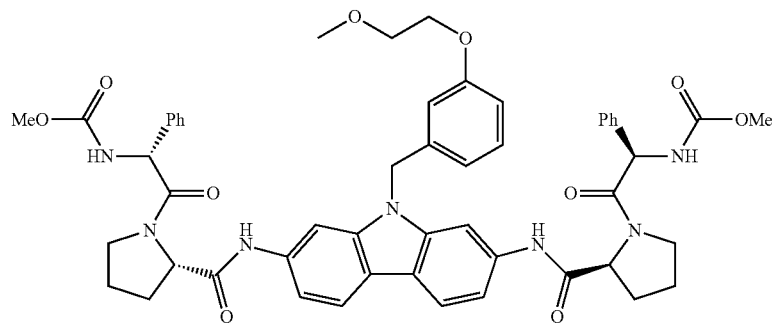 [SMILES: COCCOc1cccc(Cn2c3cc(NC(=O)[C@@H]4CCCN4C(=O)[C@H](NC(=O)OC)c4ccccc4)ccc3c3ccc(NC(=O)[C@@H]4CCCN4C(=O)[C@H](NC(=O)OC)c4ccccc4)cc32)c1]

Step (1). Preparation of 2,7-dibromo-9-(3-(2-methoxyethoxy)benzyl)-9H-carbazole The method in Step (1) of Example 1 was performed, and a target compound (388 mg, 91.9%) was obtained by using 3-((2,7-dibromo-9H-carbazole-9-yl)methyl)phenol (372 g, 0.863 mmol) and 2-methoxy-bromoethane (97 μL, 1.035 mmol).

$^1$H NMR (400 MHz, CDCl$_3$) δ 7.87 (d, J=8.3 Hz, 2H), 7.47 (d, J=1.5 Hz, 2H), 7.37 (dd, J=8.3, 1.6 Hz, 2H), 7.22 (t, J=7.9 Hz, 1H), 6.82 (dd, J=8.2, 2.1 Hz, 1H), 6.71 (d, J=7.6 Hz, 1H), 6.66-6.65 (m, 1H), 5.27 (s, 2H), 4.04-4.02 (m, 2H), 3.70-3.68 (m, 2H), 3.43 (s, 3H); $^{13}$C NMR (100 MHz, CDCl$_3$) δ 159.33, 141.53, 137.68, 130.10, 123.07, 121.53, 121.43, 119.98, 118.75, 113.13, 112.20, 70.91, 67.17, 59.23, 46.53.

Step (2). Preparation of N,N'-(9-(3-(2-methoxyethoxy)benzyl)-9H-carbazole-2,7-diyl)bis(1,1-diphenylmethaneimine)

The method in Step (2) of Example 1 was performed, and a target compound (296 mg, 72.4%) was obtained by using 2,7-dibromo-9-(3-(2-methoxyethoxy)benzyl)-9H-carbazole (388 mg, 0.793 mmol).

$^1$H NMR (400 MHz, CDCl$_3$) δ 7.83-7.81 (m, 4H), 7.77 (d, J=8.2 Hz, 2H), 7.52-7.48 (m, 2H), 7.46-7.42 (m, 4H), 7.25-7.14 (m, 11H), 6.84 (dd, J=8.2, 1.9 Hz, 1H), 6.72 (d, J=1.4 Hz, 2H), 6.67 (dd, J=8.2, 1.7 Hz, 2H), 6.55-6.52 (m, 2H), 5.16 (s, 2H), 4.04-4.02 (m, 2H), 3.75-3.73 (m, 2H), 3.46 (s, 3H); $^{13}$C NMR (100 MHz, CDCl$_3$) δ 168.02, 159.10, 149.27, 141.58, 139.95, 138.78, 136.52, 130.65, 129.71, 129.50, 129.36, 128.52, 128.23, 127.95, 119.75, 119.16, 118.87, 113.93, 113.01, 112.81, 101.50, 71.02, 67.09, 59.22, 46.37.

Step (3). Preparation of 9-(3-(2-methoxyethoxy)benzyl)-9H-carbazole-2,7-diamine dihydrochloride The method in Step (3) of Example 1 was performed, and a target compound (153 mg, 82.1%) was obtained by using N,N'-(9-(3-(2-(methoxyethoxy)benzyl)-9H-carbazole-2,7-diyl)bis(1,1-diphenylmethaneimine) (296 mg, 0.429 mmol).

$^1$H NMR (400 MHz, DMSO-d$_6$) δ 10.53 (bs, 6H), 8.27 (d, J=8.2 Hz, 2H), 7.63 (d, J=1.4 Hz, 2H), 7.27 (dd, J=8.3, 1.6 Hz, 2H), 7.18 (t, J=7.9 Hz, 1H), 6.81 (dd, J=8.2, 2.2 Hz, 1H), 6.70-6.66 (m, 2H), 5.58 (s, 2H), 4.02-3.99 (m, 2H), 3.58-3.55 (m, 2H), 3.23 (s, 3H); $^{13}$C NMR (100 MHz, DMSO-d$_6$) δ 159.20, 141.16, 138.84, 131.16, 130.46, 122.16, 121.38, 119.18, 115.21, 113.60, 113.34, 104.62, 70.73, 67.25, 58.55, 46.32.

Step (4). Preparation of dimethyl ((1R,1'R)-((2S,2'S)-(((9-(3-(2-methoxyethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (45 mg, 41.6%) was obtained by using 9-(3-(2-methoxyethoxy)benzyl)-9H-carbazole-2,7-diamine dihydrochloride (50 mg, 0.115 mmol).

$^1$H NMR (400 MHz, CDCl$_3$) δ 9.55 (s, 2H), 7.70-7.65 (m, 4H), 7.46-7.45 (m, 4H), 7.40-7.36 (m, 6H), 7.22-7.21 (m, 2H), 7.11 (t, J=7.9 Hz, 1H), 6.73-7.70 (m, 2H), 6.63 (s, 1H), 6.22 (d, J=6.8 Hz, 2H), 5.56 (d, J=6.9 Hz, 2H), 5.26-5.13 (m, 2H), 4.76-4.75 (m, 2H), 4.03-3.98 (m, 2H), 3.97-3.91 (m, 2H), 3.66 (t, J=4.7 Hz, 2H), 3.60 (s, 6H), 3.38 (s, 3H), 3.35-3.29 (m, 2H), 2.41-2.37 (m, 2H), 2.30-2.23 (m, 2H), 1.97-1.87 (m, 4H); $^{13}$C NMR (100 MHz, CDCl$_3$) δ 169.81, 168.88, 158.97, 156.09, 140.86, 138.96, 136.61, 136.06, 129.52, 129.13, 128.72, 127.94, 119.62, 119.28, 119.08, 113.30, 112.73, 111.94, 111.94, 99.88, 70.98, 66.99, 61.67, 59.08, 57.30, 52.26, 47.45, 45.87, 28.56, 24.73. LC/MS (ESI-TOF) m/z calcd for C$_{52}$H$_{56}$N$_7$C$_{10}$ [M+H]$^+$: 938.41 found 938.35.

Example 42. Preparation of dimethyl ((1R,1'R)-((2S,2'S)-(((9-(1-phenyldecyl)-9H-carbazole-2,7-diyl)bis(azanediyl))bis(carbonyl))bis(pyrrolidine-2,1-diyl))bis(2-oxo-1-phenylethane-2,1-diyl))dicarbamate

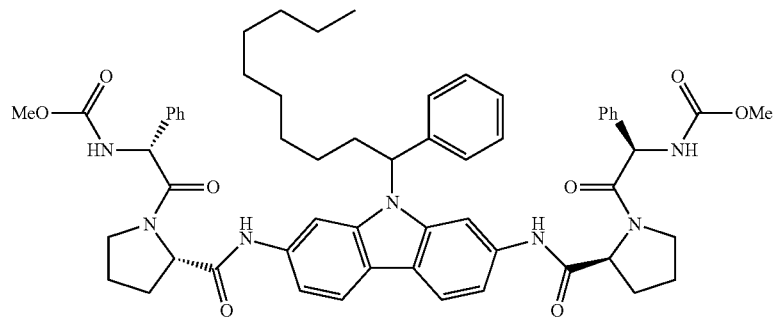 [SMILES: CCCCCCCCCC(c1ccccc1)n1c2cc(NC(=O)[C@@H]3CCCN3C(=O)[C@H](NC(=O)OC)c3ccccc3)ccc2c2ccc(NC(=O)[C@@H]3CCCN3C(=O)[C@H](NC(=O)OC)c3ccccc3)cc21]

Step (1). Preparation of (1-bromodecyl)benzene

The method in Step (1) of Example 29 was performed, and 1.04 g (3.51 mmol, 93.7%) of a target compound was obtained by using n-decylbenzene (1 mL, 3.74 mmol) and NBS (0.80 g, 4.49 mmol).

$^1$H NMR (400 MHz, CDCl$_3$) δ 7.40-7.25 (m, 5H), 4.95 (t, J=7.5 Hz, 1H), 2.29-2.24 (m, 1H), 2.16-2.12 (m, 1H), 1.31-1.25 (m, 14H), 0.87 (t, J=6.9 Hz, 3H); $^{13}$C NMR (100 MHz, CDCl$_3$) δ 142.36, 128.66, 128.26, 127.27, 55.85, 40.02, 31.87, 29.49, 29.40, 29.27, 28.92, 28.26, 22.68, 14.12.

Step (2). Preparation of 2,7-dibromo-9-(1-phenyldecyl)-9H-carbazole

The method in Step (2) of Example 29 was performed, and a target compound (317 mg, 38.1%) was obtained by using 2,7-dibromo-9H-carbazole (500 mg, 1.54 mmol) and (1-bromodecyl)benzene (503 mg, 1.69 mmol).

$^1$H NMR (400 MHz, CDCl$_3$) δ 7.78 (d, J=8.3 Hz, 2H), 7.48 (d, J=1.2 Hz, 2H), 7.26 (dd, J=1.6, 8.3 Hz, 2H), 7.20-7.09 (m, 5H), 5.65 (q, J=5.2 Hz, 1H), 2.57-2.47 (m, 1H), 2.43-2.35 (m, 1H), 1.36-0.99 (m, 13H), 0.97-0.88 (m, 1H), 0.82 (t, J=7.1 Hz, 3H); $^{13}$C NMR (100 MHz, CDCl$_3$) δ 141.44, 139.46, 128.95, 127.90, 126.71, 122.99, 121.87, 121.56, 119.89, 113.66, 58.01, 32.02, 31.57, 29.62, 29.50, 29.49, 29.41, 26.76, 22.87, 14.37.

Step (3). Preparation of N,N'-(9-(1-phenyldecyl)-9H-carbazole-2,7-diyl)bis(1,1-diphenylmethaneimine)

The method in Step (2) of Example 1 was performed, and a target compound (148 mg, 35.9%) was obtained by using 2,7-dibromo-9-(1-phenyldecyl)-9H-carbazole (300 mg, 0.55 mmol) and benzophenoneimine (0.20 mL, 1.22 mmol).

$^1$H NMR (400 MHz, CDCl$_3$) δ 7.74-7.70 (m, 6H), 7.47-7.37 (m, 6H), 7.21-7.14 (m, 9H), 7.06-7.03 (m, 6H), 6.61-6.59 (m, 4H), 5.38 (q, J=5.2 Hz, 1H), 2.28-2.14 (m, 2H), 1.29-1.14 (m, 12H), 1.02-0.98 (m, 1H), 0.86 (t, J=6.9 Hz, 3H), 0.82-0.77 (m, 1H); $^{13}$C NMR (100 MHz, CDCl$_3$) δ 167.94, 148.88, 140.34, 139.93, 136.59, 130.61, 129.48, 129.32, 128.40, 128.38, 128.20, 127.91, 127.09, 126.71, 119.58, 119.36, 113.62, 102.58, 57.14, 31.89, 30.97, 29.64, 29.50, 29.46, 29.31, 26.62, 22.69, 14.14

Step (4). Preparation of 9-(1-phenyldecyl)-9H-carbazole-2,7-diamine dihydrochloride The method in Step (3) of Example 1 was performed, and a target compound (53 mg, 66.9%) was obtained by using N,N'-(9-(1-phenyldecyl)-9H-carbazole-2,7-diyl)bis(1,1-diphenylmethaneimine) (121 mg, 0.16 mmol).

$^1$H NMR (400 MHz, MeOD) δ 8.37 (d, J=7.7 Hz, 2H), 7.65 (d, J=4.1 Hz, 2H), 7.36-7.29 (m, 7H), 6.13 (q, J=5.2 Hz, 1H), 2.72-2.65 (m, 2H), 1.42-1.36 (m, 2H), 1.23-1.14 (m, 12H), 0.84 (t, J=6.8 Hz, 3H); $^{13}$C NMR (75 MHz, MeOD) δ 142.58, 140.79, 130.26, 130.02, 128.90, 127.86, 124.07, 123.43, 115.69, 106.92, 59.44, 32.96, 32.47, 30.52, 30.43, 30.41, 30.24, 27.81, 23.64, 14.44.

Step (5). Preparation of dimethyl ((1R,1'R)-((2S,2'S)-(((9-(1-phenyldecyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (46 mg, 56.1%) was obtained by using 9-(1-phenyldecyl)-9H-carbazole-2,7-diamine dihydrochloride (40 mg, 0.08 mmol) and ((R)-2-((methoxycarbonyl)amino)-2-phenylacetyl)-L-proline (56 mg, 0.18 mmol).

$^1$H NMR (400 MHz, CDCl$_3$) δ 9.25 (s, 2H), 8.05-8.03 (m, 2H), 7.89 (d, J=8.3 Hz, 2H), 7.47-7.29 (m, 14H), 7.27-7.22 (m, 3H), 6.03 (t, J=6.6 Hz, 2H), 5.86-5.80 (m, 1H), 5.45 (d, J=7.0 Hz, 2H), 4.77 (d, J=7.9 Hz, 2H), 3.77 (t, J=9.0 Hz, 2H), 3.62 (s, 6H), 3.20 (q, J=7.7 Hz, 2H), 2.72-2.70 (m, 1H), 2.54-2.42 (m, 3H), 2.16-2.04 (m, 2H), 1.89-1.82 (m, 2H), 1.79-1.72 (m, 2H), 1.33-1.10 (m, 13H), 1.03-1.02 (m, 1H), 0.84 (t, J=7.0 Hz, 3H); $^{13}$C NMR (75 MHz, CDCl$_3$) δ 170.50, 168.14, 156.37, 141.10, 140.31, 140.13, 135.72, 129.25, 128.89, 128.50, 128.46, 128.03, 127.18, 126.90, 119.70, 119.61, 112.08, 111.98, 101.76, 61.52, 57.79, 57.53, 52.40, 47.13, 31.83, 31.52, 31.33, 29.70, 29.51, 29.42, 29.22, 27.34, 26.79, 24.63, 22.63, 14.11. LC/MS (ESI-TOF) m/z calcd for C$_{58}$H$_{67}$N$_7$O$_8$Na [M+Na]$^+$: 1012.50 found 1012.35.

Example 43. Preparation of dimethyl ((1R,1'R)-((2S,2'S)-(((9-(2-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate

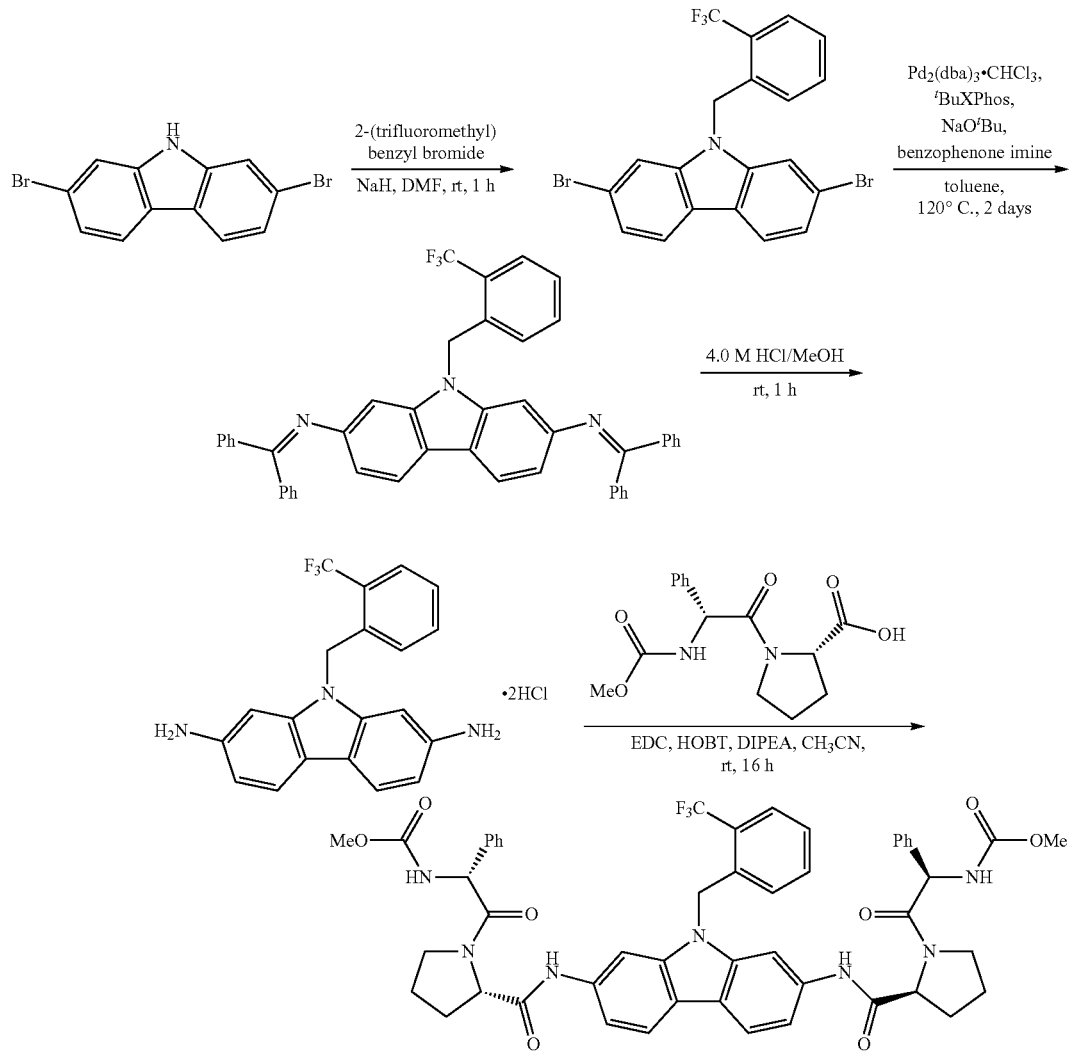

Step (1). Preparation of 2,7-dibromo-9-(2-trifluoromethyl)benzyl)-9H-carbazole The method in Step (1) of Example 1 was performed, and a target compound (743 mg, 100%) was obtained by using 2,7-dibromo-9H-carbazole (500 mg, 1.538 mmol) and 2-(trifluoromethyl)benzyl bromide (0.30 mL, 2.0 mmol).

$^1$H NMR (400 MHz, CDCl$_3$) δ 7.93 (d, J=8.0 Hz, 2H), 7.82 (d, J=7.6 Hz, 1H), 7.42 (dd, J=8.3, 1.6 Hz, 2H), 7.39-7.36 (m, 3H), 7.29-7.25 (m, 1H), 6.51 (d, J=7.8 Hz, 1H), 5.51 (s, 2H); $^{13}$C NMR (100 MHz, CDCl$_3$) δ 141.38, 134.46, 132.63, 127.75, 126.39, 123.49, 121.59, 121.47, 120.23, 111.98, 43.10, 43.06.

Step (2). Preparation of N,N'-(9-(2-(trifluoromethyl)benzyl)-9H-carbazole-2,7-diyl)bis(1,1-diphenylmethineimine)

The method in Step (2) of Example 1 was performed, and a target compound (854 mg, 81.0%) was obtained by using 2,7-dibromo-9-(2-(trifluoromethyl)benzyl)-9H-carbazole (745 mg, 1.542 mmol).

$^1$H NMR (400 MHz, CDCl$_3$) δ 7.87-7.81 (m, 6H), 7.75 (d, J=7.7 Hz, 1H), 7.52-7.47 (m, 2H), 7.44-7.40 (m, 4H), 7.36 (t, J=7.6 Hz, 1H), 7.22-7.14 (m, 11H), 6.79 (dd, J=8.2, 1.5 Hz, 2H), 6.62 (d, J=1.1 Hz, 2H), 6.33 (d, J=7.8 Hz, 1H), 5.41 (s, 2H); $^{13}$C NMR (100 MHz, CDCl$_3$) δ 168.18, 149.51, 141.43, 139.84, 136.55, 135.57, 132.49, 130.76, 129.47, 129.38, 128.49, 128.27, 127.92, 127.10, 126.86, 119.98, 119.25, 114.66, 101.19, 60.45, 42.78.

Step (3). Preparation of 9-(2-(trifluoromethyl)benzyl)-9H-carbazole-2,7-diamine dihydrochloride The method in Step (3) of Example 1 was performed, and a target compound (208 mg, 38.9%) was obtained by using N,N'-(9-(2-(trifluoromethyl)benzyl)-9H-carbazole-2,7-diyl)bis(1,1-diphenylmethineimine) (854 mg, 1.249 mmol).

$^1$H NMR (400 MHz, DMSO-d$_6$) δ 10.42 (bs 6H), 8.33 (d, J=8.3 Hz, 2H), 7.87 (d, J=7.4 Hz, 1H), 7.48 (t, J=7.5 Hz, 1H), 7.43-7.40 (m, 3H), 7.30 (dd, J=8.3, 1.7 Hz, 2H), 6.35 (d, J=7.7 Hz, 1H), 5.77 (s, 2H); $^{13}$C NMR (100 MHz, DMSO-d$_6$) 146.24, 143.22, 137.42, 133.51, 128.38, 128.07, 127.01, 126.95, 120.56, 117.49, 110.40, 96.06, 43.50.

Step (4). Preparation of dimethyl ((1R,1'R)-((2S,2'S)-(((9-(2-(trifluoromethyl)benzyl)-9H-carbazole-2,7-diyl)bis(azanediyl))biscarbonyl))bis(pyrrolidine-2,1-diyl))bis(2-oxo-1-phenylethane-2,1-diyl))dicarbamate The method in Example 2 was performed, and a target compound (51 mg, 46.9%) was obtained by using 9-(2-(trifluoromethyl)benzyl)-9H-carbazole-2,7-diamine dihydrochloride (50 mg, 0.117 mmol) and ((R)-2-((methoxycarbonyl)amino)-2-phenylacetyl)-L-proline (85.8 mg, 0.280 mmol).

$^1$H NMR (400 MHz, CDCl$_3$) δ 9.65 (s, 2H), 7.68 (d, J=7.6 Hz, 1H), 7.59 (d, J=8.2 Hz, 2H), 7.41-7.31 (m, 15H), 7.28-7.21 (m, 1H), 7.11 (t, J=7.5 Hz, 1H), 6.68-6.67 (m, 1H), 6.34 (d, J=7.7 Hz, 1H), 5.57 (d, J=7.2 Hz, 2H), 5.22-5.11 (m, 2H), 4.77-4.76 (m, 2H), 3.87-3.83 (m, 2H), 3.46 (s, 6H), 3.28-3.22 (m, 2H), 2.39-2.37 (m, 2H), 2.24-2.21 (m, 2H), 1.88-1.79 (m, 4H); $^{13}$C NMR (100 MHz, CDCl$_3$) δ 170.00, 168.53, 156.08, 140.83, 136.78, 136.53, 135.93, 132.26, 129.15, 128.64, 127.92, 126.83, 126.64, 119.77, 119.08, 112.02, 99.17, 61.48, 57.34, 52.09, 47.32, 28.09, 24.74.

Example 44. Preparation of dimethyl ((1R,1'R)-((2S,2'S)-(((9-(3-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate

Step (1). Preparation of 2,7-dibromo-9-(3-trifluoromethyl)benzyl)-9H-carbazole The method in Step (1) of Example 1 was performed, and a target compound (446 mg, 100%) was obtained by using 2,7-dibromo-9H-carbazole (300 mg, 0.923 mmol) and 3-(trifluoromethyl)benzyl bromide (0.18 mL, 1.20 mmol).

$^1$H NMR (400 MHz, CDCl$_3$) δ 7.91 (d, J=8.3 Hz, 2H), 7.55 (d, J=7.5 Hz, 1H), 7.48-7.44 (m, 3H), 7.40-7.36 (m, 3H), 7.10 (d, J=7.7 Hz, 1H), 5.42 (s, 2H); $^{13}$C NMR (100 MHz, CDCl$_3$) δ 141.41, 137.08, 129.70, 129.26, 124.86, 123.44, 123.08, 121.70, 121.61, 120.14, 112.01, 46.30.

Step (2). Preparation of N,N'-(9-(3-(trifluoromethyl)benzyl)-9H-carbazole-2,7-diyl)bis(1,1-diphenylmethaneimine)

The method in Step (2) of Example 1 was performed, and a target compound (574 mg, 54.6%) was obtained by using 2,7-dibromo-9-(3-(trifluoromethyl)benzyl)-9H-carbazole (743 mg, 1.538 mmol).

$^1$H NMR (400 MHz, CDCl$_3$) δ 7.82-7.78 (m, 6H), 7.55 (d, J=8.0 Hz, 1H), 7.51-7.47 (m, 2H), 7.44-7.41 (m, 4H), 7.32-7.29 (m, 2H), 7.20-7.12 (m, 10H), 6.91 (d, J=7.8 Hz, 1H), 6.72 (dd, J=8.2, 1.5 Hz, 2H), 6.65 (d, J=1.1 Hz, 2H), 5.21 (s, 2H); $^{13}$C NMR (100 MHz, CDCl$_3$) δ 168.17, 149.45, 141.37, 139.88, 138.33, 136.49, 130.75, 129.49, 129.38, 128.53, 128.27, 127.93, 119.98, 119.28, 114.43, 101.15, 45.97.

Step (3). Preparation of 9-(3-(trifluoromethyl)benzyl)-9H-carbazole-2,7-diamine dihydrochloride The method in Step (3) of Example 1 was performed, and a target compound (264 mg, 73.4%) was obtained by using N,N'-(9-(3-(trifluoromethyl)benzyl)-9H-carbazole-2,7-diyl)bis(1,1-diphenylmethaneimine) (574 mg, 0.839 mmol).

$^1$H NMR (400 MHz, DMSO-d$_6$) δ 10.50 (bs, 6H), 8.27 (d, J=8.3 Hz, 2H), 7.63-7.60 (m, 4H), 7.50 (t, J=7.7 Hz, 1H), 7.29 (dd, J=8.3, 1.6 Hz, 2H), 7.22 (d, J=7.8 Hz, 1H), 5.77 (s, 2H); $^{13}$C NMR (100 MHz, DMSO-d$_6$) δ 146.06, 143.18, 140.74, 131.07, 130.33, 124.85, 124.81, 124.81, 124.10, 124.06, 120.51, 117.51, 110.27, 96.27, 46.21.

Step (4). Preparation of dimethyl ((1R,1'R)-((2S,2'S)-(((9-(3-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (51 mg, 46.9%) was obtained by using 9-(3-(trifluoromethyl)benzyl)-9H-carbazole-2,7-diamine dihydrochloride (50 mg, 0.117 mmol) and ((R)-2-((methoxycarbonyl)amino)-2-phenylacetyl)-L-proline (85.8 mg, 0.280 mmol).

$^1$H NMR (400 MHz, CDCl$_3$) δ 9.59 (s, 2H), 7.67 (d, J=8.2 Hz, 2H), 7.56 (s, 2H), 7.40-7.33 (m, 12H), 7.29-7.25 (m, 2H), 7.20-7.15 (m, 2H), 6.10 (d, J=7.0 Hz, 2H), 5.52 (d, J=7.0 Hz, 2H), 5.26-5.14 (m, 2H), 4.73-7.70 (m, 2H), 3.91-3.88 (m, 2H), 3.55 (s, 6H), 3.33-3.27 (m, 2H), 2.38-

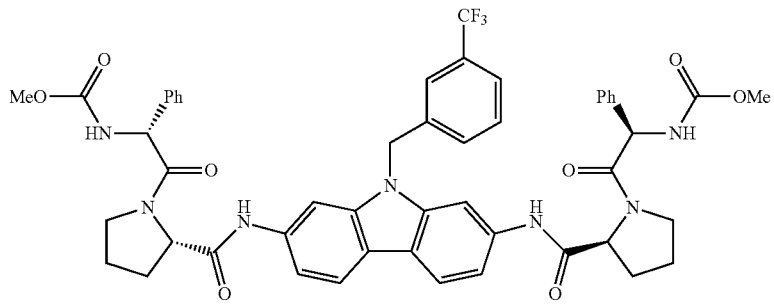 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3cccc(C(F)(F)F)c3)c2c1)c1ccccc1]

2.33 (m, 2H), 2.30-2.22 (m, 2H), 1.98-1.88 (m, 4H); $^{13}$C NMR (100 MHz, CDCl$_3$) δ 169.79, 169.08, 155.98, 140.59, 139.25, 136.67, 136.18, 130.03, 129.16, 129.08, 128.76, 127.88, 119.76, 119.11, 112.25, 99.66, 61.68, 57.24, 52.23, 47.51, 28.88, 24.73.

Example 45. Preparation of dimethyl ((1R,1'R)-((2S,2'S)-(((9-(4-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

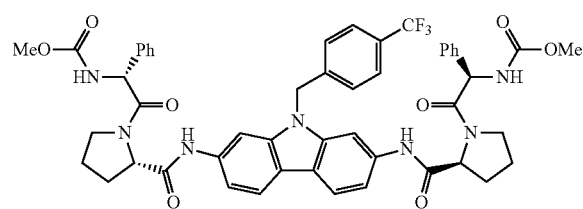 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(Cc3ccc(C(F)(F)F)cc3)c2c1)c1ccccc1]

Step (1). Preparation of 2,7-dibromo-9-(4-(trifluoromethyl)benzyl)-9H-carbazole

The method in Step (1) of Example 1 was performed, and a target compound (713 mg, 100%) was obtained by using 2,7-dibromo-9H-carbazole (500 mg, 1.540 mmol) and 4-(trifluoromethyl)benzyl bromide (0.31 mL, 2.0 mmol).

$^1$H NMR (400 MHz, CDCl$_3$) δ 7.96 (d, J=8.3 Hz, 2H), 7.59 (d, J=8.2 Hz, 2H), 7.47 (d, J=1.4 Hz, 2H), 7.42 (dd, J=8.3, 1.6 Hz, 2H), 7.21 (d, J=8.0 Hz, 2H), 5.48 (s, 2H); $^{13}$C NMR (100 MHz, CDCl$_3$) δ 141.38, 140.00, 126.47, 126.10, 126.06, 123.43, 121.70, 121.58, 120.14, 112.01, 46.25.

Step (2). Preparation of N,N'-(9-(4-(trifluoromethyl)benzyl)-9H-carbazole-2,7-diyl)bis(1,1-diphenylmethaneimine)

The method in Step (2) of Example 1 was performed, and a target compound (489 mg, 46.4%) was obtained by using 2,7-dibromo-9-(4-(trifluoromethyl)benzyl)-9H-carbazole (744 mg, 1.540 mmol).

$^1$H NMR (400 MHz, CDCl$_3$) δ 7.81-7.76 (m, 6H), 7.50-7.41 (m, 8H), 7.20-7.13 (m, 6H), 7.12-7.09 (m, 4H), 6.92 (d, J=8.0 Hz, 2H), 6.73 (dd, J=8.2, 1.7 Hz, 2H), 6.58 (d, J=1.4 Hz, 2H), 5.19 (s, 2H); $^{13}$C NMR (100 MHz, CDCl$_3$) δ 168.16, 149.41, 141.20, 139.82, 136.39, 130.71, 129.45, 129.33, 128.48, 127.86, 126.51, 125.62, 125.59, 119.93, 114.41, 100.91, 45.82.

Step (3). Preparation of 9-(4-(trifluoromethyl)benzyl)-9H-carbazole-2,7-diamine dihydrochloride The method in Step (3) of Example 1 was performed, and a target compound (224 mg, 88.1%) was obtained by using N,N'-(9-(4-(trifluoromethyl)benzyl)-9H-carbazole-2,7-diyl)bis(1,1-diphenylmethaneimine) (489 mg, 0.715 mmol).

$^1$H NMR (400 MHz, DMSO-d$_6$) δ 10.57 (bs, 6H), 8.29 (d, J=8.3 Hz, 2H), 7.68 (d, J=8.2 Hz, 2H), 7.62 (d, J=1.2 Hz, 2H), 7.33-7.29 (m, 4H), 5.77 (s, 2H); $^{13}$C NMR (100 MHz, DMSO-d$_6$) δ 142.10, 141.05, 131.16, 127.69, 126.20, 126.17, 122.21, 121.50, 115.42, 104.63, 45.98.

Step (4). Preparation of dimethyl ((1R,1'R)-((2S,2'S)-(((9-(4-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (53 mg, 28.9%) was obtained by using 9-(4-(trifluoromethyl)benzyl)-9H-carbazole-2,7-diamine dihydrochloride (70 mg, 0.197 mmol) and ((R)-2-((methoxycarbonyl)amino)-2-phenylacetyl)-L-proline (145 mg, 0.473 mmol).

$^1$H NMR (400 MHz, CDCl$_3$) δ 9.68 (s, 2H), 7.63-7.61 (m, 4H), 7.46-7.44 (m, 6H), 7.41-7.35 (m, 6H), 7.21-7.19 (m, 4H), 6.20 (d, J=7.0 Hz, 2H), 5.60 (d, J=7.1 Hz, 2H), 5.26-5.19 (m, 2H), 4.74-4.71 (m, 2H), 3.99-3.94 (m, 2H), 3.66-3.59 (m, 6H), 3.40-3.34 (m, 2H), 2.37-2.27 (m, 4H), 2.03-1.99 (m, 2H), 1.91-1.88 (m, 2H); $^{13}$C NMR (100 MHz, CDCl$_3$) δ 169.59, 169.28, 155.94, 141.52, 140.21, 136.88, 136.19, 129.13, 128.74, 127.80, 127.26, 125.54, 125.50, 119.70, 118.90, 111.94, 99.25, 61.75, 57.16, 52.28, 47.65, 45.29, 29.11, 24.79.

Example 46. Preparation of dimethyl ((1R,1'R)-((2S,2'S)-(((9-(nonane-5-yl)-9H-carbazole-2,7-diyl)bis(azanediyl))bis(carbonyl))bis(pyrrolidine-2,1-diyl))bis(2-oxo-1-phenylethane-2,1-diyl)) dicarbamate

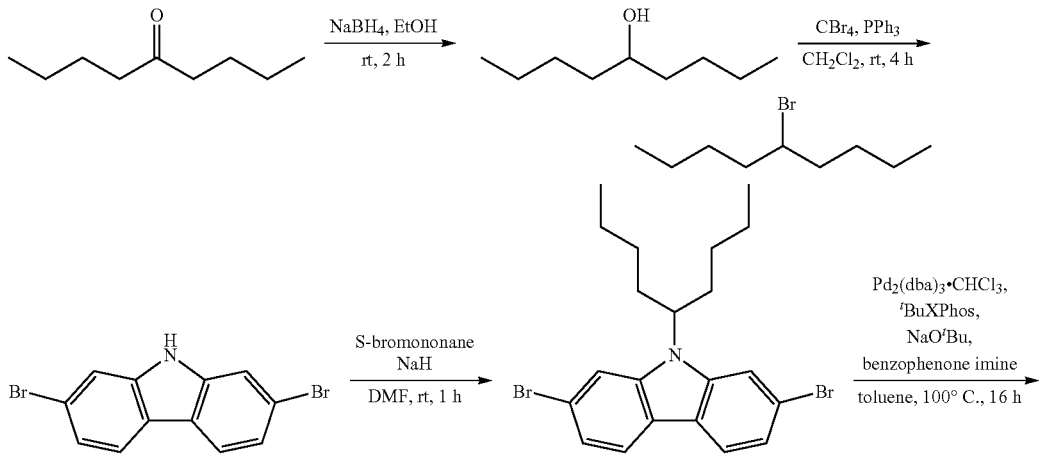

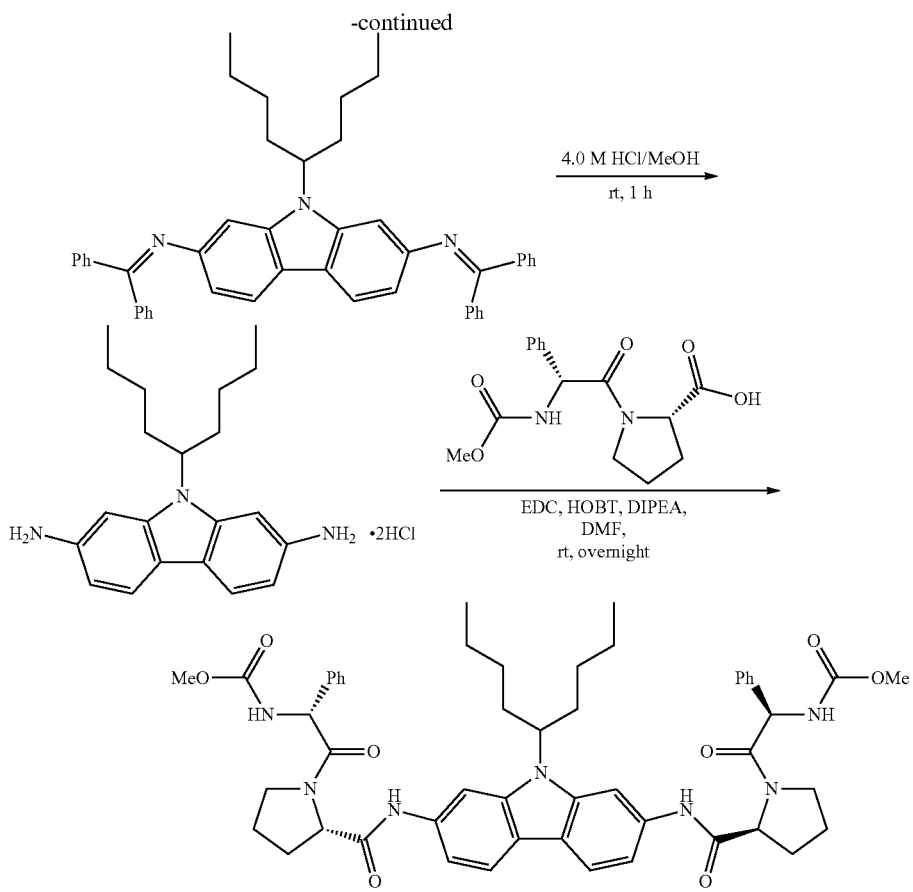

Step (1). Preparation of nonane-5-ol

Nonane-5-one (1.0 mL, 5.65 mmol), NaBH$_4$ (70 mg, 1.85 mmol), and ethanol (4 mL) were added to a reaction vessel under a dry argon atmosphere, and then the resulting mixture was stirred at room temperature for 2 hours. It was confirmed by TLC that the reaction was completed, and then the reaction mixture was filtered and concentrated under reduced pressure, and then distilled and washed twice with brine, and then extracted by separating the organic layer with ethyl acetate. The separated organic layer was dried over anhydrous sodium sulfate, and then filtered and concentrated under reduced pressure. The concentrated solution was purified by using a chromatography method (hexane/ethyl acetate, 20/1) to obtain a desired compound (558 mg, 68.5%).

$^1$H NMR (400 MHz, CDCl$_3$) δ 3.60-3.57 (m, 1H), 1.45-1.28 (m, 13H), 0.91 (t, J=7.1 Hz, 6H); $^{13}$C NMR (100 MHz, CDCl$_3$) δ 72.03, 37.19, 27.86, 22.78, 14.10.

Step (2). Preparation of 5-bromononane

Nonane-5-ol (558 mg, 3.87 mmol), CCr$_4$ (1.56 g, 4.70 mmol), and CH$_2$Cl$_2$ (5 mL) were added to a reaction vessel under a dry argon atmosphere, and then the resulting mixture was stirred at room temperature for 4 hours. It was confirmed by TLC that the reaction was completed, and then the reaction mixture was filtered and concentrated under reduced pressure, and then hexane was added to the reaction mixture, and the resulting mixture was filtered to obtain a desired compound (636 mg, 79.4%).

$^1$H NMR (400 MHz, CDCl$_3$) δ 4.10-3.92 (m, 1H), 1.84-1.79 (m, 4H), 1.55-1.49 (m, 2H), 1.42-1.29 (m, 6H), 0.92 (t, J=7.2 Hz, 6H); $^{13}$C NMR (100 MHz, CDCl$_3$) 58.80, 38.92, 29.76, 22.20, 13.97

Step (3). Preparation of 2,7-dibromo-9-(nonane-5-yl)-9H-carbazole

The method in Step (1) of Example 1 was performed, and a target compound (271 mg, 39.1%) was obtained by using 2,7-dibromo-9H-carbazole (500 mg, 1.540 mmol) and (5-bromononane) (356 mg, 1.69 mmol).

$^1$H NMR (400 MHz, CDCl$_3$) δ 7.93 (d, J=7.8 Hz, 2H), 7.73 (d, J=6.8 Hz, 1H), 7.58 (d, J=7.0 Hz, 1H), 7.39-7.36 (m, 2H), 4.48-4.41 (m, 1H), 2.25-2.24 (m, 2H), 1.99-1.92 (m, 2H), 1.32-1.19 (m, 6H), 1.00-0.97 (m, 2H), 0.81 (t, J=7.2 Hz, 6H); $^{13}$C NMR (100 MHz, CDCl$_3$) δ 122.59, 122.35, 121.44, 119.74, 114.49, 112.11, 57.07, 33.28, 28.95, 22.42, 13.84

Step (4). Preparation of N,N'-(9-(nonane-5-yl)-9H-carbazole-2,7-diyl)bis(1,1-diphenylmethaneimine)

The method in Step (2) of Example 1 was performed, and a target compound (169 mg, 46.8%) was obtained by using 2,7-dibromo-9-(nonane-5-yl)-9H-carbazole (250 mg, 0.554 mmol).

Step (5). Preparation of 9-(nonane-5-yl)-9H-carbazole-2,7-diamine dihydrochloride The method in Step (3) of Example 1 was performed, and a target compound (71 mg, 69.1%) was obtained by using N,N'-(9-(nonane-5-yl)-9H-carbazole-2,7-diyl)bis(1,1-diphenylmethaneimine) (116 mg, 0.178 mmol).

$^1$H NMR (400 MHz, CDCl$_3$) δ 7.71-7.66 (m, 2H), 6.77-6.53 (m, 4H), 4.33-4.26 (m, 1H), 3.72 (s, 6H), 2.24-2.14 (m, 2H), 1.88-1.79 (m, 2H), 1.31-1.12 (m, 6H), 1.09-0.97 (m, 2H), 0.77 (t, J=7.2 Hz, 6H); $^{13}$C NMR (100 MHz, CDCl$_3$) δ 143.84, 143.22, 119.76, 108.03, 97.73, 94.93, 56.21, 33.25, 39.13, 22.60, 13.97.

Step (6). Preparation of dimethyl ((1R,1'R)-((2S,2'S)-(((9-(nonane-5-yl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (39 mg, 34.1%) was obtained by using 9-(4-(trifluoromethyl)benzyl)-9H-carbazole-2,7-diamine dihydrochloride (50 mg, 0.13 mmol) and ((R)-2-((methoxycarbonyl)amino)-2-phenylacetyl)-L-proline (85 mg, 0.28 mmol).

$^1$H NMR (400 MHz, CDCl$_3$) δ 9.37 (s, 2H), 8.34-8.18 (m, 2H), 7.86-7.81 (m, 2H), 7.46-7.33 (m, 10H), 7.08 (t, J=8.3 Hz, 2H), 6.21 (d, J=7.0 Hz, 2H), 5.49 (d, J=7.1 Hz, 2H), 4.82 (d, J=7.4 Hz, 2H), 4.57-4.50 (m, 1H), 3.81 (t, J=8.2 Hz, 2H), 3.63 (s, 6H), 3.23 (q, J=8.6 Hz, 2H), 2.56-2.52 (m, 2H), 2.35-2.27 (m, 2H), 2.18-2.11 (m, 2H), 1.93-1.75 (m, 6H), 1.30-1.16 (m, 6H), 1.01-0.92 (m, 2H), 0.74 (t, J=7.0 Hz, 6H); $^{13}$C NMR (100 MHz, CDCl$_3$) δ 170.59, 168.34, 156.42, 142.84, 139.30, 135.83, 129.27, 128.90, 128.05, 119.75, 118.82, 111.63, 102.98, 61.60, 57.60, 56.67, 52.42, 47.19, 33.38, 29.06, 28.99, 27.41, 24.69, 22.58, 22.55, 13.96. LC/MS (ESI-TOF) m/z calcd for C$_{51}$H$_{61}$N$_7$O$_5$ [M+Na]$^+$: 922.45 found 922.60.

Example 47. Preparation of dimethyl ((1R,1'R)-((2S,2'S)-(((9-(cyclopentylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate

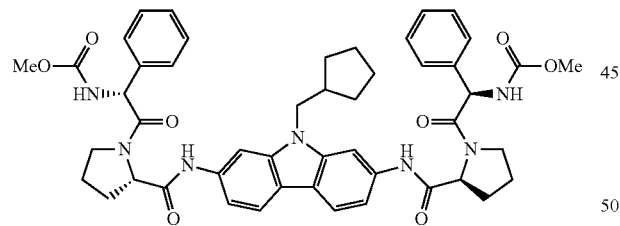

Step (1). Preparation of 2,7-dibromo-9-(cyclopentylmethyl)-9H-carbazole

The method in Step (1) of Example 1 was performed, and a target compound (281 mg, 44.9%) was obtained by using 2,7-dibromo-9H-carbazole (500 mg, 1.540 mmol) and bromomethylcyclopentane (0.22 mL, 1.69 mmol).

$^1$H NMR (400 MHz, CDCl$_3$) δ 7.86 (d, J=11.0 Hz, 2H), 7.53 (d, J=2.0 Hz, 2H), 7.32 (dd, J=2.1, 11.0 Hz, 2H), 4.11 (d, J=10.1 Hz, 2H), 2.59-2.44 (m, 1H), 1.76-1.65 (m, 4H), 1.62-1.50 (m, 2H), 1.37-1.27 (m, 2H); $^{13}$C NMR (100 MHz, CDCl$_3$) δ 141.60, 122.52, 121.46, 121.23, 119.65, 112.28, 48.04, 40.12, 30.81, 24.84.

Step (2). Preparation of N,N'-(9-(cyclopentylmethyl)-9H-carbazole-2,7-diyl)bis(1,1-diphenylmethaneimine)

The method in Step (2) of Example 1 was performed, and a target compound (74 mg, 18.4%) was obtained by using 2,7-dibromo-9-(cyclopentylmethyl)-9H-carbazole (270 mg, 0.66 mmol).

$^1$H NMR (400 MHz, CDCl$_3$) δ 7.78-7.75 (m, 4H), 7.73-7.71 (m, 2H), 7.47-7.39 (m, 6H), 7.22-7.19 (m, 6H), 7.18-7.14 (m, 4H), 6.67-6.63 (m, 4H), 3.82 (d, J=7.4 Hz, 2H), 2.08-1.97 (m, 1H), 1.58-1.50 (m, 2H), 1.48-1.31 (m, 4H), 1.02-0.94 (m, 2H); $^{13}$C NMR (100 MHz, CDCl$_3$) δ 167.84, 148.85, 141.44, 140.12, 136.66, 130.61, 129.67, 129.38, 128.46, 128.21, 127.97, 119.64, 118.96, 113.82, 101.39, 47.55, 39.64, 30.60, 24.89.

Step (3). Preparation of 9-(cyclopentylmethyl)-9H-carbazole-2,7-diamine dihydrochloride The method in Step (3) of Example 1 was performed, and a target compound (33 mg, 78.3%) was obtained by using N,N'-(9-(cyclopentylmethyl)-9H-carbazole-2,7-diyl)bis(1,1-diphenylmethaneimine) (74 mg, 0.12 mmol).

$^1$H NMR (400 MHz, MeOD) δ 8.28 (d, J=11.1 Hz, 2H), 7.64 (d, J=2.1 Hz, 2H), 7.27 (dd, J=2.4, 11.0 Hz, 2H), 4.38 (d, J=10.0 Hz, 2H), 2.66-2.56 (m, 1H), 1.81-1.66 (m, 6H), 1.62-1.48 (m, 2H); $^{13}$C NMR (100 MHz, MeOD) δ 163.76, 142.92, 130.87, 123.13, 115.07, 105.26, 46.09, 41.42, 31.57, 25.80.

Step (4). Preparation of dimethyl ((1R,1'R)-((2S,2'S)-(((9-(cyclopentylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (39 mg, 54.1%) was obtained by using 9-(cyclopentylmethyl)-9H-carbazole-2,7-diamine dihydrochloride (30 mg, 0.09 mmol) and ((R)-2-((methoxycarbonyl)amino)-2-phenylacetyl)-L-proline (58 mg, 0.19 mmol).

$^1$H NMR (400 MHz, CDCl$_3$) δ 9.68 (s, 2H), 7.59-7.52 (m, 4H), 7.45-7.44 (m, 4H), 7.36-7.35 (m, 6H), 7.14-7.12 (m, 2H), 6.32 (d, J=7.0 Hz, 2H), 5.57 (d, J=7.1 Hz, 2H), 4.71 (q, J=4.0 Hz, 2H), 3.96-3.90 (m, 4H), 3.59 (s, 6H), 3.34 (q, J=8.2 Hz, 2H), 2.40-2.27 (m, 5H), 2.03-1.86 (m, 4H), 1.61-1.48 (m, 4H), 1.45-1.42 (m, 2H), 1.26-1.20 (m, 2H); $^{13}$C NMR (100 MHz, CDCl$_3$) δ 169.69, 168.90, 156.01, 140.84, 136.87, 135.81, 129.15, 128.74, 127.89, 119.44, 118.76, 111.21, 99.72, 61.80, 57.23, 52.29, 47.57, 46.76, 40.20, 30.76, 30.43, 28.78, 24.82, 24.78, 24.71. LC/MS (ESI-TOF) m/z calcd for C$_{45}$H$_{53}$N$_7$O$_8$ [M+Na]$^+$: 378.39 found 878.45.

Example 48. Preparation of dimethyl ((1R,1'R)-((2S,2'S)-(((9-(cyclohexylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

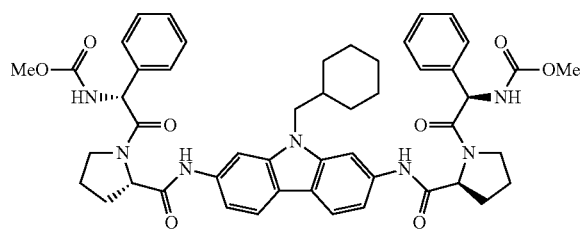 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(CC3CCCCC3)c2c1)c1ccccc1]

Step (1). Preparation of 2,7-dibromo-9-(cyclohexylmethyl)-9H-carbazole

The method in Step (1) of Example 1 was performed, and a target compound (438 mg, 67.5%) was obtained by using 2,7-dibromo-9H-carbazole (500 mg, 1.540 mmol) and bromomethylcyclohexane (0.24 mL, 1.69 mmol).

$^1$H NMR (400 MHz, CDCl$_3$) δ 7.71 (d, J=8.3 Hz, 2H), 7.42 (d, J=1.5 Hz, 2H), 7.24 (dd, J=1.7, 8.3 Hz, 2H), 3.80 (d, J=7.4 Hz, 2H), 1.91-1.81 (m, 1H), 1.63-1.52 (m, 5H), 1.11-0.94 (m, 5H); $^{13}$C NMR (100 MHz, CDCl$_3$) δ 141.76, 122.50, 121.39, 121.13, 119.70, 112.31, 49.78, 37.99, 31.37, 26.28, 25.78.

Step (2). Preparation of N,N'-(9-(cyclohexylmethyl)-9H-carbazole-2,7-diyl)bis(1,1-diphenylmethaneimine)

The method in Step (2) of Example 1 was performed, and a target compound (421 mg, 66.3%) was obtained by using 2,7-dibromo-9-(cyclohexylmethyl)-9H-carbazole (430 mg, 1.02 mmol).

$^1$H NMR (400 MHz, CDCl$_3$) δ 7.78-7.75 (m, 4H), 7.70 (dd, J=0.5, 8.0 Hz, 2H), 7.46-7.37 (m, 6H), 7.22-7.14 (m, 10H), 6.65-6.63 (m, 4H), 3.70 (d, J=7.3 Hz, 2H), 1.62-1.52 (m, 4H), 1.34-1.31 (m, 2H), 1.10-0.99 (m, 3H), 0.74 (q, J=11.8 Hz, 2H); $^{13}$C NMR (100 MHz, CDCl$_3$) δ 167.84, 148.97, 141.75, 140.19, 136.69, 130.65, 129.71, 129.41, 128.58, 128.27, 128.03, 119.67, 118.91, 113.79, 101.49, 49.45, 37.54, 31.21, 26.39, 25.73.

Step (3). Preparation of 9-(cyclohexylmethyl)-9H-carbazole-2,7-diamine dihydrochloride The method in Step (3) of Example 1 was performed, and a target compound (198 mg, 79.4%) was obtained by using N,N'-(9-(cyclohexylmethyl)-9H-carbazole-2,7-diyl)bis(1,1-diphenylmethaneimine) (421 mg, 0.68 mmol).

$^1$H NMR (400 MHz, DMSO-d$_6$) δ 9.76 (br s, 6H), 8.16 (d, J=7.9 Hz, 2H), 7.45 (d, J=1.9 Hz, 2H), 7.10 (d, J=7.8 Hz, 2H), 4.17 (d, J=7.0 Hz, 2H), 1.97-1.88 (m, 1H), 1.71-1.62 (m, 3H), 1.56-1.51 (m, 2H), 1.19-1.08 (m, 5H); $^{13}$C NMR (100 MHz, DMSO-d$_6$) δ 141.07, 131.24, 121.33, 120.28, 113.88, 103.68, 48.55, 37.50, 30.54, 25.76, 25.21.

Step (4). Preparation of dimethyl ((1R,1'R)-((2S,2'S)-(((9-(cyclohexylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate The method in Example 2 was performed, and a target compound (61 mg, 51.5%) was obtained by using 9-(cyclohexylmethyl)-9H-carbazole-2,7-diamine dihydrochloride (50 mg, 0.14 mmol) and ((R)-2-((methoxycarbonyl)amino)-2-phenylacetyl)-L-proline (92 mg, 0.30 mmol).

$^1$H NMR (400 MHz, CDCl$_3$) δ 9.68 (s, 2H), 7.53-7.51 (m, 4H), 7.45-7.44 (m, 4H), 7.35-7.34 (m, 6H), 7.15-7.13 (m, 2H), 6.38 (d, J=6.8 Hz, 2H), 5.58 (d, J=7.0 Hz, 2H), 4.73 (d, J=5.3 Hz, 2H), 3.93-3.90 (m, 2H), 3.76-3.75 (m, 2H), 3.59 (s, 6H), 3.34 (q, J=8.7 Hz, 2H), 2.39-2.27 (m, 4H), 2.04-1.85 (m, 5H), 1.61-1.48 (m, 5H), 1.09-0.97 (m, 5H); $^{13}$C NMR (100 MHz, CDCl$_3$) δ 169.58, 168.93, 155.97, 140.96, 136.95, 135.80, 129.15, 128.74, 127.90, 119.39, 118.64, 111.15, 99.71, 61.82, 57.21, 52.28, 48.74, 47.61, 38.04, 31.30, 31.19, 28.91, 26.29, 25.77, 24.85. LC/MS (ESI-TOF) m/z calcd for C$_{49}$H$_{55}$N$_7$O$_8$ [M+Na]$^+$: 892.40 found 892.55.

Example 49. Preparation of dimethyl ((1R,1'R)-((2S,2'S)-(((9-(dicyclopropylmethyl)-9H-carbazole-2,7-diyl)bis(azanediyl))bis(carbonyl))bis(pyrrolidine-2,1-diyl))bis(2-oxo-1-phenylethane-2,1-diyl)) dicarbamate

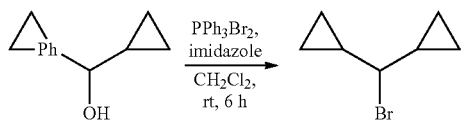

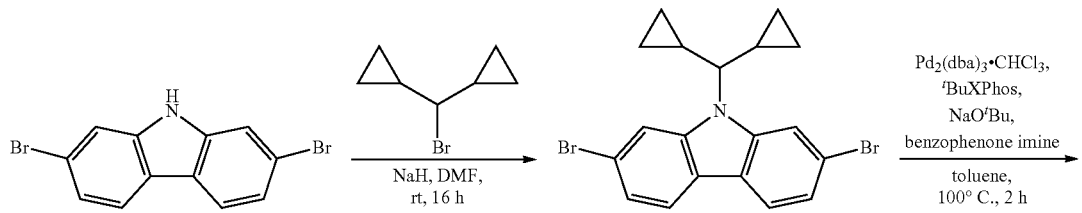

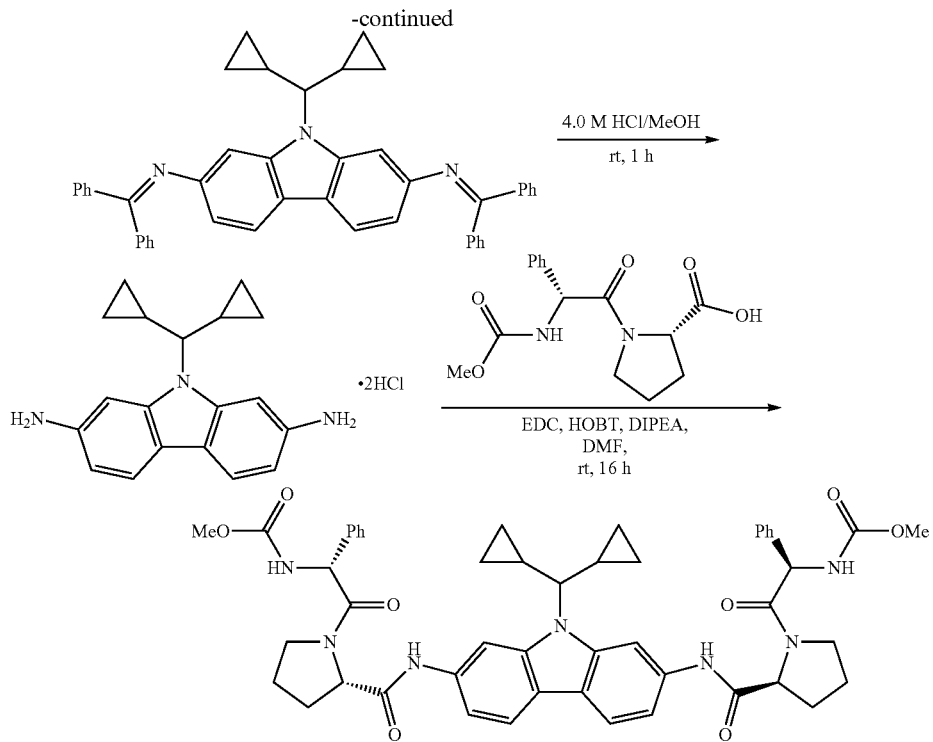

Step (1). Preparation of (bromomethylene)dicyclopropane

Dicyclopropylmethanol (1.6 g, 14.26 mmol) was dissolved in dichloromethane (32 mL) under an argon atmosphere, and then triphenylphosphine dibromide (7.225 g, 17.12 mmol) and imidazole (1.165 g, 17.12 mmol) were added thereto at 0° C. The reaction mixture was stirred at room temperature for 6 hours, and then saturated ammonium chloride was added thereto. The mixture was extracted by using dichloromethane, and the organic layer was washed with brine. The collected organic layer was dried over magnesium sulfate, and then filtered and concentrated under reduced pressure. The concentrated solution was separated and purified with column chromatography (100% hexane) to obtain a white solid target compound (1.807 g, 72.4%).

$^1$H NMR (400 MHz, CDCl$_3$) δ 5.47-5.41 (m, 1H), 5.09-5.03 (m, 1H), 3.33-3.30 (m, 2H), 2.53-2.47 (m, 2H), 1.38-1.29 (m, 1H), 0.68-0.63 (m, 2H), 0.34-0.30 (m, 2H).

Step (2). Preparation of 2,7-dibromo-9-(dicyclopropylmethyl)-9H-carbazole

The method in Step (1) of Example 1 was performed, and a target compound (1.562 g, 78.7%) was obtained by using 2,7-dibromo-9H-carbazole (1.54 g, 4.738 mmol) and (bromomethylene)dicyclopropane (1.659 g, 9.476 mmol).

$^1$H NMR (400 MHz, CDCl$_3$) δ 7.87 (d, J=6.2 Hz, 2H), 7.54 (d, J=0.9 Hz, 2H), 7.36 (dd, J=6.2, 1.0 Hz, 2H), 5.35-5.45 (m, 1H), 5.05-4.99 (m, 1H), 4.21-4.18 (m, 2H), 2.52-2.47 (m, 2H), 1.36-1.28 (m, 1H), 0.69-0.62 (m, 2H), 0.26-0.23 (m, 2H); $^{13}$C NMR (100 MHz, CDCl$_3$) δ 141.23, 137.42, 123.15, 122.52, 121.37, 121.18, 119.68, 112.13, 43.37, 31.72, 13.58, 6.52.

Step (3). Preparation of N,N'-(9-(dicyclopropylmethyl)-9H-carbazole-2,7-diyl)bis(1,1-diphenylmethaneimine)

The method in Step (2) of Example 1 was performed, and a target compound (530 mg, crude) was obtained by using 2,7-dibromo-9-(dicyclopropylmethyl)-9H-carbazole (378 mg, 0.902 mmol).

$^1$H NMR (400 MHz, CDCl$_3$) δ 7.85-7.83 (m, 4H), 7.72 (d, J=8.2 Hz, 2H), 7.55-7.45 (m, 6H), 7.30-7.25 (m, 6H), 7.24-7.21 (m, 4H), 6.78 (s, 2H), 6.63 (dd, J=8.2, 1.7 Hz, 2H), 5.46-5.39 (m, 1H), 5.01-4.95 (m, 1H), 3.99-3.95 (m, 2H), 2.19-2.13 (m, 2H), 1.39-1.32 (m, 2H), 0.72-0.68 (m, 2H), 0.35-0.31 (m, 2H); $^{13}$C NMR (100 MHz, CDCl$_3$) 5167.98, 141.08, 140.01, 136.84, 136.64, 130.72, 129.71, 129.42, 128.62, 128.26, 128.03, 123.55, 119.72, 119.14, 113.68 101.64, 43.10, 31.24, 13.57, 6.53.

Step (4). Preparation of 9-(dicyclopropylmethyl)-9H-carbazole-2,7-diamine dihydrochloride The method in Step (3) of Example 1 was performed, and a target compound (139 mg, 42.3%, 2 steps) was obtained by using N,N'-(9-(dicyclopropylmethyl)-9H-carbazole-2,7-diyl)bis(1,1-diphenylmethaneimine) (530 mg, crude).

$^1$H NMR (400 MHz, DMSO-d$_6$) 510.63 (bs, 6H), 8.24 (d, J=6.2 Hz, 2H), 7.67-7.64 (m, 2H), 7.25 (dd, J=6.2, 1.2 Hz, 2H), 5.51-5.44 (m, 1H), 4.91-4.85 (m, 1H), 4.35-4.31 (m, 2H), 2.46-2.41 (m, 2H), 1.28-1.19 (m, 1H), 0.53-0.48 (m, 2H), 0.08-0.05 (m, 2H); $^{13}$C NMR (100 MHz, DMSO-d$_6$) δ 140.89, 137.16, 130.69, 123.58, 121.99, 121.29, 114.83, 104.79, 43.25, 31.59, 13.70, 6.56.

Step (5). Preparation of dimethyl ((1R,1'R)-((2S,2'S)-(((9-(dicyclopropylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (73 mg, 61.3%) was obtained by using 9-(dicyclopropylmethyl)-9H-carbazole-2,7-diamine dihydrochloride (50 mg, 0.137 mmol) and ((R)-2-((methoxycarbonyl)amino)-2-phenylacetyl)-L-proline (101 mg, 0.329 mmol).

$^1$H NMR (400 MHz, CDCl$_3$) δ 9.66 (s, 2H), 7.63 (s, 1H), 7.56 (d, J=8.2 Hz, 2H), 7.48-7.47 (m, 4H), 7.41-7.38 (m, 7H), 7.16-7.14 (m, 2H), 6.32 (d, J=9.8 Hz, 2H), 5.61 (d, J=7.1 Hz, 2H), 5.44-5.37 (m, 1H), 4.99-4.93 (m, 1H), 4.77-4.75 (m, 2H), 4.11-4.06 (m, 4H), 3.66-3.63 (m, 6H), 3.40-3.34 (m, 2H), 2.45-2.27 (m, 6H), 2.06-1.99 (m, 2H), 1.93-1.91 (m, 2H), 1.30-1.21 (m, 1H), 0.60-0.52 (m, 2H), 0.25-0.22 (m, 2); $^{13}$C NMR (100 MHz, CDCl$_3$) δ 169.75, 168.95, 156.04, 140.40, 136.74, 136.20, 135.81, 129.15, 128.74, 127.90, 123.95, 119.46, 118.80, 111.23, 99.57, 61.77, 57.22, 52.34, 47.52, 42.52, 31.64, 28.71, 24.80, 13.39, 6.16.

Example 50. Preparation of dimethyl ((1R,1'R)-((2S,2'S)-(((9-phenethyl-9H-carbazole-2,7-diyl)bis(azanediyl))bis(carbonyl))bis(pyrrolidine-2,1-diyl))bis(2-oxo-1-phenylethane-2,1-diyl))dicarbamate

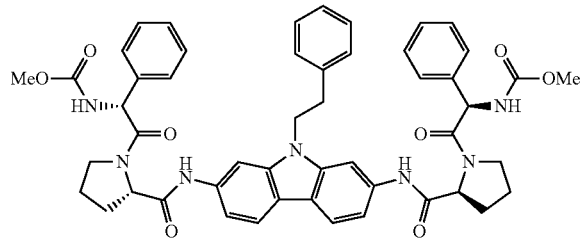 [SMILES: COC(=O)N[C@@H](C(=O)N1CCC[C@H]1C(=O)Nc1ccc2c3ccc(NC(=O)[C@@H]4CCCN4C(=O)[C@H](NC(=O)OC)c4ccccc4)cc3n(CCc3ccccc3)c2c1)c1ccccc1]

Step (1). Preparation of 2,7-dibromo-9-phenethyl-9H-carbazole

The method in Step (1) of Example 1 was performed, and 553 mg (1.29 mmol, 83.8%) of a target compound was obtained by using 2,7-dibromo-9H-carbazole (500 mg, 1.54 mmol) and (2-bromomethyl)benzene (0.24 mL, 1.69 mmol).

$^1$H NMR (400 MHz, CDCl$_3$) δ 7.79 (d, J=8.2 Hz, 2H), 7.30 (d, J=1.3 Hz, 2H), 7.27 (dd, J=1.6, 8.2 Hz, 2H), 7.24-7.19 (m, 3H), 7.06-7.04 (m, 2H), 4.31 (t, J=7.4 Hz, 2H), 3.02 (t, J=7.4 Hz, 2H); $^{13}$C NMR (100 MHz, CDCl$_3$) δ 141.13, 138.10, 128.80, 127.05, 122.71, 121.45, 121.29, 119.75, 111.99, 108.83, 45.08, 35.13.

Step (2). Preparation of N,N'-(9-phenethyl-9H-carbazole-2,7-diyl)bis(1,1-diphenylmethaneimine)

The method in Step (2) of Example 1 was performed, and a target compound (249 mg, 44.9%) was obtained by using 2,7-dibromo-9-phenethyl-9H-carbazole (500 mg, 1.17 mmol).

$^1$H NMR (400 MHz, CDCl$_3$) δ 7.79-7.77 (m, 4H), 7.69-7.67 (m, 2H), 7.48-7.39 (m, 6H), 7.27-7.14 (m, 13H), 7.07-7.05 (m, 2H), 6.67 (d, J=1.4 Hz, 2H), 6.60 (dd, J=1.7, 8.2 Hz, 2H), 4.11 (t, J=8.0 Hz, 2H), 2.66 (t, J=7.9 Hz, 2H); $^{13}$C NMR (100 MHz, CDCl$_3$) δ 168.00, 149.03, 140.94, 140.09, 138.59, 136.59, 130.71, 129.77, 129.43, 128.90, 128.63, 128.60, 128.29, 128.06, 126.59, 119.82, 119.13, 113.89, 101.36, 44.72, 34.57.

Step (3). Preparation of 9-phenethyl-9H-carbazole-2,7-diamine dihydrochloride

The method in Step (3) of Example 1 was performed, and a target compound (79 mg, 52.5%) was obtained by using N,N'-(9-phenethyl-9H-carbazole-2,7-diyl)bis(1,1-diphenylmethaneimine) (249 mg, 0.40 mmol).

$^1$H NMR (400 MHz, MeOD) δ 8.28 (d, J=8.3 Hz, 2H), 7.48 (d, J=1.6 Hz, 2H), 7.25 (dd, J=1.7, 8.3 Hz, 2H), 7.17-7.12 (m, 3H), 7.06-7.04 (m, 2H), 4.70 (t, J=6.8 Hz, 2H), 3.20 (t, J=6.8 Hz, 2H); $^{13}$C NMR (75 MHz, MeOD) δ 142.60, 139.65, 130.44, 129.98, 129.59, 127.78, 123.49, 123.18, 115.22, 105.29, 46.16, 35.73.

Step (4). Preparation of dimethyl ((1R,1'R)-((2S,2'S)-(((9-phenethyl-9H-carbazole-2,7-diyl)bis(azanediyl))bis(carbonyl))bis(pyrrolidine-2,1-diyl))bis(2-oxo-1-phenylethane-2,1-diyl))dicarbamate The method in Example 2 was performed, and a target compound (30 mg, 31.8%) was obtained by using 9-phenethyl-9H-carbazole-2,7-diamine dihydrochloride (40 mg, 0.11 mmol) and ((R)-2-((methoxycarbonyl)amino)-2-phenylacetyl)-L-proline (72 mg, 0.24 mmol).

$^1$H NMR (400 MHz, CDCl$_3$) δ 9.54 (s, 2H), 7.60-7.58 (m, 4H), 7.45-7.44 (m, 4H), 7.39-7.35 (m, 6H), 7.23-7.12 (m, 7H), 6.23 (d, J=6.9 Hz, 2H), 5.56 (d, J=7.1 Hz, 2H), 4.75 (dd, J=2.6, 8.1 Hz, 2H), 4.31-4.24 (m, 2H), 3.93-3.90 (m, 2H), 3.54 (s, 6H), 3.33 (q, J=8.2 Hz, 2H), 3.03-2.87 (m, 2H), 2.44-2.39 (m, 2H), 2.31-2.24 (m, 2H), 2.00-1.87 (m, 4H); $^{13}$C NMR (100 MHz, CDCl$_3$) δ 169.80, 168.88, 156.02, 140.26, 138.66, 136.75, 135.90, 129.17, 128.92, 128.77, 128.39, 127.91, 126.28, 119.55, 118.87, 111.36, 99.40, 61.78, 57.23, 52.31, 47.55, 43.99, 34.74, 28.73, 24.82. LC/MS (ESI-TOF) m/z calcd for C$_{50}$H$_{51}$N$_7$O$_8$Na [M+Na]$^+$: 900.37 found 900.40.

Example 51. Preparation of methyl ((R)-2-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-2-oxo-1-phenylethyl)carbamate with nitrogen and stirred for 30 minutes. Benzophenoneimine (106 μL, 0.94 mmol) was added to the mixture, and then the resulting mixture was stirred at 90° C. for 16 hours. The mixture completely reacted was cooled to room temperature, and then extracted by using ethyl acetate and distilled water, and the organic layer was dried by putting

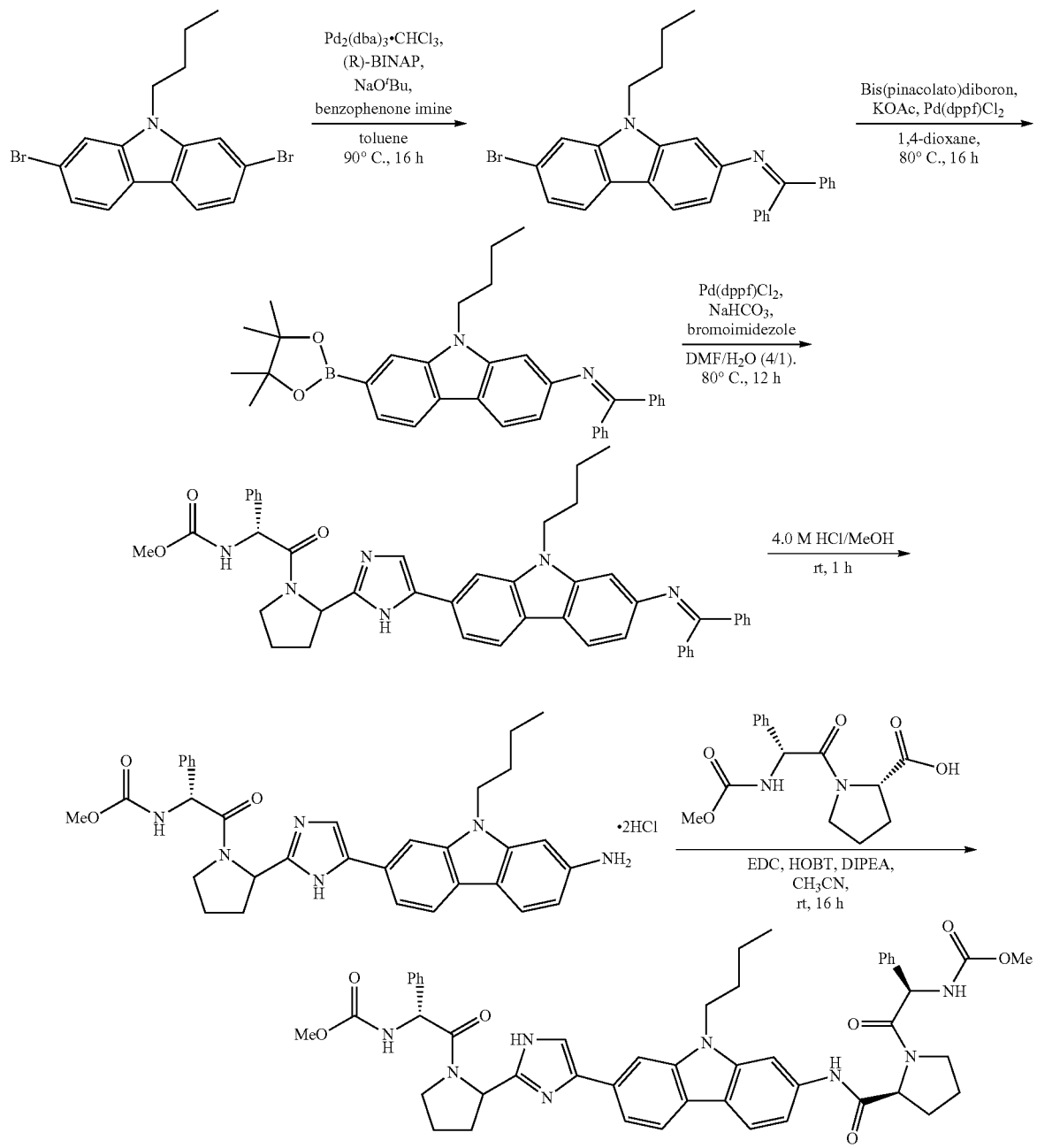

Step (1). Preparation of N-(7-bromo-9-butyl-9H-carbazole-2-yl)-1,1-diphenylmethaneimine 2,7-dibromo-9-butyl-9H-carbazole (300 mg, 0.78 mmol), Pd$_2$(dba)$_3$·CHCl$_3$ (41 mg, 0.04 mmol), (R)-(+)-(1,1'-binaphthalene-2,2'-diyl)bis(diphenylphosphine) ((R)-BINAP; 37 mg, 0.06 mmol), and NaO$^t$Bu (91 mg, 0.94 mmol) were added to toluene (4 mL). The reaction mixture was filled anhydrous sodium sulfate thereto, and then filtered and concentrated under reduced pressure. The mixture was separated and purified with column chromatography (hexane/EtOAc=20/1, v/v) to obtain a yellow solid target compound (134 mg, 35%).

$^1$H NMR (400 MHz, CDCl$_3$) δ 7.85-7.80 (m, 5H), 7.52-7.46 (m, 5H), 7.30-7.20 (m, 4H), 6.75 (m, 2H), 4.09 (t, J=7.2 Hz, 2H), 1.67 (m, 2H), 1.31 (m, 2H), 0.94 (t, J=7.2 Hz, 3H).

Step (2). Preparation of N-(9-butyl-7-(4,4,5,5-tetramethyl-1,3,2-dioxaborolane-2-yl)-9H-carbazole-2-yl)-1,1-diphenylmethaneimine The N-(7-bromo-9-butyl-9H-carbazole-2-yl)-1,1-diphenylmethaneimine (134 mg, 0.278 mmol) prepared in Step (1), [1,1'-bis(diphenylphosphino)ferocene]dichloropalladium (II) (Pd(dppf)Cl$_2$, 4.2 mg, 0.005 mmol), bis(pinacolato)diboron (66 mg, 0.26 mmol), and KOAc (31 mg, 0.31 mmol) were added to 1,4-dioxane (4 mL). The reaction mixture was filled with nitrogen and stirred at 80° C. for 16 hours. The mixture completely reacted was cooled to room temperature, and then extracted by using EtOAc and distilled water, and the organic layer was dried by putting anhydrous sodium sulfate thereto, and then filtered and concentrated under reduced pressure. The mixture was separated and purified with column chromatography (hexane/EtOAc, 25/1, v/v) to obtain a yellow solid target compound (55 mg, 99%).

$^1$H NMR (400 MHz, CDCl$_3$) δ 8.00 (d, J=0.4 Hz, 1H), 7.98 (d, J=0.8 Hz, 1H), 7.91-7.80 (m, 3H), 7.67 (d, J=0.8 Hz, 1H), 7.65-7.46 (m, 2H), 7.26-7.21 (m, 5H), 6.73 (s, 1H), 6.73 (d, J=8 Hz, 1H), 4.17 (t, J=2.8 Hz, 2H), 1.7, 1.42 (s, 12H), 1.31 (t, J=7.2 Hz, 2H), 0.93 (t, J=7.6 Hz, 3H).

Step (3). Preparation of methyl ((R)-2-((S)-2-(5-(9-butyl-7-((diphenylmethylene)amino)-9H-carbazole-2-yl)-1H-imidazole-2-yl)pyrrolidine-1-yl)-2-oxo-1-phenylethyl)carbamate The N-(9-butyl-7-(4,4,5,5-tetramethyl-1,3,2-dioxaborolane-2-yl)-9H-carbazole-2-yl)-1,1-diphenylmethaneimine (358 mg, 0.68 mmol) prepared in Step (2), Pd(dppf)Cl$_2$ (28 mg, 0.03 mmol), methyl ((R)-2-((S)-2-(5-bromo-1H-imidazole-2-yl)pyrrolidine-1-yl)-2-oxo-1-phenylethyl)carbamate (263 mg, 0.65 mmol), and sodium hydrogen carbonate (162 mg, 1.94 mmol) were added to a mixed solution of DMF (8 mL) and H$_2$O (2 mL). The reaction mixture was filled with nitrogen and stirred at 80° C. for 16 hours. The mixture completely reacted was cooled to room temperature, and then extracted by using dichloromethane and distilled water, and the organic layer was dried by putting anhydrous sodium sulfate thereto, and then filtered and concentrated under reduced pressure. The concentrated solution was separated and purified with column chromatography (EtOAc) to obtain a yellow solid target compound (81 mg, 17%).

$^1$H NMR (400 MHz, CDCl$_3$) δ 7.85 (m, 1H), 7.83 (m, 3H), 7.53 (m, 10H), 7.31 (m, 5H), 6.73 (s, 1H), 6.71 (s, 1H), 6.04 (m, 1H), 5.52 (m, 2H), 3.72 (s, 3H), 3.69 (m, 2H), 3.30 (m, 1H), 3.06 (m, 1H), 2.31 (m, 2H), 1.96 (m, 2H), 1.71 (m, 2H), 0.95 (m, 3H).

Step (4). Preparation of methyl ((R)-2-((S)-2-(5-(7-amino-9-butyl-9H-carbazole-2-yl)-1H-imidazole-2-yl)pyrrolidine-1-yl)-2-oxo-1-phenylethyl)carbamate dihydrochloride The method in Step (3) of Example 1 was performed, and a grey solid target compound (4 mg, 18%) was obtained by using methyl ((R)-2-((S)-2-(5-(9-butyl-7-((diphenylmethylene)amino)-9H-carbazole-2-yl)-1H-imidazole-2-yl)pyrrolidine-1-yl)-2-oxo-1-phenylethyl)carbamate (25 mg, 0.03 mmol).

$^1$H NMR (400 MHz, CDCl$_3$) δ 8.35 (m, 2H), 8.00 (s, 1H), 7.71 (d, J=7.6 Hz, 1H), 7.60 (m, 2H), 7.48 (m, 6H), 7.29 (d, J=8 Hz, 1H), 5.55 (s, 1H), 5.39 (m, 1H), 4.54 (m, 2H), 4.10 (m, 1H), 3.67 (s, 3H), 3.64 (m, 1H), 2.63 (m, 1H), 2.23 (m, 2H), 1.98 (m, 2H), 1.48 (m, 2H), 1.02 (t, J=7.2 Hz, 3H);

Step (5). Preparation of methyl ((R)-2-((S)-2-(5-(9-butyl-7-(2-((S)-1-((R)-2-((methoxycarbonyl)amino)-2-phenylacetyl)pyrrolidine-2-carboxamido)-9H-carbazole-2-yl)-1H-imidazole-2-yl)pyrrolidine-1-yl)-2-oxo-1-phenylethyl)carbamate EDC (18 mg, 0.09 mmol), HOBt (12 mg, 0.09 mmol), and ((R)-2-((methoxycarbonyl)amino)-2-phenylacetyl)-L-proline (18 mg, 0.06 mmol) were added to DMF (2 mL), and then the resulting mixture was stirred at room temperature for 1 hour. NMM (36 μL, 0.33 mmol) and the compound (35 mg, 0.05 mmol) prepared in Step (4) were added to the reaction mixture, and then the resulting mixture was stirred for 15 hours. The mixture completely reacted was concentrated under reduced pressure. The mixture was extracted by using ethyl acetate and distilled water, and the organic layer was dried by putting anhydrous sodium sulfate thereto, and then filtered and concentrated under reduced pressure. The concentrated solution was separated and purified with column chromatography (CH$_2$Cl$_2$/EtOAc/MeOH=15/1/1, v/v/v) to obtain a grey solid target compound (15 mg, 31%).

$^1$H NMR (400 MHz, CDCl$_3$) δ 9.42 (m, 1H), 8.07 (m, 3H), 7.64 (m, 1H), 7.50 (m, 12H), 7.08 (m, 1H), 6.13 (m, 2H), 5.53 (m, 2H), 5.39 (m, 1H), 4.87 (m, 1H), 4.30 (m, 2H), 3.88 (m, 2H), 3.72 (s, 3H), 3.68 (s, 2H), 3.34 (m, 2H), 3.00 (m, 1H), 2.55 (m, 1H), 2.31 (m, 2H), 1.91 (m, 4H), 1.43 (m, 2H), 1.30 (m, 2H), 0.97 (m, 3H). LC/MS (ESI-TOF) m/z calcd for C$_{48}$H$_{53}$N$_8$C$_7$ [M+H]$^+$: 853.41 found 853.30.

Example 52. Preparation of methyl ((R)-2-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-2-oxo-1-phenylethyl)carbamate

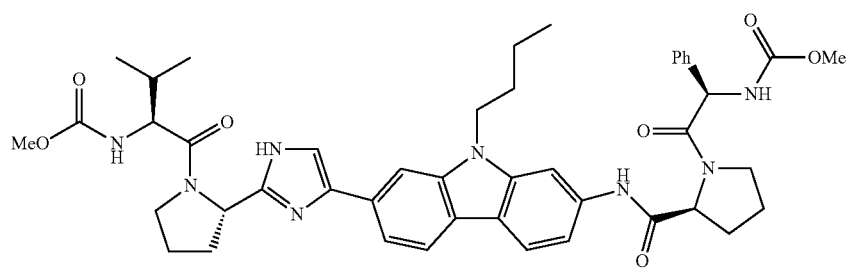 [SMILES: CCCCn1c2cc(NC(=O)[C@@H]3CCCN3C(=O)[C@H](NC(=O)OC)c3ccccc3)ccc2c2ccc(-c3c[nH]c([C@@H]4CCCN4C(=O)[C@@H](NC(=O)OC)C(C)C)n3)cc21]

Step (1). Preparation of methyl ((R)-1-((S-2-(5-(9-butyl-7-((diphenylmethylene)amino)-9H-carbazole-2-yl)-1H-imidazole-2-yl)pyrrolidine-1-yl)-3-methyl-1-oxobutane-2-yl)carbamate The method in Step (3) of Example 51 was performed, and a target compound (24 mg, 41%) was obtained by using N-(9-butyl-7-(4,4,5,5-tetramethyl-1,3,2-dioxaborolane-2-yl)-9H-carbazole-2-yl)-1,1-diphenylmethaneimine (45 mg, 0.08 mmol) and methyl ((S)-1-((S)-2-(5-bromo-1H-imidazole-2-yl)pyrrolidine-1-yl)-3-methyl-1-oxobutane-2-yl)carbamate (30 mg, 0.08 mmol).

$^1$H NMR (400 MHz, CDCl$_3$) δ 7.94 (d, J=8 Hz, 1H), 7.85 (m, 4H), 7.51 (m, 5H), 7.26 (m, 5H), 6.72 (s, 1H), 6.70 (s, 1H), 5.45 (d, J=8.4 Hz, 1H), 5.33 (m, 1H), 4.39 (m, 1H), 3.88 (m, 2H), 3.74 (s, 3H), 3.69 (m, 2H), 2.38 (m, 1H), 2.28 (m, 1H), 2.26 (m, 1H), 2.15 (m, 2H), 1.71 (m, 2H), 1.08 (m, 2H), 0.97 (m, 6H).

Step (2). Preparation of methyl ((R)-1-((S)-2-(5-(7-amino-9-butyl-9H-carbazole-2-yl)-1H-imidazole-2-yl)pyrrolidine-1-yl)-3-methyl-1-oxobutane-2-yl)carbamate dihydrochloride The method in Step (4) of Example 51 was performed, and a grey solid target compound (6 mg, 29%) was obtained by using methyl ((R)-1-((S)-2-(5-(9-butyl-7-((diphenylmethylene)amino)-9H-carbazole-2-yl)-1H-imidazole-2-yl)pyrrolidine-1-yl)-3-methyl-1-oxobutane-2-yl)carbamate (24 mg, 0.03 mmol).

$^1$H NMR (400 MHz, CDCl$_3$) δ 8.34 (d, J=6.0 Hz, 1H), 8.32 (d, J=6.0 Hz, 1H), 8.06 (s, 1H), 8.01 (s, 1H), 7.66 (dd, J=8.0, 1.2 Hz, 1H), 7.63 (s, 1H), 7.29 (dd, J=8.0, 2.0 Hz, 1H), 5.31 (m, 1H), 4.55 (t, J=7.2 Hz, 2H), 4.29 (d, J=7.2 Hz, 1H), 4.15 (m, 1H), 4.00 (m, 1H), 3.68 (s, 3H), 2.65 (m, 1H), 2.35 (m, 3H), 2.14 (m, 1H), 1.96 (m, 2H), 1.47 (m, 2H), 1.01 (m, 9H).

Step (3). Preparation of methyl ((S)-1-((S)-2-(5-(9-butyl-7-((S)-1-((R)-2-((methoxycarbonyl)amino)-2-phenylacetyl)pyrrolidine-2-carboxamido)-9H-carbazole-2-yl)-1H-imidazole-2-yl)pyrrolidine-1-yl)-3-methyl-1-oxobutane-2-yl)carbamate The method in Step (5) of Example 51 was performed, and a grey solid target compound (12 mg, 27%) was obtained by using methyl ((R)-1-((S-2-(5-(7-amino-9-butyl-9H-carbazole-2-yl)-1H-imidazole-2-yl)pyrrolidine-1-yl)-3-methyl-1-oxobutane-2-yl)carbamate dihydrochloride (25 mg, 0.04 mmol) and ((R)-2-((methoxycarbonyl)amino)-2-phenylacetyl)-L-proline (13 mg, 0.04 mmol).

$^1$H NMR (400 MHz, CDCl$_3$) δ 9.41 (m, 1H), 8.13 (s, 1H), 7.99 (m, 2H), 7.60 (m, 1H), 7.50 (m, 7H), 7.13 (m, 1H), 6.05 (m, 1H), 5.52 (d, J=6.4 Hz, 1H), 5.44 (m, 1H), 4.91 (m, 2H), 4.37 (m, 3H), 3.88 (m, 2H), 3.74 (s, 3H), 3.69 (s, 3H), 3.29 (m, 1H), 2.60-1.90 (m, 9H), 1.44 (m, 2H), 1.09 (m, 1H), 0.99 (m, 9H) LC/MS (ESI-TOF) m/z calcd for C$_{45}$H$_{55}$N$_8$C$_7$ [M+H]$^+$: 819.42 found 819.35.

Example 53. Preparation of methyl ((S)-1-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-3-methyl-1-oxobutane-2-yl)carbamate The method in Step (5) of Example 51 was performed, and a grey solid target compound (14 mg, 24%) was obtained by using methyl ((R)-1-((S-2-(5-(7-amino-9-butyl-9H-carbazole-2-yl)-1H-imidazole-2-yl)pyrrolidine-1-yl)-3-methyl-1-oxobutane-2-yl)carbamate dihydrochloride (44 mg, 0.07 mmol) and (methoxycarbonyl)-L-valyl-L-proline (20 mg, 0.07 mmol).

$^1$H NMR (400 MHz, CDCl$_3$) δ 9.59 (s, 1H), 7.96 (m, 2H), 7.74 (m, 2H), 7.29 (m, 2H), 7.02 (m, 1H), 5.46 (m, 2H), 4.94 (d, J=6.4 Hz, 1H), 4.31 (m, 3H), 3.86 (m, 3H), 3.74 (s, 6H), 3.14 (m, 1H), 2.65 (m, 1H), 2.31-1.85 (m, 8H), 1.87 (m, 2H), 1.41 (m, 2H), 1.29 (m, 2H), 1.08 (m, 9H). LC/MS (ESI-TOF) m/z calcd for C$_{42}$H$_{57}$N$_8$C$_7$ [M+H]$^+$: 785.44 found 785.45.

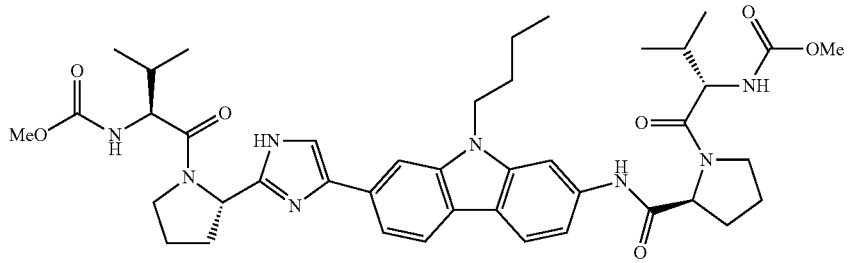 [SMILES: CCCCn1c2cc(NC(=O)[C@@H]3CCCN3C(=O)[C@@H](NC(=O)OC)C(C)C)ccc2c2ccc(-c3c[nH]c([C@@H]4CCCN4C(=O)[C@@H](NC(=O)OC)C(C)C)n3)cc21]

Example 54. Preparation of methyl ((S)-1-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-3-methyl-1-oxobutane-2-yl)carbamate

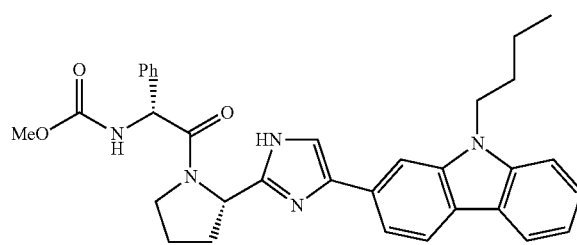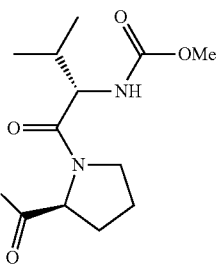

The method in Step (5) of Example 51 was performed, and a grey solid target compound (50 mg, 55%) was obtained by using methyl ((R)-2-((S)-2-(5-(7-amino-9-butyl-9H-carbazole-2-yl)-1H-imidazole-2-yl)pyrrolidine-1-yl)-2-oxo-1-phenylethyl)carbamate dihydrochloride (70 mg, 0.11 mmol) and (methoxycarbonyl)-L-valyl-L-proline (30 mg, 0.11 mmol).

$^1$H NMR (400 MHz, CDCl$_3$) δ 9.61 (s, 1H), 7.97 (m, 3H), 7.57 (s, 1H), 7.48 (m, 7H), 7.01 (m, 1H), 6.13 (br s, 1H), 5.52 (m, 3H), 4.93 (m, 1H), 4.40 (m, 1H), 4.26 (m, 2H), 3.87 (m, 2H), 3.73 (s, 3H), 3.72 (s, 3H), 3.38 (m, 2H), 2.61 (m, 1H), 2.27-2.05 (m, 7H), 1.80 (m, 2H), 1.38 (m, 3H), 1.07 (m, 9H). LC/MS (ESI-TOF) m/z calcd for C$_{45}$H$_{55}$N$_8$C$_7$ [M+H]$^+$: 819.42 found 819.10.

TEST EXAMPLES

It was confirmed that the compounds synthesized in the Examples of the present invention had anti-virus activity by means of the following Test Example 1, and it was also confirmed that several compounds were resistant to hepatitis C virus by means of the following Test Example 2.

Test Example 1. Search for Anti-Virus Activity

From human liver cells (Huh7.5.1 cell) infected by hepatitis C virus, the anti-virus effects by the compound of the present invention were measured. From HCV genotype 1 b (HCV replicon system), genotype 2a (HCV cell culture system, HCVcc), and genotype 3a, the EC$_{50}$ values were measured.

In order to measure the EC$_{50}$ value from HCV genotype 1 b, the degrees of HCV replication inhibitory activities of an experimental compound were measured. The EC$_{50}$ value was measured by treating the experimental compound with the HCV replicon systems (genotype 1 b) having Renilla luciferase (Rluc) genes and genotype 1 b non-structure genes under various concentration conditions to compare the activity degree of the luciferase after 3 days elapsed time with that of the control. The results are shown in the following Table 1.

In order to measure the EC$_{50}$ value from HCV genotype 2a, a luciferase assay was used. A JFH1 clone (JFH 5a-Rluc) virus constructed to have a Renilla luciferase enzyme (Rluc) gene in NS5A protein was infected with Huh7.5.1 cell being a host cell, and then the EC$_{50}$ value was measured by taking cells grown for 3 days by treating the experimental compound under various concentration conditions, and analyzing the activity degree of the luciferase. The results are shown in the following Table 1.

In order to measure the EC$_{50}$ value from genotype 3a, the value was measured through the luciferase activity. A HCV replicon system having firefly luciferase (Fluc) genes and genotype 3a non-structure genes was used. The HCV replicon system having the genes as described above was used to treat the experimental compound under various concentration conditions, and then 3 days later, the EC50 value was measured by comparing the luciferase activity with that of the control. The results are shown in the following Table 1.

In the following Table 1, a low BC$_{50}$ value means that the inhibitory activity value is high.

TABLE 1

| Experimental compound | Replicon EC$_{50}$ | | |
| --- | --- | --- | --- |
| | 1b type | 2a type | 3a type |
| Example 1 | 10.4 pM | | |
| Example 2 | >1 nM | | |
| Example 3 | >1 nM | | |
| Example 4 | 10 nM~100 nM | | |
| Example 5 | >100 nM | | |
| Example 6 | 19.5 pM | | |
| Example 7 | >1 nM | | |
| Example 8 | >1 nM | | |
| Example 9 | >100 nM | | |
| Example 10 | >100 nM | | |
| Example 11 | 10~100 nM | | |
| Example 12 | 1~10 nM | | |
| Example 13 | 24.6 pM | | |
| Example 14 | 20.3 pM | | |
| Example 15 | 15.7 pM | | |
| Example 16 | 18.2 pM | | |
| Example 17 | 50~250 pM | | |
| Example 18 | 50~250 pM | | |
| Example 19 | 243.5 pM | | |
| Example 20 | 221.5 pM | | |
| Example 21 | 110.6 pM | | |
| Example 22 | 250 pM~1.25 nM | | |
| Example 23 | >1 nM | | |
| Example 24 | ~10 pM | 10~100 nM | |
| Example 25 | >1 nM | | |
| Example 26 | 7.92 pM | 10~100 nM | |
| Example 27 | 1.85 pM | 10~100 nM | |
| Example 28 | 4.52 pM | 1~10 nM | |
| Example 29 | 10~100 pM | 1~10 nM | 10~100 nM |
| Example 30 | 10~100 pM | ~1 nM | 71 pM |
| Example 31 | ~10 pM | 1~10 nM | ~10 pM |
| Example 32 | 100 pM~1 nM | | 1~10 nM |
| Example 33 | 100 pM~1 nM | | 100 pM~1 nM |
| Example 34 | 10~100 pM | 1~10 nM | 10~100 pM |
| Example 35 | ~1 nM | | |
| Example 36 | 3.26 pM | | 12.59 pM |
| Example 37 | 14.5 pM | | 87.43 pM |
| Example 38 | 35.38 pM | | 81.92 pM |
| Example 39 | 1.125 pM | | 6.384 pM |
| Example 40 | 10~100 pM | | |

TABLE 1-continued

| Experimental compound | Replicon EC$_{50}$ | | |
|---|---|---|---|
| | 1b type | 2a type | 3a type |
| Example 41 | 9.65 pM | | 41.89 pM |
| Example 42 | 1.24 pM | 10~100 nM | 32.87 pM |
| Example 43 | ~10 pM | >10 nM | |
| Example 44 | ~10 pM | >10 nM | 10 pM~100 pM |
| Example 45 | ~10 pM | >10 nM | 199.2 pM |
| Example 46 | ~10 pM | | |
| Example 47 | ~10 pM | | |
| Example 48 | 7.41 pM | | 160.6 pM |
| Example 49 | 8.4 pM | >10 nM | 76.62 pM |
| Example 50 | 4.34 pM | | 183.3 pM |
| Example 51 | 14.52 pM | 387.3 pM | 193.4 pM |
| Example 52 | 12.35 pM | 170.7 pM | 148.2 pM |
| Example 53 | >10 nM | | |

Test Example 2. Search for Efficacy of Resistant Mutant

The efficacy for resistant hepatitis C virus was searched by selecting several compounds exhibiting excellent anti-virus efficacy for genotype 1 b (HCV replicon 1b) and cell culture genotype 2a (HCVcc). As a mutant resistant to hepatitis C virus, L31V and Y93H of the NS5A region, and double mutants thereof were applied. The results are shown in the following Table 2.

TABLE 2

| Experimental compound | Formula 1, R$^1$ | EC$_{50}$ | | |
|---|---|---|---|---|
| | | L31V | Y93H | Double mutant |
| BMS-790052 | | 100 pM~1 nM | 1 nM~10 nM | >1 μM |
| Example 13 | Benzyl | 100 pM~1 nM | 100 nM~1 μM | >1 μM |
| Example 14 | 4-methoxybenzyl | 100 pM~1 nM | 100 nM~1 μM | >1 μM |
| Example 15 | 1-phenylethyl | <100 pM | 10 nM~100 nM | >1 μM |
| Example 16 | Cyclopropylmethyl | 1 nM~10 nM | 10 nM~100 nM | >1 μM |
| Example 19 | Pyridine-4-ylmethyl | 1 nM~10 nM | >1 μM | >1 μM |
| Example 20 | (6-methylpyridine-2-yl)methyl | 10 nM~100 nM | >1 μM | >1 μM |
| Example 21 | 2-methoxyethyl | 10 nM~100 nM | 100 nM~1 μM | >1 μM |
| Example 26 | Octyl | 1 nM~10 nM | | |
| Example 27 | Dodecyl | 100 pM~1 nM | | |
| Example 28 | 1-phenylbutyl | <100 pM | | |
| Example 31 | 4-(hexyloxy)benzyl | <100 pM | 10 nM~100 nM | |
| Example 34 | 10-morpholinodecyl | <100 pM | 100 nM~1 μM | |
| Example 36 | 4-butoxybenzyl | 100 pM~1 nM | 100 nM~1 μM | |
| Example 39 | 3-(cyclopentyloxy)benzyl | 100 pM~1 nM | 100 nM~1 μM | |
| Example 41 | 3-(2-(2-methoxyethoxy)ethoxy)benzyl | 100 pM~1 nM | >1 μM | |
| Example 42 | 1-phenyldecyl | 100 pM~1 nM | 100 nM~1 μM | |

Meanwhile, the novel compound represented by Formula 1 according to the present invention can be formulated in various forms according to the purpose. The followings illustrate several formulation methods in which the compound represented by Formula 1 according to the present invention is contained as an active ingredient, and the present invention is not limited thereto.

FORMULATION EXAMPLES

Method of Preparing Pharmaceutical Formulations

Formulation Example 1. Tableting (Direct Pressurization)

After 5.0 mg of the active ingredient was sieved, the active ingredient was mixed with 14.1 mg of lactose, 0.8 mg of crospovidone USNF, and 0.1 mg of magnesium stearate, and the resulting mixture was subjected to pressurization to be formulated into a tablet.

Formulation Example 2. Tableting (Wet Granulation)

After 5.0 mg of the active ingredient was sieved, the active ingredient was mixed with 16.0 mg of lactose and 4.0 mg of starch. After 0.3 mg of Polysolvate 80 was dissolved in pure water, a proper amount of the resulting solution was added to the mixture and subjected to granulation. After drying, the fine grains were sieved and mixed with 2.7 mg of colloidal silicon dioxide and 2.0 mg of magnesium stearate. The resulting granules were subjected to pressurization to be formulated into a tablet.

Formulation Example 3. Powder and Capsule

After 5.0 mg of the active ingredient was sieved, the active ingredient was mixed with 14.8 mg of lactose, 10.0 mg of polyvinyl pyrrolidone, and 0.2 mg of magnesium stearate. The mixture was filled into a firm No. 5 gelatin capsule by using a suitable device.

Formulation Example 4. Injection

An injection was prepared by containing 100 mg of the active ingredient, 180 mg of mannitol, 26 mg of Na$_2$HPO$_4$.12H$_2$O, and 2,974 mg of distilled water.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A compound selected from a carbazole compound represented by the following Formula 1a or Formula 1b, a pharmaceutically acceptable salt or a hydrate thereof:

[Formula 1a]

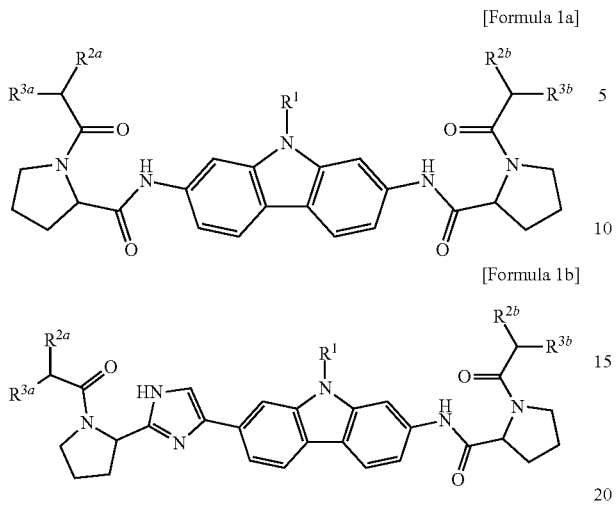

[Formula 1b]

wherein in Formula 1a or 1b, $R^1$ represents —($C_1$ to $C_{15}$ alkyl)-$R^4$, $R^{2a}$ and $R^{2b}$ are the same as or different from each other, and represent a $C_1$-$C_{10}$ alkyl group, or a $C_6$ to $C_{12}$ aryl group, $R^{3a}$ and $R^{3b}$ are the same as or different from each other, and represent —N($R^5$)—C(O)O$R^6$, $R^4$ represents a hydrogen atom, a $C_3$ to $C_7$ cycloalkyl group, di($C_3$ to $C_7$ cycloalkyl), —O$C_1$-$C_{10}$alkyl, —(O$C_1$-$C_{10}$alkyl)$_n$(O$C_1$-$C_{10}$alkyl) (here, n is an integer from 0 to 5), a $C_6$ to $C_{12}$ aryl group, a pentagonal to heptagonal heterocyclic group including 1 to 3 heteroatoms selected from nitrogen and oxygen, or a pentagonal to heptagonal heteroaryl group including 1 to 3 heteroatoms selected from nitrogen and oxygen, $R^5$ and $R^6$ represent a hydrogen atom, or a $C_1$-$C_{10}$ alkyl group, or $R^5$ and $R^6$ are optionally bonded to each other to form

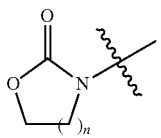

(here, n is an integer from 0 to 9), and the aryl group, the heterocyclic group, or the heteroaryl group are optionally each unsubstituted or substituted with 1 to 3 substituents selected from the group consisting of a halogen atom, nitro, amine, $C_1$-$C_{10}$ alkyl, $C_1$-$C_{10}$ haloalkyl including 1 to 15 halogen atoms, —O$C_1$-$C_{10}$alkyl, —O$C_3$-$C_7$ cycloalkyl, —(O$C_1$-$C_{10}$alkyl)$_n$(O$C_1$-$C_{10}$alkyl) (here, n is an integer from 0 to 5), and —NH—C(O)—$C_1$-$C_{10}$ alkyl.

2. The compound of claim 1, wherein $R^1$ represents a $C_1$ to $C_{15}$ alkyl group, —($C_1$-$C_{10}$ alkyl)-($C_3$ to $C_7$ cycloalkyl), —($C_1$-$C_{10}$ alkylene)-($C_3$ to $C_7$ cycloalkyl)$_2$, —($C_1$-$C_{10}$ alkyl)-(O$C_1$ to $C_6$ alkyl), —($C_1$-$C_{10}$ alkyl)(O$C_1$ to $C_6$ alkyl)$_n$(O$C_1$ to $C_6$ alkyl) (here, n is an integer from 1 to 3), —($C_1$-$C_{10}$ alkyl)-morpholine, —($C_1$-$C_{10}$ alkyl)-piperidine, —($C_1$-$C_{10}$ alkyl)-piperazine, —($C_1$-$C_{10}$ alkyl)-(N—$C_1$ to $C_6$ alkylpiperazine), —($C_1$-$C_{10}$ alkyl)-pyridine, and —($C_1$-$C_{10}$ alkyl)-phenyl, the pyridine is optionally unsubstituted or substituted with 1 and 2 substituents selected from the group consisting of $C_1$ to $C_6$ alkyl, and the phenyl is optionally unsubstituted or substituted with 1 to 3 substituents selected from the group consisting of halo, —NO$_2$, —NH$_2$, —CF$_3$, —O$C_1$ to $C_6$ alkyl, —O$C_3$-$C_7$ cycloalkyl, —(O$C_1$ to $C_6$ alkyl)$_n$(O$C_1$ to $C_6$ alkyl) (here, n is an integer from 1 to 3), and —NH—C(O)—$C_1$ to $C_6$ alkyl, $R^{2a}$ and $R^{2b}$ are the same as or different from each other, and represent a $C_1$-$C_{10}$ alkyl group, or a phenyl group, $R^{3a}$ and $R^{3b}$ are the same as or different from each other, and represent —N($R^5$)—C(O)O$R^6$, and $R^5$ and $R^6$ represent a hydrogen atom, or a $C_1$-$C_{10}$ alkyl group, or $R^5$ and $R^6$ are optionally bonded to each other to form

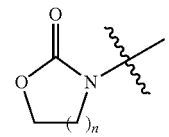

(here, n is an integer from 0 to 9).

3. The compound of claim 1, wherein the compound is selected from (Compound No. 1) dimethyl ((1R,1'R)-((2S, 2'S)-(((9-butyl-9H-carbazole-2,7-diyl)bis(azanediyl))bis (carbonyl))bis(pyrrolidine-2,1-diyl))bis(2-oxo-1-phenylethane-2,1-diyl))dicarbamate, (Compound No. 2) dimethyl ((2R,2'R)-((2S,2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 3) dimethyl ((1S,1'S)-((2S,2'S)-(((9-butyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 4) dimethyl ((2S,2'S)-((2S,2'S)-(((9-butyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 5) (2S,2'S)—N,N'-(9-butyl-9H-carbazole-2,7-diyl)bis(1-((S)-3-methyl-3-2-(2-oxooxazolidine-3-yl)butanoyl)pyrrolidine-2-carboxamide), (Compound No. 6) dimethyl ((1R,1'R)-((2S,2'S)-(((9-methyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 7) dimethyl ((2R,2'R)-((2S,2'S)-(((9-methyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 8) dimethyl ((1S,1'S)-((2S,2'S)-(((9-methyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 9) dimethyl ((2S,2'S)-((2S,2'S)-(((9-methyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 10) (2S,2'S)—N,N'-(9-methyl-9H-carbazole-2,7-diyl)bis(1-((S)-3-methyl-2-(2-oxazolidine-3-yl)butanoyl)pyrrolidine-2-carboxamide), (Compound No. 11) dimethyl ((1R,1'R)-((2S,2'S)-(((9-(2-(4-methylpiperazine-1-yl)ethyl)-9H-carbazole-2,7- diyl)bis(azanediyl))bis(carbonyl))bis(pyrrolidine-2,1-diyl))bis(2-oxo-1-phenylethane-2,1-diyl))carbamate, (Compound No. 12) dimethyl ((1R,1'R)-((2S,2'S)-(((9-(2-morpholinoethyl)-9H-carbazole-2,7-diyl)bis(azanediyl))bis(carbonyl))bis(pyrrolidine-2,1-diyl))bis(2-oxo-1-phenylethane-2,1-diyl))carbamate, (Compound No. 13) dimethyl ((1R,1'R)-((2S,2'S)-(((9-benzyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 14) dimethyl ((1R,1'R)-((2S,2'S)-(((9-(4-methoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 15) dimethyl ((1R,1'R)-((2S,2'S)-(((9-(1-phenylethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 16) dimethyl ((1R,1'R)-((2S,2'S)-(((9-(cyclopropylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 17) dimethyl ((1R,1'R)-((2S,2'S)-(((9-(pyridine-2-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 18) dimethyl ((1R,1'R)-((2S,2'S)-(((9-(pyridine-3-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 19) dimethyl ((1R,1'R)-((2S,2'S)-(((9-(pyridine-4-ylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 20) dimethyl ((1R,1R)-((2S,2'S)-(((9-((6-methylpyridine-2-yl)methyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 21) dimethyl ((1R,1'R)-((2S,2'S)-(((9-(2-methoxyethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 22) dimethyl ((1R,1'R)-((2S,2'S)-(((9-(2-(2-methoxyethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 23) dimethyl ((1R,1R)-((2S,2'S)-(((9-(2-(2-(2-methoxyethoxy)ethoxy)ethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 24) dimethyl ((1R,1'R)-((2S,2'S)-(((9-decyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 25) dimethyl ((2R,2'R)-((2S,2'S)-(((9-decyl-9H-carbazole-2,7-diyl)bis(azanediyl))bis(carbonyl))bis(pyrrolidine-2,1-diyl))bis(3-methyl-1-oxobutane-1,2-diyl))dicarbamate, (Compound No. 26) dimethyl ((1R,1'R)-((2S,2'S)-(((9-octyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 27) dimethyl ((1R,1'R)-((2S,2'S)-(((9-dodecyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 28) dimethyl ((1R,1'R)-((2S,2'S)-(((9-(1-phenylbutyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 29) dimethyl ((1R,1'R)-((2S,2'S)-(((9-(1-phenyloctyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 30) dimethyl ((1R,1'R)-((2S,2'S)-(((9-(3-(pentyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 31) dimethyl ((1R,1'R)-((2S,2'S)-(((9-(4-(hexyloxy)benzyl)-9H-carbonyl-2,7-diyl)bis(azanediyl))bis(carbonyl))bis(pyrrolidine-2,1-diyl))bis(2-oxo-1-phenylethane-2,1-diyl))dicarbamate, (Compound No. 32) dimethyl ((1R,1'R)-((2S,2'S)-(((9-(2-butoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 33) dimethyl ((1R, 1'R)-((2S,2'S)-(((9-(10-(4-methylpiperazine-1-yl)decyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 34) dimethyl ((1R,1'R)-((2S,2'S)-(((9-(10-morpholinodecyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 35) dimethyl ((1R,1'R)-((2S,2'S)-(((9-(2-(hexyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 36) dimethyl ((1R,1'R)-((2S,2'S)-(((9-(4-butoxybenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 37) dimethyl (1R,1'R)-((2S,2'S)-(((9-(3-nitrobenzyl)-9H-carbazole-2,7-diyl)bis(azanediyl))bis(carbonyl))bis(pyrrolidine-2,1-diyl))bis(2-oxo-1-phenylethane-2,1-diyl)dicarbamate, (Compound No. 38) dimethyl ((1R,1'R)-((2S,2'S)-(((9-(3-pivalamidobenzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 39) dimethyl ((1R,1'R)-((2S,2'S)-(((9-(3-(cyclopentyloxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 40) dimethyl ((1R,1'R)-((2S,2'S)-(((9-(3-(2-(2-methoxyethoxy)ethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 41) dimethyl ((1R,1'R)-((2S,2'S)-(((9-(3-(2-methoxyethoxy)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 42) dimethyl ((1R,1'R)-((2S,2'S)-(((9-(1-phenyldecyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 43) dimethyl ((1R,1'R)-((2S,2'S)-(((9-(2-(trifluoromethyl)benzyl)-9H-carbazole-2,7-diyl)bis(azanediyl))biscarbonyl))bis(pyrrolidine-2,1-diyl))bis(2-oxo-1-phenylethane-2,1-diyl))dicarbamate, (Compound No. 44) dimethyl ((1R,1'R)-((2S,2'S)-(((9-(3-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 45) dimethyl ((1R,1'R)-((2S,2'S)-(((9-(4-(trifluoromethyl)benzyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 46) dimethyl ((1R,1'R)-((2S,2'S)-(((9-(nonane-5-yl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 47) dimethyl ((1R,1'R)-((2S,2'S)-(((9-(cyclopentylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 48) dimethyl ((1R,1'R)-((2S,2'S)-(((9-(cyclohexylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 49) dimethyl R,1'R)-((2S,2'S)-(((9-(dicyclopropylmethyl)-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 50) dimethyl ((1R,1'R)-((2S,2'S)-(((9-pentyl-9H-carbazole-2,7-diyl)bis(azanediyl))bis(carbonyl))bis(pyrrolidine-2,1-diyl))bis(2-oxo-1-phenylethane-2,1-diyl))dicarbamate, (Compound No. 51) methyl ((R)-2-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-2-oxo-1-phenylethyl)carbamate, (Compound No. 52) methyl ((R)-2-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-2-oxo-1-phenylethyl)carbamate, (Compound No. 53) methyl ((S)-1-((S)-2-((9-butyl-7-(2-((S)-1-((methoxycarbonyl)-L-valyl)pyrrolidine-2-yl)-1H-imidazole-4-yl)-9H-carbazole-2-yl)carbamoyl)pyrrolidine-1-yl)-3-methyl-1-oxobutane-2-yl)carbamate, (Compound No. 54) methyl ((S)-1-((S)-2-((9-butyl-7-(2-((S)-1-((R)-2-((methoxycarbonyl)amino)-2-phenylacetyl)pyrrolidine-2-yl)-1H-imidazole-4-yl)-9H-carbazole-2-yl)carbamoyl)pyrrolidine-1-yl)-3-methyl-1-oxobutane-2-yl)carbamate, or a pharmaceutically acceptable salt or a hydrate thereof.

4. The compound of claim 1, wherein the pharmaceutically acceptable salt is a salt of inorganic acid or organic acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

5. A pharmaceutical composition comprising a compound selected from the group consisting of the carbazole compound of claim 1, a pharmaceutically acceptable salt thereof, and a hydrate thereof.

6. A method for treating liver diseases caused by hepatitis C virus selected from the group consisting of acute hepatitis C, chronic hepatitis C, cirrhosis, and hepatocellular carcinoma, said method comprising administering the compound, pharmaceutically acceptable salt or hydrate thereof of claim 1 to a subject in need thereof.

\* \* \* \* \*